(12) United States Patent
Dumont et al.

(10) Patent No.: US 6,479,487 B1
(45) Date of Patent: *Nov. 12, 2002

(54) 6, 9-DISUBSTITUTED 2-[TRANS-(4-AMINOCYCLOHEXYL)AMINO] PURINES

(75) Inventors: Jennifer A. Dumont, Flemington, NJ (US); Alan J. Bitonti, Acton, MA (US); David R. Borcherding, Bangor, PA (US); Norton P. Peet, Neshanic Station, NJ (US); H. Randall Munson, Jr., Annandale, NJ (US); Patrick W. Shum, Flemington, NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/247,053

(22) Filed: Feb. 9, 1999

Related U.S. Application Data
(60) Provisional application No. 60/135,109, filed on Feb. 26, 1998.

(51) Int. Cl.$^7$ ............... C07D 473/16; A61K 31/52; A61P 35/00; A61P 35/02

(52) U.S. Cl. ............... 514/234.2; 514/261; 514/266; 544/118; 544/277

(58) Field of Search ............... 544/277, 118; 514/261, 266, 234.2

(56) References Cited

U.S. PATENT DOCUMENTS

| | | | |
|---|---|---|---|
| 4,232,155 A | | 11/1980 | Naito ............... 544/277 |
| 5,516,631 A | * | 5/1996 | Frisch ............... 435/5 |
| 5,688,665 A | * | 11/1997 | Massague ............... 435/69.2 |
| 5,861,290 A | * | 1/1999 | Goldsmith ............... 435/172.3 |

FOREIGN PATENT DOCUMENTS

| | | | |
|---|---|---|---|
| EP | 0545413 | | 6/1993 |
| FR | 2793794 A1 | * | 11/2000 |
| WO | 9417090 | | 8/1994 |
| WO | 9602543 | | 2/1996 |
| WO | 9716452 | | 5/1997 |
| WO | 9720842 | | 6/1997 |
| WO | 9805335 | | 2/1998 |
| WO | 9907705 | | 2/1999 |
| WO | 0044750 | | 8/2000 |

OTHER PUBLICATIONS

Myers, et al of Current Pharmaceutical Design, 1997, 30, 473–502.
Kath, J.C., Oncologic, Endorcine & Metbolic, Exp. Opin. Ther. Patents (2000) 10(6):803:818.
Rosania, R.R. et al., Ashley Publication Exp. Opin. Ther. Patents (2000)10(2): 215–230.
Park, J. Biol. Chem 271, p 8161 (1996).
Park, J. Neuro Sci. 17(4), 1256 (1997).

On Line Medical Dictionary, entry for "Hyperproliferation" (undated).*
Biotech Life Science Dictionary, entry for "Hyperproliferation" (undated).*
Taber's Cyclopedic Medical Dictionary (F.A. Davis, Co), p. 793, 1387, 1985.*
Webster's Third New International Dictionary (Merriam–Webster, Inc)p. 1814, 1986.*

* cited by examiner

Primary Examiner—Mark L. Berch
(74) Attorney, Agent, or Firm—Joseph Strupczewski

(57) ABSTRACT

The present invention provides novel compounds of the formula (I)

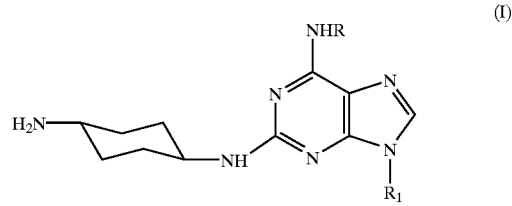

(I)

wherein

R is selected from the group consisting of R2, R2NH—, or R3R4N—R5- wherein

R2 is selected from the group consisting of $C_9$–$C_{12}$ alkyl,

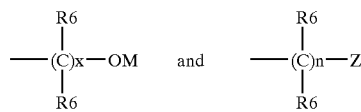

Z is selected from the group consisting of phenyl, heterocycle, cycloalkyl, and naphthanlene; and M is selected from the group consisting of hydrogen, $C_1$–$C_4$ alkyl, and wherein each $C_9$–$C_{12}$ alkyl or Z is optionally substituted with 1 to 3 substituents, which may be the same or different, and which are selected from the group consisting of D, E,

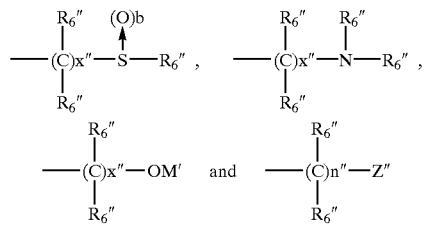

wherein each D is independently selected from the group consisting of trifluoromethyl, trifluoromethoxy, and $C_1$–$C_4$ alkoxy; each E is independently selected from the group consisting of Hal, OH, and $C_1$–$C_8$ alkyl;

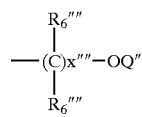

R3 and R4 are selected from the group consisting of hydrogen, $C_1$–$C_4$ alkyl and $(CH_2)_y$-phenyl, wherein y is an integer 0–8, with the proviso that R3 and R4 not both be hydrogen;

R5 is $C_1$–$C_8$ alkylene; and

R1 is selected from the group consisting of cyclopentyl, cyclopentenyl and isopropyl, and the pharmaceutically acceptable salts, optical isomers, and hydrates thereof, with the proviso that when R2 is the group

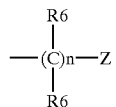

wherein n is 1 or greater; R1 is isopropyl or cyclopentyl; R6 is hydrogen, $C_1$–$C_4$ alkyl, or $(CH_2)_m$-phenyl; and Z is phenyl, heterocycle, or cycloalkyl, that Z is substituted with 1 to 3 substituents, which may be the same or different, and which are selected from the group consisting of

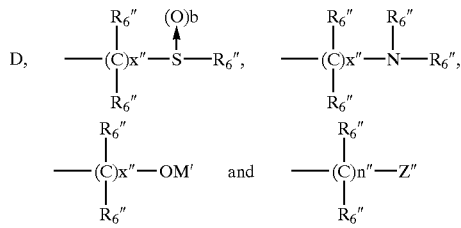

In addition, the present invention provides a method of inhibiting cyclin dependent kinases, particularly cdk-2.

The present invention also provides a method of preventing apoptosis in neuronal cells and a method of inhibiting the development of neoplasms.

193 Claims, No Drawings

6,9-DISUBSTITUTED 2-[TRANS-(4-AMINOCYCLOHEXYL)AMINO] PURINES

This application claims the benefit of U.S. Provisional Application No. 60/135,109, filed Feb. 26, 1998, which is hereby incorporated by reference.

The present invention relates to 6,9-disubstituted 2-[trans-(4-aminocyclohexyl)amino]-purines and methods of using the same for antineoplastic agents or for treatment for neuronal injury and degeneration.

BACKGROUND OF THE INVENTION

Cell division, in both normal and neoplastic cells, is a tightly controlled event which occurs by defined stages. Quiescent cells which are not actively dividing, are in the $G_0$ phase, as are those terminally differentiated or in a state of temporary arrest. The first phase is the first gap ($G_1$) phase during which the cell prepares to synthesize DNA. In late $G_1$ phase at what is termed a restriction point or R point, the cell commits to entering S phase during which DNA synthesis occurs. Upon completion of S phase, the cell enters the second gap ($G_2$) phase during which the cell prepares to divide, which is followed by mitosis, or M phase.

Initial experiments in cell cycle regulation revealed the existence of a protein called "Maturation Promoting Factor" (MPF), a heterodimer with kinase activity. Later, comparison of subsequently identified proteins and their underlying genes revealed a family of yeast genes known as cell division control (cdc) genes. Further experiments demonstrated that some of the cdc genes encode kinases, and were later called cyclin-dependent kinases (cdks). As the result of this reclassification, some cell cycle proteins have dual designations, such as cdk1 which is also known as cdc2. The kinase component of the MPF is now identified as $p34^{cdc2}$ and the regulatory subunit of MPF is now called cyclin B. Cyclins were first identified as proteins whose levels oscillated during the cell cycle and were specifically degraded at mitosis. To date, animal cyclins A–I and cdks 1–8 have been identified. To further complicate nomenclature, subtypes of cyclins and cdks have been identified, such as cyclins B1 and B2.

Subsequent research on cell regulation has demonstrated that the stages of cellular division are achieved in part by modulation cyclins and cyclin-dependent kinases (cdks). Cyclins sequentially regulate cdks and are characterized by a 100 amino acid homology region termed the "cyclin box" which is involved in binding a protein kinase partner. Cdks are closely related in sequence and size (35–40 kDa) and are defined as protein kinases activated by bound cyclin regulatory subunits. Cdks contain a conserved active-site cleft of approximately 300 amino acids that is characteristic of all eukaryotic protein kinases. Thus, both the cyclins and cdks appear to be highly conserved protein families.

Isolation of individual cyclins and cdks has enabled further identification of the roles and interactions of each component in cell cycle phase transitions. Excess levels of cdks persist throughout the cell cycle. Activation of cdks occurs upon cyclin synthesis and binding to the catalytic cdk subunit, the result of which is stimulation of the cdk serine/threonine kinase activity. Complete cdk activation requires phosphorylation on a conserved threonine residue located in the T-loop by a cyclin-dependent kinase activating kinase (CAK), which is itself a cdk/cyclin complex composed of cyclin H and cdk7, and a third protein of about 32 kDa.

Inactivation of the cdk-cyclin complex can result from the phosphorylation of a threonine and/or tyrosine residue in the ATP-binding site of the cdk or from binding of one of a number of endogenous inhibitor proteins.

In $G_1$ phase, D-type cyclins bind to several different cdks, including cdk2, cdk4, cdk5 and cdk6, but are most commonly associated with cdk4 and cdk6. D-type cyclins are thought to act as growth factor sensors, which link cell cycle progression to external cues. Cyclin E-cdk2 complexes appear in the mammalian cell cycle after the D-type cyclin-cdk complexes. Cyclin E synthesis is tightly regulated and occurs in late $G_1$ and early S phase. The cyclin E-cdk2 complex is essential for the cell to begin DNA replication.

The $G_1$ cyclins, cyclin D and cyclin E, are transiently produced proteins, with a half-life of about 20 minutes. The short half-life is thought to result from a PEST sequence in the C-terminal regions of these proteins, the degradation of which appears to be mediated by the ubiquitination pathway.

The $G_2$ cyclins, cyclin A and cyclin B, are stable throughout interphase and specifically destroyed at mitosis through an ubiquitination pathway. Both cyclin A and cyclin B2 appear to be degraded only when complexed with their cdk partner [cyclinA-cdk2 and cyclin A/B-cdk1(cdc2)]. However, cyclin B1 destruction is connected with the integrity of the mitotic apparatus at the end of metaphase. If the spindle is incorrectly assembled, or chromosomes incorrectly aligned, then cyclin B1 destruction is prevented.

Retinoblastoma protein (Rb), a 105 kDa nuclear phosphoprotein, is a substrate of cyclin-cdk complexes of cdks-2, 4 and 6 in $G_1$ phase and functions as one of the major checkpoint controls in the cell cycle via carefully orchestrated phosphorylation and dephosphorylation. In $G_0/G_1$, Rb exists in a hypophosphorylated state. As the cell progresses into late $G_1$, Rb becomes hyperphosphorylated by D-cyclin complexes, which inactivates Rb and drives the cell into S phase resulting in cell cycle progression and cell division. This state of hyperphosphorylation of Rb remains in $G_2$. During late M phase, Rb is dephosphorylated, thus returning to the hypophosphorylated state. Phosphorylation of the Rb protein alters its binding characteristics; in the hypophosphorylated state, Rb binds to and sequesters specific transcription factors, such as E2F, the binding of which prevents the exit from the $G_1$ phase. Once cdks hyperphosphorylate Rb, the transcription factors are released which can then activate transcription of genes necessary for S phase progression, for example, thymdine kinase, myc, myb, dihydrofolate reductase, and DNA polymerase-α.

Localization of cyclin-CDK complexes is also very suggestive about the role each complex plays in the pathway. Nuclear cyclins A and E bind to p107 and p130, possibly because they are in the nucleus. Mammalian cyclin B1 accumulates in the cytoplasm in $G_2$ phase and translocates into the nucleus at the beginning of mitosis. Cyclin B associates with the spindle apparatus, in particular with the spindle caps, and it is thought that the cyclin B-cdc2 kinase may be involved in the formation of the spindle through phosphorylating components of the mitotic apparatus. In addition, cyclin B1 is part of a feedback mechanism ensuring correct assembly of the metaphase mitotic apparatus. Human cyclin B2 is almost exclusively associated with the membrane compartment, and in particular the Golgi apparatus. Cyclin B2-cdc2 is involved in the disassembly of the Golgi apparatus when cells enter mitosis.

Cdc2-cyclin B kinase is a key mitotic factor which appears to be highly conserved and is thought to be involved in cell cycle transitions in all eukaryotic cells. Histone H1 is a substrate for cdc2-cyclin B; histone H1 is selectively phosphorylated on specific sites in mitosis, which is thought to be important for chromatin condensation. The cdc2-cyclin B complex also phosphorylates lamin, which is responsible for nuclear lamina breakdown. The nuclear lamina is made up of a polymer of lamin subunits that are hyperphosphorylated at mitosis, and this phosphorylation is responsible for their disassembly. Lamins are part of the intermediate filament family of proteins, and cdc2-cyclin B phosphorylates a subset of the sites phosphorylated at mitosis on the cytoplasmic intermediate filament subunits, vimentin and desmin. Thus, the cdc2-cyclin B complex is involved in the reorganization of the cell architecture at mitosis.

In addition, cdc2-cyclin B is involved in the reorganization of microfilaments, through phosphorylation of non-muscle caldesmon, an 83 kDa protein that binds to actin and calmodulin, and inhibits actomyosin ATPase activity. At mitosis, caldesmon is phosphorylated by cdc2-cyclin B, which weakens its affinity for actin and causes it to dissociate from microfilaments.

Cdc2-cyclin B is implicated in actomyosin filament regulation, by phosphorylating the myosin in the contractile ring, which divides the cell into two (cytokinesis). In metaphase, the myosin II regulatory light chain (MLC) is phosphorylated on two main sites at the N-terminus. Once phosphorylated, the myosin is prevented from interacting with actin. At anaphase, these two sites are dephosphorylated.

Cdc2-cyclin B also plays a role in reorganization of the membrane compartment at mitosis. For example, cdc2-cyclin B phosphorylates rab1Ap and rab4p. When rab4p is phophorylated by cdc2-cyclin B, it dissociates from the membrane compartment.

At mitosis, most forms of transcription are inhibited. Again, cdc2-cyclin B plays a role in inhibition of pol III-mediated transcription by phosphorylating TFIIIB. Given that pol I, pol II and pol III-mediated transcription share several common factors, such as TATA-binding protein (TBA), it is likely that cdc2-cyclin B is involved in down-regulating all forms of transcription at mitosis.

Given the importance of cyclin/cdk complexes in triggering cell cycle division, they are under tight regulatory mechanisms. Since their initial discovery, cyclins and cdks have been shown to interact with other transcription factors and proteins involved in a broad range of cellular pathways. Cdk7 has been identified as a component in transcription factor IIH (TFIIH), which contains the RNA polymerase II C-terminal domain (CTD) kinase activity. More recently, cdk8 which partners with cyclin C, has also been discovered to phosphorylate the CTD of RNA polymerase II, but does not appear to possess CAK activity. Thus, it is clear that cdks participate in a broad range of cellular functions in addition to cell cycle regulation. CDK-inhibitor proteins (CDIs) are small proteins that bind and inactivate specific cyclin-CDK complexes, or monmeric CDKs. These inhibitors can be grouped into two families based on sequence and functional similarities. The INK4 family includes $p15^{INK4B}$, $p16^{INK4}$, p18 and p19 which specifically bind cdk4 and cdk6. $p16^{INK4}$ and $p15^{INK4B}$ contain four ankyrin repeats and, in addition to sharing significant homology, are encoded by adjacent genes on the 9p12 locus.

High cellular levels of p16 results in inactivation of cdk4 because p16 binds cyclinD-cdk4 and cyclin D-cdk6 complexes. The gene for $p16^{INK4}$ (MTS1) is recognized as a potential tumor suppressor gene, as it is rearranged, deleted or mutated in a large number of tumor cell lines, and in some primary tumors. In one study of hereditary melanoma, about half the families had germline mutations in the $p16^{INK4}$ gene. Rb is a repressor of $p16^{INK4}$. Inactivation of cellular Rb, either by mutation or viral antigens, correlates with increased levels of $p16^{INK4}$. $P16^{INK4}$, $p15^{INK4B}$, and p18 inhibit binding of cyclin D with cdk4 and cdk6.

The second family of CDIs is the Kip/Cip family which includes $p21^{Cip1,WAF-1}$, $p27^{Kip1}$ and $p57^{Kip2}$ $p27^{KIP1}$ is present in proliferating cells in a latent or masked form. Upon stimulation, $p27^{KIP1}$ is unmasked and binds to and inhibits cyclin-CDK4/6 complexes. The Kip/Cip family proteins have strong homology in the N-terminus, the region that binds the cyclin-cdk complexes. The Kip/Cip family proteins preferentially bind to and inhibits cyclin-cdk complexes involved in the $G_1$ and S phase complexes over those involved in the M phase.

P21 (also known as WAF1, Cip1 and Sdi1) is induced by p53 and forms a ternary complex with proliferating cell nuclear antigen (PCNA), a subunit of DNA polymerase δ in several cyclin-CDK2 complexes, including cyclins A, D1 and E. $P21^{WAF-1}$ expression in growing, quiescent and senescent cells correlates with a role as a negative regulator of S phase entry. $P21^{WAF-1}$ mRNA is upregulated as cells become senescent or quiescent, and after serum stimulation of quiescent cells, and decreases as cells enter S phase. p21 inactivates cyclin E-cdk2, cyclin A-cdk2, and cyclins D1-, D2- and D3-cdk4 complexes.

Genetic analysis of numerous human tumors reveals a disproportionate numer of altered cell cycle proteins, and it is this aberration that is thought to cause abnormal cell cycle. For example, cyclin D1 is the bcl-1/PRAD1 proto-oncogene that is either overexpressed or deregulated in a variety of human tumors. The cyclin D1/CCND1 gene, located at chromosome 11q13, is amplified in a number of cancers, mainly breast and non-small cell lung carcinomas. This correlates with the observation that overexpression of cyclin D1 is a common feature in the tumors with this specific 11q13 amplicon. The gene for p16 is rearranged, deleted or mutated in a large number of tumour cell lines, and in some primary tumours. Mutations in cdk4, specifically an Arg24Cys mutation, has been identified in two unrelated hereditary melanoma families. This mutation was found in 11/11 of the melanoma patients, 2/17 unaffecteds and 0/5 spouses (Zuo, L., et al., *Nature Genetics* 12 1996:97–99). This mutation has a specific effect on the $p16^{INK4a}$ binding domain of cdk4, but has no affect on the ability to bind to cyclin D and form a functional kinase. As a result of this mutation, the cyclin D/cdk4 complex is resistant to normal physiological inhibition by $p16^{INK4a}$. Other studies have demonstrated that about half the familial melanoma kindreds show evidence of linkage to the region of chromosome 9p21 that contains the $p16^{INK4a}$ gene. The types of $p16^{INK4a}$ mutations identified include a nonsense mutation, splice donor mutation, an unidentified mutation that prevents $p16^{INK4a}$ transcription, and 3 missense mutants that are unable to bind to cdk4 or cdk6. Overexpression of cdk4 as a result of gene amplification has been identified in a study of 32 glioma cell lines (He, J., et al., *Cancer Res.* 54:5804–5807, 1994). This alteration was observed among the ten cases having intact p16 genes. Genetic analysis of glioma cell lines revealed that 24 of 32 glioma cell lines had one of two alternative genetic alterations, each of which indicates that increased cdk4 kinase activity is important to glial tumor development. Cdk4 maps to the long arm of chromosome 12 and is found overexpressed in certain tumors because of its amplification as a component of an amplicon that includes other relevant genes, such as SAS and MDM2. All of the above conditions lead to activation of cdk4. Overexpression of cyclins B1 and E in leukemic and solid tumor cell lines, as well as altered patterns of cyclin E expression in breast cancer has also been reported.

Cellular hyperproliferation occurs in a number of disease states. The most common hyperproliferative diseases are neoplasms, which are typically named according to the original source of the hyperproliferative tissue. Neoplasms are defined as new growths of animal or plant tissue that resemble more or less the tissue from which it arises, but serve no physiologic function, and are benign, potentially malignant or malignant in character. Neoplasms arise as the result of loss of normal controls, leading to unregulated growth. Neoplastic cells may lack differentiation and acquire the ability to invade local tissues and metastasize. Neoplasms may develop in any type of tissue of any organ at any age. The incidence, and mortality rate, of neoplasms generally increases with age, with certain neoplasms having peak incidence between the ages of 60 and 80 (e.g. prostate, stomach and colon). However, other neoplasms have a peak incidence from birth to 10 years of age (e.g. acute lymphoblastic leukemia). Diet, exposure to carcinogens, particularly use of tobacco, and familial predispositions also affect incidence of particular neoplasms.

Neoplastic cells differ from normal cells in a number of important aspects, including loss of differentiation, increased invasiveness and decreased drug sensitivity. Another important difference is the unchecked growth of cells, which is thought to result from loss of normal cellular control mechanisms of these cells are either deactivated, bypassed or otherwise disregarded, leaving the neoplastic cells to proliferate without regard to the normal controlling mechanisms. Neoplasm is an abnormal mass of tissue, the growth of which exceeds and is uncoordinated with that of the normal tissue, and persists in the same excessive manner after cessation of the stimuli which evoked the change.

Neoplasms are classified as either benign or malignant. Benign neoplasms exhibit slow, localized growth that is usually circumscribed due to their encapsulation by a fibrous connective tissue capsule. Whereas benign neoplasms rarely cause the death of the organism, untreated malignant neoplasms have a high probability of killing the organism. Malignant neoplasms are generally nonencapsulated, and usually exhibit a more rapid growth rate. Malignant neoplasms often invade surrounding tissues and vessel and spread to distant body sites. Malignant neoplasms are generically described as "cancer" or as "tumors"; the latter term denotes swelling.

Myeloproliferative disorders are a group of disorders characterized by abnormal proliferation by one or more hematopoietic cell lines or connective tissue elements. Four disorders are normally included as myeloproliferative disorders: polycythemia vera (primary polycythemia; Vaquez' Disease), myelofibrosis (agnogenic myeloid metaplasia), chronic myelogenous leukemia and primary (essential) thrombocythemia. Acute leukemia, especially erythroleukemia, and paroxysmal nocternal hemoglobinuria are also classified as myeloproliferative disorders. Each of these disorders is identified according to its predominant feature or site of proliferation. Although each results from proliferation of different cells, each has been shown to be caused by a clonal proliferation arising at the level of a pluripotent stem cell, which causes varying degrees of abnormal proliferation of erythroid, myeloid, and megakaryocytic precursors in the bone marrow. All myeloproliferative disorders have a tendency to terminate in acute leukemia.

Leukemias are malignant neoplasms of the blood-forming tissues. At least two viruses are associated with causing leukemias in humans. The Epstein-Barr virus is associated with Burkitt's lymphoma and the human T-cell lymphotropic virus, also called human acute leukemia/lymphoma virus (HTLV-1) has been linked to some T cell leukemias and lymphomas. Exposure, especially prolonged exposure to chemical agents, such as benzene and some antineoplastics, or to ionizing radiation, genetic predisposition (e.g. Down's syndrome) and some familial disorders (e.g. Fanconi's anemia) result in predispositions to leukemias.

Development of leukemias appears to occur through a single cell cycle through two or more steps with subsequent proliferation and clonal expansion. Leukemias are currently classified according to their cellular maturity; acute leukemias are predominantly undifferentiated cell populations and chronic leukemias are more mature cell forms. Acute leukemias are further divided into lymphoblastic (ALL, also known as acute lymphocytic leukemia) and myeloid (AML, also known as acute myelocytic, myelogenous, myeloblastic, myelomonoblastic) types. They may be further classified by morphologic and cytochemical appearance according to the French-American-British (FAB) classification or according to type and degree of differentiation. Chronic leukemias are classified as either lymphocytic (CLL) or myelocytic (CML). CLL is characterized by the appearance of mature lymphocytes in the blood, bone marrow and lymphoid organs. CML is characterized by the predominance of granulocytic cells of all stages of differentiation in blood, bone marrow, liver, spleen and other organs.

Myelodysplastic Syndrome (MDS) is characterized as a clonal proliferative disorder in which a normal or hypercellular bone marrow is associated with anemia and dysmyelopoiesis. Hemapoietic cells which may proliferate include erythroid, myeloid and megakaryocytic forms. MDS is a relatively new designation of group of disorders known as Preleukemia, Refractory Anemias, Ph-Chromosome-Negative Chronic Myelocytic Leukemia, Chronic Myelomonocytic Leukemia and Agnogenic Myeloid Metaplasia. The FAB system provides further classification of Myelofibrosis.

Lymphomas are a heterogeneous group of neoplasms arising in the reticuloendothelial and lymphatic systems. The major types of lymphomas are Hodgkin's disease and non-Hodgkin's lymphoma, as well as the rarer Burkitt's lymphoma and mycosis fungoides. Hodgkin's disease is a chronic disease with lymphoreticular proliferation of unknown cause that may present in localized or disseminated form, and is further classified according to four histopathologic profiles. Non-Hodgkin's lymphomas are a heterogeneous group of diseases consisting of neoplastic proliferation of lymphoid cells that usually disseminate throughout the body. The former terms, lymphosarcoma and reticulum cell sarcoma, are now being replaced with terms that reflect that cell of origin and biology of the disease. The Rappaport classification is based on the histopathology; on the degree of the differentiation of the tumor; and on whether the growth pattern is diffuse or nodular. The Lukes and Collins classification is based upon the cell of origin, specifically whether it is T cell or B cell derived, histiocytic (or monocytic) origin or unclassifiable. The International Panel Working Formulation of the National Cancer Institute categorizes non-Hodgkin's lymphomas using the above classifications.

Burkitt's lymphoma is a highly undifferentiated B cell lymphoma that tends to involve sites other than the lymph nodes and reticulendoethlial system. Burkitt's lymphoma, unlike other lymphomas, has a specific geographic distribution, which suggests an unidentified insect vector and an infectious agent. Evidence points to the herpes like Epstein-Barr virus.

Mycosis fungoides is an uncommon chronic T cell lymphoma primarily affecting the skin and occasionally internal organs.

Plasma cell dyscrasias (PCDs), or monoclonal gammopathy, are disorders characterized by the disproportionate proliferation of one clone of cells normally engaged in immunoglobulin (Ig) synthesis, and the presence of a structurally and electrophoretically homogeneous IG or polypeptide subunit in serum or urine. The disorders may be primarily asymptomatic to progressive, overt neoplasms (e.g., multiple myeloma). The disorder results from disproportionate proliferation of one clone producing a specific Ig: IgG, IgM, IgA, IgD or IgE.

Multiple myeloma, also known as plasma cell myeloma or myelomatosis, is a progressive neoplastic disease characterized by marrow plasma cell tumors and overproduction of an intact monoclonal Ig (IgG, IgA, IgD or IgE) or Bence Jones protein, which is free monoclonal κ or λ light chains. Diffuse osteoporosis or discrete osteolytic lesions arise due to replacement by expanding plasma cell tumors or a osteoclast-activating factor secreted by malignant plasma cells.

Macroglobulinemia, or primary or Waldenstrom's macroglobulinemia, is a plasma cell dyscrasia involving B cells that normally synthesize and secrete IgM. Macroglobulinemia is distinct from myeloma and other PCDs, and resembles a lymphomatous disease. Many patients have symptoms of hyperviscosity, fatigue, weakness, skin and mucosal bleeding and so forth.

Heavy chain diseases are neoplastic plasma cell dyscrasias characterized by the overproduction of homogenous γ, α, μ, and δ Ig heavy chains. These disorders result in incomplete monoclonal Igs. The clinical picture is more like lymphoma than multiple myeloma.

Hypersplenism is a syndrome in which circulating cytopenia is associated with splenomegaly. Treatment of patients with hypersplenism requires therapy for the underlying disease, not splenectomy. Lymphoproliferative and myeloproliferative diseases are some, but not the sole, causes of hypersplenism. Myeloproliferative disorders causing hypersplenism include polycythemia vera, myelofibrosis with myeloid metaplasia, chronic myelogenous leukemia and essential thrombocythemia. Chronic lymphocytic leukemia and the lymphomas (including Hodgkin's disease) are specific lymphoproliferative disorders that may cause hypersplenism.

Lung tissue is the site for both benign and malignant primary tumors, as well as the site of metastasis from cancers of many other organs and tissues. Cigarette smoking causes an overwhelming percentage of lung cancers, estimated at over ninety percent of the cases in men and about seventy percent of the cases in women. Exposure to occupational agents such as asbestos, radiation, arsenic, chromates, nickel, chloromethyl ethers, poison gas, and coke oven emissions is also associated with lung cancer. The most common types of lung cancer are squamous cell, small and large cell and adenocarcinoma.

About ninety-five percent of the stomach cancers are carcinoma; less common are lymphomas and leiomyosarcomas. Gastric carcinomas are classified according to gross appearance; protruding, penetrating (the tumor has a sharp, well-circumscribed border and may be ulcerated) and spreading or miscellaneous, which has characteristics of two of the other types.

Pancreatic cancers may be exocrine tumors, which are mostly adenocarcinomas arising from duct cells rather than the acinar cells, or endocrine tumors, which include insulinoama. Gastrin-producing pancreatic tumors involving cells of the non-β-type or in the duodenal wall can cause Zollinger-Ellison Syndrome, a syndrome marked by hypergastrinemeia. Sometimes other endocrine abnormalities, particularly with the parathyroids, or pituitary and adrenal glands cause a polyglandular disorder known as multiple endocring neoplasia (MEN). Non-β islet cell tumors may cause a syndrome known as Vipoma Syndrome, which is characterized by prolonged massive watery diarrhea.

Neoplasms of the bowel include tumors of the small intestine, tumors of the large intestine, and cancer of the colon and rectum. Benign small intestine tumors may arise from jejunal and ileal neoplasms, including leiomyomas, lipomas, neurofibromas, and fibromas. Malignant small intestine tumors, such as adenocarcinomas, are uncommon, and typically arise in the proximal jejunum. Patients with Crohn's disease of the small intestine are more prone to such adenocarcinomas rather than patients with Crohn's disease of the colon. In patients with Crohn's disease, the tumors tend to occur distally in the bypassed or inflamed loops of the bowel. Carcinoid tumors typically arise in the small bowel, especially the ileum, and in about half the cases, multiple tumors exist. Kaposi's sarcoma, which occurs frequently in transplant recipients and AIDS patients, have gastrointestinal involvement in about half the cases. Lesions may occur anywhere in the GI tract, but are usually found in the stomach, small intestine, or distal colon.

Tumors of the large bowel include polyps of the colon and rectum. Polyps are a mass of tissue that arises from the bowel wall and protrudes into the lumen. Polyps are classified on the basis of their histology, as tubular adenomas, tubulovillous adenomas, villous adenomas, hyperplastic polyps, hamartomas, juvenile polyps, polypoid carcinomas, pseudopolyps, lipomas, leiomyomas and even rarer tumors.

Malignant tumors may also arise in the anorectum. These are epidermoid (squamous cells) carcinoma of the anorectum which comprise about three to five percent of rectal and anal cancers.

In Western countries, cancer of the colon and rectum are second to lung cancer in accounting for more new cases each year. In the USA, about 75,000 people died of these cancers in 1989; about 70% occurred in the rectum and sigmoid colon, and 95% were adenocarcinomas.

Neoplasms of the liver include benign neoplasms, which are relatively common but often undetected, and malignant neoplasms. Hepatocellular adenoma is the most important benign liver neoplasm. Asymptomatic small hemangiomas occur in one to five percent of adults. Bile duct adenomas and other mesenchymal neoplasms also occur, but are relatively rare. Malignant neoplasms of the liver are the most common form of hepatic tumor, and the liver is a frequent site of bloodborne metastases, usually from lung, breast, colon, pancreas and stomach primary tumors. The incidence of hepatocellular carcinoma is linked with chronic hepatitis B virus in certain parts of Africa and Southeast Asia. In North America, Europe and other areas of low prevelence, most of the patients have underlying cirrhosis. Fibrolamellar carcinoma is a distant variant of hepatocellular carcinoma with characteristic morphology of malignant hepatocytes enmeshed in lamellar fibrous tissue. Fibrolamellar carcinoma usually affects relatively young adults, and has no association with preexisting cirrhosis, chronic hepatitis B virus infection or other known risk factors. Other primary malignancies of the liver include cholangiocarcinoma (a tumor arising from intrahepatic biliary epithelium), hepatoblastoma (which is one of the most common cancers in infants) and angiosarcoma (which is associated with industrial exposure to vinyl chloride). Leukemia and related disorders may involve hepatic tissues, thought to be the result of infiltration with abnormal cells.

Multiple Endocrine Neoplasia (MEN) Syndromes are a group of genetically distinct familial diseases involving adenomatous hyperplasia and malignant tumor formation in several endocrine glands. Three distinct syndromes have been identified. Type I (MEN-I) is characterized by tumors of the parathyroid glands, pancreatic islets, and the pituitary. Type II (MEN-II) is characterized by medullary carcinoma of the thyroid, pheochromocytoma and hperparthyroidism. Type III (MEN-III) is characterized by multiple mucosal neuromas, medullary carcinoma of the thyroid, and pheochromocytoma.

Carcinoid syndrome is usually caused by metastatic intestinal carcinoid tumors that secrete excessive amount of vasoactive substances, including serotonin, bradykinin, histamine, prostaglandins and polypeptide hormones. Abnormal levels of these subtances cause a variety of symptoms, often episodic cutaneous flushing, cyanosis, abdominal cramps, diarrhea, and valvular heart disease.

Neoplasms of the bone and joints may be benign or malignant. Benign tumors of the bone include osteochondromas (osteocartilaginous exostoses), which are the most common benign bone tumors in children between ages 10 to 20, benign chondromas (which are located within the bone), which occur most commonly in children and young adults between the ages 10 to 30, chondroblastoma (which arises in an epiphysis), which is rare, but most common in children between the ages of 10 to 20, chondromyxofibromas, osteoid osteoma, giant cell tumors and fibromatous lesions. Primary malignant tumors of the bone include osteogenic sarcoma (osteosarcoma), which is the second most common primary bone tumor, fibrosarcomas, malignant fibrous histiocytoma, chondrosarcomas, mesenchymal chondrosarcoma, Ewing's tumor (Ewing's sarcoma), malignant lymphoma of bone, multiple myeloma, and malignant giant cell tumor.

Primary cancers of other tissues may metastasize to bone tissue. The most common are carcinomas arising in the breast, lung, prostate, kidney, and thyroid.

Central nervous system (CNS) neoplasms are generally classified according to the organ. Primary intracranial neoplasms are subdivided into six classes: tumors of (1) the skull; (2) the meninges; (3) the cranial nerves; (4) the neuroglia and ependyma; (5) pituitary or pineal gland; and (6) those of congenital origin. Skull neoplasms include osteoma, hemangioma, granuloma, xanthoma, and osteitis deformans. The meninges neoplasms include meningioma, sarcoma, and glomatosis. The cranial nerve neoplasms include glioma of the optic nerve, and schwannoma of the 8th and 5th cranial nerves. The neuroglia neoplasms include gliomas and ependymomas. The pituitary or pineal body neoplasms include pituitary adenoma and pinealoma. The congenital origin neoplams include craniopharyngioma, chordoma, germinoma, teratoma, dermoid cyst, agioma and hemangioblastoma.

Spinal cord neoplasms are lesions that compress the spinal cord or its roots, arising from the cord parenchyma, roots, meninges, or vertebrae. Primary spinal cord neoplasms are much less common than intracranial tumors. Metastatic lesions are common and may arise from carcinomas of the lung, breast, prostate, kidney, thyroid or lymphoma.

Genitourinary neoplasms occur at any age and in both sexes; however, they account for about 30% of cancer in the male and 4% in the female. Adenocarcinoma of the prostate accounts for a significant number of malignancies in men over 50. Prostate adenocarcinoma is thought to be hormone related and its pathology is typically glandular. Carcinoma of the kidney, adenocarcinoma, is only about one to two percent of adult cancers, but most solid kidney tumors are malignant. Wilms' tumors, an embryonal adenomyosarcoma of the kidneys, occurs fetally and is often not diagnosed for several years. Renal pelvis and ureter neoplasms are histologically similar. Urinary bladder neoplasms may be induced by known urinary carcinogens such as aniline dyes, and the most common is transitional cell carcinoma, less common is squamous cell carcinoma. Rarer genitourinary neoplasms include carcinoma of the urethra, and penis. Neoplasms of the testis account for the majority of solid malignancies in males under 30. Most malignant testicular tumors arise from the primordial germ cell and are classified according to the cell type involved.

Breast cancer is the most common cancer in women. In the USA, the cumulative risk for women of all ages of developing breast cancer is about 10%, but that of dying from the disease is only about 3.6%. However, the risk increases with age, a family history of breast cancer, exposure to radiation, and even diet is implicated in higher risk.

Breast cancers are routinely typed for estrogen- and progesterone-receptor analysis. About two thirds of the patients have estrogen-receptor positive (ER+) breast tumors. Tumors which are progesterone positive are thought to have functional estrogen receptor and the presence of both receptors gives a greater likelihood of favorable response to endocrine treatment than the presence of just one receptor. Endocrine therapy, usually tamoxifen, is preferred in estrogen receptor-positive tumors. Estrogens and androgens are also effective, but less favored due to undesirable side effects induced by higher levels of these hormones than other forms of endocrine treatment. Breast cancer may metastasize to almost any organ in the body, but most common sites of metastatisis are the lung, liver, bone, lymph nodes and skin.

Lobular carcinoma in situ (LCIS) or lobular neoplasia, is most frequently found in premenopausal women. Ductal carcinoma in situ (DCIS) occurs in both pre- and postmenopausal women. DCIS forms a palpable mass. LCIS and DCIS account for about 90% of all breast cancers. The rarer forms, medullary and tubular lesions, have a somewhat better prognosis.

The most common gynecologic neoplasms are endometrial carcinomas, which ranks fourth in frequency after breast, colorectal and lung cancers in women. Endometrial carcinomas are characterized by their clinical staging, ranging from in situ at stage 0, to metastasis to distant organs at stage IVB. Endometrial carcinomas typically produce estrogen and the current treatment approaches are surgery and progesterone therapy.

Ovarian cancers account for about 18% of all gynecologic neoplasms. About 80% of malignant ovarian cancers arise from the ovarian epithelium and are classified according to their histology. Tumors may also arise from germ cells or stroma.

Vulvar carcinoma accounts for about 3–4% of all gynecologic neoplasms. Vulvar carcinoma usually occurs after menopause, and about 90% are squamous cell carcinomas. About 4% are basal cell carcinomas and the rest include intraepithelial carcinomas, adnocarcinoma of Bartholin's gland, fibrosarcoma and melanoma.

Vaginal carinoma accounts for about 1% of gynecologic malignancies, with a peak incidence from about ages 45 to 65. About 95% of vaginal carcinomas are squamous cell carcinoma. Primary carcinoma of the oviduct is rare, and typically spread directly or by the lymphatics.

Trophoblastic disease or neoplams of trophoblastic origin, can follow intra- or extrauterine pregnancy. A degenerating pregancy results in a hydatidiform mole of which about 80% are benign.

Neoplasms may arise in the ear canal and affect hearing. Ceruminomas also arise, are typically malignant despite appearing benign histologically and are treated by surgical removal. Basal cell and squamous cell carcinomas frequently develop on the external ear as the result from regular sun exposure, and are also typically treated by surgical removal. The middle ear may be the site of squamous cell carcinomas. Nonchromaffin paragangliomas may arise in the temporal bone.

The most common malignant tumor in the nose and paranasal sinuses is squamous cell carcinoma; less common are adenoid cystic and mucoepidermod carcinomas, malignant mixed tumors, adenocarcinomas, lymphomas, fibrosarcomas, osteosarcomas, chondrosarcomas, and melanomas.

Squamous cell carcinoma of the nasopharynx is more commonly observed in children and young adults.

The most common malignancies of the upper respiratory tract are squamous cell carcinomas of the tonsil and of the larynx. Both are more common in males and are associated with tobacco smoking and ethanol ingestion; about 85% of patients with cancer of the head or neck have a history of ethanol and tobacco consumption.

In the head and neck, about 90% of the cancers are squamous cell (epidermoid) carcinoma. Melanomas, lymphomas and sarcomas are relatively rare forms of primary head and neck cancers. Cancers of the head and neck are classified according to the size and site of involvement of the primary neoplasm; number and size of metastases to the cervical lymph nodes; and evidence of distant metastases.

Ophthalmologic cancers may arise in the skin of the eyelids and may be benign or neoplastic. Common benign growths are xanthelasmas, which form yellow-white flat plaques of lipid material subcutaneously. Basal cell carcinomas are more common; treatment is typically surgical removal or radiation therapy. Other less common malignant tumors are squamous cell or meibomian gland carcinomas and other types of melanomas. The most common primary ocular malignancy is malignant melanoma of the choroid.

Tumors also arise in the skin tissue, and include benign tumors such as moles, lipomas and the like, as well as malignant tumors. About 40–50% of malignant melanomas arise from melanocytes in moles. Malignant skin cancers are either basal cell or squamous cell carcinomas and frequently arise in sun-exposed areas of skin. They are the most common malignancies, and the incidence is rising. Less common malignancies include malignant melanoma, Paget's disease of the nipple or estramammary Patent's, Kaposi's sarcoma (KS), and cutaneous T cell lymphoma (mycosis fungiodes). The incidence of KS is increasing as the result of the increased incidence of AIDS. KS arises in about one third of patients with AIDS.

Oral cancers account for about 5% of cancers in men and 2% of cancers in women. The most common form of oral cancer is squamous cell carcinoma. Incidence increases with age and risk factors, particularly tobacco and alcohol consumption.

Surgery is the oldest effective form of treatment of neoplasms. Success is largely achieved if the neoplasm is detected in its early stages and has not metastasized. Radiation is also important therapy, and is the favored therapy of many neoplasms such as Hodgkin's disease, early stage non-Hodgkin's lymphomas, and squamous cell carcinoma of the head and neck. Radiation has proven very successful as an adjunct to surgery and antineoplastic drugs.

Antineoplastic drugs are also useful in the treatment of neoplasms, and are classified according to their mechanism of action. Numerous combinations, typically of antineoplastic drugs with differing mechanisms of action, have proven to be particularly effective therapy, permit lower doses and frequently minimize negative side effects. Antineoplastic drugs frequently target fundamental biological processes necessary for cell replication or growth.

Alkylating agents, such as mechlorethamin and cyclophosphamide, alkylate DNA, and restrict DNA replication.

Antimetabolites, which are directed to disruption of necessary cell division pathways, include:

Folate antagonists bind to dehydrofolate reductase and interfere with pyrimidine synthesis. Folate antagonists are S-phase specific. Methotrexate is a very commonly used antineoplastic folate antagonist.

Purine antagonists block de novo purine synthesis and are S-phase specific. 6-Mercaptopurine is an example of a purine antagonist.

Pyrimidine antagonists interfere with thymidylate synthase to reduce thymidine production and are S-phase specific. A frequently used pyrimidine antagonist is 5-fluorouracil.

Cytarabine inhibits DNA polymerase and is S-phase specific.

Plant alkyloids include vincas, such as vinblastine and vincristine, and podophyllotoxins, such as etoposide. Plant alkyloids are effective in the metaphase and inhibit mitosis by a variety of mechanisms including altering microtubular proteins.

Antibiotics include doxorubicin and daunomycin, which intercalate between DNA strands to inhibit the uncoiling of DNA; bleomycin, which causes incisions in DNA strands; and mitomycin, which inhibits DNA synthesis by acting as a bifunctional alkylator.

Nitrosureas include carmustine and lomustine and alkylate DNA or cause carbamoylate amino acids in proteins.

Inorganic ions, such as cisplatin, cause inter- and intracalation of DNA strands to inhibit the uncoiling of DNA.

Biologic Response Modifiers, such as the interferons, have antiproliferative effects, but their specific role is not known. Interferons include α (leukocyte) interferon, β (fibroblast) interferon and γ (lymphocyte) interferon.

Enzymes, such as asparaginase, are also used to alter metabolic pathways important in cancerous cells. Asparaginase depletes the cell of asparagine, on which leukemic cells depend.

Hormones and their analogs, such as tamoxifen, flutamide and progesterone, have non-specific effects but are useful to treat certain neoplams which are known to be hormone responsive, especially breast, ovarian and prostate neoplasms. Tamoxifen, frequently used in the treatment of breast neoplasms, places cells at rest, and binds to the estrogen receptor. Flutamide, frequently used in the treatment of prostate neoplasms, binds the androgen receptor.

Cytokinins are naturally occurring and artificial plant growth regulators. Natural cytokinins tend to be non-specific inhibitors of various protein kinases. The molecular mechanisms by which cytokinins regulate cell growth and division are still being determined. Studies have indicated that cytokinins may increase accessibility of the DNA template, activate RNA polymerases, affect polyadenylation and secondary structure of mRNA and stimulate formation and activity of polyribosomes. Cytokinins are thought to affect cell division by interacting with regulatory proteins of the cell cycle. Both cytokinins and cyclin-dependent kinases (cdks) act at multiple and similar control points of cell cycle, for example, at the $G_1/S$ and $G_2/M$ transitions and S and M phases.

Olomoucine, 6-(benzylamino)-2-[(2-hydroxyethyl) amino]-9-methylpurine, was first discovered as an herbicide. More recently, it has been discovered that Olomoucine is an artificial cytokinin, which specifically inhibit some cdks, including $p34^{cdc2}$/cyclin B kinases, at micromolar concentration, but has no effect on other major protein kinases such as cAMP- and cGMP-dependent kinases, and protein kinase C. Olomoucine has recently been shown to have good selectivity for the CDK-cyclin protein kinases, but only has moderate inhibitory activity, with an $IC_{50}$ of about 7 $\mu$M. Vesely, J., et al., *Eur. J. Biochem.*, 1994, 224, 771–786. A 2.4 A crystal structure of olomucine co-crystallized with cdk2 revealed that the purine portion of olomoucine binds in the conserved ATP binding pocket, while the benzylamino group extends into a region of the active site unique to the cdk2 kinases.

Roscovitine, 2-(1-ethyl-2-hydroxyethylamino)-6-benzylamino-9-isopropylpurine, is a recently synthesized purine which has been shown to have selectivity towards some cyclin-dependent kinases and to be 10-fold more active on cdk2 and cdc2 than olomoucine (Meijer, L., et al., *Eur. J. Biochem.*, 243:527–536, 1997 and PCT/FR96/01905). Meijer et al report that most kinases are not significantly inhibited by roscovitine. However, cdc 2-cyclin B, cdk 2-cyclin A, cdk 2-cyclin E and cdk 5-p35 are substantially inhibited with $IC_{50}$ values of 0.65, 0.7, 0.7 and 0.2 $\mu$M, respectively. In contrast, roscovitine displayed $IC_{50}$ values of greater than 100 $\mu$M for cdk 4-cyclin D1 and cdk 6-cyclin D2.

Havlicek, L., et al., *J. Med. Chem.* (1997)40:408–412 report that Roscovitine, and related analogs substituted in the 2, 6 and/or 9 positions, inhibit $p34cdc^2$ cyclin B kinases. None of the analogs had superior $IC_{50}$ values over the (R) enantiomer of Roscovitine, which had an $IC_{50}$ value of 0.2 $\mu$M. The (S) enantiomer had an $IC_{50}$ value of 0.8 $\mu$M; the racemic mixture (R/S) had an $IC_{50}$ value of 0.65 $\mu$M. These authors conclude that the $N^6$-benzyl substituent of Roscovitine was superior over the isopentenyl or cyclohexylmethyl substituents.

The National Cancer Institute (NCI) is a US Government-run organization directed at the discovery and development of novel therapeutic oncology products. In 1985, the NCI established a new cancer screening strategy involving human tumor cell lines in an in vitro assay as the primary cancer screen. A total of sixty human tumor cell lines, derived from seven cancer types (lung, colon, melanoma, renal, ovarian, brain and leukemia) were selected for inclusion in the NCI panel (Grever, M. R., et al., *Seminars in Oncology*, 19:1992:622–638). The protocols used in the assays have also been reported in the literature. American Type Tissue Collection (ATCC) acts as a depository for these and other tumor cell lines. Useful human tumor cell lines include the following:

MCF7: human breast adenocarcinoma, hormone-dependent;

MDA-MB-23 1: human breast adenocarcinoma, hormone-independent;

HT-29: human colon adenocarcinoma, moderately well-differentiated grade II;

HCT-15: human colon adenocarcinoma;

A549: human non-small cell lung carcinoma;

DMS-1 14: human small cell lung carcinoma;

PC-3: human prostate adenocarcinoma, hormone-independent; and

DU 145: human prostate carcinoma, hormone-independent.

Skehan, P., et al., *J. Natl. Cancer Inst.* 82: 1107–1112, 1990 sets forth useful protocols for using such tumor cell lines for screening antineoplastic drugs.

Meijer, et al., supra, report that roscovitine inhibits the proliferation of the NCI disease-oriented in vitro screen, i.e., 60 human tumour cell lines comprising nine tumour types (leukemia, non-small cell lung cancer, colon cancer, central nervous system cancer, melanoma, ovarian cancer, renal cancer, prostate cancer, breast cancer) with an average $IC_{50}$ value of 16 $\mu$M. The results of individual tumour lines were not reported.

Two distinct cdk inhibitors, flavopiridol and olomoucine, suppress the death of neuronal PC12 cells and sympathetic neurons in two model systems of neuronal survival (Park et al., *J. Biol. Chem.* 271(14):8161–8169, 1996). The concentration of each required to promote survival correlated with the amount required to inhibit proliferation. Neuronal apoptosis is an important aspect of both nervous system development and a component of neuronal injury and disease.

The PC12 cell line was initially derived from a rat adrenal medullary pheochromocytoma. When grown in serum-containing medium, PC12 cells divide and resemble precursors of adrenal chromaffin cells and sympathetic neurons. Upon addition of nerve growth factor (NGF), PC12 cells attain the phenotypic properties of sympathetic neurons. Upon removal of either serum or serum and NGF, both naive and neuronally differentiated PC12 cells undergo apoptosis, which is analogous to the response of sympathetic neurons.

The role of cell cycle regulation in apoptosis may be demonstrated by withdrawal of NGF or serum which results in uncoordinated cell cycle progression and cell death from naive PC-12 cells. Cdk inhibitors did not prevent the death of these proliferation competent naive PC-12 cells after removal of trophic support. Post-mitotic differentiated or sympathetic neurons are hypothesized to attempt inappropriate re-entry of the cell cycle following withdrawal of NGF which results in cell death. However, exposure to flavopiridol or olomoucine which inhibit cdks prevented apoptosis in these cells.

Changes in the activity of cdks and cyclins are observed during apoptosis of many different cell types. Camptothecin- or araC-induced apoptosis of HL60 cells is associated with elevated cdc2 activity and cyclin E-associated kinase activity. Camptothecin-induced apoptosis of RKO cells is associated with an increase in expression of cyclin D1.

Camptothecin causes apoptotic death of rat cerebral cortical neurons. Morris and Geller, *J. Cell Biol.* 134:757–770 (1996). Camptothecin-treated nonproliferating neuronally differentiated PC12 cells die within 6 days after treatment, and cultured rat sympathetic neurons die within 5 days after treatment, even in the presence of NGF. Park et al., *J. Neurosci.* 17(4):1256–1270(1997). However, administration of either both, or individual olomoucine or flavopiridol, in the presence or absence of camptothecin resulted in approximately 30% cell death at day 6. Maximal protection of PC12 cells, or rat sympathetic neurons, from death was observed with 1 μM flavopiridol and 200 μM olomoucine, which are the minimum concentrations that fully inhibit DNA synthesis by proliferating PC12 cells. Administration of iso-olomoucine, an inactive analog of olomoucine, failed to prevent the cell death of camptothecin-treated neuronal cells Flavopiridol and olomoucine were also shown to protect against camptothecin-induced cortical neuronal death. Park et al., *J. Neurosci.* 17(4):1256–1270(1997). The $IC_{50}$ values of flavopiridol and olomoucine were 0.1 μM and 100 μM, respectively. Administration of iso-olomoucine failed to prevent the cell death of camptothecin-treated neuronal cells.

There are several implications of the above observations. It is well recognized that patients treated with radiation or antineoplastic agents experience undesirable side effects, including developing new neoplasms or undesirable cellular apoptosis. For example, some patients treated with high-dose araC for refractory leukemia develop a cerebellar toxicity syndrome, characterized by loss of Purkinje neurons. Winkelman and Hinges, *Ann Neurol.* 14:520–527 (1983) and Vogel and Horouipian, *Cancer* 71:1303–1308 (1993). Patients treated with cis-platinum have been reported to develop periperal neuropathies. Wallach, et al., *J. Fla. Med. Assoc.* 79:821–822(1992) and Mansfield and Castillo, *AJNR Am. J. Neuroradiol.* 15:1178–1180(1994). In view of these observations, either co-administration or sole administration of the present compounds in the treatment of neoplasms would reduce or preclude cellular apoptosis, in particular, neuronal damage caused by treatment with antineoplastic agents or radiation.

Cerebrovascular disease is the most common cause of neurologic disability in Western countries. The major specific types of cerebrovascular disease are cerebral insufficiency due to transient disturbances of blood flow, infarction, hemmorrhage, and arteriovenous malformation. Stroke generally denotes ischemic lesions. Undesirable neuronal apoptosis occurs in cerebrovascular disease. Treatment with inhibitors of cdks may be an approach to prevent is neuronal injury and degeneration in such cases.

SUMMARY OF THE INVENTION

The present invention provides novel compounds of the formula (I)

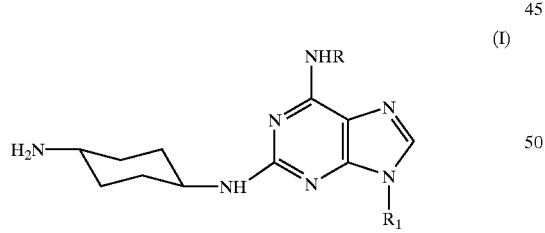

wherein R is selected from the group consisting of R2, R2NH-, or R3R4N—R5- wherein
R2 is selected from the group consisting of $C_9$–$C_{12}$ alkyl,

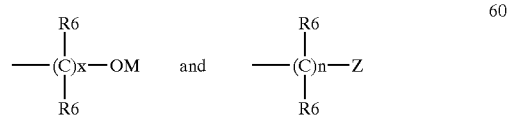

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; n is an integer 0–8; Z is selected from the group consisting of phenyl, heterocycle, cycloalkyl, and naphthanlene; and M is selected from the group consisting of hydrogen, $C_1$–$C_4$ alkyl,

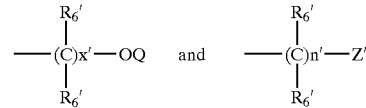

wherein each R6' is independently selected from the group consisting of hydrogen, $C_3$–$C_8$ cycloalkyl, $C_1$–$C_4$ alkyl, and $(CH_2)_{m'}$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and napthalene; and
wherein each $C_9$–$C_{12}$ alkyl or Z is optionally substituted with 1 to 3 substituents, which may be the same or different, and which are selected from the group consisting of D, E,

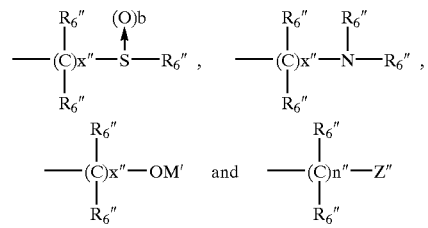

wherein each D is independently selected from the group consisting of trifluoromethyl, trifluoromethoxy, and $C_1$–$C_4$ alkoxy; each E is independently selected from the group consisting of Hal, OH, and $C_1$–$C_8$ alkyl; b is an integer 0–2; Z" is selected from the group consisting of phenyl, heterocycle, cycloalkyl, and naphthalene; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

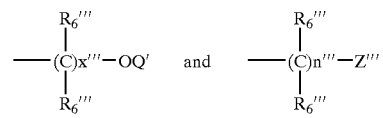

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and napthalene,
wherein the groups M' and Z" may be optionally substituted with the groups D', E' or

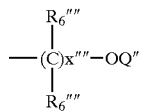

wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl;

R3 and R4 are selected from the group consisting of hydrogen, $C_1$–$C_4$ alkyl and $(CH_2)_y$-phenyl, wherein y is an integer 0–8, with the proviso that R3 and R4 not both be hydrogen;

R5 is $C_1$–$C_8$ alkylene; and

R1 is selected from the group consisting of cyclopentyl, cyclopentenyl and isopropyl, and the pharmaceutically acceptable salts, optical isomers, and hydrates thereof, with the proviso that when R2 is the group

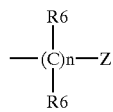

wherein n is 1 or greater; R1 is isopropyl or cyclopentyl; R6 is hydrogen, $C_1$–$C_4$ alkyl, or $(CH_2)$-phenyl; and Z is phenyl, heterocycle, or cycloalkyl, that Z is substituted with 1 to 3 substituents, which may be the same or different, and which are selected from the group consisting of

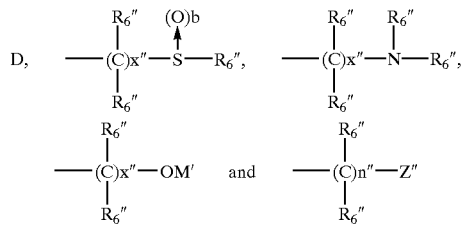

wherein D, b, R6", x", n", M', and Z" are as previously defined.

In addition, the present invention provides a method of inhibiting cell cycle progression. More specifically, the present invention provides a method of inhibiting cdk-2.

The present invention also provides a method of preventing apoptosis in neuronal cells. A particularly preferred method of the present invention is preventing apoptosis of neuronal cells induced by antineoplastic agents or resulting from cerebrovascular disease. Another preferred embodiment of the present invention is the method of preventing apoptosis induced by oxygen depletion. A more preferred invention provides a method of preventing apoptosis induced cerebrovascular disease. Another preferred invention provides a method of preventing apoptosis induced by stroke or infarction.

The present invention provides a method of inhibiting the development of neoplasms. The present invention provides a method for treating a patient afflicted with a neoplastic disease state comprising administering a compound of the formula provided. It is preferred that the amount administered is a therapeutically effective amount of a compound of the formula. A preferred method of the present invention administers a single compound of the formula provided. Alternatively, a preferred method of the present invention administers an amount of a compound of the formula in conjunction with other antineoplastic agents.

In addition, the present invention provides a composition comprising an assayable amount of a compound of Formula (I) in admixture or otherwise in association with an inert carrier. The present invention also provides a pharmaceutical composition comprising an effective inhibitory amount of a compound of Formula (I) in admixture or otherwise in association with one or more pharmaceutically acceptable carriers or excipients.

DETAILED DESCRIPTION OF THE INVENTION

The present invention provides novel compounds of the formula (I)

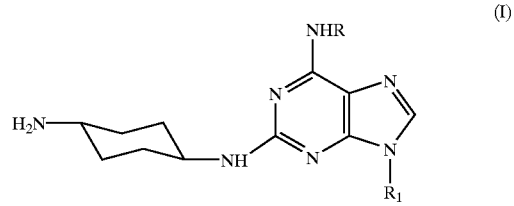

wherein R is selected from the group consisting of R2, R2NH-, or R3R4N—R5- wherein R2 is selected from the group consisting of $C_9$–$C_{12}$ alkyl,

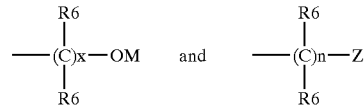

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; n is an integer 0–8; Z is selected from the group consisting of phenyl, heterocycle, cycloalkyl, and naphthanlene; and M is selected from the group consisting of hydrogen, $C_1$–$C_4$ alkyl,

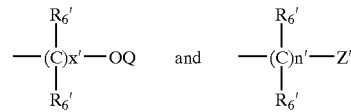

wherein each R6' is independently selected from the group consisting of hydrogen, $C_3$–$C_8$ cycloalkyl, $C_1$–$C_4$ alkyl, and $(CH_2)_m$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and napthalene; and wherein each $C_9$–$C_{12}$ alkyl or Z is optionally substituted with 1 to 3 substituents, which may be the same or different, and which are selected from the group consisting of D, E,

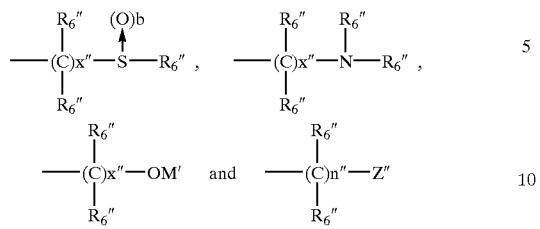

wherein each D is independently selected from the group consisting of trifluoromethyl, trifluoromethoxy, and $C_1-C_4$ alkoxy; each E is independently selected from the group consisting of Hal, OH, and $C_1-C_8$ alkyl; b is an integer 0–2; Z" is selected from the group consisting of phenyl, heterocycle, cycloalkyl, and naphthalene; each R6" is independently selected from the group consisting of hydrogen, $C_3-C_8$ cycloalkyl, $C_1-C_4$ alkyl, and $(CH_2)_{m''}$-phenyl, wherein m" is an integer 0–8; n" is an integer 0–8; x" is an integer 1–8; and M' is selected from the group consisting of hydrogen, $C_1-C_4$ alkyl,

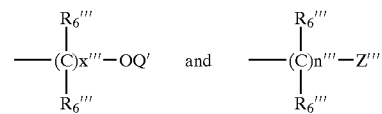

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and napthalene, wherein the groups M' and Z" may be optionally substituted with the groups D', E' or

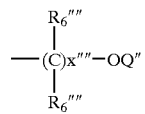

wherein each R6"" is independently selected from the group consisting of hydrogen, $C_3-C_8$ cycloalkyl, $C_1-C_4$ alkyl, and $(CH_2)_{m''''}$-phenyl, wherein m"" is an integer 0–8; x"" is an integer 0–8; Q" is hydrogen, $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1-C_8$ alkyl;

R3 and R4 are selected from the group consisting of hydrogen, $C_1-C_4$ alkyl and $(CH_2)_y$-phenyl, wherein y is an integer 0–8, with the proviso that R3 and R4 not both be hydrogen;

R5 is $C_1-C_8$ alkylene; and

R1 is selected from the group consisting of cyclopentyl, cyclopentenyl and isopropyl, and the pharmaceutically acceptable salts, optical isomers, and hydrates thereof, with the proviso that when R2 is the group

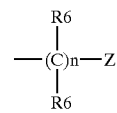

wherein n is 1 or greater; R1 is isopropyl or cyclopentyl; R6 is hydrogen, $C_1-C_4$ alkyl, or $(CH_2)_m$-phenyl; and Z is phenyl, heterocycle, or cycloalkyl, that Z is substituted with 1 to 3 substituents, which may be the same or different, and which are selected from the group consisting of

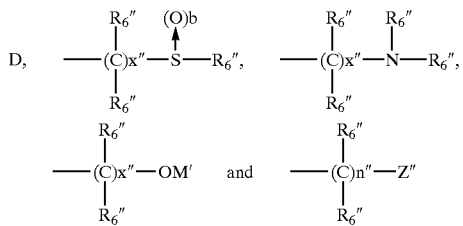

wherein D,b,R6",x",n",M', and Z" are as previously defined.

As used herein, the term "heterocycle" means any closed-ring moiety in which one or more of the atoms of the ring are an element other than carbon and includes, but is not limited to the following: piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, and isoquinolinyl.

As used herein, the term "$C_1-C_4$ alkyl" refers to a saturated or unsaturated, straight of branched chain hydrocarbyl radical of from one to four carbon atoms and includes, but is not limited to the following: methyl, ethyl, propyl, isopropyl, 1-propenyl, 2-propenyl, n-butyl, isobutyl, tertiary butyl, sec-butyl, 1-butenyl, 2-butenyl, 3-butenyl, and the like.

As used herein, the term "$C_1-C_8$ alkyl" refers to a saturated or unsaturated, straight or branched chain hydrocarbyl radical of from one to eight carbon atoms and includes, but is not limited to the following: methyl, ethyl, propyl, isopropyl, 1-propenyl, 2-propenyl, n-butyl, isobutyl, tertiary butyl, sec-butyl, 1-butenyl, 2-butenyl, 3-butenyl, pentyl, neopentyl, hexyl, heptyl, octyl, and the like.

As used herein, the term "$C_9-C_{12}$ alkyl" refers to a saturated or unsaturated, straight or branched chain hydrocarbyl radical of from nine to twelve carbon atoms and includes, but is not limited to the following: nonyl, decyl, undecyl, and dodecyl, and the like.

As used herein, the term "$C_1-C_8$ alkylene" refers to a saturated or unsaturated, straight of branched chain hydrocarbylene radical of from one to eight carbon atoms and includes, but is not limited to the following: methylene, ethylene, propylene, isopropylene, 1-propenylene, 2-propenylene, n-butylene, isobutylene, tertiary butylene, sec-butylene, 1-butenylene, 2-butenylene, 3-butenylene, pentylene, neopentylene, hexylene, heptylene, octylene, and the like.

As used herein, the term "cycloalkyl" refers to a saturated or unsaturated alicyclic moiety containing three to eight carbon atoms and includes, but is not limited to, the following: cyclopropyl, cyclobutyl, cyclopentyl, cyclohexyl, cycloheptyl, cyclooctyl, and the like.

As used herein, the designation

refers to a sulfur atom which is optionally oxidized to a sulfoxide (b=1) or a sulfone (b=2).

As used herein, the term "Hal" refers to a halogen moiety and includes fluoro, chloro, bromo, and iodo moieties.

As used herein, the term "optical isomer" or "optical isomers" refers to any of the various stereo isomeric configurations which may exists for a given compounds of Formula (I).

As used herein, the term "hydrate" or "hydrates" refers to the reaction product of one or more molecules of water with a compound of formula (I) in which the H—OH bond is not split and includes monohydrates as well as multihydrates.

As used herein, the term "pharmaceutically acceptable salts" refers to the reaction product of one or more molecules of any non-toxic, organic or inorganic acid with the compounds of Formula (I). Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include mono, di and tricarboxylic acids. Illustrative of such acids are, for example, acetic acid, glycolic acid, lactic acid, pyruvic acid, malonic acid, succinic acid, glutaric acid, fumaric acid, malic acid acid, tartaric acid, citric acid, ascorbic acid, maleic acid, hydroxymaleic acid, benzoic acid, hydroxybenzoic acid, phenylacetic acid, cinnamic acid, salacylic acid, 2-phenoxybenzoic acid and sulfonic acids such as methane sulfonic acid, trifluoromethane sulfonic acid and 2-hydroxyethane sulfonic acid.

The compounds of Formula (I) can be prepared by utilizing procedures and techniques well known and appreciated by one of ordinary skill in the art. A general synthetic scheme for preparing these compounds is set forth in Scheme A wherein all substituents, unless otherwise indicated, are as previously defined.

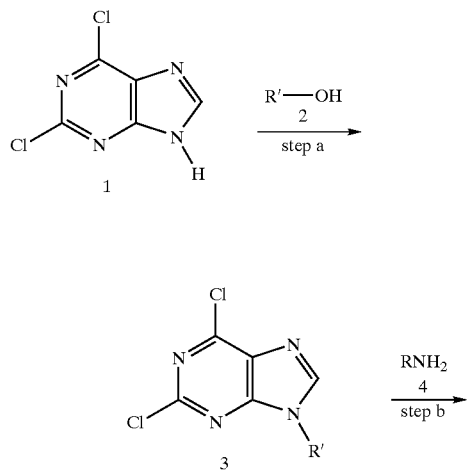

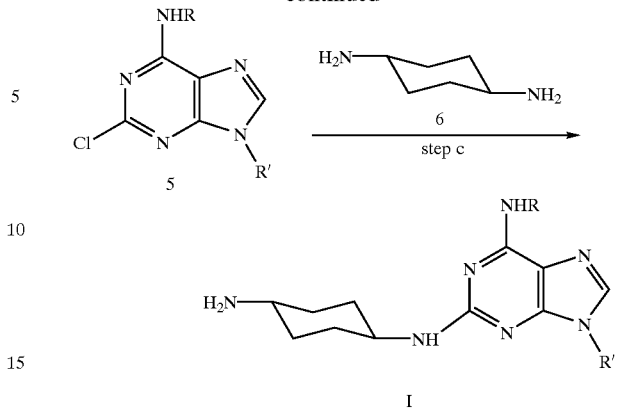

In Scheme A, step a, 2,6-dichloropurine (1) is reacted with the appropriate alcohol of structure 2 to give the corresponding 9-substituted-2,6-dichloropurine compound of structure 3 using techniques and procedures well known to one of ordinary skill in the art.

For example, 2,6-dichloropurine (1) can be reacted with the appropriate alcohol of structure 2 in the presence of triphenylphosphine and diethyl azodicarboxylate in a suitable anhydrous aprotic solvent, such as tetrahydrofuran. The reactants are typically stirred together at room temperature for a period of time ranging from 5 hours to 5 days. The resulting 9-substituted-2,6-dichloropurine of structure 3 may be recovered from the reaction zone by extractive methods as is known in the art or more typically, the resulting 9-substituted-2,6-dichloropurine of structure 3 is recovered by removal of solvent following by charging directly onto a silica gel column and eluting with a sutiable solvent, such as methylene chloride or mixture of solvents, such as a mixture of hexane and ethyl acetate. The crude 9-substituted-2,6-dichloropurine of structure 3 may then be purified by chromatography or may be used in the next step without purification.

In step b, the 6-chloro functionality of the 9-substituted-2,6-dichloropurine of structure 3 is reacted with an appropriate amine of structure 4 to give the corresponding 9-substituted-6-amino-2-chloropurine compound of structure 5.

For example, the 9-substituted-2,6-dichloropurine of structure 3 can be reacted with the appropriate amine of structure 4 in a suitable anhydrous polar solvent such as ethanol. The reactants are typically stirred together at reflux temperatures for a period of time ranging from 30 minutes to 3 days. The resulting 9-substituted-6-amino-2-chloropurine of structure 5 is recovered from the reaction zone by extractive methods as are known in the art, or, if the 9-substituted-6-amino-2-chloropurine of structure 5 precipitates out of solution, it may be recovered by filtration.

In step c, the 2-chloro functionality of the 9-substituted-6-amino-2-chloropurine of structure 5 is reacted with 1,4-cyclohexanediamine (6) to give the corresponding compound of Formula I.

For example, the appropriate 9-substituted-6-amino-2-chloropurine of structure 5 can be reacted with a molar excess of 1,4-cyclohexanediamine (6). The reactants are typically placed in a pressure tube, sealed, and heated at a temperature of from about 80° C. to about 150° C. for a period of time ranging from 30 minutes to 3 days. The resulting compound of Formula I is recovered from the reaction zone by extractive methods as are known in the art and may be purified by chromatography.

Starting materials for use in the general synthetic procedures outlined in Scheme A are readily available to one of ordinary skill in the art. For example, certain 4-aminopiperidines and 3-aminopyrrolidines of structure 4 may be prepared as described in Schemes B and C below.

Starting amines of structure 4 for use in Scheme A which are 4-amino-1-piperidine and 3-amino-1-pyrrolidine derivatives (structure 4') may be prepared as shown in Scheme B, wherein all substituents, unless otherwise indicated, are as previously defined.

Scheme B

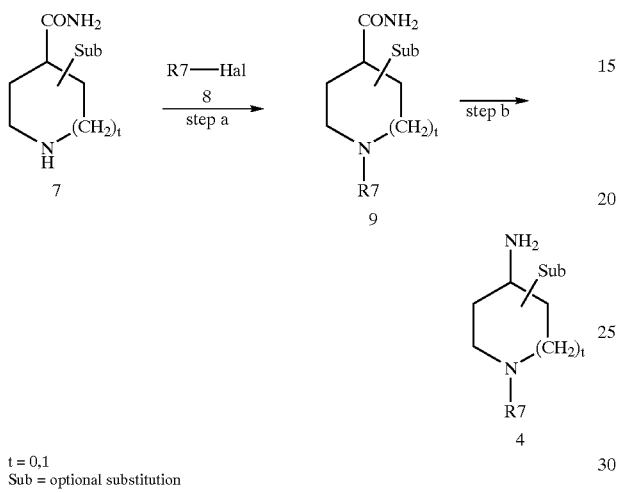

t = 0,1
Sub = optional substitution pyrrolidine derivatives (structure 4') may be prepared as shown in Scheme C, wherein all substituents, unless otherwise indicated, are as previously defined.

Scheme C

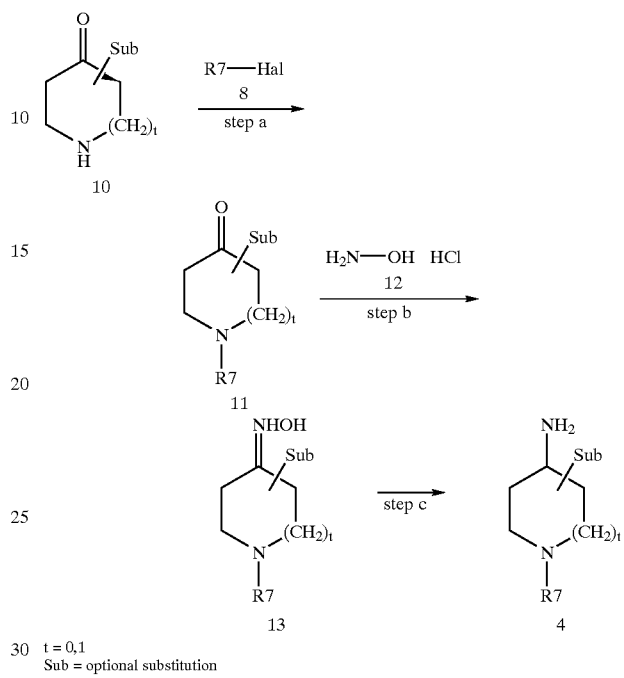

t = 0,1
Sub = optional substitution

In Scheme B, step a, the free amino functionality of an appropriate 4-carboxamide-1-piperidine or 3-carboxamide-1-pyrrolidine derivative of structure 7 is reacted with the appropriate alkyl halide of structure 8 to give the corresponding 4-carboxamide-1-alkylated-piperidine or 3-carboxamide-1-alkylated-pyrrolidine of structure 9.

For example, the 4-carboxamide-1-piperidine or 3-carboxamide-1-pyrrolidine of structure 7 can be reacted with the appropriate alkyl halide of structure 8 in a suitable aprotic organic solvent, such as 3-pentanone, in the presence of a suitable base, such as cesium carbonate, and a catalytic amount of a suitable alkylation catalyst, such as potassium iodide. The reactants are typically stirred together at reflux temperature for a period of time ranging from 30 minutes to 12 hours. The resulting 4-carboxamide- -alkylated-piperidine or 3-carboxamide-1-alkylated pyrrolidine of structure 9 is recovered from the reaction zone by filtration and evaporation of solvent In step b, the carboxamide functionality of the appropriate 4-carboxamide-1-alkylated piperidine or 3-carboxamide-1-alkylated pyrrolidine of structure 9 is dehydrogenated to give the corresponding 4-amino-1-alkylated-piperidine or 3-amino-1- alkylated-pyrrolidine of structure 4'.

For example, the appropriate 4-carboxamide-1-alkylated piperidine or 3-carboxamide-1-alkylated pyrrolidine of structure 9 is reacted with a molar excess of bis (trifluoroacetoxy)-iodobenzene in a suitable aprotic polar solvent such as acetonitrile. The reactants are typically stirred together at a temperature of about 50° C. to about 95° C. for a period of time ranging from 30 minutes to 5 hours. The resulting 4-amino-1-alkylated-piperidine or 3-amino-1-alkylated-pyrrolidine of structure 4' is recovered from the reaction zone by extractive methods as are known in the art.

Alternatively, starting amines of structure 4 for use in Scheme A which are 4-amino-1-piperidine and 3-amino-1-

Scheme C, step a, the free amino functionality of an appropriate 4-piperidone or 3-pyrrolidone derivative of structure 10 is reacted with the appropriate alkyl halide of structure 8 to give the corresponding 1-alkylated-4-piperidone or 1-alkylated-3-pyrrolidone of structure 11.

For example, the 4-piperidone or 3-pyrrolidone of structure 10 can be reacted with the appropriate alkyl halide of structure 8 in a suitable aprotic organic solvent, such as 3-pentanone, in the presence of a suitable base, such as cesium carbonate, and a catalytic amount of a suitable alkylation catalyst, such as potassium iodide. The reactants are typically stirred together at reflux temperature for a period of time ranging from 30 minutes to 12 hours. The resulting 1-alkylated-4-piperidone or 1-alkylated-3-pyrrolidone of structure 11 is recovered from the reaction zone by filtration and evaporation of solvent.

In step b, the ketone functionality of the appropriate 1-alkylated-4-piperidone or 1-alkylated-3-pyrrolidone of structure 11 is reacted with hydroxylamine hydrochloride (12) to give the corresponding 1-alkylated-4-piperidone oxime or 1-alkylated-3-pyrrolidone oxime of structure 13.

For example, the 1-alkylated-4-piperidone or 1-alkylated-3-pyrrolidone of structure 11 is reacted with hydroxylamine hydrochloride (12) in the presence of a suitable base, such as sodium acetate in a suitable protic solvent, such as aqueous ethanol. The reactants are typically stirred together at reflux temperatures for a period of time ranging from 30 minutes to 5 hours. The resulting 1-alkylated-4-piperidone oxime or 1-alkylated-3-pyrrolidone oxime of structure 13 is recovered from the reaction zone by extractive methods as are known in the art.

In step c, the oxime functionality of the appropriate 1-alkylated-4-piperidone oxime or 1-alkylated-3-pyrrolidone oxime of structure 13 is reduced to give the corresponding 4-amino-1-piperidine and 3-amino-1-pyrrolidine derivatives (structure 4').

For example, the 1-alkylated-4-piperidone oxime or 1-alkylated-3-pyrrolidone oxime of structure 13 is reacted with a suitable reducing agent, such as lithium aluminum hydride, in a suitable anhydrous solvent, such as tetrahydrofuran under an inert atmosphere. The reactants are typically stirred together at reflux temperature for a period of time ranging from 30 minutes to 5 hours. The resulting 4-amino-1-piperidine and 3-amino-1-pyrrolidine derivatives (structure 4') is recovered from the reaction zone by extractive methods as are known in the art.

The following examples present typical syntheses as described in Scheme A. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; "μM" refers to micromolar, and "APCI" refers to Atmospheric Pressure Chemical Ionization. Rf values are determined by an AQ 4×50 column (YMC) with a linear gradient from 100% C to 100% D in four minutes with a two minute hold at 100% D, where C is 5:95 acetonitrile:water with 0.1% TFA, and D is 95:5 acetonitrile:water with 0.085% TFA. Molecular ion determinations were made using a Finnigan MAT SSQ-7:10 mass spectrometer.

EXAMPLE 1

2-[Trans-(4-aminocyclohexyl)amino]-6-[(4-trifluorobenzyl)amino]-9-cyclopentylpurine dihydrochloride Scheme A, step a: 2.6-Dichloro-9-cyclopentylpurine Dissolve cyclopentanol (260 mg, 3.02 mmol), 2,6-dichloropurine (680 mg, 3.60 mmol) and triphenyl phosphine (950 mg, 3.60 mmol) in dry THF (20 mL) and cool to 0° C. Add diethyl azodicarboxylate (570 μL, 3.60 mmol) dropwise over a period of 15 minutes under a nitrogen atmosphere. Stir the resulting solution for 60 hours at room temperature. Evaporate the solvent in vacuo, charge directly onto a silica gel column, and elute with methylene chloride to give the title compound as a crude mixture.

Scheme A, step b: 2-Chloro-6-[(4-trifluorobenzyl)amino]-9-cyclopentylpurine

Dissolve 2,6-dichloro-9-cyclopentylpurine (3.00 mmol), 4-trifluorobenzylamine (3.00 mmol) and triethylamine (835 μL, 6.00 mmol) in dry ethanol (20 mL). Heat at reflux for 15 hours, cool, and filter the solid to give the title compound.

Scheme A, step c: 2-[Trans-(4-aminocyclohexyl)amino]-6-[(4-trifluorobenzyl)amino]-9-cyclopentylpurine dihydrochloride Mix 2-chloro-6-[(4-trifluorobenzyl)amino]-9-cyclopentylpurine (0.287 mmol) and 1,4-cyclohexanediamine (2.00 g, excess) in a pressure tube, seal and heat to 140° C. for 18 hours. Cool the reaction mixture, add $CH_2Cl_2$ (40 mL) and wash with $H_2O$ (2×20 mL). Dry ($MgSO_4$), evaporate the solvent in vacuo, and purify by silica gel chromatography (10:1 drops $CH_2Cl_2$/MeOH/$NH_4OH$) to give the title compound. Convert to the hydrochloride salt.

CIMS ($NH_3$) 474 ($MH^+$); Rf (min.) =0.58

EXAMPLE 2

2-[Trans-(4-aminocyclohexyl)amino]-6-(2-chlorophenylhydrazino)-9-cyclopentylpurine dihydrochloride Scheme A, step b: 2-Chloro-6-(2-chlorophenylhydrazino)-9-cyclopentylpurine 2-Chloro-6-(2-chlorophenylhydrazino)-9-cyclopentylpurine is prepared from 2,6-dichloro-9-cyclopentylpurine, 2-chlorophenylhydrazine, and triethylamine essentially as described above in Example 1, Scheme A, step b.

Scheme A, step, c: 2-[Trans-(4-aminocyclohexyl)amino]-6-(2-chlorophenylhydrazino)-9-cyclopentylpurine dihydrochloride 2-[Trans-(4-aminocyclohexyl)amino]-6-(2-chlorophenylhydrazino)-9-cyclopentylpurine dihydrochloride is prepared from 2-chloro-6-(2-chlorophenylhydrazino)-9-cyclopentylpurine essentially as described in Example 1, Scheme A, step c.

CIMS ($NH_3$) 475 ($MH^+$); Rf (min.)=3.49

EXAMPLE 3

2-[Trans-(4-aminocyclohexyl)amino]-6-(3,4,5-trimethoxybenzylamino)-9-cyclopentylpurine dihydrochloride Scheme A, step b: 2-Chloro-6-(3,4,5-trimethoxybenzylamino)-9-cyclopentylpurine 2-Chloro-6-(3,4,5-trimethoxybenzylamino)-9-cyclopentylpurine is prepared from 2,6-dichloro-9-cyclopentylpurine, 3,4,5-trimethoxybenzylamine, and triethylamine essentially as described above in Example 1, Scheme A, step b.

Scheme A, step c: 2-[Trans-(4-aminocyclohexyl)amino]-6-(3,4 5-trimethoxybenzylamino)-9-cyclopentylpurine dihydrochloride 2-[Trans-(4-aminocyclohexyl)amino]-6-(3,4,5-trimethoxybenzylamino)-9-cyclopentylpurine dihydrochloride is prepared from 2-chloro-6-(3,4,5-trimethoxybenzylamino)-9-cyclopentylpurine essentially as described in Example 1, Scheme A, step c.

CIMS ($NH_3$) 496 ($MH^+$); Rf (min.)=3.42

EXAMPLE 4

2-[Trans-(4-aminocyclohexyl)amino]-6-[(2,6-dimethoxybenzyl)amino]-1-9-cyclopentylpurine dihydrochloride Scheme A, step b: 2-Chloro-6-[(2,6-dimethoxybenzyl)amino]-9-cyclopentylpurine 2-Chloro-6-[(2,6-dimethoxybenzyl)amino]-9-cyclopentylpurine is prepared from 2,6-dichloro-9-cyclopentylpurine, 2,6-dimethoxybenzylamine, and triethylamine essentially as described above in Example 1, Scheme A, step b.

Scheme A, step c: 2-[Trans-(4-aminocyclohexyl)amino]-6-[(2.6-dimethoxybenzyl)amino -9-cyclopentylpurine dihydrochloride 2-[Trans-(4-aminocyclohexyl)amino]-6-[(2,6-dimethoxybenzyl)amino]-9-cyclopentylpurine dihydrochloride is prepared from 2-chloro-6-[(2,6-dimethoxybenzyl)amino]-9-cyclopentylpurine essentially as described in Example 1, Scheme A, step c.

CIMS ($NH_3$) 466 ($MH^+$); Rf (min.) 2.29

EXAMPLE 5

2-[Trans-(4-aminocyclohexyl)amino]-6-[(4-trifluoromethoxy)phenylamino]-9-cyclopentylpurine dihydrochloride Scheme A, step b: 2-Chloro-6-[(4-trifluoromethoxy)phenylamino]-9-cyclopentylpurine 2-Chloro-6-[(4-trifluoromethoxy)phenylamino]-9-cyclopentylpurine is prepared from 2,6-dichloro-9- cyclopentylpurine, 4-trifluoromethoxyaniline, and triethylamine essentially as described above in Example 1, Scheme A, step b.

Scheme A, step c: 2-[Trans-(4-aminocyclohexyl)amino]-6-[(4-trifluoromethoxy)phenylamino]-9-cyclopentylpurine dihydrochloride 2-[Trans-(4-aminocyclohexyl)amino]-6-[(4-trifluoromethoxy)phenylamino]-9-cyclopentylpurine dihydrochloride is prepared from 2-chloro-6-[(4-trifluoromethoxy)phenylamino]-9-cyclopentylpurine essentially as described in Example 1, Scheme A, step c.

CIMS (NH$_3$) 476 (MH$^+$); Rf (min.)=4.00

EXAMPLE 6

2-[Trans-(4-aminocyclohexyl)amino]-6-[2-(diethylamino)ethylamino]-9-cyclopentylpurine trihydrochloride Scheme A step b: 2-Chloro-6-[2-(diethylamino)ethylamino]-9-cyclopentylpurine 2-Chloro-6-[2-(diethylamino)ethylamino]-9-cyclopentylpurine is prepared from 2,6-dichloro-9-cyclopentylpurine, 2-diethylaminoethylamine, and triethylamine essentially as described above in Example 1, Scheme A, step b.

Scheme A, step c: 2-[Trans-(4-aminocyclohexyl)amino]-6-[2-(diethylamino)ethylamino]-9-cyclopentylpurine trihydrochloride 2-[Trans-(4-aminocyclohexyl)amino]-6-[2-(diethylamino)ethylamino]-9-cyclopentylpurine trihydrochloride is prepared from 2-chloro-6-[2-(diethylamino)ethylamino]-9-cyclopentylpurine essentially as described in Example 1, Scheme A, step c.

CIMS (NH$_3$) 415 (MH$^+$); Rf(min.) 3.15

EXAMPLE 7

2-[Trans-(4-aminocyclohexyl)amino]-6-[(1-napthyl)methylamino]-9-cyclopentylpurine dihydrochloride Scheme A, step b: 2-Chloro-6-[(1-napthyl)methylamino]-9-cyclopentylpurine 2-Chloro-6-[(1-napthyl)methylamino]-9-cyclopentylpurine is prepared from 2,6-dichloro-9-cyclopentylpurine, 1-(aminomethyl)naphthylene, and triethylamine essentially as described above in Example 1, Scheme A, step b.

Scheme A, step c: 2-[Trans-(4-aminocyclohexyl)amino]-6-r(1-napthyl)methylamino]-9-cyclopentylpurine dihydrochloride 2-[Trans-(4-aminocyclohexyl)amino]-6-[( 1-napthyl)methylamino]-9-cyclopentylpurine dihydrochloride is prepared from 2-chloro-6-[(1-napthyl)methylamino]-9-cyclopentylpurine essentially as described in Example 1, Scheme A, step c.

CIMS (NH$_3$) 456 (MH$^+$); Rf (min.)=3.43

EXAMPLE 8

2-[Trans-(4-aminocyclohexyl)amino]-6-[(4-methoxybenzyl)amino]-9-cyclopentylpurine dihydrochloride Scheme A, step b: 2-Chloro-6-[(4-methoxybenzyl)amino]-9-cyclopentylpurine 2-Chloro-6-[(4-methoxybenzyl)amino]-9-cyclopentylpurine is prepared from 2,6-dichloro-9-cyclopentylpurine, 4-methoxybenzylamine, and triethylamine essentially as described above in Example 1, Scheme A, step b.

Scheme A, step c: 2-[Trans-(4-aminocyclohexyl)amino]-6-[(4-methoxybenzyl)amino]-9-cyclopentylpurine dihydrochloride 2-[Trans-(4-aminocyclohexyl)amino]-6-[(4-methoxybenzyl)amino]-9-cyclopentylpurine dihydrochloride is prepared from 2-chloro-6-[(4-methoxybenzyl)amino]-9-cyclopentylpurine essentially as described in Example 1, Scheme A, step c.

CIMS (NH$_3$) 436 (MH$^+$); Rf (min.)=2.28

EXAMPLE 9

2-[Trans-(4-aminocyclohexyl)amino]-6-[(3-(5-methoxyindolyl))-2-ethylamino]-9-cyclopentylpurine dihydrochloride Scheme A, step b: 2-Chloro-6-[(3-(5-methoxyindolyl))-2-ethylamino]-9-cyclopentylpurine 2-Chloro-6-[(3-(5-methoxyindolyl))-2-ethylamino]-9-cyclopentylpurine is prepared from 2,6-dichloro-9-cyclopentylpurine, 5-methoxytryptamine, and triethylamine essentially as described above in Example 1, Scheme A, step b.

Scheme A, step c: 2-[Trans-(4-aminocyclohexyl)amino]-6-[(3-(5-methoxyindolyl))-2-ethylamino]-9-cyclopentylpurine dihydrochloride 2-[Trans-(4-aminocyclohexyl)amino]-6-[(3-(5-methoxyindolyl))-2-ethylamino]-9-cyclopentylpurine dihydrochloride is prepared from 2-chloro-6-[(3-(5-methoxyindolyl))-2-ethylamino]-9-cyclopentylpurine essentially as described in Example 1, Scheme A, step c.

CIMS (NH$_3$) 489 (MH$^+$); Rf (min.)=3.44

EXAMPLE 10

2-[Trans-(4-aminocyclohexyl)amino]-6-[4-(hydroxymethyl)cyclohexanemethylamino]-9-cyclopentylpurine dihydrochloride Scheme A, step b: 2-Chloro-6-[4-(hydroxymethyl)cyclohexanemethylamino]-9-cyclopentylpurine 2-Chloro-6-[4-(hydroxymethyl)cyclohexanemethylamino]-9-cyclopentylpurine is prepared from 2,6-dichloro-9-cyclopentylpurine, 4-(aminomethyl)cyclohexanemethanol, and triethylamine essentially as described above in Example 1, Scheme A, step b.

Scheme A, step c: 2-[Trans-(4-aminocyclohexyl)amino]-6-[4-(hydroxymethyl)cyclohexanemethylamino]-9-cyclopentylpurine dihydrochloride 2-[Trans-(4-aminocyclohexyl)amino]-6-[4-(hydroxymethyl)cyclohexanemethylamino]-9-cyclopentylpurine dihydrochloride is prepared from 2-chloro-6-[4-(hydroxymethyl)cyclohexanemethylamino]-9-cyclopentylpurine essentially as described in Example 1, Scheme A, step c.

CIMS (NH$_3$) 442 (MH$^+$); Rf (min.)=3.34

EXAMPLE 11

2-[Trans-(4-aminocyclohexyl)amino]-6-[2-fluorophenylhydrazino]-9-cyclopentylpurine dihydrochloride Scheme A, step b: 2-Chloro-6-[2-fluorophenylhydrazino]-9-cyclopentylpurine 2-Chloro-6-[2-fluorophenylhydrazino]-9-cyclopentylpurine is prepared from 2,6-dichloro-9-cyclopentylpurine, 2-fluorophenylhydrazine, and triethylamine essentially as described above in Example 1, Scheme A, step b.

Scheme A, step c: 2-[Trans-(4-aminocyclohexyl)amino]-6-[2-fluorophenylhydrazino]-9-cyclopentylpurine dihydrochloride 2-[Trans-(4-aminocyclohexyl)amino]-6-[2-fluorophenylhydrazino]-9-cyclopentylpurine dihydrochloride is prepared from 2-chloro-6-[2-fluorophenylhydrazino]-9-cyclopentylpurine essentially as described in Example 1, Scheme A, step c.

CIMS (NH$_3$) 425 (MH$^+$); Rf (min.)=3.41

EXAMPLE 12

2-[Trans-(4-aminocyclohexyl)amino]-6-[(2-methoxybenzyl)amino]-9-cyclopentylpurine dihydrochloride Scheme A, step b: 2-Chloro-6-[(2-methoxybenzyl)amino]-9-cyclopentylpurine 2-Chloro-6-[(2-methoxybenzyl)amino]-9-cyclopentylpurine is prepared from 2,6-dichloro-9-cyclopentylpurine, 2-methoxybenzylamine, and triethylamine essentially as described above in Example 1, Scheme A, step b.

Scheme A, step c: 2-[Trans-(4-aminocyclohexyl)amino]-6-[(2-methoxybenzyl)amino]-9-cyclopentylpurine dihydrochloride 2-[Trans-(4-aminocyclohexyl)amino]-6-[(2-methoxybenzyl)amino]-9-cyclopentylpurine dihydrochloride is prepared from 2-chloro-6-[(2-methoxybenzyl)amino]-9-cyclopentylpurine essentially as described in Example 1, Scheme A, step c.

CIMS (NH3) 436 (MH); Rf (min.)=2.30

EXAMPLE 13

2-[Trans-(4-aminocyclohexyl)amino]-6-[(2,3-dimethoxybenzyl)amino]-9-cyclopentylpurine dihydrochloride Scheme A, step b: 2-Chloro-6-[(2,3-dimethoxybenzyl)amino]-9-cyclopentylpurine 2-Chloro-6-[(2,3-dimethoxybenzyl)amino]-9-cyclopentylpurine is prepared from 2,6-dichloro-9-cyclopentylpurine, 2,3-dimethoxybenzylamine, and triethylamine essentially as described above in Example 1, Scheme A, step b.

Scheme A, step c: 2-[Trans-(4-aminocyclohexyl)amino]-6-[(2,3-dimethoxybenzyl)amino]-9-cyclopentylpurine dihydrochloride 2-[Trans-(4-aminocyclohexyl)amino]-6-[(2,3-dimethoxybenzyl)amino]-9-cyclopentylpurine dihydrochloride is prepared from 2-chloro-6-[(2,3-dimethoxybenzyl)amino]-9-cyclopentylpurine essentially as described in Example 1, Scheme A, step c.

CIMS (NH$_3$) 466 (MH$^+$); Rf (min.)=2.29

EXAMPLE 14

2-[Trans-(4-aminocyclohexyl)amino]-6-[2-(4-methoxyphenyl)ethylamino]-9-cyclopentylpurine dihydrochloride Scheme A, step b: 2-Chloro-6-[2-(4-methoxyphenyl)ethylamino]-9-cyclopentylpurine 2-Chloro-6-[2-(4-methoxyphenyl)ethylamino]-9-cyclopentylpurine is prepared from 2,6-dichloro-9-cyclopentylpurine, 2-(4-methoxyphenyl)ethylamine, and triethylamine essentially as described above in Example 1, Scheme A, step b.

Scheme A, step c: 2-[Trans-(4-aminocyclohexyl)amino]-6-[2-(4-methoxyphenyl)ethylamino]-9-cyclopentylpurine dihydrochloride 2-[Trans-(4-aminocyclohexyl)amino]-6-[2-(4-methoxyphenyl)ethylamino]-9-cyclopentylpurine dihydrochloride is prepared from 2-chloro-6-[2-(4-methoxyphenyl)ethylamino]-9-cyclopentylpurine essentially as described in Example 1, Scheme A, step c.

CIMS (NH$_3$) 450 (MH$^+$); Rf (min.)=3.53

EXAMPLE 15

2-[Trans-(4-aminocyclohexyl)amino]-6-[3-(2-methoxyethoxy)propylamino]-9-cyclopentylpurine dihydrochloride Scheme A, step b: 2-Chloro-6-[3-(2-methoxyethoxy)propylamino]-9-cyclopentylpurine 2-Chloro-6-[3-(2-methoxyethoxy)propylamino]-9-cyclopentylpurine is prepared from 2,6-dichloro-9-cyclopentylpurine, 3-(2-methoxyethoxy)propylamine, and triethylamine essentially as described above in Example 1, Scheme A, step b.

Scheme A, step c: 2-[Trans-(4-aminocyclohexyl)amino]-6-[3-(2-methoxyethoxy)propylamino]-9-cyclopentylpurine dihydrochloride 2-[Trans-(4-aminocyclohexyl)amino]-6-[3-(2-methoxyethoxy)propylamino]-9-cyclopentylpurine dihydrochloride is prepared from 2-chloro-6-[3-(2-methoxyethoxy)propylamino]-9-cyclopentylpurine essentially as described in Example 1, Scheme A, step c.

CIMS (NH$_3$) 432 (MH); Rf (min.)=3.31

EXAMPLE 16

2-[Trans-(4-aminocyclohexyl)amino]-6-(2-methoxyethylamino)-9-cyclopentylpurine dihydrochloride Scheme A, step b: 2-Chloro-6-(2-methoxyethylamino)-9-cyclopentylpurine 2-Chloro-6-(2-methoxyethylamino)-9-cyclopentylpurine is prepared from 2,6-dichloro-9-cyclopentylpurine, 2-methoxyethylamine, and triethylamine essentially as described above in Example 1, Scheme A, step b.

Scheme A, step c: 2-[Trans-(4-aminocyclohexyl)amino]-6-(2-methoxyethylamino)-9-cyclopentylpurine dihydrochloride 2-[Trans-(4-aminocyclohexyl)amino]-6-(2-methoxyethylamino)-9-cyclopentylpurine dihydrochloride is prepared from 2-chloro-6-(2-methoxyethylamino)-9-cyclopentylpurine essentially as described in Example 1, Scheme A, step c.

CIMS (NH$_3$) 374 (MH$^+$); Rf (min.)=3.23

EXAMPLE 17

2-[Trans-(4-aminocyclohexyl)amino]-6-[(2,4-dimethoxybenzyl)amino]-9-cyclopentylpurine dihydrochloride Scheme A, step b: 2-Chloro-6-[(2,4-dimethoxybenzyl)amino]-9-cyclopentylpurine 2-Chloro-6-[(2,4-dimethoxybenzyl)amino]-9-cyclopentylpurine is prepared from 2,6-dichloro-9-cyclopentylpurine, 2,4-dimethoxybenzylamine, and triethylamine essentially as described above in Example 1, Scheme A, step b.

Scheme A, step c: 2-[Trans-(4-aminocyclohexyl)amino]-6-[(2,4-dimethoxybenzyl)amino]-9-cyclopentylpurine dihydrochloride 2-[Trans-(4-aminocyclohexyl)amino]-6-[(2,4-dimethoxybenzyl)amino]-9-cyclopentylpurine dihydrochloride is prepared from 2-chloro-6-[(2,4-dimethoxybenzyl)amino]-9-cyclopentylpurine essentially as described in Example 1, Scheme A, step c.

CIMS (NH$_3$) 466 (MH$^+$); Rf (min.)=2.29

EXAMPLE 18

2-[Trans-(4-aminocyclohexyl)amino]-6-[(3-diethylamino)propylamino]-9-cyclopentylpurine dihydrochloride Scheme A, step b: 2-Chloro-6-[(3-diethylamino)propylamino]-9-cyclopentylpurine 2-Chloro-6-[(3-diethylamino)propylamino]-9-cyclopentylpurine is prepared from 2,6-dichloro-9-cyclopentylpurine, 3-diethylaminopropylamine, and triethylamine essentially as described above in Example 1, Scheme A, step b.

Scheme A, step c: 2-[Trans-(4-aminocyclohexyl)amino]-6-[(3-diethylamino)propylamino]-9-cyclopentylpurine dihydrochloride 2-[Trans-(4-aminocyclohexyl)amino]-6-[(3-diethylamino)propylamino]-9-cyclopentylpurine dihydrochloride is prepared from 2-chloro-6-[(3-diethylamino)propylamino]-9-cyclopentylpurine essentially as described in Example 1, Scheme A, step c.

CIMS (NH$_3$) 429 (MH$^+$); Rf (min.)=3.13

EXAMPLE 19

2-[Trans-(4-aminocyclohexyl)amino]-6-[(3.4-dimethoxybenzyl)amino]-9-(2-propyl)purine dihydrochloride Scheme A, step a: 2.6-Dichloro-9-(2-propyl)purine 2,6-Dichloro-9-(2-propyl)purine is prepared from 2,6-dichloropurine and isopropanol essentially as described in Example 1, Scheme A, step a, but substituting isopropanol for cyclopentanol.

Scheme A, step b: 2-Chloro-6-[(3,4-dimethoxybenzyl)amino]-9-(2-propyl)purine

2-Chloro-6-[(3,4-dimethoxybenzyl)amino]-9-(2-propyl)purine is prepared from 2,6-dichloro-9-(2-propyl)purine, 3,4-dimethoxybenzylamine, and triethylamine essentially as described above in Example 1, Scheme A, step b.

Scheme A, step c: 2-[Trans-(4-aminocyclohexyl)amino]-6-[(3,4-dimethoxybenzyl)amino]-9-(2-propyl)purine dihydrochloride 2-[Trans-(4-aminocyclohexyl)amino]-6-[(3,4-dimethoxybenzyl)amino]-9-(2-propyl)purine dihydrochloride is prepared from 2-chloro-6-[(3,4-dimethoxybenzyl)amino]-9-(2-propyl)purine essentially as described in Example 1, Scheme A, step c.

CIMS (NH$_3$) 440 (MH$^+$); Rf((min.)=3.33

EXAMPLE 20

2-[Trans-(4-aminocyclohexyl)amino]-6-[2,6-dichlorophenylhydrazino]-9-cyclopentylpurine dihydrochloride Scheme A, step b: 2-Chloro-6-[2,6-dichlorophenylhydrazino]-9-cyclopentylpurine 2-Chloro-6-[2,6-dichlorophenylhydrazino]-9-cyclopentylpurine is prepared from 2,6-dichloro-9-cyclopentylpurine, 2,6-dichlorophenylhydrazine, and triethylamine essentially as described above in Example 1, Scheme A, step b.

Scheme A, step c: 2-[Trans-(4-aminocyclohexyl)amino]-6-[2,6-dichlorophenylhydrazino]-9-cyclopentylpurine dihydrochloride 2-[Trans-(4-aminocyclohexyl)amino]-6-[2,6-dichlorophenylhydrazino]-9-cyclopentylpurine dihydrochloride is prepared from 2-chloro-6-[2,6-dichlorophenylhydrazino]-9-cyclopentylpurine essentially as described in Example 1, Scheme A, step c.

CIMS (NH$_3$) 475 (MH$^+$); Rf (min.)=3.43

EXAMPLE 21

2-[Trans-(4-aminocyclohexyl)amino]-6-(3-fluorophenylamino)-9-cyclopentylpurine dihydrochloride Scheme A, step b: 2-Chloro-6-(3-fluorophenylamino)-9-cyclopentylpurine 2-Chloro-6-(3-fluorophenylamino)-9-cyclopentylpurine is prepared from 2,6-dichloro-9-cyclopentylpurine, 3-fluoroaniline, and triethylamine essentially as described above in Example 1, Scheme A, step b.

Scheme A, step c: 2-[Trans-(4-aminocyclohexyl)amino]-6-(3-fluorophenylamino)-9-cyclopentylpurine dihydrochloride 2-[Trans-(4-aminocyclohexyl)amino]-6-(3-fluorophenylamino)-9-cyclopentylpurine dihydrochloride is prepared from 2-chloro-6-(3-fluorophenylamino)-9-cyclopentylpurine essentially as described in Example 1, Scheme A, step c.

CIMS (NH$_3$) 448 (MH$^+$); Rf (min.) 3.44

EXAMPLE 22

2-[Trans-(4-aminocyclohexyl)amino]-6-(3-methoxypropylamino)-9-cyclopentylpurine dihydrochloride Scheme A, step b: 2-Chloro-6-(3-methoxypropylamino)-9-cyclopentylpurine 2-Chloro-6-(3-methoxypropylamino)-9-cyclopentylpurine is prepared from 2,6-dichloro-9-cyclopentylpurine, 3-methoxypropylamine, and triethylamine essentially as described above in Example 1, Scheme A, step b.

Scheme A, step c: 2-[Trans-(4-aminocyclohexyl)amino]-6-(3-methoxypropylamino)-9-cyclopentylpurine dihydrochloride 2-[Trans-(4-aminocyclohexyl)amino]-6-(3-methoxypropylamino)-9-cyclopentylpurine dihydrochloride is prepared from 2-chloro-6-(3-methoxypropylamino)-9-cyclopentylpurine essentially as described in Example 1, Scheme A, step c.

CIMS (NH$_3$) 388 (MH$^+$); Rf (min.)=3.29

EXAMPLE 23

2-[Trans-(4-aminocyclohexyl)amino]-6-[(4-pentyl)phenylamino]-9-cyclopentylpurine dihydrochloride Scheme A, step b: 2-Chloro-6-[(4-pentyl)phenylamino]-9-cyclopentylpurine 2-Chloro-6-[(4-pentyl)phenylamino]-9-cyclopentylpurine is prepared from 2,6-dichloro-9-cyclopentylpurine, 4-butylphenylamine, and triethylamine essentially as described above in Example 1, Scheme A, step b.

Scheme A, step c: 2-[Trans-(4-aminocyclohexyl)amino]-6-[(4-pentyl)phenylamino]-9-cyclopentylpurine dihydrochloride 2-[Trans-(4-aminocyclohexyl)amino]-6-[(4-pentyl)phenylamino]-9-cyclopentylpurine dihydrochloride is prepared from 2-chloro-6-[(4-pentyl)phenylamino]-9-cyclopentylpurine essentially as described in Example 1, Scheme A, step c.

CIMS (NH$_3$) 462 (MH$^+$); Rf (min.)=4.15

EXAMPLE 24

(+/−)-2-[Trans-(4-aminocyclohexyl)amino]-6-[(α-cyclopropyl-4-chlorobenzyl)amino]-9-cyclopentylpurine dihydrochloride Scheme A, step b: 2-Chloro-6-[(α-cyclopropyl-4-chlorobenzyl)amino]-9-cyclopentylpurine 2-Chloro-6-[(α-cyclopropyl-4-chlorobenzyl)amino]-9-cyclopentylpurine is prepared from 2,6-dichloro-9-cyclopentylpurine, α-cyclopropyl-4-chlorobenzylamine, and triethylamine essentially as described above in Example 1, Scheme A, step b.

Scheme A, step c: 2-[Trans-(4-aminocyclohexyl)amino]-6-[(α-cyclopropyl-4-chlorobenzyl)amino]-9-cyclopentylpurine dihydrochloride 2-[Trans-(4-aminocyclohexyl)amino]-6-[(α-cyclopropyl-4-chlorobenzyl)amino]-9-cyclopentylpurine dihydrochloride is prepared from 2-chloro-6-[(α-cyclopropyl4-chlorobenzyl)amino]-9-cyclopentylpurine essentially as described in Example 1, Scheme A, step c.

CIMS ($H_3$) 480 ($MH^+$) Rf (min.)=2.35

EXAMPLE 25

2-[Trans-(4-aminocyclohexyl)amino]-6-[(2-trifluorobenzyl)amino]-9-cyclopentylpurine dihydrochloride Scheme A, step b: 2-Chloro-6-[(2-trifluorobenzyl)amino]-9-cyclopentylpurine 2-Chloro-6-[(2-trifluorobenzyl)amino]-9-cyclopentylpurine is prepared from 2,6-dichloro-9-cyclopentylpurine, 2-trifluorobenzylamine, and triethylamine essentially as described above in Example 1, Scheme A, step b.

Scheme A, step c: 2-[Trans-(4-aminocyclohexyl)amino]-6-[(2-trifluorobenzyl)amino]-9-cyclopentylpurine dihydrochloride 2-[Trans-(4-aminocyclohexyl)amino]-6-[(2-trifluorobenzyl)amino]-9-cyclopentylpurine dihydrochloride is prepared from 2-chloro-6-[(2-trifluorobenzyl)amino]-9-cyclopentylpurine essentially as described in Example 1, Scheme A, step c.

CIMS ($NH_3$) 474 ($MH^+$); Rf (min.)=2.31

EXAMPLE 26

2-[Trans-(4-aminocyclohexyl)amino]-6-(2-hydroxyethoxyethylamino)-9-cyclopentylpurine dihydrochloride Scheme A, step b: 2-Chloro-6-(2-hydroxyethoxyethylamino)-9-cyclopentylpurine 2-Chloro-6-(2-hydroxyethoxyethylamino)-9-cyclopentylpurine is prepared from 2,6-dichloro-9-cyclopentylpurine, 2-(2-aminoethoxy)ethanol, and triethylamine essentially as described above in Example 1, Scheme A, step b.

Scheme A, step c: 2-[Trans-(4-aminocyclohexyl)amino]-6-(2-hydroxyethoxyethylamino)-9-cyclopentylpurine dihydrochloride 2-[Trans-(4-aminocyclohexyl)amino]-6-(2-hydroxyethoxyethylamino)-9-cyclopentylpurine dihydrochloride is prepared from 2-chloro-6-(2-hydroxyethoxyethylamino)-9-cyclopentylpurine essentially as described in Example 1, Scheme A, step c.

CIMS ($NH_3$) 404 ($MH^+$); Rf (min.)=3.16

EXAMPLE 27

2-[Trans-(4-aminocyclohexyl)amino]-6-[2-(3-methoxyphenyl)ethylamino]-9-cyclopentylpurine dihydrochloride Scheme A, step b: 2-Chloro-6-[2-(3-methoxyphenyl)ethylamino]-9-cyclopentylpurine 2-Chloro-6-[2-(3-methoxyphenyl)ethylamino]-9-cyclopentylpurine is prepared from 2,6-dichloro-9-cyclopentylpurine, 2-(3-methoxyphenyl)ethylamine, and triethylamine essentially as described above in Example 1, Scheme A, step b.

Scheme A, step c: 2-[Trans-(4-aminocyclohexyl)amino]-6-[2-(3-methoxyphenyl)ethylamino]-9-cyclopentylpurine dihydrochloride 2-[Trans-(4-aminocyclohexyl)amino]-6-[2-(3-methoxyphenyl)ethylamino]-9-cyclopentylpurine dihydrochloride is prepared from 2-chloro-6-[2-(3-methoxyphenyl)ethylamino]-9-cyclopentylpurine essentially as described in Example 1, Scheme A, step c.

CIMS ($NH_3$) 450 ($MH^+$); Rf (min.)=3.54

EXAMPLE 28

2-[Trans-(4-aminocyclohexyl)amino]-6-[(3 5-dimethoxybenzyl)amino]-9-cyclopentylpurine dihydrochloride Scheme A, step b: 2-Chloro-6-[(3,5-dimethoxybenzyl)amino]-9-cyclopentylpurine 2-Chloro-6-[(3,5-dimethoxybenzyl)amino]-9-cyclopentylpurine is prepared from 2,6-dichloro-9-cyclopentylpurine, 3,5-dimethoxybenzylamine, and triethylamine essentially as described above in Example 1, Scheme A, step b.

Scheme A, step c: 2-[Trans-(4-aminocyclohexyl)amino]-6-[(3 5-dimethoxybenzyl)amino]-9-cyclopentylpurine dihydrochloride 2-[Trans-(4-aminocyclohexyl)amino]-6-[(3,5-dimethoxybenzyl)amino]-9-cyclopentylpurine dihydrochloride is prepared from 2-chloro-6-[(3,5-dimethoxybenzyl)amino]-9-cyclopentylpurine essentially as described in Example 1, Scheme A, step c.

CIMS ($NH_3$) 466 ($MH^+$); Rf (min.)=2.27

EXAMPLE 29

2-[Trans-(4-aminocyclohexyl)amino]-6-(4-methoxybutylamino)-9-cyclopentylpurine dihydrochloride Scheme A, step b: 2-Chloro-6-(4-methoxybutylamino)-9-cyclopentylpurine 2-Chloro-6-(4-methoxybutylamino)-9-cyclopentylpurine is prepared from 2,6-dichloro-9-cyclopentylpurine, 4-methoxybutylamine, and triethylamine essentially as described above in Example 1, Scheme A, step b.

Scheme A, step c: 2-[Trans-(4-aminocyclohexyl)amino]-6-(4-methoxybutylamino)-9-cyclopentylpurine dihydrochloride 2-[Trans-(4-aminocyclohexyl)amino]-6-(4-methoxybutylamino)-9-cyclopentylpurine dihydrochloride is prepared from 2-chloro-6-(4-methoxybutylamino)-9-cyclopentylpurine essentially as described in Example 1, Scheme A, step c.

CIMS ($NH3$) 388 ($MH^+$); Rf (min.)=3.29

EXAMPLE 30

2-[Trans-(4-aminocyclohexyl)amino]-6-[(2,3-dimethoxybenzyl)amino]-9-(2-propyl)purine dihydrochloride Scheme A, step b: 2-Chloro-6-[(2,3-dimethoxybenzyl)amino]-9-(2-propyl)purine 2-Chloro-6-[(2,3-dimethoxybenzyl)amino]-9-(2-propyl)purine is prepared from 2,6-dichloro-9-(2-propyl)purine (see Example 19 for preparation), 2,3-dimethoxybenzylamine, and triethylamine essentially as described above in Example 1, Scheme A, step b.

Scheme A, step c: 2-[Trans-(4-aminocyclohexyl)amino]-6-[(2,3-dimethoxybenzyl)amino]-9-(2-propyl)purine dihydrochloride 2-[Trans-(4-aminocyclohexyl)amino]-6-[(2,3-dimethoxybenzyl)amino]-9-(2-propyl)purine dihydrochloride is prepared from 2-chloro-6-[(2,3-dimethoxybenzyl)amino]-9-(2-propyl)purine essentially as described in Example 1, Scheme A, step c.

CIMS (NH$_3$) 440 (MH$^+$); Rf (min.)=3.39

EXAMPLE 31

2-[Trans-(4-aminocyclohexyl)amino]-6-[2-(phenylamino[]ethylamino]-9-cyclopentylpurine trihydrochloride Scheme A, step b: 2-Chloro-6-[2-(phenylamino)ethylamino]-9-cyclopentylpurine 2-Chloro-6-[2-(phenylamino)ethylamino]-9-cyclopentylpurine is prepared from 2,6-dichloro-9-cyclopentylpurine, N-phenylethylenediamine, and triethylamine essentially as described above in Example 1, Scheme A, step b.

Scheme A, step c: 2-[Trans-(4-aminocyclohexyl)amino]-6-[2-(phenylamino)ethylamino]-9-cyclopentylpurine trihydrochloride 2-[Trans-(4-aminocyclohexyl)amino]-6-[2-(phenylamino)ethylamino]-9-cyclopentylpurine trihydrochloride is prepared from 2-chloro-6-[2-(phenylamino)ethylamino]-9-cyclopentylpurine essentially as described in Example 1, Scheme A, step c.

CIMS (NH$_3$) 435 (MH$^+$); Rf (min.)=3.34

EXAMPLE 32

2-[Trans-(4-aminocyclohexyl)amino]-6-(phenylamino)-9-cyclopentylpurine dihydrochloride Scheme A, step b: 2-Chloro-6-(phenylamino)-9-cyclopentylpurine 2-Chloro-6-(phenylamino)-9-cyclopentylpurine is prepared from 2,6-dichloro-9-cyclopentylpurine, aniline, and triethylamine essentially as described above in Example 1, Scheme A, step b.

Scheme A, step c: 2-[Trans-(4-aminocyclohexyl amino]-6-(phenylamino)-9-cyclopentylpurine dihydrochloride 2-[Trans-(4-aminocyclohexyl)amino]-6-(phenylamino)-9-cyclopentylpurine dihydrochloride is prepared from 2-chloro-6-(phenylamino)-9-cyclopentylpurine essentially as described in Example 1, Scheme A, step c.

CIMS (NH$_3$) 392 (MH$^+$); Rf (min.)=3.35

EXAMPLE 33

2-[Trans-(4-aminocyclohexyl)amino]-6-[4-(1-benzyl)piperidinylamino]-9-cyclopentylpurine trihydrochloride Scheme A, step b: 2-Chloro-6-[4-(1-benzyl)piperidinylamino]-9-cyclopentylpurine 2-Chloro-6-[4-(1-benzyl)piperidinylamino]-9-cyclopentylpurine is prepared from 2,6-dichloro-9-cyclopentylpurine, 4-amino-1-benzylpiperidine, and triethylamine essentially as described above in Example 1, Scheme A, step b.

Scheme A, step c: 2-[Trans-(4-aminocyclohexyl)amino]-6-[4-(1-benzyl)piperidinylamino]-9-cyclopentylpurine trihydrochloride 2-[Trans-(4-aminocyclohexyl)amino]-6-[4-(1-benzyl)piperidinylamino]-9-cyclopentylpurine trihydrochloride is prepared from 2-chloro-6-[4-(1-benzyl)piperidinylamino]-9-cyclopentylpurine essentially as described in Example 1, Scheme A, step c.

CIMS (NH$_3$) 489 (MH$^+$); Rf (min.)=3.29

EXAMPLE 34

2-[Trans-(4-aminocyclohexyl)amino]-6-[3,4-dimethoxybenzyl)amino]-9-cyclopentylpurine dihydrochloride Scheme A, step b: 2-Chloro-6-[3,4-dimethoxybenzyl)amino]-9-cyclopentylpurine 2-Chloro-6-[3,4-dimethoxybenzyl)amino]-9-cyclopentylpurine is prepared from 2,6-dichloro-9-cyclopentylpurine, 3,4-dimethoxybenzylamine, and triethylamine essentially as described above in Example 1, Scheme A, step b.

Scheme A, step c: 2-[Trans-(4-aminocyclohexyl)amino]-6-[3,4-dimethoxybenzyl)amino]-9-cyclopentylpurine dihydrochloride 2-[Trans-(4-aminocyclohexyl)amino]-6-[3,4-dimethoxybenzyl)amino]-9-cyclopentylpurine dihydrochloride is prepared from 2-chloro-6-[3,4-dimethoxybenzyl)amino]-9-cyclopentylpurine essentially as described in Example 1, Scheme A, step c.

CIMS (NH$_3$) 466 (MH$^+$); Rf (min.)=2.25

EXAMPLE 35

2-[Trans-(4-aminocyclohexyl)amino]-6-[(3-iodobenzyl)amino]-9-(2-cyclopentenyl)purine hydrochloride Scheme A, step a: 2,6-Dichloro-9-cyclopentenylpurine 2,6-Dichloro-9-cyclopentenylpurine is prepared from 2,6-dichloropurine and cyclopentenol essentially as described in Example 1, Scheme A, step a, but substituting cyclopentenol for cyclopentanol.

Scheme A, step b: 2-Chloro-6-[(3-iodobenzyl)amino]-9-cyclopentenylpurine

2-Chloro-6-[(3-iodobenzyl)amino]-9-cyclopentenylpurine is prepared from 2,6-dichloro-9-cyclopentenylpurine, 3-iodobenzylamine, and triethylamine essentially as described above in Example 1, Scheme A, step b.

Scheme A, step c: 2-[Trans-(4-aminocyclohexyl)amino]-6-[(3-iodobenzyl)amino]-9-cyclopentenylpurine 2-[Trans-(4-aminocyclohexyl)amino]-6-[(3-iodobenzyl)amino]-9-cyclopentenylpurine hydrochloride is prepared from 2-chloro-6-[(3-iodobenzyl)amino]-9-cyclopentenylpurine essentially as described in Example 1, Scheme A, step c.

CIMS (NH$_3$) 530 (MH$^+$)

EXAMPLE 36

2-[Trans-(4-aminocyclohexyl)amino]-6-(dodecylamino)-9-cyclopentylpurine dihydrochloride Scheme A, step b: 2-Chloro-6-(dodecylamino)-9-cyclopentylpurine 2-Chloro-6-(dodecylamino)-9-cyclopentylpurine is prepared from 2,6-dichloro-9-cyclopentylpurine, n-dodecylamine, and triethylamine essentially as described above in Example 1, Scheme A, step b.

Scheme A, step c: 2-[Trans-(4-aminocyclohexyl)amino]-6-(dodecylamino)-9-cyclopentylpurine dihydrochloride 2-[Trans-(4-aminocyclohexyl)amino]-6-(dodecylamino)-9-cyclopentylpurine dihydrochloride is prepared from 2-chloro-6-(dodecylamino)-9-cyclopentylpurine essentially as described in Example 1, Scheme A, step c.
CIMS (NH$_3$) 484 (MH$^+$); Rf (min.)=5.09

EXAMPLE 37

2-[Trans-(4-aminocyclohexyl)amino]-6-[(4-methoxybenzyl)amino]-9-(2-propyl)purine dihydrochloride Scheme A, step b: 2-Chloro-6-[(4-methoxybenzyl) amino]-9-(2-propyl)purine 2Chloro-6-[(4-methoxybenzyl)amino]-9-(2-propyl) purine is prepared from 2,6-dichloro-9-(2-propyl)purine (see Example 19 for preparation), 4-methoxybenzylamine, and triethylamine essentially as described above in Example 1, Scheme A, step b.

Scheme A, step c: 2-[Trans-(4-aminocyclohexyl)amino]-6-[(4-methoxybenzyl)amino]-9-(2-propyl)purine dihydrochloride 2-[Trans-(4-aminocyclohexyl)amino]-6-[(4-methoxybenzyl)amino]-9-(2-propyl)purine dihydrochloride is prepared from 2-chloro-6-[(4-methoxybenzyl)amino]-9-(2-propyl)purine essentially as described in Example 1, Scheme A, step c.
CIMS (NH$_3$) 410 (MH$^+$); Rf (min.)=3.37

EXAMPLE 38

2-[Trans-(4-aminocyclohexyl)amino]-6-[4-(1-(4-chlorobenzyl))piperidinylamino]-9-cyclopentylpurine Preparation of 4-Amino-1-(4-chlorobenzyl)piperidine
Method 1
Scheme B, step a: 4-Carboxamide-1-(4-chlorobenzyl) piperidine Dissolve isonipecotamide (39 mmol) in 3-pentanone (25 mL) and heat to reflux. Add cesium carbonate (24 mmol) and a catalytic amount of potassium iodide (2 spatula tips, cat) followed by 4-chlorobenzyl chloride (47 mmol). Stir and reflux for 5 hours. Filter the hot solution through celite, wash the filter cake with hot acetone (4×20 mL), combine the filtrate and washings, and evaporate the solvent in vacuo and residue was recrystallized from acetone to give the title compound.

Scheme B, step b: 4-Amino-1-(4-chlorobenzyl)piperidine

Dissolve bis(trifluoroacetoxy)iodobenzene (84 mmol) in acetonitrile (20 mL) and dilute with water (20 mL). Add 4-carboxamide-1-(4-chlorobenzyl)piperidine (7 mmol) and heat for overnight at 65° C. Cool the mixture (ice bath), add water (60 mL), followed by concentrated HCl. Extract with ether (2×). The aqueous layer was concentrated in vacuo, and the residue was dissolved in water in 40 mL of water. Basify with aqueous sodium carbonate, and extract into methylene chloride, the organic layer was drived over Na$_2$SO$_4$, filtered and the solvent was evaporated in vacuo to give the title compound.
Method 2
Scheme C, step a: 1-(4-Chlorobenzyl)-4-piperidone Dissolve 4-piperidone (17 mmol) in 3-pentanone (25 mL) and heat to reflux. Add cesium carbonate (19 mmol) and a catalytic amount of potassium iodide, followed by 4-chlorobenzyl chloride (20 mmol). Stir and reflux for 4 hours. Filter the hot suspension, wash the residue with hot acetone (4×20 mL), combine the filtrate and washings, and evaporate the solvent in vacuo to give the title compound.

Scheme C, step b: 1-(4-Chlorobenzyl)-4-piperidone oxime

Dissolve 1-(4-chlorobenzyl)-4-piperidone (0.0456 mmol), hydroxylamine hydrochloride (0.0456 mmol) and sodium acetate (0.0456 mmol) in aqueous ethanol (450 mL). Stir approximately 30 minutes to 2 hours while warming. Add methylene chloride (450 mL), separate the organic phase, and extract the aqueous phase with methylene chloride (100 mL). Combine the organic phases and dry (MgSO$_4$). Evaporate the solvent in vacuo to give the title compound.

Scheme C, step c: 4-Amino-1-(4-chlorobenzyl)piperidine

Add 1-(4-chlorobenzyl)-4-piperidone oxime (1.87 mmol) to a solution of lithium aluminum hydride (2.5 mL of a 1M solution in tetrahydrofuran) and place under a nitrogen atmosphere. Heat at reflux for 2 hours, cool and pour into dilute aqueous sodium hydroxide. Extract with a mixture of ethyl ether/ethyl acetate (2×), wash with aqueous sodium chloride and dry (MgSO$_4$). Evaporate the solvent in vacuo to give the title compound.

Scheme A, step b: 2-Chloro-6-[4-(1-(4-chlorobenzyl)) piperidinylamino]-9-cyclopentylpurine 2-Chloro-6-[4-(1-(4-chlorobenzyl))piperidinylamino]-9-cyclopentylpurine is prepared from 2,6-dichloro-9-cyclopentylpurine, 4-amino-1-(4-chlorobenzyl)piperidine, and triethylamine essentially as described above in Example 1, Scheme A, step b.

Scheme A, step c: 2-[Trans-(4-aminocyclohexyl)amino]-6-[4-(1-(4-chlorobenzyl))piperidinylamino]-9-cyclopentylpurine 2-[Trans-(4-aminocyclohexyl)amino]-6-[4-(1-(4-chlorobenzyl))piperidinylamino]-9-cyclopentylpurine is prepared from 2-chloro-6-[4-(1-(4-chlorobenzyl)) piperidinylamino]-9-cyclopentylpurine essentially as described in Example 1, Scheme A, step c.
Rf: (min)=2.29; purity 94%; MS (APCI): 523 M$^{+1}$

EXAMPLE 39

2-[Trans-(4-aminocyclohexyl)amino]-6-[4-(1-(4-methoxybenzyl))piperidinylamino]-9-cyclopentylpurine Preparation of 4-Amino-1-(4-methoxybenzyl)piperidine
Method 1
Scheme B, step a: 4-Carboxamide-1-(4-methoxybenzyl) piperidine 4–Carboxamide-1-(4-methoxybenzyl)piperidine may be prepared from isonipecotamide and 4-methoxybenzyl chloride essentially as described above in Example 38, Scheme B, step a.

Scheme B, step b: 4-Amino-1-(4-methoxybenzyl)piperidine

4-Amino-1-(4-methoxybenzyl)piperidine is prepared from 4-carboxamide-1-(4-methoxybenzyl)piperidine essentially as described above in Example 38, Scheme B, step b.
Method 2
Scheme C, step a: 1-(4-Methoxybenzyl)-4-piperidone 1-(4-Methoxybenzyl)-4-piperidone is prepared from 4-piperidone and 4-methoxybenzyl chloride essentially as described above in Example 38, Scheme C, step a.

Scheme C, step b: 1-(4-Methoxybenzyl)-4-piperidone oxime 1-(4-Methoxybenzyl)-4-piperidone oxime is prepared from 1-(4-methoxybenzyl)-4-piperidone and hydroxylamine hydrochloride essentially as described above in Example 38, Scheme C, step b.

Scheme C, step c: 4-Amino-1-(4-methoxybenzyl)piperidine

4-Amino-1-(4-methoxybenzyl)piperidine is prepared from 1-(4-methoxybenzyl)-4-piperidone oxime essentially as described above in Example 38, Scheme C, step c.

Scheme A, step b: 2-Chloro-6-[4-(1-(4-methoxybenzyl)) piperidinylamino]-9-cyclopentylpurine 2-Chloro-6-[4-(1-(4-methoxybenzyl))piperidinylamino]-9-cyclopentylpurine is prepared from 2,6-dichloro-9- cyclopentylpurine, 4-amino-1-(4-methoxybenzyl) piperidine, and triethylamine essentially as described above in Example 1, Scheme A, step b.

Scheme A, step c: 2-[Trans-(4-aminocyclohexyl)amino]-6-[4-(1-(4-methoxybenzyl))piperidinylamino]-9-cyclopentylpurine 2-[Trans-(4-aminocyclohexyl)amino]-6-[4-(1-(4-methoxybenzyl))piperidinylamino]-9-cyclopentylpurine is prepared from 2-chloro-6-[4-(1-(4-methoxybenzyl)) piperidinylamino]-9-cyclopentylpurine essentially as described in Example 1, Scheme A, step c.

Rf: (min)=2.26; purity 100%; MS (APCI): 519 M$^{+1}$

EXAMPLE 40

2-[Trans-(4-aminocyclohexyl)amino]-6-[4-(1-(4-methylbenzyl))piperidinylamino]-9-cyclopentylpurine Preparation of 4-Amino-1-(4-methylbenzyl)piperidine
Method 1
Scheme B, step a: 4-Carboxamide-1-(4-methylbenzyl) piperidine 4-Carboxamide-1-(4-methylbenzyl)piperidine may be prepared from isonipecotamide and α-chloro-p-xylene essentially as described above in Example 38, Scheme B, step a.

Scheme B, step b: 4-Amino-1-(4-methylbenzyl)piperidine
4-Amino-1-(4-methylbenzyl)piperidine is prepared from 4-carboxamide-1-(4-methylbenzyl)piperidine essentially as described above in Example 38, Scheme B, step b.
Method 2
Scheme C, step a: 1-(4-Methylbenzyl)-4-piperidone
1-(4-Methylbenzyl)-4-piperidone is prepared from 4-piperidone and α-chloro-p-xylene essentially as described above in Example 38, Scheme C, step a.
Scheme C, step b: 1-(4-Methylbenzyl)-4-piperidone oxime
1-(4-Methylbenzyl)-4-piperidone oxime is prepared from 1-(4-methylbenzyl)-4-piperidone and hydroxylamine hydrochloride essentially as described above in Example 38, Scheme C, step b.
Scheme C, step c: 4-Amino-1-(4-methylbenzyl)piperidine
1-Amino-1-(4-methylbenzyl)piperidine is prepared from 1-(4-methylbenzyl)-4-piperidone oxime essentially as described above in Example 38, Scheme C, step c.
Scheme A, step b: 2-Chloro-6-[4-(1-(4-methylbenzyl)) piperidinylamino]-9-cyclopentylpurine 2-Chloro-6-[4-(1-(4-methylbenzyl))piperidinylamino]-9-cyclopentylpurine is prepared from 2,6-dichloro-9-cyclopentylpurine, 4-amino-1-(4-methylbenzyl)piperidine, and triethylamine essentially as described above in Example 1, Scheme A, step b.

Scheme A, step c: 2-[Trans-(4-aminocyclohexyl)amino]-6-[4-(1-(4-methylbenzyl))piperidinylamino]-9-cyclopentylpurine 2-[Trans-(4-aminocyclohexyl)amino]-6-[4-(1-(4-methylbenzyl))piperidinylamino]-9-cyclopentylpurine is prepared from 2-chloro-6-[4-(1-(4-methylbenzyl)) piperidinylamino]-9-cyclopentylpurine essentially as described in Example 1, Scheme A, step c.

Rf: (min)=2.26; purity 100%; MS (APCI): 503 M$^{+1}$

EXAMPLE 41

2-[Trans-(4-aminocyclohexyl)amino]-6-[4-(1-(3-methoxybenzyl))piperidinylamino]-9-cyclopentylpurine Preparation of 4-Amino-1-(3-methoxybenzyl)piperidine
Method 1
Scheme B, step a: 4-Carboxamide-1-(3-methoxybenzyl) piperidine
4-Carboxamide-1-(3-methoxybenzyl)piperidine may be prepared from isonipecotamide and 3-methoxybenzyl chloride essentially as described above in Example 38, Scheme B, step a.

Scheme B, step b: 4-Amino-1-(3-methoxybenzyl)piperidine
4-Amino-1-(3-methoxybenzyl)piperidine is prepared from 4-carboxamide-1-(3-methoxybenzyl)piperidine essentially as described above in Example 38, Scheme B, step b.
Method 2
Scheme C, step a: 1-(3-Methoxybenzyl)-4-piperidone
1-(3-Methoxybenzyl)-4-piperidone is prepared from 4-piperidone and 3-methoxybenzyl chloride essentially as described above in Example 38, Scheme C, step a.
Scheme C, step b: 1-(3-Methoxybenzyl)-4-piperidone oxime
1-(3-Methoxybenzyl)-4-piperidone oxime is prepared from 1-(3-methoxybenzyl)-4-piperidone and hydroxylamine hydrochloride essentially as described above in Example 38, Scheme C, step b.
Scheme C, step c: 4-Amino-1-(3-methoxybenzyl)piperidine
4-Amino-1-(3-methoxybenzyl)piperidine is prepared from 1-(3-methoxybenzyl)-4-piperidone oxime essentially as described above in Example 38, Scheme C, step c.
Scheme A, step b: 2-Chloro-6-[4-(1-(3-methoxybenzyl)) piperidinylamino]-9-cyclopentylpurine 2-Chloro-6-[4-(1-(3-methoxybenzyl))piperidinylamino]-9-cyclopentylpurine is prepared from 2,6-dichloro-9-cyclopentylpurine, 4-amino-1-(3-methoxybenzyl) piperidine, and triethylamine essentially as described above in Example 1, Scheme A, step b.

Scheme A, step c: 2-[Trans-(4-aminocyclohexyl)amino]-6-[4-(1-(3-methoxybenzyl))piperidinylamino]-9-cyclopentylpurine 2-[Trans-(4-aminocyclohexyl)amino]-6-[4-(1-(3-methoxybenzyl))piperidinylamino]-9-cyclopentylpurine is prepared from 2-chloro-6-[4-(1-(3-methoxybenzyl)) piperidinylamino]-9-cyclopentylpurine essentially as described in Example 1, Scheme A, step c.

Rf: (min)=2.27; purity 99%; MS (APCI): 519 M$^{+1}$

EXAMPLE 42

2-[Trans-(4-aminocyclohexyl)amino]-6-[4-(1-(3-chlorobenzyl))piperidinylamino]-9-cyclopentylpurine Preparation of 4-Amino-1-(3-chlorobenzyl)piperidine
Method 1
Scheme B, step a: 4-Carboxamide-1-(3-chlorobenzyl) piperidine 4-Carboxamide-1-(3-chlorobenzyl)piperidine may be prepared from isonipecotamide and 3-chlorobenzyl chloride essentially as described above in Example 38, Scheme B, step a.

Scheme B, step b: 4-Amino-1-(3-chlorobenzyl)piperidine
4-Amino-1-(3-chlorobenzyl)piperidine is prepared from 4-carboxamide-1-(3-chlorobenzyl)piperidine essentially as described above in Example 38, Scheme B, step b.
Method 2
Scheme C, step a: 1-(3-Chlorobenzyl)-4-piperidone
1-(3-Chlorobenzyl)-4-piperidone is prepared from 4-piperidone and 3-chlorobenzyl chloride essentially as described above in Example 38, Scheme C, step a.
Scheme C, step b: 1-(3-Chlorobenzyl)-4-piperidone oxime
1-(3-Chlorobenzyl)-4-piperidone oxime is prepared from 1-(3-chlorobenzyl)-4-piperidone and hydroxylamine hydrochloride essentially as described above in Example 38, Scheme C, step b.

Scheme C, step c: 4-Amino-1-(3-chlorobenzyl)piperidine

4-Amino-1-(3-chlorobenzyl)piperidine is prepared from 1-(3-chlorobenzyl)-4-piperidone oxime essentially as described above in Example 38, Scheme C, step c.

Scheme A, step b: 2-Chloro-6-[4-(1-(3-chlorobenzyl))piperidinylamino]-9-cyclopentylpurine 2-Chloro-6-[4-(1-(3-chlorobenzyl))piperidinylamino]-9-cyclopentylpurine is prepared from 2,6-dichloro-9-cyclopentylpurine, 4-amino-1-(3-chlorobenzyl)piperidine, and triethylamine essentially as described above in Example 1, Scheme A, step b.

Scheme A, step c: 2-[Trans-(4-aminocyclohexyl)amino]-6-[4-(1-(3-chlorobenzyl))piperidinylamino]-9-cyclopentylpurine 2-[Trans-(4-aminocyclohexyl)amino]-6-[4-(1-(3-chlorobenzyl))piperidinylamino]-9-cyclopentylpurine is prepared from 2-chloro-6-[4-(1-(3-chlorobenzyl))piperidinylamino]-9-cyclopentylpurine essentially as described in Example 1, Scheme A, step c.

Rf: (min)=2.25; purity 95%; MS (APCI): S23 M$^{+1}$

EXAMPLE 43

2-[Trans-(4-aminocyclohexyl)amino]-6-[4-(1-(2-chlorobenzyl))piperidinylamino]-9-cyclopentylpurine Preparation of 4-Amino-1-(2-chlorobenzyl)piperidine
Method 1
Scheme B, step a: 4-Carboxamide-1-(2-chlorobenzyl)piperidine 4-Carboxamide-1-(2-chlorobenzyl)piperidine may be prepared from isonipecotamide and 2-chlorobenzyl chloride essentially as described above in Example 38, Scheme B, step a.

Scheme B, step b: 4-Amino-1-(2-chlorobenzyl)piperidine

4-Amino-1-(2-chlorobenzyl)piperidine is prepared from 4-carboxamide-1-(2-chlorobenzyl)piperidine essentially as described above in Example 38, Scheme B, step b.
Method 2
Scheme C, step a: 1-(2-chlorobenzyl)-4-piperidone 1-(2-Chlorobenzyl)-4-piperidone is prepared from 4-piperidone and 2-chlorobenzyl chloride essentially as described above in Example 38, Scheme C, step a.

Scheme C, step b: 1-(2-Chlorobenzyl)-4-piperidone oxime 1-(2-Chlorobenzyl)-4-piperidone oxime is prepared from 1-(2-chlorobenzyl)-4-piperidone and hydroxylamine hydrochloride essentially as described above in Example 38, Scheme C, step b.

Scheme C, step c: 4-Amino-1-(2-chlorobenzyl)piperidine

4-Amino-1-(2-chlorobenzyl)piperidine is prepared from 1-(2-chlorobenzyl)-4-piperidone oxime essentially as described above in Example 38, Scheme C, step c.

Scheme A, step b: 2-Chloro-6-[4-(1-(2-chlorobenzyl))piperidinylamino]-9-cyclopentylpurine 2-Chloro-6-[4-(1-(2-chlorobenzyl))piperidinylamino]-9-cyclopentylpurine is prepared from 2,6-dichloro-9-cyclopentylpurine, 4-amino-1-(2-chlorobenzyl)piperidine, and triethylamine essentially as described above in Example 1, Scheme A, step b.

Scheme A, step c: 2-[Trans-(4-aminocyclohexyl)amino]-6-[4-(1-(2-chlorobenzyl))piperidinylamino]-9-cyclopentylpurine 2-[Trans-(4-aminocyclohexyl)amino]-6-[4-(1-(2-chlorobenzyl))piperidinylamino]-9-cyclopentylpurine is prepared from 2-chloro-6-[4-(1-(2-chlorobenzyl))piperidinylamino]-9-cyclopentylpurine essentially as described in Example 1, Scheme A, step c.

Rf: (min)=2.25; purity 92%; MS (APCI): 523 M$^{+1}$

EXAMPLE 44

2-[Trans-(4-aminocyclohexyl)amino]-6-[4-(1-(2-methylbenzyl))piperidinylamino]-9-cyclopentylpurine Preparation of 4-Amino-1-(2-methylbenzyl)piperidine
Method 1
Scheme B, step a: 4-Carboxamide-1-(2-methylbenzyl)piperidine 4-Carboxamide-1-(2-methylbenzyl)piperidine may be prepared from isonipecotamide and α-chloro-o-xylene essentially as described above in Example 38, Scheme B, step a.

Scheme B, step b: 4-Amino-1-(2-methylbenzyl)piperidine

4-Amino-1-(2-methylbenzyl)piperidine is prepared from 4-carboxamide-1-(2-methylbenzyl)piperidine essentially as described above in Example 38, Scheme B, step b.
Method 2
Scheme C, step a: 1-(2-Methylbenzyl)-4-piperidone 1-(2-Methylbenzyl)-4-piperidone is prepared from 4-piperidone and α-chloro-o-xylene essentially as described above in Example 38, Scheme C, step a.

Scheme C, step) b: 4-Amino-1-(2-methylbenzyl)piperidine oxime

4-Amino-1-(2-methylbenzyl)piperidine oxime is prepared from 4-amino-1-(2-methylbenzyl)piperidine and hydroxylamine hydrochloride essentially as described above in Example 38, Scheme C, step b.

Scheme C, step c: 4-Amino-1-(2-methylbenzyl)piperidine

4-Amino-1-(2-methylbenzyl)piperidine is prepared from essentially as described above in Example 38, Scheme C, step c.

Scheme A, step b: 2-Chloro-6-[4-(1-(2-methylbenzyl))piperidinylamino]-9-cyclopentylpurine 2-Chloro-6-[4-(1-(2-methylbenzyl))piperidinylamino]-9-cyclopentylpurine is prepared from 2,6-dichloro-9-cyclopentylpurine, 4-amino-1-(2-methylbenzyl)piperidine, and triethylamine essentially as described above in Example 1, Scheme A, step b.

Scheme A, step c: 2-[Trans-(4-aminocyclohexyl)amino]-6-[4-(1-(2-methylbenzyl))piperidinylamino]-9-cyclopentylpurine 2-[Trans-(4-aminocyclohexyl)amino]-6-[4-(1-(2-methylbenzyl))piperidinylamino]-9-cyclopentylpurine is prepared from 2-chloro-6-[4-(1-(2-methylbenzyl))piperidinylamino]-9-cyclopentylpurine essentially as described in Example 1, Scheme A, step c.

Rf: (min)=2.26; purity 98%; MS (APCI): 503 M$^{+1}$

EXAMPLE 45

2-[Trans-(4-aminocyclohexyl)amino]-6-[4-(1-(2,6-dichlorobenzyl))piperidinylamino]-9-cyclopentylpurine Preparation of 4-Amino-1-(2,6-dichlorobenzyl)piperidine
Method 1
Scheme B, step a: 4-Carboxamide-1-(2,6-dichlorobenzyl)piperidine 4-Carboxamide-1-(2,6-dichlorobenzyl)piperidine may be prepared from isonipecotamide and α,2,6-trichlorotoluene essentially as described above in Example 38, Scheme B, step a.

Scheme B, step b: 4-Amino-1-(2,6-dichlorobenzyl)piperidine

4-Amino-1-(2,6-dichlorobenzyl)piperidine is prepared from 4-carboxamide-1-(2,6-dichlorobenzyl)piperidine essentially as described above in Example 38, Scheme B, step b.

Method 2
Scheme C, step a: 1-(2,6-Dichlorobenzyl)-4-piperidone 1-(2,6-Dichlorobenzyl)-4-piperidone is prepared from 4-piperidone and α,2,6-trichlorotoluene essentially as described above in Example 38, Scheme C, step a.

Scheme C, step b: 1-(2,6-Dichlorobenzyl)-4-piperidone oxime 1-(2,6-Dichlorobenzyl)-4-piperidone oxime is prepared from 1-(2,6-dichlorobenzyl)-4-piperidone and hydroxylamine hydrochloride essentially as described above in Example 38, Scheme C, step b.

Scheme C, step c: 4-Amino-1-(2,6-dichlorobenzyl)piperidine

4-Amino-1-(2,6-dichlorobenzyl)piperidine is prepared from 1-(2,6-dichlorobenzyl)-4-piperidone oxime essentially as described above in Example 38, Scheme C, step c.

Scheme A, step b: 2-Chloro-6-[4-(1-(2,6-dichlorobenzyl))piperidinylamino]-9-cyclopentylpurine 2-Chloro-6-[4-(1-(2,6-dichlorobenzyl))piperidinylamino]-9-cyclopentylpurine is prepared from 2,6-dichloro-9-cyclopentylpurine, 4-amino-1-(2,6-dichlorobenzyl)piperidine (made according to the Method 1 of Example 45), and triethylamine essentially as described above in Example 1, Scheme A, step b.

Scheme A, step c: 2-[Trans-(4-aminocyclohexyl)amino]-6-[4-(1-(2,6-dichlorobenzyl))piperidinylamino]-9-cyclopentylpurine 2-[Trans-(4-aminocyclohexyl)amino]-6-[4-(1-(2,6-dichlorobenzyl))piperidinylamino]-9-cyclopentylpurine is prepared from 2-chloro-6-[4-(1-(2,6-dichlorobenzyl))piperidinylamino]-9-cyclopentylpurine essentially as described in Example 1, Scheme A, step c.

Rf: (min) 2.28; purity 98%; MS (APCI): 557M$^{+1}$.

EXAMPLE 46

2-[Trans-(4-aminocyclohexyl)amino]-6-[4-(1-(4-trifluoromethylbenzyl))piperidinylamino]-9-cyclopentylpurine Preparation of 4-Amino-1-(4-trifluoromethylbenzyl)piperidine
Method 1
Scheme B, step a: 4-Carboxamide-1-(4-trifluoromethylbenzyl)piperidine 4-Carboxamide-1-(4-trifluoromethylbenzyl)piperidine may be prepared from isonipecotamide and α'-chloro-α,α,α-trifluoro-p-xylene essentially as described above in Example 38, Scheme B, step a.

Scheme B, step b: 4-Amino-1-(4-trifluoromethylbenzyl)piperidine

4-Amino-1-(4-trifluoromethylbenzyl)piperidine is prepared from 4-carboxamide-1-(4-trifluoromethylbenzyl)piperidine essentially as described above in Example 38, Scheme B, step b.

Method 2
Scheme C, step a: 1-(4-Trifluoromethylbenzyl)-4-piperidone 1-(4-Trifluoromethylbenzyl)-4-piperidone is prepared from 4-piperidone and α'-chloro-α,α,α-trifluoro-p-xylene essentially as described above in Example 38, Scheme C, step a.

Scheme C, step b: 1-(4-Trifluoromethylbenzyl)-4-piperidone oxime 1-(4-Trifluoromethylbenzyl)-4-piperidone oxime is prepared from 1-(4-trifluoromethylbenzyl)-4-piperidone and hydroxylamine hydrochloride essentially as described above in Example 38, Scheme C, step b.

Scheme C, step c: 4-Amino-1-(4-trifluoromethylbenzyl)piperidine

4-Amino-1-(4-trifluoromethylbenzyl)piperidine is prepared from 1-(4-trifluoromethylbenzyl)-4-piperidone oxime essentially as described above in Example 38, Scheme C, step c.

Scheme A, step b: 2-Chloro-6-[4-(1-(4-trifluoromethylbenzyl))piperidinylamino]-9-cyclopentylpurine 2-Chloro-6-[4-(1-(4-trifluoromethylbenzyl))piperidinylamino]-9-cyclopentylpurine is prepared from 2,6-dichloro-9-cyclopentylpurine, 4-amino-i-(4-trifluoromethylbenzyl)piperidine, and triethylamine essentially as described above in Example 1, Scheme A, step b.

Scheme A, step c: 2-[Trans-(4-aminocyclohexyl)amino]-6-[4-(1-(4-trifluoromethylbenzyl))piperidinylamino]-9-cyclopentylpurine 2-[Trans-(4-aminocyclohexyl)amino]-6-[4-(1-(4-trifluoromethylbenzyl))piperidinylamino]-9-cyclopentylpurine is prepared from 2-chloro-6-[4-(1-(4-trifluoromethylbenzyl))piperidinylamino]-9-cyclopentylpurine essentially as described in 4 Example 1, Scheme A, step c.

Rf: (min) 2.38; purity 100%; MS (APCI): 557 M$^{+1}$

EXAMPLE 47

(+/−)-2-[Trans-(4-aminocyclohexyl)amino]-6-[4-(1-(α-methylbenzyl))piperidinylamino]-9-cyclopentylpurine Preparation of (R,S)-4-Amino-1-(α-methylbenzyl)piperidine
Method 1
Scheme B, step a: 4-Carboxamide-1-(α-methylbenzyl)piperidine 4-Carboxamide-1-(α-methylbenzyl)piperidine may be prepared from isonipecotamide and α-methylbenzyl bromide essentially as described above in Example 38, Scheme B, step a.

Scheme B, step b: (R,S)-4-Amino-1-(α-methylbenzyl)piperidine (R,S)-4-Amino-1-(α-methylbenzyl)piperidine is prepared from 4-carboxamide-1-(α-methylbenzyl)piperidine essentially as described above in Example 38, Scheme B, step b.
Method2
Scheme C, step a: 1-(α-Methylbenzyl)-4-piperidone 1-(α-Methylbenzyl)-4-piperidone is prepared from 4-piperidone and α-methylbenzyl bromide essentially as described above in Example 38, Scheme C, step a.

Scheme C, step b: 1-(α-Methylbenzyl)-4-piperidone oxime 1-(α-Methylbenzyl)-4-piperidone oxime is prepared from 1-(α-methylbenzyl)-4-piperidone and hydroxylamine hydrochloride essentially as described above in Example 38, Scheme C, step b.

Scheme C, step c: (R,S)-4-Amino-1-(α-methylbenzyl)piperidine (R,S)-4-Amino-1-(α-methylbenzyl)piperidine is prepared from 1-(α-methylbenzyl)-4-piperidone oxime essentially as described above in Example 38, Scheme C, step c.

Scheme A, step b: 2-Chloro-6-[4-(1-(α-methylbenzyl))piperidinylamino]-9-cyclopentylpurine 2-Chloro-6-[4-(1-(α-methylbenzyl))piperidinylamino]-9-cyclopentylpurine is prepared from 2,6-dichloro-9-cyclopentylpurine, (R,S)-4-amino-1-(α-methylbenzyl)piperidine, and triethylamine essentially as described above in Example 1, Scheme A, step b.

Scheme A, step c: 2-[Trans-(4-aminocyclohexyl)amino]-6-[4-(1 -(α-methylbenzyl)piperidinylamino]-9-cyclopentylpurine 2-[Trans-(4-aminocyclohexyl)amino]-6-[4-(1-(α-methylbenzyl))piperidinylamino]-9-cyclopentylpurine is prepared from 2-chloro-6-[4-(1-(α-methylbenzyl))piperidinylamino]-9-cyclopentylpurine essentially as described in Example 1, Scheme A, step c.

EXAMPLE 48

2-[Trans-(4-aminocyclohexyl)amino]-6-[4-(1-(3-phenoxypropyl))piperidinylamino]-9-cyclopentylpurine Preparation of 4-Amino-1-(3-phenoxypropyl)piperidine Method 1

Scheme B, step a: 4-Carboxamide-1-(3-phenoxypropyl)piperidine

4-Carboxamide-1-(3-phenoxypropyl)piperidine may be prepared from isonipecotamide and 1-chloro-3-phenoxypropane essentially as described above in Example 38, Scheme B, step a.

Scheme B, step b: 4-Amino-1-(3-phenoxypropyl)piperidine

4-Amino-1-(3-phenoxypropyl)piperidine is prepared from 4-carboxamide-1-(3-phenoxypropyl)piperidine essentially as described above in Example 38, Scheme B, step b.

Method 2

Scheme C step a: 1-(3-Phenoxypropyl)-4-piperidone 1-(3-Phenoxypropyl)-4-piperidone is prepared from 4-piperidone and 1-chloro-3-phenoxypropane essentially as described above in Example 38, Scheme C, step a.

Scheme C, step b: 1-(3-Phenoxypropyl)-4-piperidone oxime 1-(3-Phenoxypropyl)-4-piperidone oxime is prepared from 1-(3-phenoxypropyl)-4-piperidone and hydroxylamine hydrochloride essentially as described above in Example 38, Scheme C, step b.

Scheme C, step c: 4-Amino-1-(3-phenoxypropyl)piperidine

4-Amino-1-(3-phenoxypropyl)piperidine is prepared from 1-(3-phenoxypropyl)-4-piperidone oxime essentially as described above in Example 38, Scheme C, step c.

Scheme A, step b: 2-Chloro-6-[4-(1-(3-phenoxypropyl!)piperidinylamino]-9-cyclopentylpurine 2-Chloro-6-[4-(1-(3-phenoxypropyl))piperidinylamino]-9-cyclopentylpurine is prepared from 2,6-dichloro-9-cyclopentylpurine, 4-amino-1-(3-phenoxypropyl)piperidine, and triethylamine essentially as described above in Example 1, Scheme A, step b.

Scheme A, step c: 2-[Trans-(4-aminocyclohexyl)amino]-6-[4-(1-(3-phenoxypropyl))]piperidinylamino]-9-cyclopentylpurine 2-[Trans-(4-aminocyclohexyl)amino]-6-[4-(1-(3-phenoxypropyl))piperidinylamino]-9-cyclopentylpurine is prepared from 2-chloro-6-[4-(1-(3-phenoxypropyl))piperidinylamino]-9-cyclopentylpurine essentially as described in Example 1, Scheme A, step c.

EXAMPLE 49

2-[Trans-(4-aminocyclohexyl)amino]-6-[4-(1-(2-phenoxyethyl))piperidinylamino]-9-cyclopentylpurine Preparation of 4-Amino-1-(2-phenoxyethyl)piperidine Method 1

Scheme B, step a: 4-Carboxamide-1-(2-phenoxyethyl)piperidine

4-Carboxamide-1-(2-phenoxyethyl)piperidine may be prepared from isonipecotamide and 1-chloro-2-phenoxyethane essentially as described above in Example 38, Scheme B, step a.

Scheme B, step b: 4-Amino-1-(2-phenoxyethyl)piperidine

4-Amino-1-(2-phenoxyethyl)piperidine is prepared from 4-carboxamide-1-(2-phenoxyethyl)piperidine essentially as described above in Example 38, Scheme B, step b.

Method 2

Scheme C, step a: 1-(2-Phenoxyethyl)-4-piperidone 1-(2-Phenoxyethyl)-4-piperidone is prepared from 4-piperidone and 1-chloro-2-phenoxyethane essentially as described above in Example 38, Scheme C, step a.

Scheme C, step b: 1-(2-Phenoxyethyl)-4-piperidone oxime 1-(2-Phenoxyethyl)-4-piperidone oxime is prepared from 1-(2-phenoxyethyl)-4-piperidone and hydroxylamine hydrochloride essentially as described above in Example 38, Scheme C, step b.

Scheme C, step c: 4-Amino-1-(2-phenoxyethyl)piperidine

4-Amino-1-(2-phenoxyethyl)piperidine is prepared from 1-(2-phenoxyethyl)-4-piperidone oxime essentially as described above in Example 38, Scheme C, step c.

Scheme A, step b: 2-Chloro-6-[4-(1-(2-phenoxyethyl))piperidinylamino]-9-cyclopentylpurine 2-Chloro-6-[4-(1-(2-phenoxyethyl))piperidinylamino]-9-cyclopentylpurine is prepared from 2,6-dichloro-9-cyclopentylpurine, 4-amino-1-(2-phenoxyethyl)piperidine, and triethylamine essentially as described above in Example 1, Scheme A, step b.

Scheme A, step c: 2-[Trans-(4-aminocyclohexyl)amino]-6-[4-(1-(2-phenoxyethyl))piperidine)amino]-9-cyclopentylpurine 2-[Trans-(4-aminocyclohexyl)amino]-6-[4-(1-(2-phenoxyethyl))piperidinylamino]-9-cyclopentylpurine is prepared from 2-chloro-6-[4-(1-(2-phenoxyethyl))piperidinylamino]-9-cyclopentylpurine essentially as described in Example 1, Scheme A, step c.

EXAMPLE 50

2-[Trans-(4-aminocyclohexyl)amino]-6-[4-(1-(2-phenylethyl))piperidinylamino]-9-cyclopentylpurine Preparation of 4-Amino-1-(2-phenylethyl)piperidine Method 1

Scheme B, step a: 4-Carboxamide-1-(2-phenylethyl)piperidine

4-Carboxamide-1-(2-phenylethyl)piperidine may be prepared from isonipecotamide and (2-chloroethyl)benzene essentially as described above in Example 38, Scheme B, step a.

Scheme B, step b: 4-Amino-1-(2-phenylethyl)piperidine

4-Amino-1-(2-phenylethyl)piperidine is prepared from 4-carboxamide-1-(2-phenylethyl)piperidine essentially as described above in Example 38, Scheme B, step b.

Method 2

Scheme C, step a: 1-(2-Phenylethyl)-4-piperidone 1-(2-phenylethyl)-4-piperidone is prepared from 4-piperidone and (2-chloroethyl)benzene essentially as described above in Example 38, Scheme C, step a.

Scheme C, step b: 1-(2-Phenylethyl)-4-piperidone oxime 1-(2-Phenylethyl)-4-piperidone oxime is prepared from 1-(2-phenylethyl)-4-piperidone and hydroxylamine hydrochloride essentially as described above in Example 38, Scheme C, step b.

Scheme C, step c: 4-Amino-1-(2-phenylethyl)piperidine

4-Amino-1-(2-phenylethyl)piperidine is prepared from 1-(2-phenylethyl)-4-piperidone oxime essentially as described above in Example 38, Scheme C, step c.

Scheme A, step b: 2-Chloro-6-[4-(1-(2-phenylethyl))piperidinylamino]-9-cyclopentylpurine 2-Chloro-6-[4-(1-(2-phenylethyl))piperidinylamino]-9-cyclopentylpurine is prepared from 2,6-dichloro-9-cyclopentylpurine, 4-amino-1-(2-phenylethyl)piperidine, and triethylamine essentially as described above in Example 1, Scheme A, step b.

Scheme A, step c: 2-[Trans-(4-aminocyclohexyl)amino]-6-[4-(1-(2-phenylethyl))piperidinylamino]-9-cyclopentylpurine 2-[Trans-(4-aminocyclohexyl)amino]-6-[4-(1-(2-phenylethyl))piperidinylamino]-9-cyclopentylpurine is prepared from 2-chloro-6-[4-(1-(2-phenylethyl))piperidinylamino]-9-cyclopentylpurine essentially as described in Example 1, Scheme A, step c.

EXAMPLE 51

2-[Trans-(4-aminocyclohexyl)amino]-6-[4-(1-propyl)piperidinylamino]-9-cyclopentylpurine Preparation of 4-Amino-1-propylpiperidine
Method 1
Scheme B, step a: 4-Carboxamide-1-propylpiperidine 4-Carboxamide-1-propylpiperidine may be prepared from isonipecotamide and 1-chloropropane essentially as described above in Example 38, Scheme B, step a.
Scheme B, step b:4-Amino-1-propylpiperidine 4-Amino-1-propylpiperidine is prepared from 4-carboxamide-1-propylpiperidine essentially as described above in Example 38, Scheme B, step b.
Method 2
Scheme C, step a: 1-Propyl-4-piperidone 1-Propyl4-piperidone is prepared from 4-piperidone and 1-chloropropane essentially as described above in Example 38, Scheme C, step a.
Scheme C, step b: 1-Propyl-4-piperidone oxime 1-Propyl-4-piperidone oxime is prepared from 1-propyl-4-piperidone and hydroxylamine hydrochloride essentially as described above in Example 38, Scheme C, step b.
Scheme C, step c: 4-Amino-1-propylpiperidine 4-Amino-1-propylpiperidine is prepared from 1-propyl-4-piperidone oxime essentially as described above in Example 38, Scheme C, step c.
Scheme A, step b: 2-Chloro-6-[4-(1-propyl)piperidinylamino]-9-cyclopentylpurine 2-Chloro-6-[4-(1-propyl)piperidinylamino]-9-cyclopentylpurine is prepared from 2,6-dichloro-9-cyclopentylpurine, 4-amino-1-propylpiperidine, and triethylamine essentially as described above in Example 1, Scheme A, step b.
Scheme A, step c: 2-[Trans-(4-aminocyclohexyl)amino]-6-[4-(1-propyl)piperidinylamino]-9-cyclopentylpurine 2-[Trans-(4-aminocyclohexyl)amino]-6-[4-(1-propyl)piperidinylamino]-9-cyclopentylpurine is prepared from 2-chloro-6-[4-(1-propyl)piperidinylamino]-9-cyclopentylpurine essentially as described in Example 1, Scheme A, step c.

EXAMPLE 52

2-[Trans-(4-aminocyclohexyl)amino]-6-[4-(1-cyclopropylmethyl)piperidinylamino]-9-cyclopentylpurine Preparation of 4-Amino-1-cyclopropylmethylpiperidine
Method 1
Scheme B, step a: 4-Carboxamide-1-cyclopropylmethylpiperidine 4-Carboxamide-1-cyclopropylmethylpiperidine may be prepared from isonipecotamide and (chloromethyl)cyclopropane essentially as described above in Example 38, Scheme B, step a.
Scheme B, step b: 4-Amino-1-cyclopropylmethylpiperidine 4-Amino-1- cyclopropylmethylpiperidine is prepared from 4-carboxamide-1-cyclopropylmethylpiperidine essentially as described above in Example 38, Scheme B, step b.
Method 2
Scheme C, step a: 1-(Cyclopropylmethyl)-4-piperidone 1-(Cyclopropylmethyl)-4-piperidone is prepared from 4-piperidone and (chloromethyl)cyclopropane essentially as described above in Example 38, Scheme C, step a.
Scheme C, step b: 1-(Cyclopropylmethyl)-4-piperidone oxime 1-(Cyclopropylmethyl)-4-piperidone oxime is prepared from 1-(cyclopropylmethyl)-4-piperidone and hydroxylamine hydrochloride essentially as described above in Example 38, Scheme C, step b.
Scheme C, step c: 4-Amino-1-cyclopropylmethylpiperidine 4-Amino-1-cyclopropylmethylpiperidine is prepared from 1-(cyclopropylmethyl)-4-piperidone oxime essentially as described above in Example 38, Scheme C, step c.
Scheme A, step b: 2-Chloro-6-[4-(1-cyclopropylmethyl)piperidinylamino]-9-cyclopentylpurine 2-Chloro-6-[4-(1-cyclopropylmethyl)piperidinylamino]-9-cyclopentylpurine is prepared from 2,6-dichloro-9-cyclopentylpurine, 4-amino-1-cyclopropylmethylpiperidine, and triethylamine essentially as described above in Example 1, Scheme A, step b.
Scheme A, step c: 2-[Trans-(4-aminocyclohexyl)amino]-6-[4-(1-cyclopropylmethyl)piperidinylamino]-9-cyclopentylpurine 2-[Trans-(4-aminocyclohexyl)amino]-6-[4-(1-cyclopropylmethyl)piperidinylamino]-9-cyclopentylpurine is prepared from 2-chloro-6-[4-(1-cyclopropylmethyl)piperidinylamino]-9-cyclopentylpurine essentially as described in Example 1, Scheme A, step c.

Rf: (min)=2.19; purity 100%; MS (APCI): 454 $M^{+1}$

EXAMPLE 53

2-[Trans-(4-aminocyclohexyl)amino]-6-[4-(1-(2-pyridinylmethyl))piperidinylamino]-9-cyclopentylpurine Preparation of 4-Amino-1-(2-pyridinylmethyl)piperidine
Method 1
Scheme B, step a: 4-Carboxamide-1-(2-pyridinylmethyl)piperidine 4-Carboxamide-1-(2-pyridinylmethyl)piperidine may be prepared from isonipecotamide and 2-picolyl chloride hydrochloride essentially as described above in Example 38, Scheme B, step a.
Scheme B, step b:4-Amino-1-(2-pyridinylmethyl)piperidine 4-amino-1-(2-pyridinylmethyl)piperidine is prepared from 4-carboxamide-1-(2-pyridinylmethyl)piperidine essentially as described above in Example 38, Scheme B, step b.
Method 2
Scheme C, step a: 1-(2-Pyridinylmethyl)-4-piperidone 1-(2-Pyridinylmethyl)-4-piperidone is prepared from 4-piperidone and 2-picolyl chloride hydrochloride essentially as described above in Example 38, Scheme C, step a.
Scheme C, step b: 1-(2-Pyridinylmethyl)-4-piperidone oxime 1-(2-Pyridinylmethyl)-4-piperidone oxime is prepared from 1-(2-pyridinylmethyl)-4-piperidone and hydroxylamine hydrochloride essentially as described above in Example 38, Scheme C, step b.
Scheme C, step c: 4-Amino-1-(2-pyridinylmethyl)piperidine 4-Amino-1-(2-pyridinylmethyl)piperidine is prepared from 1-(2-pyridinylmethyl)-4-piperidone oxime essentially as described above in Example 38, Scheme C, step c.
Scheme A, step b: 2-Chloro-6-[4-(1-(2-pyridinylmethyl))piperidinylamino]-9-cyclopentylpurine 2-Chloro-6-[4-(1-(2-pyridinylmethyl))piperidinylamino]-9-cyclopentylpurine is prepared from 2,6-dichloro-9-cyclopentylpurine, 4-amino-1-(2-pyridinylmethyl)piperidine, and triethylamine essentially as described above in Example 1, Scheme A, step b.

Scheme A, step c: 2-[Trans-(4-aminocyclohexyl)amino]-6-[4-(1-(2-pyridinylmethyl))piperidinylamino]-9-cyclopentylpurine 2-[Trans-(4-aminocyclohexyl)amino]-6-[4-(1-(2-pyridinylmethyl))piperidinylamino]-9-cyclopentylpurine is prepared from 2-chloro-6-[4-(1-(2-pyridinylmethyl))piperidinylamino]-9-cyclopentylpurine essentially as described in Example 1, Scheme A, step c.

EXAMPLE 54

2-[Trans-(4-aminocyclohexyl)amino]-6-[4-(1-(3-pyridinylmethyl))piperidinylamino]-9-cyclopentylpurine Preparation of 4-Amino-1-(3-pyridinylmethyl)piperidine
Method 1
Scheme B, step a: 4-Carboxamide-1-(3-pyridinylmethyl)piperidine
   4-Carboxamide-1-(3-pyridinylmethyl)piperidine may be prepared from isonipecotamide and 3-picolyl chloride hydrochloride essentially as described above in Example 38, Scheme B, step a.
Scheme B, step b: 4-Amino-1-(3-pyridinylmethyl)piperidine
   4-Amino-1-(3-pyridinylmethyl)piperidine is prepared from 4-carboxamide-1-(3-pyridinylmethyl)piperidine essentially as described above in Example 38, Scheme B, step b.
Method 2
Scheme C, step a: 1-(3-Pyridinylmethyl)-4-piperidone
   1-(3-Pyridinylmethyl)-4-piperidone is prepared from 4-piperidone and 3-picolyl chloride hydrochloride essentially as described above in Example 38, Scheme C, step a.
Scheme C, step b: 1-(3-Pyridinylmethyl)-4-piperidone oxime
   1-(3-Pyridinylmethyl)-4-piperidone oxime is prepared from 1-(3-pyridinylmethyl)-4-piperidone and hydroxylamine hydrochloride essentially as described above in Example 38, Scheme C, step b.
Scheme C, step c: 4-Amino-1-(3-pyridinylmethyl)piperidine
   4-Amino-1-(3-pyridinylmethyl)piperidine is prepared from 1-(3-pyridinylmethyl)-4-piperidone oxime essentially as described above in Example 38, Scheme C, step c.
Scheme A, step b: 2-Chloro-6-[4-(1-(3-pyridinylmethyl))piperidinylamino]-9-cyclopentylpurine
   2-Chloro-6-[4-(1-(3-pyridinylmethyl))piperidinylamino]-9-cyclopentylpurine is prepared from 2,6-dichloro-9-cyclopentylpurine, 4-amino-1-(3-pyridinylmethyl)piperidine, and triethylamine essentially as described above in Example 1, Scheme A, step b.
Scheme A, step c: 2-[Trans-(4-aminocyclohexyl)amino]-6-[4-(1-(3-pyridinylmethyl))piperidinylamino]-9-cyclopentylpurine
   2-[Trans-(4-aminocyclohexyl)amino]-6-[4-(1-(3-pyridinylmethyl))piperidinylamino]-9-cyclopentylpurine is prepared from 2-chloro-6-[4-(1-(3-pyridinylmethyl))piperidinylamino]-9-cyclopentylpurine essentially as described in Example 1, Scheme A, step c.

EXAMPLE 55

2-[Trans-(4-aminocyclohexyl)amino]-6-[4-(1-(4-pyridinylmethyl))piperidinylamino]-9-cyclopentylpurine Preparation of 4-Amino-1-(4-pyridinylmethyl)piperidine
Method 1
Scheme B, step a: 4-Carboxamide-1-(4-pyridinylmethyl)piperidine
   4-Carboxamide-1-(4-pyridinylmethyl)piperidine may be prepared from isonipecotamide and 4-picolyl chloride hydrochloride essentially as described above in Example 38, Scheme B, step a.
Scheme B, step b: 4-Amino-1-(4-pyridinylmethyl)piperidine
   4-Amino-1-(4-pyridinylmethyl)piperidine is prepared from 4-carboxamide-1-(4-pyridinylmethyl)piperidine essentially as described above in Example 38, Scheme B, step b.
Method 2
Scheme C, step a: 1-(4-Pyridinylmethyl)-4-piperidone
   1-(4-Pyridinylmethyl)-4-piperidone is prepared from 4-piperidone and 4-picolyl chloride hydrochloride essentially as described above in Example 38, Scheme C, step a.
Scheme C, step b: 1-(4-Pyridinylmethyl)-4-piperidone oxime
   1-(4-Pyridinylmethyl)-4-piperidone oxime is prepared from 1-(4-pyridinylmethyl)-4-piperidone and hydroxylamine hydrochloride essentially as described above in Example 38, Scheme C, step b.
Scheme C, step c: 4-Amino-1-(4-pyridinylmethyl)piperidine
   4-Amino-1-(4-pyridinylmethyl)piperidine is prepared from 1-(4-pyridinylmethyl)-4-piperidone oxime essentially as described above in Example 38, Scheme C, step c.
Scheme A, step b: 2-Chloro-6-[4-(1-(4-pyridinylmethyl))piperidinylamino]-9-cyclopentylpurine
   2-Chloro-6-[4-(1-(4-pyridinylmethyl))piperidinylamino]-9-cyclopentylpurine is prepared from 2,6-dichloro-9-cyclopentylpurine, 4-amino-1-(4-pyridinylmethyl)piperidine, and triethylamine essentially as described above in Example 1, Scheme A, step b.
Scheme A, step c: 2-[Trans-(4-aminocyclohexyl)amino]-6-[4-(1-(4-pyridinylmethyl))piperidinylamino]-9-cyclopentylpurine
   2-[Trans-(4-aminocyclohexyl)amino]-6-[4-(1-(4-pyridinylmethyl))piperidinylamino]-9-cyclopentylpurine is prepared from 2-chloro-6-[4-(1-(4-pyridinylmethyl))piperidinylamino]-9-cyclopentylpurine essentially as described in Example 1, Scheme A, step c.

EXAMPLE 56

2-[Trans-(4-aminocyclohexyl)amino]-6-[4-(1-(3-(2,4-dimethylisoxazolyl))methyl)piperidinylamino]-9-cyclopentylpurine Preparation of 4-Amino-1-(3-(2,4-dimethylisoxazolyl)methylpiperidine
Method 1
Scheme B, step a: 4-Carboxamide-1-(3-(2,4-dimethylisoxazolyl)methyl)piperidine
   4-Carboxamide-1-(3-(2,4-dimethylisoxazolyl)methyl)piperidine may be prepared from isonipecotamide and 2,4-dimethyl-3-chloromethyl-isoxazole essentially as described above in Example 38, Scheme B, step a.
Scheme B, step b: 4-Amino-1-(3-(2,4-dimethylisoxazolyl)methylpiperidine
   4-Amino-1-(3-(2,4-dimethylisoxazolyl)methylpiperidine is prepared from 4-carboxamide-1-(3-dimethylisoxazolyl)methyl)piperidine essentially as described above in Example 38, Scheme B, step
Method 2
Scheme C, step a: 1-(3-(2,4-Dimethylisoxazolyl)methyl)-4-piperidone
   1-(3-(2,4-Dimethylisoxazolyl)methyl)-4-piperidone is prepared from 4-piperidone and 2,4-dimethyl-3-chloromethyl-isoxazole essentially as described above in Example 38, Scheme C, step a.
Scheme C, step b: 1-(3-(2,4-Dimethylisoxazolyl)methyl)-4-piperidone oxime
   1-(3-(2,4-Dimethylisoxazolyl)methyl)-4-piperidone oxime is prepared from 1-(3-(2,4-dimethylisoxazolyl)methyl)-4-piperidone and hydroxylamine hydrochloride essentially as described above in Example 38, Scheme C, step b.

Scheme C, step c: 4-Amino-1-(3-(2,4-dimethylisoxazolyl) methylpiperidine

4-Amino-1-(3-(2,4-dimethylisoxazolyl)methylpiperidine is prepared from 1-(3-(2,4-dimethylisoxazolyl)methyl)-4-piperidone oxime essentially as described above in Example 38, Scheme C, step c.

Scheme A, step b: 2-Chloro-6-[4-(1-(3-(2,4-dimethylisoxazolyl))methyl)piperidinylamino]-9-cyclopentylpurine 2-Chloro-6-[4-(1-(3-(2,4-dimethylisoxazolyl))methyl) piperidinylamino]-9-cyclopentylpurine is prepared from 2,6-dichloro-9-cyclopentylpurine, 4-amino-1-(3-(2,4-dimethylisoxazolyl)methylpiperidine, and triethylamine essentially as described above in Example 1, Scheme A, step b.

Scheme A, step c: 2-[Trans-(4-aminocyclohexyl)amino]-6-[4-(1-(3-(2,4-dimethylisoxazolyl))methyl[]piperidinylamino]-9-cyclopentylpurine 2-[Trans-(4-aminocyclohexyl)amino]-6-[4-(1-(3-(2,4-dimethylisoxazolyl))methyl)piperidinylamino]-9-cyclopentylpurine is prepared from 2-chloro-6-[4-(1-(3-(2,4-dimethylisoxazolyl))methyl)piperidinylamino]-9-cyclopentylpurine essentially as described in Example 1, Scheme A, step c.

EXAMPLE 57

(R,S)-2-[Trans-(4-aminocyclohexyl)amino]-6-[4-(1-benzyl-3-methyl)piperidinylamino]-9-cyclopentylpurine Preparation of (R,S)-4-Amino-1-benzyl-3-methylpiperidine
Method 1
Scheme B, step a: (R,S)-4-Carboxamide-1-benzyl-3-methylpiperidine (R,S)-4-Carboxamide-1-benzyl-3-methylpiperidine may be prepared from (R,S)-4-carboxamide-3-methylpiperidine and benzyl chloride essentially as described above in Example 38, Scheme B, step a, substituting (R,S)-4-carboxamide-3-methylpiperidine for isonipecotamide.

Scheme B, step b: (R,S)-4-Amino-1-benzyl-3-methylpiperidine (R,S)-4-Amino-1-benzyl-3-methylpiperidine is prepared from (R,S)-4-carboxamide-1-benzyl-3-methylpiperidine essentially as described above in Example 38, Scheme B, step b.

Method 2
Scheme C, step a: (R,S)-1- Benzyl-3-methyl-4-piperidone (R,S)-1-Benzyl-3-methyl-4-piperidone is prepared from (R,S)-3-methyl-4-piperidone and benzyl chloride essentially as described above in Example 38, Scheme C, step a, substituting (R,S)-3-methyl-4-piperidone for 4-piperidone.

Scheme C, step b: (R,S)-1-Benzyl -3-methyl-4-piperidone oxime (R,S)-1-Benzyl-3-methyl-4-piperidone oxime is prepared from (R,S)-1- benzyl-3-methyl-4-piperidone and hydroxylamine hydrochloride essentially as described above in Example 38, Scheme C, step b.

Scheme C, step c: (R,S)-4-Amino-1-benzyl-3-methylpiperidine (R,S)-4-Amino-1-benzyl-3-methylpiperidine is prepared from (R,S)-1-benzyl-3-methyl-4-piperidone oxime essentially as described above in Example 38, Scheme C, step c.

Scheme A, step b: (R,S)-2-Chloro-6-[4-(1-benzyl-3-methyl) !piperidinylamino]-9-cyclopentylpurine (R,S)-2-Chloro-6-[4-(1-benzyl-3-methyl) piperidinylamino]-9-cyclopentylpurine is prepared from 2,6-dichloro-9-cyclopentylpurine, (R,S)-4-amino-1-benzyl-3-methylpiperidine, and triethylamine essentially as described in Example 1, Scheme A, step b.

Scheme A, step c: (R,S)-2-[Trans-(4-aminocyclohexyl) amino]-6-[4-(1-benzyl-3-methyl)piperidinylamino]-9-cyclopentylpurine (R,S)-2-[Trans-(4-aminocyclohexyl)amino]-6-[4-(1-benzyl-3-methyl)piperidinylamino]-9-cyclopentylpurine is prepared from (R,S)-2-chloro-6-[4-(1-benzyl-3-methyl) piperidinylamino]-9-cyclopentylpurine essentially as described in Example 1, Scheme A, step c.

EXAMPLE 58a (R)-2-[Trans-(4-aminocyclohexyl)amino]-6-[3-(1-benzyl)pyrrolidinylamino]-9-cyclopentylpurine Scheme A, step b: (R)-2-Chloro-6-[3-(1-benzyl) pyrrolidinylamino]-9-cyclopentylpurine (R)-2-Chloro-6-[3-(1-benzyl)pyrrolidinylamino]-9-cyclopentylpurine is prepared from 2,6-dichloro-9-cyclopentylpurine, (R)-4-amino-1-benzyl-pyrrolidine, and triethylamine essentially as described above in Example 1, Scheme A, step b.

Scheme A, step c: (R)-2-[Trans-(4-aminocyclohexyl) amino]-6-[3-(1-benzyl)pyrrolidinylamino]-9-cyclopentylpurine (R)-2-[Trans-(4-aminocyclohexyl)amino]-6-[3-(1-benzyl)pyrrolidinylamino]-9-cyclopentylpurine is prepared from (R)-2-chloro-6-[3-(1-benzyl)pyrrolidinylamino]-9-cyclopentylpurine essentially as described in Example 1, Scheme A, step c.

EXAMPLE 58b (S)-2-[Trans-(4-aminocyclohexyl)amino]-6-[3-(1-benzyl)pyrrolidinylamino]-9-cyclopentylpurine Scheme A, step b: (S)-2-Chloro-6-[3-(1-benzyl) pyrrolidinylamino]-9-cyclopentylpurine (S)-2-Chloro-6-[3-(1-benzyl)pyrrolidinylamino]-9-cyclopentylpurine is prepared from 2,6-dichloro-9-cyclopentylpurine, (S)-4-amino-1-benzyl-pyrrolidine, and triethylamine essentially as described above in Example 1, Scheme A, step b.

Scheme A, step c: (S)-2-[Trans-(4-aminocyclohexyl) amino]-6-[3-(1-benzyl)pyrrolidinylamino]-9-cyclopentylpurine (S)-2-[Trans-(4-aminocyclohexyl)amino]-6-[3-(1-benzyl)pyrrolidinylamino]-9-cyclopentylpurine is prepared from (S)-2-chloro-6-[3-(1-benzyl)pyrrolidinylamino]-9-cyclopentylpurine essentially as described in Example 1, Scheme A, step c.

EXAMPLE 59

2-[Trans-(4-aminocyclohexyl)amino]-6-[4-(1-butyl) piperidinylamino]-9-cyclopentylpurine Preparation of 4-Amino-1-butylpiperidine
Method 1
Scheme B, step a: 4-Carboxamide-1-butylpiperidine 4-Carboxamide-1-butylpiperidine may be prepared from isonipecotamide and 1-chlorobutane essentially as described above in Example 38, Scheme B, step a.

Scheme B, step b: 4-Amino-1-butylpiperidine

4-Amino-1-butylpiperidine is prepared from 4-carboxamide-1-butylpiperidine essentially as described above in Example 38, Scheme B, step b.

Method 2
Scheme C, step a: 1-Butyl-4-piperidone

1-Butyl-4-piperidone is prepared from 4-piperidone and 1-chlorobutane essentially as described above in Example 38, Scheme C, step a.

Scheme C, step b: 1-Butyl-4-piperidone oxime

1-Butyl-4-piperidone oxime is prepared from 1-butyl-4-piperidone and hydroxylamine hydrochloride essentially as described above in Example 38, Scheme C, step b.

Scheme C, step c: 4-Amino-1-butylpiperidine

4-Amino-1-butylpiperidine is prepared from 1-butyl-4-piperidone oxime essentially as described above in Example 38, Scheme C, step c.

Scheme A, step b: 2-Chloro-6-[4-(1-butyl)piperidinylamino]-9-cyclopentylpurine

2-Chloro-6-[4-(1-butyl)piperidinylamino]-9-cyclopentylpurine is prepared from 2,6-dichloro-9-cyclopentylpurine, 4-amino-1-butylpiperidine, and triethylamine essentially as described above in Example 1, Scheme A, step b.

Scheme A, step c: 2-[Trans-(4-aminocyclohexyl)amino]-6-[4-(1-butyl)piperidinylamino]-9-cyclopentylpurine 2-[Trans-(4-aminocyclohexyl)amino]-6-[4-(1-butyl)piperidinylamino]-9-cyclopentylpurine is prepared from 2-chloro-6-[4-(1-butyl)piperidinylamino]-9-cyclopentylpurine essentially as described in Example 1, Scheme A, step c.

EXAMPLE 60

2-[Trans-(4-aminocyclohexyl)amino]-6-[4-(1-(2-methylthioethyl)piperidinylamino]-9-cyclopentylpurine Preparation of 4-Amino-1-(2-methylthioethyl)piperidine
Method 1
Scheme B, step a: 4-Carboxamide-1-(2-methylthioethyl)piperidine 4-Carboxamide-1-(2-methylthioethyl)piperidine may be prepared from isonipecotamide and 1-chloro-2-thiomethoxyethane essentially as described above in Example 38, Scheme B, step a.

Scheme B, step b: 4-Amino-1-(2-methylthioethyl)piperidine

4-Amino-1-(2-methylthioethyl)piperidine is prepared from 4-carboxamide-1-(2-thiomethoxyethyl)piperidine essentially as described above in Example 38, Scheme B, step b.

Method 2
Scheme C, step a: 1-(2-methylthioethyl)-4-piperidone 1-(2-methylthioethyl)piperidone is prepared from 4-piperidone and 1-chloro-2-thiomethoxyethane essentially as described above in Example 38, Scheme C, step a.

Scheme C, step b: 1-(2-methylthioethyl)-4-piperidone oxime 1-(2-methylthioethyl)-4-piperidone oxime is prepared from 1-(2-thiomethoxyethyl)-4-piperidone and hydroxylamine hydrochloride essentially as described above in Example 38, Scheme C, step b.

Scheme C, step c: 4-Amino-1-(2-methylthioethyl)piperidine

4-Amino-1-(2-methylthioethyl)piperidine is prepared from 1-(2-thiomethoxyethyl)-4-piperidone oxime essentially as described above in Example 38, Scheme C, step c.

Scheme A, step b: 2-Chloro-6-[4-(1-(2-thiomethoxyethyl)piperidinylamino]-9-cyclopentylpurine 2-Chloro-6-[4-(1-(2-thiomethoxyethyl)piperidinylamino]-9-cyclopentylpurine is prepared from 2,6-dichloro-9-cyclopentylpurine, 4-amino-1-(2-thiomethoxyethyl)piperidine, and triethylamine essentially as described above in Example 1, Scheme A, step b.

Scheme A, step c: 2-[Trans-(4-aminocyclohexyl)amino]-6-[4-(1-(2-methylthioethyl)piperidinylamino]-9-cyclopentylpurine 1-[Trans-(4-aminocyclohexyl)amino]-6-[4-(1-(2-methylthioethyl)piperidinylamino]-9-cyclopentylpurine is prepared from 2-chloro-6-[4-(1-(2-methylthioethyl)piperidinylamino]-9-cyclopentylpurine essentially as described in Example 1, Scheme A, step c.

EXAMPLE 61

2-[Trans-(4-aminocyclohexyl)amino]-6-[4-(1-(2-phenylsulfinyl)ethyl)piperidinylamino]-9-cyclopentylpurine Preparation of 4-Amino-1-(2-phenylsulfinylethyl)piperidine
Method 1
Scheme B, step a: 4-Carboxamide-1-(2-phenylsulfinylethyl)piperidine 4-Carboxamide-1-(2-phenylsulfinylethyl)piperidine may be prepared from isonipecotamide and 1-chloro-2-phenylsulfinylethane essentially as described above in Example 38, Scheme B, step a.

Scheme B, step b: 4-Amino-1-(2-phenylsulfinylethyl)piperidine

4-Amino-1-(2-phenylsulfinylethyl)piperidine is prepared from 4-carboxamide-1-(2-phenylsulfinylethyl)piperidine essentially as described above in Example 38, Scheme B, step b.

Method 2
Scheme C, step a: 1-(2-Phenylsulfinylethyl)-4-piperidone 1-(2-Phenylsulfinylethyl)-4-piperidone is prepared from 4-piperidone and 1-chloro-2-phenylsulfinylethane essentially as described above in Example 38, Scheme C, step a.

Scheme C, step b: 1-(2-Phenylsulfinylethyl)-4-piperidone oxime 1-(2-Phenylsulfinylethyl)-4-piperidone oxime is prepared from 1-(2-phenylsulfinylethyl)-4-piperidone and hydroxylamine hydrochloride essentially as described above in Example 38, Scheme C, step b.

Scheme C, step c: 4-Amino-1-(2-phenylsulfinylethyl)piperidine

4-Amino-1-(2-phenylsulfinylethyl)piperidine is prepared from 1-(2-phenylsulfinylethyl)-4-piperidone oxime essentially as described above in Example 38, Scheme C, step c.

Scheme A, step b: 2-Chloro-6-[4-(1-(2-phenylsulfinyl)ethyl)piperidinylamino]-9-cyclopentylpurine 2-Chloro-6-[4-(1-(2-phenylsulfinyl)ethyl)piperidinylamino]-9-cyclopentylpurine is prepared from 2,6-dichloro-9-cyclopentylpurine, 4-amino-1-(2-phenylsulfinylethyl)piperidine, and triethylamine essentially as described above in Example 1, Scheme A, step b.

Scheme A, step c: 2-[Trans-(4-aminocyclohexyl)amino]-6-[4-(1-(2-phenylsulfinyl)ethyl)piperidinylamino]-9-cyclopentylpurine 2-[Trans-(4-aminocyclohexyl)amino]-6-[4-(1-(2-phenylsulfinyl)ethyl)piperidinylamino]-9-cyclopentylpurine is prepared from 2-chloro-6-[4-(1-(2-phenylsulfinyl)ethyl)piperidinylamino]-9-cyclopentylpurine essentially as described in Example 1, Scheme A, step c.

EXAMPLE 62

2-[Trans-(4-aminocyclohexyl)amino]-6-[4-(1-(3-hydroxy)propyl)piperidinylamino]-9-cyclopentylpurine Preparation of 4-Amino-1-(3-hydroxypropyl)piperidine
Method 1
Scheme B, step a: 4-Carboxamide-1-(3-hydroxypropyl)piperidine 4-Carboxamide-1-(3-hydroxypropyl)piperidine may be prepared from isonipecotamide and 3-chloro-1-propanol essentially as described above in Example 38, Scheme B, step a.

Scheme B, step b: 4-Amino-1-(3-hydroxypropyl)piperidine
  4-Amino-1-(3-hydroxypropyl)piperidine is prepared from 4-carboxamide-1-(3-hydroxypropyl)piperidine essentially as described above in Example 38, Scheme B, step b.
Method 2
Scheme C, step a: 1-(3-Hydroxypropyl)-4-piperidone
  1-(3-Hydroxypropyl)-4-piperidone is prepared from 4-piperidone and 3-chloro-1-propanol essentially as described above in Example 38, Scheme C, step a.
Scheme C, step b: 1-(3-Hydroxypropyl)-4-piperidone oxime
  1-(3-Hydroxypropyl)-4-piperidone oxime is prepared from 1-(3-hydroxypropyl)-4-piperidone and hydroxylamine hydrochloride essentially as described above in Example 38, Scheme C, step b.
Scheme C, step c: 4-Amino-1-(3-hydroxypropyl)piperidine
  4-Amino-1-(3-hydroxypropyl)piperidine is prepared from 1-(3-hydroxypropyl)-4-piperidone oxime essentially as described above in Example 38, Scheme C, step c.
Scheme A, step b: 2-Chloro-6-[4-(1-(3-hydroxy)propyl)piperidinylamino]-9-cyclopentylpurine
  2-Chloro-6-[4-(1-(3-hydroxy)propyl)piperidinylamino]-9-cyclopentylpurine is prepared from 2,6-dichloro-9-cyclopentylpurine, 4-amino-1-(3-hydroxypropyl)piperidine, and triethylamine essentially as described above in Example 1, Scheme A, step b.
Scheme A, step c: 2-[Trans-(4-aminocyclohexyl)amino]-6-[4-(1-(3-hydroxy)propyl)piperidinylamino]-9-cyclopentylpurine
  2-[Trans-(4-aminocyclohexyl)amino]-6-[4-(1-(3-hydroxy)propyl)piperidinylamino]-9-cyclopentylpurine is prepared from 2-chloro-6-[4-(1-(3-hydroxy)propyl)piperidinylamino]-9-cyclopentylpurine essentially as described in Example 1, Scheme A, step c.

EXAMPLE 63

2-[Trans-(4-aminocyclohexyl)amino]-6-[4-(1-(3-methoxy)propyl)piperidinylamino]-9-cyclopentylpurine Preparation of 4-Amino-1-(3-methoxypropyl)piperidine
Method 1
Scheme B, step a: 4-Carboxamide-1-(3-methoxypropyl)piperidine
  4-Carboxamide-1-(3-methoxypropyl)piperidine may be prepared from isonipecotamide and 1-chloro-3-methoxypropane essentially as described above in Example 38, Scheme B, step a.
Scheme B, step b: 4-Amino-1-(3-methoxypropyl)piperidine
  4-Amino-1-(3-methoxypropyl)piperidine is prepared from 4-carboxamide-1-(3-methoxypropyl)piperidine essentially as described above in Example 38, Scheme B, step b.
Method 2
Scheme C, step a: 1-(3-Methoxypropyl)-4-piperidone
  1-(3-Methoxypropyl)-4-piperidone is prepared from 4-piperidone and 1-chloro-3-methoxypropane essentially as described above in Example 38, Scheme C, step a.
Scheme C, step b: 1-(3-Methoxypropyl)-4-piperidone oxime
  1-(3-Methoxypropyl)-4-piperidone oxime is prepared from 1-(3-methoxypropyl)-4-piperidone and hydroxylamine hydrochloride essentially as described above in Example 38, Scheme C, step b.
Scheme C, step c: 4-Amino-1-(3-methoxypropyl)piperidine
  4-Amino-1-(3-methoxypropyl)piperidine is prepared from 1-(3-methoxypropyl)-4-piperidone oxime essentially as described above in Example 38, Scheme C, step C.
Scheme A, step b: 2-Chloro-6-[4-(1-(3-methoxy)propyl)piperidinylamino]-9-cyclopentylpurine
  2-Chloro-6-[4-(1-(3-methoxy)propyl)piperidinylamino]-9-cyclopentylpurine is prepared from 2,6-dichloro-9-cyclopentylpurine, 4-amino-1-(3-methoxypropyl)piperidine, and triethylamine essentially as described above in Example 1, Scheme A, step b.
Scheme A, step) c: 2-[Trans-(4-aminocyclohexyl)amino]-6-[4-(1-(3-methoxy)propyl)piperidinylamino]-9-cyclopentylpurine
  2-[Trans-(4-aminocyclohexyl)amino]-6-[4-(1-(3-methoxy)propyl)piperidinylamino]-9-cyclopentylpurine is prepared from 2-chloro-6-[4-(1-(3-methoxy)propyl)piperidinylamino]-9-cyclopentylpurine essentially as described in Example 1, Scheme A, step C.

EXAMPLE 64

2-[Trans-(4-aminocyclohexyl)amino]-6-[4-(1-(3-ethoxy)propyl)piperidinylamino]-9-cyclopentylpurine Preparation of 4-Amino-1-(3-ethoxypropyl)piperidine
Method 1
Scheme B, step a: 4-Carboxamide-1-(3-ethoxypropyl)piperidine
  4-Carboxamide-1-(3-ethoxypropyl)piperidine may be prepared from isonipecotamide and 1-chloro-3-ethoxypropane essentially as described above in Example 38, Scheme B, step a.
Scheme B, step b: 4-Amino-1-(3-ethoxypropyl)piperidine
  4-Amino-1-(3-ethoxypropyl)piperidine is prepared from 4-carboxamide-1-(3-ethoxypropyl)piperidine essentially as described above in Example 38, Scheme B, step b.
Method 2
Scheme C, step a: 1-(3-Ethoxypropyl)-4-piperidone
  1-(3-Ethoxypropyl)-4-piperidone is prepared from 4-piperidone and 1-chloro-3-ethoxypropane essentially as described above in Example 38, Scheme C, step a.
Scheme C, step b: 1-(3-Ethoxypropyl)-4-piperidone oxime
  1-(3-Ethoxypropyl)-4-piperidone oxime is prepared from 1-(3-ethoxypropyl)-4-piperidone and hydroxylamine hydrochloride essentially as described above in Example 38, Scheme C, step b.
Scheme C, step c: 4-Amino-1-(3-ethoxypropyl)piperidine
  4-Amino-1-(3-ethoxypropyl)piperidine is prepared from 1-(3-ethoxypropyl)-4-piperidone oxime essentially as described above in Example 38, Scheme C, step c.
Scheme A, step b:. 2-Chloro-6-[4-(1-(3-ethoxy)propyl)piperidinylamino]-9-cyclopentylpurine
  2-Chloro-6-[4-(1-(3-ethoxy)propyl)piperidinylamino]-9-cyclopentylpurine is prepared from 2,6-dichloro-9-cyclopentylpurine, 4-amino-1-(3-ethoxypropyl)piperidine, and triethylamine essentially as described above in Example 1, Scheme A, step b.
Scheme A, step c: 2-[Trans-(4-aminocyclohexyl)amino]-6-[4-(1-(3-ethoxy)propyl)piperidinylamino]-9-cyclopentylpurine
  2-[Trans-(4-aminocyclohexyl)amino]-6-[4-(1-(3-ethoxy)propyl)piperidinylamino]-9-cyclopentylpurine is prepared from 2-chloro-6-[4-(1-(3-ethoxy)propyl)piperidinylamino]-9-cyclopentylpurine essentially as described in Example 1, Scheme A, step c.

EXAMPLE 65

2-[Trans-(4-aminocyclohexyl)amino]-6-[4-(1-(3-propoxy)propyl)piperidinylamino]-9-cyclopentylpurine Preparation of 4-Amino-1-(3-propoxypropyl)piperidine
Method 1
Scheme B, step a: 4-Carboxamide-1-(3-propoxypropyl)piperidine
  4-Carboxamide-1-(3-propoxypropyl)piperidine may be prepared from isonipecotamide and 1-chloro-3-propoxypropane essentially as described above in Example 38, Scheme B, step a.

Scheme B, step b: 4-Amino-1-(3-propoxypropyl)piperidine

4-Amino-1-(3-propoxypropyl)piperidine is prepared from 4-carboxamide-1-(3-propoxypropyl)piperidine essentially as described above in Example 38, Scheme B, step b.

Method 2

Scheme C, step a: 1-(3-Propoxypropyl)-4-piperidone 1-(3-Propoxypropyl)-4-piperidone is prepared from 4-piperidone and 1-chloro-3-propoxypropane essentially as described above in Example 38, Scheme C, step a.

Scheme C, step b: 1-(3-Propoxypropyl)-4-piperidone oxime 1-(3-Propoxypropyl)-4-piperidone oxime is prepared from 1-(3-propoxypropyl)-4-piperidone and hydroxylamine hydrochloride essentially as described above in Example 38, Scheme C, step b.

Scheme C, step c: 4-Amino-1-(3-propoxypropyl)piperidine

4-Amino-1-(3-propoxypropyl)piperidine is prepared from 1-(3-propoxypropyl)-4-piperidone oxime essentially as described above in Example 38, Scheme C, step c.

Scheme A, step b: 2-Chloro-6-[4-(1-(3-propoxy)propyl)piperidinylamino]-9-cyclopentylpurine 2-Chloro-6-[4-(1-(3-propoxy)propyl)piperidinylamino]-9-cyclopentylpurine is prepared from 2,6-dichloro-9-cyclopentylpurine, 4-amino-1-(3-propoxypropyl)piperidine, and triethylamine essentially as described above in Example 1, Scheme A, step b.

Scheme A, step c: 2-[Trans-(4-aminocyclohexyl)amino]-6-[4-(1-(3-propoxy)propyl)piperidinylamino]-9-cyclopentylpurine 2-[Trans-(4-aminocyclohexyl)amino]-6-[4-(1-(3-propoxy)propyl)piperidinylamino]-9-cyclopentylpurine is prepared from 2-chloro-6-[4-(1-(3-propoxy)propyl)piperidinylamino]-9-cyclopentylpurine essentially as described in Example 1, Scheme A, step c.

EXAMPLE 66

2-[Trans-(4-aminocyclohexyl)amino]-6-[4-(1-(3-butoxy)propyl)piperidinylamino]-9-cyclopentylpurine Preparation of 4-Amino-1-(3-butoxypropyl)piperidine Method 1

Scheme B, step a: 4-Carboxamide-1-(3-butoxypropyl)piperidine

4-Carboxamide-1-(3-butoxypropyl)piperidine may be prepared from isonipecotamide and 1-chloro-3-butoxypropane essentially as described above in Example 38, Scheme B, step a.

Scheme B, step b: 4-Amino-1-(3-butoxypropyl)piperidine

4-Amino-1-(3-butoxypropyl)piperidine is prepared from 4-carboxamide-1-(3-butoxypropyl)piperidine essentially as described above in Example 38, Scheme B, step b.

Method 2

Scheme C, step a: 1-(3-Butoxypropyl)-4-piperidone 1-(3-Butoxypropyl)-4-piperidone is prepared from 4-piperidone and 1-chloro-3-butoxypropane essentially as described above in Example 38, Scheme C, step a.

Scheme C, step b: 1-(3-Butoxypropyl)-4-piperidone oxime 1-(3-Butoxypropyl)-4-piperidone oxime is prepared from 1-(3-butoxypropyl)-4-piperidone and hydroxylamine hydrochloride essentially as described above in Example 38, Scheme C, step b.

Scheme C, step c: 4-Amino-1-(3-butoxypropyl)piperidine

4-Amino-1-(3-butoxypropyl)piperidine is prepared from 1-(3-butoxypropyl)-4-piperidone oxime essentially as described above in Example 38, Scheme C, step c.

Scheme A, step b: 2-Chloro-6-[4-(1-(3-butoxy)propyl)piperidinylamino]-9-cyclopentylpurine 2-Chloro-6-[4-(1-(3-butoxy)propyl)piperidinylamino]-9-cyclopentylpurine is prepared from 2,6-dichloro-9-cyclopentylpurine, 4-amino-1-(3-butoxypropyl)piperidine, and triethylamine essentially as described above in Example 1, Scheme A, step b.

Scheme A, step c: 2-[Trans-(4-aminocyclohexyl)amino]-6-[4-(1-(3-butoxy)propyl)piperidinylamino]-9-cyclopentylpurine 2-[Trans-(4-aminocyclohexyl)amino]-6-[4-(1-(3-butoxy)propyl)piperidinylamino]-9-cyclopentylpurine is prepared from 2-chloro-6-[4-(1-(3-butoxy)propyl)piperidinylamino]-9-cyclopentylpurine essentially as described in Example 1, Scheme A, step c.

EXAMPLE 67

2-[Trans-(4-aminocyclohexyl)amino]-6-[4-(1-(3-benzyloxy)propyl)piperidinylamino]-9-cyclopentylpurine Preparation of 4-Amino-1-(3-benzyloxypropyl)piperidine Method 1

Scheme B, step a: 4-Carboxamide-1-(3-benzyloxypropyl)piperidine

4-Carboxamide-1-(3-benzyloxypropyl)piperidine may be prepared from isonipecotamide and 1-chloro-3-benzyloxypropane essentially as described above in Example 38, Scheme B, step a.

Scheme B, step b: 4-Amino-1-(3-benzyloxypropyl)piperidine

4-Amino-1-(3-benzyloxypropyl)piperidine is prepared from 4-carboxamide-1-(3-benzyloxypropyl)piperidine essentially as described above in Example 38, Scheme B, step b.

Method 2

Scheme C, step a: 1-(3-Benzyloxypropyl)-4-piperidone 1-(3-Benzyloxypropyl)-4-piperidone is prepared from 4-piperidone and 1-chloro-3-benzyloxypropane essentially as described above in Example 38, Scheme C, step a.

Scheme C, step b: 1-(3-Benzyloxypropyl)-4-piperidone oxime 1-(3-Benzyloxypropyl)-4-piperidone oxime is prepared from 1-(3-benzyloxypropyl)-4-piperidone and hydroxylamine hydrochloride essentially as described above in Example 38, Scheme C, step b.

Scheme C, step c: 4-Amino-1-(3-benzyloxypropyl)piperidine

4-Amino-1-(3-benzyloxypropyl)piperidine is prepared from 1-(3-benzyloxypropyl)-4-piperidone oxime essentially as described above in Example 38, Scheme C, step c.

Scheme A, step b: 2-Chloro-6-[4-(1-(3-benzyloxy)propyl)piperidinylamino]-9-cyclopentylpurine 2-Chloro-6-[4-(1-(3-benzyloxy)propyl)piperidinylamino]-9-cyclopentylpurine is prepared from 2,6-dichloro-9-cyclopentylpurine, 4-amino-1-(3-benzyloxypropyl)piperidine, and triethylamine essentially as described above in Example 1, Scheme A, step b.

Scheme A, step c: 2-[Trans-(4-aminocyclohexyl)amino]-6-[4-(1-(3-benzyloxy)propyl)piperidinylamino]-9-cyclopentylpurine 2-[Trans-(4-aminocyclohexyl)amino]-6-[4-(1-(3-benzyloxy)propyl)piperidinylamino]-9-cyclopentylpurine is prepared from 2-chloro-6-[4-(1-(3-benzyloxy)propyl)piperidinylamino]-9-cyclopentylpurine essentially as described in Example 1, Scheme A, step c.

EXAMPLE 68

2-[Trans-(4-aminocyclohexyl)amino]-6-[4-(1-(3-(2-phenylethyleneoxy)propyl)piperidinylamino]-9-cyclopentylpurine Preparation of 4-Amino-1-(3-(2-phenylethyleneoxy)propyl) piperidine Method 1

Scheme B, step a: 4-Carboxamide-1-(3-(2-phenylethyleneoxy)propyl)piperidine

4-Carboxamide-1-(3-(2-phenylethyleneoxy)propyl) piperidine may be prepared from isonipecotamide and 1-chloro-3-(2-phenylethyleneoxy)propane essentially as described above in Example 38, Scheme B, step a.

Scheme B, step b: 4-Amino-1-(3-(2-phenylethyleneoxy)propyl)piperidine

4-Amino-1-(3-(2-phenylethyleneoxy)propyl)piperidine is prepared from 4-carboxamide-1-(3-(2-phenylethyleneoxy)propyl)piperidine essentially as described above in Example 38, Scheme B, step b.

Method 2

Scheme C, step a: 1-(3-(2-Phenylethyleneoxy)-4-piperidone 1-(3-(2-Phenylethyleneoxy)-4-piperidone is prepared from 4-piperidone and 1-chloro-3-(2-phenylethyleneoxy)propane essentially as described above in Example 38, Scheme C, step a.

Scheme C, step b: 1-(3-(2-Phenylethyleneoxy)-4-piperidone oxime 1-(3-(2-Phenylethyleneoxy)-4-piperidone oxime is prepared from 1-(3-(2-phenylethyleneoxy)-4-piperidone and hydroxylamine hydrochloride essentially as described above in Example 38, Scheme C, step b.

Scheme C, step c: 4-Amino-1-(3-(2-phenylethyleneoxy)propyl)piperidine

4-Amino-1-(3-(2-phenylethyleneoxy)propyl)piperidine is prepared from 1-(3-(2-phenylethyleneoxy)-4-piperidone oxime essentially as described above in Example 38, Scheme C, step c.

Scheme A, step b: 2-Chloro-6-[4-(1-(3-(2-phenylethyleneoxy)propyl)piperidinylamino]-9-cyclopentylpurine 2-Chloro-6-[4-(1-(3-(2-phenylethyleneoxy)propyl)piperidinylamino]-9-cyclopentylpurine is prepared from 2,6-dichloro-9-cyclopentylpurine, 4-amino-1-(3-(2-phenylethyleneoxy)propyl)piperidine, and triethylamine essentially as described above in Example 1, Scheme A, step b.

Scheme A, step c: 2-[Trans-(4-aminocyclohexyl)amino]-6-[4-(1-(3-(2-phenylethyleneoxy)propyl)piperidinylamino]-9-cyclopentylpurine 2-[Trans-(4-aminocyclohexyl)amino]-6-[4-(1-(3-(2-phenylethyleneoxy)propyl)piperidinylamino]-9-cyclopentylpurine is prepared from 2-chloro-6-[4-(1-(3-(2-phenylethyleneoxy)propyl)piperidinylamino]-9-cyclopentylpurine essentially as described in Example 1, Scheme A, step c.

EXAMPLE 69

2-[Trans-(4-aminocyclohexyl)amino]-6-[4-(1-(3-(3-phenylpropyleneoxy)propyl)piperidinylamino]-9-cyclopentylpurine Preparation of 4-Amino-1-(3-(3-phenylpropyleneoxy)propyl)piperidine Method 1

Scheme B, step a: 4-Carboxamide-1-(3-(3-phenylpropyleneoxy)propyl)piperidine

4-Carboxamide-1-(3-(3-phenylpropyleneoxy)propyl) piperidine may be prepared from isonipecotamide and 1-chloro-3-(3-phenylpropyleneoxy)propane essentially as described above in Example 38, Scheme B, step a.

Scheme B, step b: 4-Amino-1-(3-(3-phenylpropyleneoxy)propyl)piperidine

4-Amino-1-(3-(3-phenylpropyleneoxy)propyl)piperidine is prepared from 4-carboxamide-1-(3-(3-phenylpropyleneoxy)propyl)piperidine essentially as described above in Example 38, Scheme B, step b.

Method 2

Scheme C, step a: 1-(3-(3-Phenylpropyleneoxy)propyl)-4-piperidone 1-(3-(3-Phenylpropyleneoxy)propyl)-4-piperidone is prepared from 4-piperidone and 1-chloro-3-(3-phenylpropyleneoxy)propane essentially as described above in Example 38, Scheme C, step a.

Scheme C, step b: 1-(3-(3-Phenylpropyleneoxy)propyl)-4-piperidone oxime 1-(3-(3-Phenylpropyleneoxy)propyl)-4-piperidone oxime is prepared from 1-(3-(3-phenylpropyleneoxy)propyl)-4-piperidone and hydroxylamine hydrochloride essentially as described above in Example 38, Scheme C, step b.

Scheme C, step c: 4-Amino-1-(3-(3-phenylpropyleneoxy)propyl)piperidine

4-Amino-1-(3-(3-phenylpropyleneoxy)propyl)piperidine is prepared from 1-(3-(3-phenylpropyleneoxy)propyl)-4-piperidone oxime essentially as described above in Example 38, Scheme C, step c.

Scheme A, step b: 2-Chloro-6-[4-(1-(3-(3-phenylpropyleneoxy)propyl)piperidinylamino]-9-cyclopentylpurine 2-Chloro-6-[4-(1-(3-(3-phenylpropyleneoxy)propyl) piperidinylamino]-9-cyclopentylpurine is prepared from 2,6-dichloro-9-cyclopentylpurine, 4-amino-1-(3-(3-phenylpropyleneoxy)propyl)piperidine, and triethylamine essentially as described above in Example 1, Scheme A, step b.

Scheme A, step c: 2-[Trans-(4-aminocyclohexyl)amino]-6-[4-(1-(3-(3-phenylpropyleneoxy)propyl)piperidinylamino]-9-cyclopentylpurine 2-[Trans-(4-aminocyclohexyl)amino]-6-[4-(1-(3-(3-phenylpropyleneoxy)propyl)piperidinylamino]-9-cyclopentylpurine is prepared from 2-chloro-6-[4-(1-(3-(3-phenylpropyleneoxy)propyl)piperidinylamino]-9-cyclopentylpurine essentially as described in Example 1, Scheme A, step c.

EXAMPLE 70

2-[Trans-(4-aminocyclohexyl)amino]-6-[4-(1-(3-(4-phenylbutyleneoxy)propyl)piperidinylamino]-9-cyclopentylpurine Preparation of 4-Amino-1-(3-(4-phenylbutyleneoxy)propyl) piperidine Method 1

Scheme B, step a: 4-Carboxamide-1-(3-(4-phenylbutyleneoxy)propyl)piperidine

4-Carboxamide-1-(3-(4-phenylbutyleneoxy)propyl) piperidine may be prepared from isonipecotamide and 1-chloro-3-(4-phenylbutyleneoxy)propane essentially as described above in Example 38, Scheme B, step a.

Scheme B, step b: 4-Amino-1-(3-(4-phenylbutyleneoxy)propyl)piperidine

4-Amino-1-(3-(4-phenylbutyleneoxy)propyl)piperidine is prepared from 4-carboxamide-1-(3-(4-phenylbutyleneoxy)propyl)piperidine essentially as described above in Example 38, Scheme B, step b.

Method 2
Scheme C, step a: 1-(3-(4-Phenylbutyleneoxy)propyl)-4-piperidone 1-(3-(4-Phenylbutyleneoxy)propyl)-4-piperidone is prepared from 4-piperidone and 1-chloro-3-(4-phenylbutyleneoxy)propane essentially as described above in Example 38, Scheme C, step a.

Scheme C, step b: 1-(3-(4-Phenylbutyleneoxy)propyl)-4-piperidone oxime 1-(3-(4-Phenylbutyleneoxy)propyl)-4-piperidone oxime is prepared from 1-(3-(4-phenylbutyleneoxy)propyl)-4-piperidone and hydroxylamine hydrochloride essentially as described above in Example 38, Scheme C, step b.

Scheme C, step c: 4-Amino-1-(3-(4-phenylbutyleneoxy)propyl)piperidine

4-Amino-1-(3-(4-phenylbutyleneoxy)propyl)piperidine is prepared from 1-(3-(4-phenylbutyleneoxy)propyl)-4-piperidone oxime essentially as described above in Example 38, Scheme C, step c.

Scheme A, step b: 2-Chloro-6-[4-(1-(3-(4-phenylbutyleneoxy)propyl)piperidinylamino]-9-cyclopentylpurine 2-Chloro-6-[4-(1-(3-(4-phenylbutyleneoxy)propyl)piperidinylamino]-9-cyclopentylpurine is prepared from 2,6-dichloro-9-cyclopentylpurine, 4-amino-1-(3-(4-phenylbutyleneoxy)propyl)piperidine, and triethylamine essentially as described above in Example 1, Scheme A, step b.

Scheme A, step c: 2-[Trans-(4-aminocyclohexyl)amino]-6-[4-(1-(3-(4-phenylbutyleneoxy)propyl)piperidinylamino]-9-cyclopentylpurine 2-[Trans-(4-aminocyclohexyl)amino]-6-[4-(1-(3-(4-phenylbutyleneoxy)propyl)piperidinylamino]-9-cyclopentylpurine is prepared from 2-chloro-6-[4-(1-(3-(4-phenylbutyleneoxy)propyl)piperidinylamino]-9-cyclopentylpurine essentially as described in Example 1, Scheme A, step c.

EXAMPLE 71

2-[Trans-(4-aminocyclohexyl)amino]-6-[4-(1-(4-hydroxy)butyl)piperidinylamino]-9-cyclopentylpurine Preparation of 4-Amino-1-(4-hydroxybutyl)piperidine
Method 1
Scheme B, step a: 4-Carboxamide-1-(4-hydroxybutyl)piperidine 4-Carboxamide-1-(4-hydroxybutyl)piperidine may be prepared from isonipecotamide and 4-chloro-1-butanol essentially as described above in Example 38, Scheme B, step a.

Scheme B, step b: 4-Amino-1-(4-hydroxybutyl)piperidine

4-Amino-1-(4-hydroxybutyl)piperidine is prepared from 4-carboxamide-1-(4-hydroxybutyl)piperidine essentially as described above in Example 38, Scheme B, step b.

Method 2
Scheme C, step a: 1-(4-Hydroxybutyl)-4-piperidone 1-(4-Hydroxybutyl)-4-piperidone is prepared from 4-piperidone and 4-chloro-1-butanol essentially as described above in Example 38, Scheme C, step a.

Scheme C, step b: 1-(4-Hydroxybutyl)-4-piperidone oxime 1-(4-Hydroxybutyl)-4-piperidone oxime is prepared from 1-(4-hydroxybutyl)-4-piperidone and hydroxylamine hydrochloride essentially as described above in Example 38, Scheme C, step b.

Scheme C, step c: 4-Amino-1-(4-hydroxybutyl)piperidine

4-Amino-1-(4-hydroxybutyl)piperidine is prepared from 1-(4-hydroxybutyl)-4-piperidone oxime essentially as described above in Example 38, Scheme C, step c.

Scheme A, step b: 2-Chloro-6-[4-(1-(4-hydroxy)butyl)piperidinylamino]-9-cyclopentylpurine 2-Chloro-6-[4-(1-(4-hydroxy)butyl)piperidinylamino]-9-cyclopentylpurine is prepared from 2,6-dichloro-9-cyclopentylpurine, 4-amino-1-(4-hydroxybutyl)piperidine, and triethylamine essentially as described above in Example 1, Scheme A, step b.

Scheme A, step c: 2-[Trans-(4-aminocyclohexyl)amino]-6-[4-(1-(4-hydroxy)butyl)piperidinylamino]-1-9-cyclopentylpurine 2-[Trans-(4-aminocyclohexyl)amino]-6-[4-(1-(4-hydroxy)butyl)piperidinylamino]-9-cyclopentylpurine is prepared from 2-chloro-6-[4-(1-(4-hydroxy)butyl)piperidinylamino]-9-cyclopentylpurine essentially as described in Example 1, Scheme A, step c.

EXAMPLE 72

2-[Trans-(4-aminocyclohexyl)amino]-6-[4-(1-(4-methoxy)butyl)piperidinylamino]-9-cyclopentylpurine Preparation of 4-Amino-1-(4-methoxybutyl)piperidine
Method 1
Scheme B, step a: 4-Carboxamide-1-(4-methoxybutyl)piperidine 4-Carboxamide-1-(4-methoxybutyl)piperidine may be prepared from isonipecotamide and 1-chloro-4-methoxybutane essentially as described above in Example 38, Scheme B, step a.

Scheme B, step b: 4-Amino-1-(4-methoxybutyl)piperidine

4-Amino-1-(4-methoxybutyl)piperidine is prepared from 4-carboxamide-1-(4-methoxybutyl)piperidine essentially as described above in Example 38, Scheme B, step b.

Method 2
Scheme C, step a: 1-(4-Methoxybutyl)-4-piperidone 1-(4-Methoxybutyl)-4-piperidone is prepared from 4-piperidone and 1-chloro-4-methoxybutane essentially as described above in Example 38, Scheme C, step a.

Scheme C, step b: 1-(4-Methoxybutyl)-4-piperidone oxime 1-(4-Methoxybutyl)-4-piperidone oxime is prepared from 1-(4-methoxybutyl)-4-piperidone and hydroxylamine hydrochloride essentially as described above in Example 38, Scheme C, step b.

Scheme C, step c: 4-Amino-1-(4-methoxybutyl)piperidine

4-Amino-1-(4-methoxybutyl)piperidine is prepared from 1-(4-methoxybutyl)-4-piperidone oxime essentially as described above in Example 38, Scheme C, step c.

Scheme A, step b: 2-Chloro-6-[4-(1-(4-methoxy)butyl)piperidinylamino]-9-cyclopentylpurine 2-Chloro-6-[4-(1-(4-methoxy)butyl)piperidinylamino]-9-cyclopentylpurine is prepared from 2,6-dichloro-9-cyclopentylpurine, 4-amino-1-(4-methoxybutyl)piperidine, and triethylamine essentially as described above in Example 1, Scheme A, step b.

Scheme A, step c: 2-[Trans-(4-aminocyclohexyl)amino]-6-[4-(1-(4-methoxy)butyl)piperidinylamino]-9-cyclopentylpurine 2-[Trans-(4-aminocyclohexyl)amino]-6-[4-(1-(4-methoxy)butyl)piperidinylamino]-9-cyclopentylpurine is prepared from 2-chloro-6-[4-(1-(4-methoxy)butyl)piperidinylamino]-9-cyclopentylpurine essentially as described in Example 1, Scheme A, step c.

EXAMPLE 73

2-[Trans-(4-aminocyclohexyl)amino]-6-[4-(1-(4-ethoxy)butyl)piperidinylamino]-9-cyclopentylpurine Preparation of 4-Amino-1-(4-ethoxybutyl)piperidine
Method 1
Scheme B, step a: 4-Carboxamide-1-(4-ethoxybutyl)piperidine
    4-Carboxamide-1-(4-ethoxybutyl)piperidine may be prepared from isonipecotamide and 1-chloro-4-ethoxybutane essentially as described above in Example 38, Scheme B, step a.
Scheme B, step b: 4-Amino-1-(4-ethoxybutyl)piperidine
    4-Amino-1-(4-ethoxybutyl)piperidine is prepared from 4-carboxamide-1-(4-ethoxybutyl)piperidine essentially as described above in Example 38, Scheme B, step b.
Method 2
Scheme C, step a: 1-(4-Ethoxybutyl)-4-piperidone
    1-(4-Ethoxybutyl)-4-piperidone is prepared from 4-piperidone and 1-chloro-4-ethoxybutane essentially as described above in Example 38, Scheme C, step a.
Scheme C, step b: 1-(4-Ethoxybutyl)-4-piperidone oxime
    1-(4-Ethoxybutyl)-4-piperidone oxime is prepared from 1-(4-ethoxybutyl)-4-piperidone and hydroxylamine hydrochloride essentially as described above in Example 38, Scheme C, step b.
Scheme C, step c: 4-Amino-1-(4-ethoxybutyl)piperidine
    4-Amino-1-(4-ethoxybutyl)piperidine is prepared from 1-(4-ethoxybutyl)-4-piperidone oxime essentially as described above in Example 38, Scheme C, step c.
Scheme A, step b: 2-Chloro-6-[4-(1-(4-ethoxy)butyl)piperidinylamino]-9-cyclopentylpurine
    2-Chloro-6-[4-(1-(4-ethoxy)butyl)piperidinylamino]-9-cyclopentylpurine is prepared from 2,6-dichloro-9-cyclopentylpurine, 4-amino-1-(4-ethoxybutyl)piperidine, and triethylamine essentially as described above in Example 1, Scheme A, step b.
Scheme A, step c: 2-[Trans-(4-aminocyclohexyl)amino]-6-[4-(1-(4-ethoxy)butyl)piperidinylamino]-9-cyclopentylpurine
    2-[Trans-(4-aminocyclohexyl)amino]-6-[4-(1-(4-ethoxy)butyl)piperidinylamino]-9-cyclopentylpurine is prepared from 2-chloro-6-[4-(1-(4-ethoxy)butyl)piperidinylamino]-9-cyclopentylpurine essentially as described in Example 1, Scheme A, step c.

EXAMPLE 74

2-[Trans-(4-aminocyclohexyl)amino]-6-[4-(1-(4-propoxy)butyl)piperidinylamino]-9-cyclopentylpurine Preparation of 4-Amino-1-(4-propoxybutyl)piperidine
Method 1
Scheme B, step a: 4-Carboxamide-1-(4-propoxybutyl)piperidine
    4-Carboxamide-1-(4-propoxybutyl)piperidine may be prepared from isonipecotamide and 1-chloro-4-propoxybutane essentially as described above in Example 38, Scheme B, step a.
Scheme B, step b: 4-Amino-1-(4-propoxybutyl)piperidine
    4-Amino-1-(4-propoxybutyl)piperidine is prepared from 4-carboxamide-1-(4-propoxybutyl)piperidine essentially as described above in Example 38, Scheme B, step b.
Method 2
Scheme C, step a: 1-(4-Propoxybutyl)-4-piperidone
    1-(4-Propoxybutyl)-4-piperidone is prepared from 4-piperidone and 1-chloro-4-propoxybutane essentially as described above in Example 38, Scheme C, step a.
Scheme C, step b: 1-(4-Propoxybutyl)-4-piperidone oxime
    1-(4-Propoxybutyl)-4-piperidone oxime is prepared from 1-(4-propoxybutyl)-4-piperidone and hydroxylamine hydrochloride essentially as described above in Example 38, Scheme C, step b.
Scheme C, step c: 4-Amino-1-(4-propoxybutyl)piperidine
    4-Amino-1-(4-propoxybutyl)piperidine is prepared from 1-(4-propoxybutyl)-4-piperidone oxime essentially as described above in Example 38, Scheme C, step c.
Scheme A, step b: 2-Chloro-6-[4-(1-(4-propoxy)butyl)piperidinylamino]-9-cyclopentylpurine
    2-Chloro-6-[4-(1-(4-propoxy)butyl)piperidinylamino]-9-cyclopentylpurine is prepared from 2,6-dichloro-9-cyclopentylpurine, 4-amino-1-(4-propoxybutyl)piperidine, and triethylamine essentially as described above in Example 1, Scheme A, step b.
Scheme A, step c: 2-[Trans-(4-aminocyclohexyl)amino]-6-[4-(1-(4-propoxy)butyl)piperidinylamino]-9-cyclopentylpurine
    2-[Trans-(4-aminocyclohexyl)amino]-6-[4-(1-(4-propoxy)butyl)piperidinylamino]-9-cyclopentylpurine is prepared from 2-chloro-6-[4-(1-(4-propoxy)butyl)piperidinylamino]-9-cyclopentylpurine essentially as described in Example 1, Scheme A, step c.

EXAMPLE 75

2-[Trans-(4-aminocyclohexyl)amino]-6-[4-(1-(4-butoxy)butyl)piperidinylamino]-9-cyclopentylpurine Preparation of 4-Amino-1-(4-butoxybutyl)piperidine
Method 1
Scheme B, step a: 4-Carboxamide-1-(4-butoxybutyl)piperidine
    4-Carboxamide-1-(4-butoxybutyl)piperidine may be prepared from isonipecotamide and 1-chloro-4-butoxybutane essentially as described above in Example 38, Scheme B, step a.
Scheme B, step b: 4-Amino-1-(4-butoxybutyl)piperidine
    4-Amino-1-(4-butoxybutyl)piperidine is prepared from 4-carboxamide-1-(4-butoxybutyl)piperidine essentially as described above in Example 38, Scheme B, step b.
Method 2
Scheme C, step a: 1-(4-Butoxybutyl)-4-piperidone
    1-(4-Butoxybutyl)-4-piperidone is prepared from 4-piperidone and 1-chloro-4-butoxybutane essentially as described above in Example 38, Scheme C, step a.
Scheme C, step b: 1-(4-Butoxybutyl)-4-piperidone oxime
    1-(4-Butoxybutyl)-4-piperidone oxime is prepared from 1-(4-butoxybutyl)-4-piperidone and hydroxylamine hydrochloride essentially as described above in Example 38, Scheme C, step b.
Scheme C, step c: 4-Amino-1-(4-butoxybutyl)piperidine
    4-Amino-1-(4-butoxybutyl)piperidine is prepared from 1-(4-butoxybutyl)-4-piperidone oxime essentially as described above in Example 38, Scheme C, step c.
Scheme A, step b: 2-Chloro-6-[4-(1-(4-butoxy)butyl)piperidinylamino]-9-cyclopentylpurine
    2-Chloro-6-[4-(1-(4-butoxy)butyl)piperidinylamino]-9-cyclopentylpurine is prepared from 2,6-dichloro-9-cyclopentylpurine, 4-amino-1-(4-butoxybutyl)piperidine, and triethylamine essentially as described above in Example 1, Scheme A, step b.
Scheme A, step c: 2-[Trans-(4-aminocyclohexyl)amino]-6-[4-(1-(4-butoxy)butyl)piperidinylamino]-9-cyclopentylpurine
    2-[Trans-(4-aminocyclohexyl)amino]-6-[4-(1-(4-butoxy)butyl)piperidinylamino]-9-cyclopentylpurine is prepared from 2-chloro-6-[4-(1-(4-butoxy)butyl)piperidinylamino]-

EXAMPLE 76

2-[Trans-(4-aminocyclohexyl)amino]-6-[4-(1-(4-benzyloxy)butyl)piperidinylamino]-9-cyclopentylpurine Preparation of 4-Amino-1-(4-benzyloxybutyl)piperidine
Method 1
Scheme B, step a: 4-Carboxamide-1-(4-benzyloxybutyl)piperidine 4-Carboxamide-1-(4-benzyloxybutyl)piperidine may be prepared from isonipecotamide and 1-chloro-4-benzyloxybutane essentially as described above in Example 38, Scheme B, step a.

Scheme B, step b: 4-Amino-1-(4-benzyloxybutyl)piperidine

4-Amino-1-(4-benzyloxybutyl)piperidine is prepared from 4-carboxamide-1-(4-benzyloxybutyl)piperidine essentially as described above in Example 38, Scheme B, step b.

Method 2
Scheme C, step a: 1-(4-Benzyloxybutyl)-4-piperidone 1-(4-Benzyloxybutyl)-4-piperidone is prepared from 4-piperidone and 1-chloro-4-benzyloxybutane essentially as described above in Example 38, Scheme C, step a.

Scheme C, step b: 1-(4-Benzyloxybutyl)-4-piperidone oxime 1-(4-Benzyloxybutyl)-4-piperidone oxime is prepared from 1-(4-benzyloxybutyl)-4-piperidone and hydroxylamine hydrochloride essentially as described above in Example 38, Scheme C, step b.

Scheme C, step c: 4-Amino-1-(4-benzyloxybutyl)piperidine

4-Amino-1-(4-benzyloxybutyl)piperidine is prepared from 1-(4-benzyloxybutyl)-4-piperidone oxime essentially as described above in Example 38, Scheme C, step c.

Scheme A, step b: 2-Chloro-6-[4-(1-(4-benzyloxy)butyl)piperidinylamino]-9-cyclopentylpurine 2-Chloro-6-[4-(1-(4-benzyloxy)butyl)piperidinylamino]-9-cyclopentylpurine is prepared from 2,6-dichloro-9-cyclopentylpurine, 4-amino-1-(4-benzyloxybutyl)piperidine, and triethylamine essentially as described above in Example 1, Scheme A, step b.

Scheme A, step c: 2-[Trans-(4-aminocyclohexyl)amino]-6-[4-(1-(4-benzyloxy)butyl)piperidinylamino]-9-cyclopentylpurine 2-[Trans-(4-aminocyclohexyl)amino]-6-[4-(1-(4-benzyloxy)butyl)piperidinylamino]-9-cyclopentylpurine is prepared from 2-chloro-6-[4-(1-(4-benzyloxy)butyl)piperidinylamino]-9-cyclopentylpurine essentially as described in Example 1, Scheme A, step c.

EXAMPLE 77

2-[Trans-(4-aminocyclohexyl)amino]-6-[4-(1-(4-(2-phenylethyleneoxy)butyl)piperidinylamino]-9-cyclopentylpurine Preparation of 4-Amino-1-(4-(2-phenylethyleneoxy)butyl)piperidine
Method 1
Scheme B, step a: 4-Carboxamide-1-(4-(2-phenylethyleneoxy)butyl)piperidine 4-Carboxamide-1-(4-(2-phenylethyleneoxy)butyl)piperidine may be prepared from isonipecotamide and 1-chloro-4-(2-phenylethyleneoxy)butane essentially as described above in Example 38, Scheme B, step a.

Scheme B, step b: 4-Amino-1-(4-(2-phenylethyleneoxy)butyl)piperidine

4-Amino-1-(4-(2-phenylethyleneoxy)butyl)piperidine is prepared from 4-carboxamide-1-(4-(2-phenylethyleneoxy)butyl)piperidine essentially as described above in Example 38, Scheme B, step b.

Method 2
Scheme C, step a: 1-(4-(2-Phenylethyleneoxy)butyl)-4-piperidone 1-(4-(2-Phenylethyleneoxy)butyl)-4-piperidone is prepared from 4-piperidone and 1-chloro-4-(2-phenylethyleneoxy)butane essentially as described above in Example 38, Scheme C, step a.

Scheme C, step b: 1-(4-(2-Phenylethyleneoxy)butyl)-4-piperidone oxime 1-(4-(2-Phenylethyleneoxy)butyl)-4-piperidone oxime is prepared from 1-(4-(2-phenylethyleneoxy)butyl)-4-piperidone and hydroxylamine hydrochloride essentially as described above in Example 38, Scheme C, step b.

Scheme C, step c: 4-Amino-1-(4-(2-phenylethyleneoxy)butyl)piperidine

4-Amino-1-(4-(2-phenylethyleneoxy)butyl)piperidine is prepared from 1-(4-(2-phenylethyleneoxy)butyl)-4-piperidone oxime essentially as described above in Example 38, Scheme C, step c.

Scheme A, step b: 2-Chloro-6-[4-(1-(4-(2-phenylethyleneoxy)butyl)piperidinylamino]-9-cyclopentylpurine 2-Chloro-6-[4-(1-(4-(2-phenylethyleneoxy)butyl)piperidinylamino]-9-cyclopentylpurine is prepared from 2,6-dichloro-9-cyclopentylpurine, 4-amino-1-(4-(2-phenylethyleneoxy)butyl)piperidine, and triethylamine essentially as described above in Example 1, Scheme A, step b.

Scheme A, step c: 2-[Trans-(4-aminocyclohexyl)amino]-6-[4-(1-(4-(2-phenylethyleneoxy)butyl)piperidinylamino]-9-cyclopentylpurine 2-[Trans-(4-aminocyclohexyl)amino]-6-[4-(1-(4-(2-phenylethyleneoxy)butyl)piperidinylamino]-9-cyclopentylpurine is prepared from 2-chloro-6-[4-(1-(4-(2-phenylethyleneoxy)butyl)piperidinylamino]-9-cyclopentylpurine essentially as described in Example 1, Scheme A, step c.

EXAMPLE 78

2-[Trans-(4-aminocyclohexyl)amino]-6-[4-(1-(4-(3-phenylpropyleneoxy)butyl)piperidinylamino]-9-cyclopentylpurine Preparation of 4-Amino-1-(4-(3-phenylpropyleneoxy)butyl)piperidine
Method 1
Scheme B, step a: 4-Carboxamide-1-(4-(3-phenylpropyleneoxy)butyl)piperidine 4-Carboxamide-1-(4-(3-phenylpropyleneoxy)butyl)piperidine may be prepared from isonipecotamide and 1-chloro-(4-(3-phenylpropyleneoxy)butane essentially as described above in Example 38, Scheme B, step a.

Scheme B, step b: 4-Amino-1-(4-(3-phenylpropyleneoxy)butyl)piperidine

4-Amino-1-(4-(3-phenylpropyleneoxy)butyl)piperidine is prepared from 4-carboxamide-1-(4-(3-phenylpropyleneoxy)butyl)piperidine essentially as described above in Example 38, Scheme B, step b.

Method 2
Scheme C, step a: 1-(4-(3-Phenylpropyleneoxy)butyl)-4-piperidone 1-(4-(3-Phenylpropyleneoxy)butyl)-4-piperidone is prepared from 4-piperidone and 1-chloro-(4-(3-phenylpropyleneoxy)butane essentially as described above in Example 38, Scheme C, step a.

Scheme C, step b: 1-(4-(3-Phenylpropyleneoxy)butyl)-4-piperidone oxime 1-(4-(3-Phenylpropyleneoxy)butyl)-4-piperidone oxime is prepared from 1-(4-(3-phenylpropyleneoxy)butyl)-4-piperidone and hydroxylamine hydrochloride essentially as described above in Example 38, Scheme C, step b.

Scheme C, step2 c: 4-Amino-1-(4-(3-phenylpropyleneoxy)butyl)piperidine

4-Amino-1-(4-(3-phenylpropyleneoxy)butyl)piperidine is prepared from 1-(4-(3-phenylpropyleneoxy)butyl)-4-piperidone oxime essentially as described above in Example 38, Scheme C, step c.

Scheme A, step b: 2-Chloro-6-[4-(1-(4-(3-phenylpropyleneoxy)butyl)piperidinylamino]-9-cyclopentylpurine 2-Chloro-6-[4-(1-(4-(3-phenylpropyleneoxy)butyl)piperidinylamino]-9-cyclopentylpurine is prepared from 2,6-dichloro-9-cyclopentylpurine, 4-amino-1-(4-(3-phenylpropyleneoxy)butyl)piperidine, and triethylamine essentially as described above in Example 1, Scheme A, step b.

Scheme A, step c: 2-[Trans-(4-aminocyclohexyl)amino]-6-[4-(1-(4-(3-phenylpropyleneoxy)butyl)piperidinylamino]-9-cyclopentylpurine 2-[Trans-(4-aminocyclohexyl)amino]6-[4-(1-(4-(3-phenylpropyleneoxy)butyl)piperidinylamino]-9-cyclopentylpurine is prepared from 2-chloro-6-[4-(1-(4-(3-phenylpropyleneoxy)butyl)piperidinylamino]-9-cyclopentylpurine essentially as described in Example 1, Scheme A, step c.

EXAMPLE 79

2-[Trans-(4-aminocyclohexyl)amino]-6-[4-(1-(4-(4-phenylbutyleneoxy)butyl)piperidinylamino]-9-cyclopentylpurine Preparation of 4-Amino-1-(4-(4-phenylbutyleneoxy)butyl)piperidine Method 1

Scheme B, step a: 4-Carboxamide-1-(4-(4-phenylbutyleneoxy)butyl)piperidine

4-Carboxamide-1-(4-(4-phenylbutyleneoxy)butyl)piperidine may be prepared from isonipecotamide and 1-chloro-4-(4-phenylbutyleneoxy)butane essentially as described above in Example 38, Scheme B, step a.

Scheme B, step b: 4-Amino-1-(4-(4-phenylbutyleneoxy)butyl)piperidine

4-Amino-1-(4-(4-phenylbutyleneoxy)butyl)piperidine is prepared from 4-carboxamide-1-(4-(4-phenylbutyleneoxy)butyl)piperidine essentially as described above in Example 38, Scheme B, step b.

Method 2

Scheme C, step a: 1-(4-(4-Phenylbutyleneoxy)butyl)-4-piperidone 1-(4-(4-Phenylbutyleneoxy)butyl)-4-piperidone is prepared from 4-piperidone and 1-chloro-4-(4-phenylbutyleneoxy)butane essentially as described above in Example 38, Scheme C, step a.

Scheme C, step b: 1-(4-(4-Phenylbutyleneoxy)butyl)-4-piperidone oxime 1-(4-(4-Phenylbutyleneoxy)butyl)-4-piperidone oxime is prepared from 1-(4-(4-phenylbutyleneoxy)butyl)-4-piperidone and hydroxylamine hydrochloride essentially as described above in Example 38, Scheme C, step b.

Scheme C, step c: 4-Amino-1-(4-(4-phenylbutyleneoxy)butyl)piperidine

4-Amino-1-(4-(4-phenylbutyleneoxy)butyl)piperidine is prepared from 1-(4-(4-phenylbutyleneoxy)butyl)-4-piperidone oxime essentially as described above in Example 38, Scheme C, step c.

Scheme A, step b: 2-Chloro-6-[4-(1-(4-(4-phenylbutyleneoxy)butyl)piperidinylamino]-9-cyclopentylpurine 2-Chloro-6-[4-(1-(4-(4-phenylbutyleneoxy)butyl)piperidinylamino]-9-cyclopentylpurine is prepared from 2,6-dichloro-9-cyclopentylpurine, 4-amino-1-(4-(4-phenylbutyleneoxy)butyl)piperidine, and triethylamine essentially as described above in Example 1, Scheme A, step b.

Scheme A, step c: 2-[Trans-(4-aminocyclohexyl)amino]-6-[4-(1-(4-(4-phenylbutyleneoxy)butyl)piperidinylamino]-9-cyclopentylpurine 2-[Trans-(4-aminocyclohexyl)amino]-6-[4-(1-(4-(4-phenylbutyleneoxy)butyl)piperidinylamino]-9-cyclopentylpurine is prepared from 2-chloro-6-[4-(1-(4-(4-phenylbutyleneoxy)butyl)piperidinylamino]-9-cyclopentylpurine essentially as described in Example 1, Scheme A, step c.

EXAMPLE 80

2-[Trans-(4-aminocyclohexyl)amino]-6-[4-(1-(5-hydroxypentyl))piperidinylamino]-9-cyclopentylpurine Preparation of 4-Amino-1-(5-hydroxypentyl)piperidine Method 1

Scheme B, step a: 4-Carboxamide-1-(5-hydroxypentyl)piperidine

4-Carboxamide-1-(5-hydroxypentyl)piperidine may be prepared from isonipecotamide and 1-chloro-5-hydroxypentane essentially as described above in Example 38, Scheme B, step a.

Scheme B, step b: 4-Amino-1-(5-hydroxypentyl)piperidine

4-Amino-1-(5-hydroxypentyl)piperidine is prepared from 4-carboxamide-1-(5-3hydroxypentyl)piperidine essentially as described above in Example 38, Scheme B, step b.

Method 2

Scheme C, step a: 1-(5-Hydroxypentyl)-4-piperidone 1-(5-Hydroxypentyl)-4-piperidone is prepared from 4-piperidone and 1-chloro-5-hydroxypentane essentially as described above in Example 38, Scheme C, step a.

Scheme C, step b: 1-(5-Hydroxypentyl)-4-piperidone oxime 1-(5-Hydroxypentyl)-4-piperidone oxime is prepared from 1-(5-hydroxypentyl)-4-piperidone and hydroxylamine hydrochloride essentially as described above in Example 38, Scheme C, step b.

Scheme C, step c: 4-Amino-1-(5-hydroxypentyl)piperidine

4-Amino-1-(5-hydroxypentyl)piperidine is prepared from 1-(5-hydroxypentyl)-4-piperidone oxime essentially as described above in Example 38, Scheme C, step c.

Scheme A, step b: 2-Chloro-6-[4-(1-(5-hydroxypentyl)piperidinylamino]-9-cyclopentylpurine 2-Chloro-6-[4-(1-(5-hydroxypentyl))piperidinylamino]-9-cyclopentylpurine is prepared from 2,6-dichloro-9-cyclopentylpurine, 4-amino-1-(5-hydroxypentyl)piperidine, and triethylamine essentially as described above in Example 1, Scheme A, step b.

Scheme A, step c: 2-[Trans-(4-aminocyclohexyl)amino]-6-[4-(1-(5-hydroxypentyl))piperidinylamino]-9-cyclopentylpurine 2-[Trans-(4-aminocyclohexyl)amino]-6-[4-(1-(5-hydroxypentyl))piperidinylamino]-9-cyclopentylpurine is prepared from 2-chloro-6-[4-(1-(5-hydroxypentyl))piperidinylamino]-9-cyclopentylpurine essentially as described in Example 1, Scheme A, step c.

EXAMPLE 81

2-[Trans-(4-aminocyclohexyl)amino]-6-[4-(1-(5-methoxypentyl)piperidinylamino]-9-cyclopentylpurine Preparation of 4-Amino-(5-methoxypentyl)piperidine
Method 1
Scheme B, step a: 4-Carboxamide-1-(5-methoxypentyl)piperidine 4-Carboxamide-1-(5-methoxypentyl)piperidine may be prepared from isonipecotamide and 1-chloro-5-methoxypentane essentially as described above in Example 38, Scheme B, step a.

Scheme B, step b: 4-Amino-(5-methoxypentyl)piperidine

4-Amino-(5-methoxypentyl)piperidine is prepared from 4-carboxamide-1-(5-methoxypentyl)piperidine essentially as described above in Example 38, Scheme B, step b.

Method 2
Scheme C, step a: 1-(5-Methoxypentyl)-4-piperidone 1-(5-Methoxypentyl)-4-piperidone is prepared from 4-piperidone and 1-chloro-5-methoxypentane essentially as described above in Example 38, Scheme C, step a.

Scheme C, step b: 1-(5-Methoxypentyl)-4-piperidone oxime 1-(5-Methoxypentyl)-4-piperidone oxime is prepared from 1-(5-methoxypentyl)-4-piperidone and hydroxylamine hydrochloride essentially as described above in Example 38, Scheme C, step b.

Scheme C, step c: 4-Amino-(5-methoxypentyl)piperidine

4-Amino-(5-methoxypentyl)piperidine is prepared from 1-(5-methoxypentyl)-4-piperidone oxime essentially as described above in Example 38, Scheme C, step c.

Scheme A, step b: 2-Chloro-6-[4-(1-(5-methoxypentyl))piperidinylamino]-9-cyclopentylpurine 2-Chloro-6-[4-(1-(5-methoxypentyl))piperidinylamino]-9-cyclopentylpurine is prepared from 2,6-dichloro-9-cyclopentylpurine, 4-amino-(5-methoxypentyl)piperidine, and triethylamine essentially as described above in Example 1, Scheme A, step b.

Scheme A, step c: 2-[Trans-(4-aminocyclohexyl)amino]-6-[4-(1-(5-methoxypentyl))piperidinylamino]-9-cyclopentylpurine 2-[Trans-(4-aminocyclohexyl)amino]-6-[4-(1-(5-methoxypentyl))piperidinylamino]-9-cyclopentylpurine is prepared from 2-chloro-6-[4-(1-(5-methoxypentyl))piperidinylamino]-9-cyclopentylpurine essentially as described in Example 1, Scheme A, step c.

EXAMPLE 82

2-[Trans-(4-aminocyclohexyl)amino]-6-[4-(1-(5-ethoxypentyl)piperidinylamino]-9-cyclopentylpurine Preparation of 4-Amino-1-(5-ethoxypentyl)piperidine
Method 1
Scheme B, step a: 4-Carboxamide-1-(5-ethoxypentyl)piperidine 4-Carboxamide-1-(5-ethoxypentyl)piperidine may be prepared from isonipecotamide and 1-chloro-5-ethoxypentane essentially as described above in Example 38, Scheme B, step a.

Scheme B, step b: 4-Amino-1-(5-ethoxypentyl)piperidine

4-Amino-1-(5-ethoxypentyl)piperidine is prepared from 4-carboxamide-1-(5-ethoxypentyl)piperidine essentially as described above in Example 38, Scheme B, step b.

Method 2
Scheme C, step a: 1-(5-Ethoxypentyl)-4-piperidone 1-(5-Ethoxypentyl)-4-piperidone is prepared from 4-piperidone and 1-chloro-5-ethoxypentane essentially as described above in Example 38, Scheme C, step a.

Scheme C, step b: 1-(5-Ethoxypentyl)-4-piperidone oxime 1-(5-Ethoxypentyl)-4-piperidone oxime is prepared from 1-(5-ethoxypentyl)-4-piperidone and hydroxylamine hydrochloride essentially as described above in Example 38, Scheme C, step b.

Scheme C, step c: 4-Amino-1-(5-ethoxypentyl)piperidine

4-Amino-1-(5-ethoxypentyl)piperidine is prepared from 1-(5-ethoxypentyl)-4-piperidone oxime essentially as described above in Example 38, Scheme C, step c.

Scheme A, step, b: 2-Chloro-6-[4-(1-(5-ethoxypentyl))piperidinylamino]-9-cyclopentylpurine 2-Chloro-6-[4-(1-(5-ethoxypentyl))piperidinylamino]-9-cyclopentylpurine is prepared from 2,6-dichloro-9-cyclopentylpurine, 4-amino-1-(5-ethoxypentyl)piperidine, and triethylamine essentially as described above in Example 1, Scheme A, step b.

Scheme A, step c: 2-[Trans-(4-aminocyclohexyl)amino]-6-[4-(1-(5-ethoxypentyl))piperidinylamino]-9-cyclopentylpurine 2-[Trans-(4-aminocyclohexyl)amino]-6-[4-(1-(5-ethoxypentyl))piperidinylamino]-9-cyclopentylpurine is prepared from 2-chloro-6-[4-(1-(5-ethoxypentyl))piperidinylamino]-9-cyclopentylpurine essentially as described in Example 1, Scheme A, step c.

EXAMPLE 83

2-[Trans-(4-aminocyclohexyl)amino]-6-[4-(1-(5-propoxypentyl))piperidinylamino]-9-cyclopentylpurine Preparation of 4-Amino-1-(5-propoxypentyl)piperidine
Method 1
Scheme B, step a: 4-Carboxamide-1-(5-propoxypentyl)piperidine 4-Carboxamide-1-(5-propoxypentyl)piperidine may be prepared from isonipecotamide and 1-chloro-5-propoxypentane essentially as described above in Example 38, Scheme B, step a.

Scheme B, step b: 4-Amino-1-(5-propoxypentyl)piperidine

4-Amino-1-(5-propoxypentyl)piperidine is prepared from 4-carboxamide-1-(5-propoxypentyl)piperidine essentially as described above in Example 38, Scheme B, step b.

Method 2
Scheme C, step a: 1-(5-Propoxypentyl)-4-piperidone 1-(5-Propoxypentyl)-4-piperidone is prepared from 4-piperidone and 1-chloro-5-propoxypentane essentially as described above in Example 38, Scheme C, step a.

Scheme C, step b: 1-(5-Propoxypentyl)-4-piperidone oxime 1-(5-Propoxypentyl)-4-piperidone oxime is prepared from 1-(5-propoxypentyl)-4-piperidone and hydroxylamine hydrochloride essentially as described above in Example 38, Scheme C, step b.

Scheme C, step c: 4-Amino-1-(5-propoxypentyl)piperidine

4-Amino-1-(5-propoxypentyl)piperidine is prepared from 1-(5-propoxypentyl)-4-piperidone oxime essentially as described above in Example 38, Scheme C, step c.

Scheme A, step b: 2-Chloro-6-[4-(1-(5-propoxypentyl))piperidinylamino]-9-cyclopentylpurine 2-Chloro-6-[4-(1-(5-propoxypentyl))piperidinylamino]-9-cyclopentylpurine is prepared from 2,6-dichloro-9-cyclopentylpurine, 4-amino-1-(5-propoxypentyl)piperidine, and triethylamine essentially as described above in Example 1, Scheme A, step b.

Scheme A, step c: 2-[Trans-(4-aminocyclohexyl)amino]-6-[4-(1-(5-propoxypentyl))piperidinylamino]-9-cyclopentylpurine 2-[Trans-(4-aminocyclohexyl)amino]-6-[4-(1-(5-propoxypentyl))piperidinylamino]-9-cyclopentylpurine is prepared from 2-chloro-6-[4-(1-(5-propoxypentyl))piperidinylamino]-9-cyclopentylpurine essentially as described in Example 1, Scheme A, step c.

EXAMPLE 84

2-[Trans-(4-aminocyclohexyl)amino]-6-[4-(1-(5-butoxypentyl))piperidinylamino]-9-cyclopentylpurine Preparation of 4-Amino-1-(5-butoxypentyl)piperidine
Method 1
Scheme B, step a: 4-Carboxamide-1-(5-butoxypentyl)piperidine 4-Carboxamide-1-(5-butoxypentyl)piperidine may be prepared from isonipecotamide and 1-chloro-5-butoxypentane essentially as described above in Example 38, Scheme B, step a.
Scheme B, step b: 4-Amino-1-(5-butoxypentyl)piperidine 4-Amino-1-(5-butoxypentyl)piperidine is prepared from 4-carboxamide-1-(5-butoxypentyl)piperidine essentially as described above in Example 38, Scheme B, step b.
Method 2
Scheme C, step a: 1-(5-Butoxypentyl)-4-piperidone 1-(5-Butoxypentyl)-4-piperidone is prepared from 4-piperidone and 1-chloro-5-butoxypentane essentially as described above in Example 38, Scheme C, step a.
Scheme C, step b: 1-(5-Butoxypentyl-4-piperidone oxime 1-(5-Butoxypentyl)-4-piperidone oxime is prepared from 1-(5-butoxypentyl)-4-piperidone and hydroxylamine hydrochloride essentially as described above in Example 38, Scheme C, step b.
Scheme C, step c: 4-Amino-1-(5-butoxypentyl)piperidine 4-Amino-1-(5-butoxypentyl)piperidine is prepared from 1-(5-butoxypentyl)-4-piperidone oxime essentially as described above in Example 38, Scheme C, step c.
Scheme A, step b: 2-Chloro-6-[4-(1-(5-butoxypentyl))piperidinylamino]-9-cyclopentylpurine 2-Chloro-6-[4-(1-(5-butoxypentyl))piperidinylamino]-9-cyclopentylpurine is prepared from 2,6-dichloro-9-cyclopentylpurine, 4-amino-1-(5-butoxypentyl)piperidine, and triethylamine essentially as described above in Example 1, Scheme A, step b.
Scheme A, step c: 2-[Trans-(4-aminocyclohexyl)amino]-6-[4-(1-(5-butoxypentyl))piperidinylamino]-9-cyclopentylpurine 2-[Trans-(4-aminocyclohexyl)amino]-6-[4-(1-(5-butoxypentyl))piperidinylamino]-9-cyclopentylpurine is prepared from 2-chloro-6-[4-(1-(5-butoxypentyl))piperidinylamino]-9-cyclopentylpurine essentially as described in Example 1, Scheme A, step c.

EXAMPLE 85

2-[Trans-(4-aminocyclohexyl)amino]-6-[4-(1-(5-benzyloxypentyl))piperidinylamino]-9-cyclopentylpurine Preparation of 4-Amino-1-(5-benzyloxypentyl)piperidine
Method 1
Scheme B, step a: 4-Carboxamide-1-(5-benzyloxypentyl)piperidine 4-Carboxamide-1-(5-benzyloxypentyl)piperidine may be prepared from isonipecotamide and 1-chloro-5-benzyloxypentane essentially as described above in Example 38, Scheme B, step a.
Scheme B, step b: 4-Amino-1-(5-benzyloxypentyl)piperidine 4-Amino-1-(5-benzyloxypentyl)piperidine is prepared from 4-carboxamide-1-(5-benzyloxypentyl)piperidine essentially as described above in Example 38, Scheme B, step b.
Method 2
Scheme C, step a: 1-(5-Benzyloxypentyl-4-piperidone 1-(5-Benzyloxypentyl)-4-piperidone is prepared from 4-piperidone and 1-chloro-5-benzyloxypentane essentially as described above in Example 38, Scheme C, step a.
Scheme C, step b: 1-(5-Benzyloxypentyl)-4-piperidone oxime 1-(5-Benzyloxypentyl)-4-piperidone oxime is prepared from 1-(5-benzyloxypentyl)-4-piperidone and hydroxylamine hydrochloride essentially as described above in Example 38, Scheme C, step b.
Scheme C, step c: 4-Amino-1-(5-benzyloxypentyl)piperidine 4-Amino-1-(5-benzyloxypentyl)piperidine is prepared from 1-(5-benzyloxypentyl)-4-piperidone oxime essentially as described above in Example 38, Scheme C, step c.
Scheme A, step b: 2-Chloro-6-[4-(1-(5-benzyloxypentyl))piperidinylamino]-9-cyclopentylpurine 2-Chloro-6-[4-(1-(5-benzyloxypentyl))piperidinylamino]-9-cyclopentylpurine is prepared from 2,6-dichloro-9-cyclopentylpurine, 4-amino-1-(5-benzyloxypentyl)piperidine, and triethylamine essentially as described above in Example 1, Scheme A, step b.
Scheme A, step c: 2-[Trans-(4-aminocyclohexyl)amino]-6-[4-(1-(5-benzyloxypentyl))piperidinylamino]-9-cyclopentylpurine 2-[Trans-(4-aminocyclohexyl)amino]-6-[4-(1-(5-benzyloxypentyl))piperidinylamino]-9-cyclopentylpurine is prepared from 2-chloro-6-[4-(1-(5-benzyloxypentyl))piperidinylamino]-9-cyclopentylpurine essentially as described in Example 1, Scheme A, step c.

EXAMPLE 86

2-[Trans-(4-aminocyclohexyl)amino]-6-[4-(1-(5-(2-phenylethyleneoxy)pentyl))piperidinylamino]-9-cyclopentylpurine Preparation of 4-Amino-1-(5-(2-phenylethyleneoxy)pentyl)piperidine
Method 1
Scheme B, step a: 4-Carboxamide-1-(5-(2-phenylethyleneoxy)pentyl)piperidine 4-Carboxamide-1-(5-(2-phenylethyleneoxy)pentyl)piperidine may be prepared from isonipecotamide and 1-chloro-5-(2-phenylethyleneoxy)pentane essentially as described above in Example 38, Scheme B, step a.
Scheme B, step b: 4-Amino-1-(5-(2-phenylethyleneoxy)pentyl)piperidine 4-Amino-1-(5-(2-phenylethyleneoxy)pentyl)piperidine is prepared from 4-carboxamide-1-(5-(2-phenylethyleneoxy)pentyl)piperidine essentially as described above in Example 38, Scheme B, step b.
Method 2
Scheme C, step a: 1-(5-(2-Phenylethyleneoxy)pentyl)-4-piperidone 1-(5-(2-Phenylethyleneoxy)pentyl)-4-piperidone is prepared from 4-piperidone and 1-chloro-5-(2-phenylethyleneoxy)pentane essentially as described above in Example 38, Scheme C, step a.
Scheme C, step b: 1-(5-(2-Phenylethyleneoxy)pentyl)-4-piperidone oxime 1-(5-(2-Phenylethyleneoxy)pentyl)-4-piperidone oxime is prepared from 1-(5-(2-phenylethyleneoxy)pentyl)-4- piperidone and hydroxylamine hydrochloride essentially as described above in Example 38, Scheme C, step b.

Scheme C, step c: 4-Amino-1-(5-(2-phenylethyleneoxy)pentyl)piperidine

4-Amino-1-(5-(2-phenylethyleneoxy)pentyl)piperidine is prepared from 1-(5-(2-phenylethyleneoxy)pentyl)-4-piperidone oxime essentially as described above in Example 38, Scheme C, step c.

Scheme A, step b: 2-Chloro-6-[4-(1-(5-(2-phenylethyleneoxy)pentyl))piperidinylamino]-9-cyclopentylpurine 2-Chloro-6-[4-(1-(5-(2-phenylethyleneoxy)pentyl))piperidinylamino]-9-cyclopentylpurine is prepared from 2,6-dichloro-9-cyclopentylpurine, 4-amino-1-(5-(2-phenylethyleneoxy)pentyl)piperidine, and triethylamine essentially as described above in Example 1, Scheme A, step b.

Scheme A, step c: 2-[Trans-(4-aminocyclohexyl)amino]-6-[4-(1-(5-(2-phenylethyleneoxy)pentyl))piperidinylamino]-9-cyclopentylpurine 2-[Trans-(4-aminocyclohexyl)amino]-6-[4-(1-(5-(2-phenylethyleneoxy)pentyl))piperidinylamino]-9-cyclopentylpurine is prepared from 2-chloro-6-[4-(1-(5-(2-phenylethyleneoxy)pentyl))piperidinylamino]-9-cyclopentylpurine essentially as described in Example 1, Scheme A, step c.

EXAMPLE 87

2-[Trans-(4-aminocyclohexyl)amino]-6-[4-(1-(5-(3-phenylpropyleneoxy)pentyl))piperidinylamino]-9-cyclopentylpurine Preparation of 4-Amino-1-(5-(3-phenylpropyleneoxy)pentyl)piperidine Method 1

Scheme B, step a: 4-Carboxamide-1-(5-(3-phenylpropyleneoxy)pentyl)piperidine

4-Carboxamide-1-(5-(3-phenylpropyleneoxy)pentyl)piperidine may be prepared from isonipecotamide and 1-chloro-5-(3-phenylpropyleneoxy)pentane essentially as described above in Example 38, Scheme B, step a.

Scheme B, step b: 4-Amino-1-(5-(3-phenylpropyleneoxy)pentyl)piperidine

4-Amino-1-(5-(3-phenylpropyleneoxy)pentyl)piperidine is prepared from 4-carboxamide-1-(5-(3-phenylpropyleneoxy)pentyl)piperidine essentially as described above in Example 38, Scheme B, step b.

Method 2

Scheme C, step a: 1-(5-(3-Phenylpropyleneoxy)pentyl)-4-piperidone 1-(5-(3-Phenylpropyleneoxy)pentyl)-4-piperidone is prepared from 4-piperidone and 1-chloro-5-(3-phenylpropyleneoxy)pentane essentially as described above in Example 38, Scheme C, step a.

Scheme C, step b: 1-(5-(3-Phenylpropyleneoxy)pentyl)-4-piperidone oxime 1-(5-(3-Phenylpropyleneoxy)pentyl)-4-piperidone oxime is prepared from 1-(5-(3-phenylpropyleneoxy)pentyl)-4-piperidone and hydroxylamine hydrochloride essentially as described above in Example 38, Scheme C, step b.

Scheme C, step c: 4-Amino-1-(5-(3-phenylpropyleneoxy)pentyl)piperidine

4-Amino-1-(5-(3-phenylpropyleneoxy)pentyl)piperidine is prepared from 1-(5-(3-phenylpropyleneoxy)pentyl)-4-piperidone oxime essentially as described above in Example 38, Scheme C, step c.

Scheme A, step b: 2-Chloro-6-[4-(1-(5-(3-phenylpropyleneoxy)pentyl))piperidinylamino]-9-cyclopentylpurine 2-Chloro-6-[4-(1-(5-(3-phenylpropyleneoxy)pentyl))piperidinylamino]-9-cyclopentylpurine is prepared from 2,6-dichloro-9-cyclopentylpurine, 4-amino-1-(5-(3-phenylpropyleneoxy)pentyl)piperidine, and triethylamine essentially as described above in Example 1, Scheme A, step b.

Scheme A, step c: 2-[Trans-(4-aminocyclohexyl)amino]-6-[4-(1-(5-(3-phenylpropyleneoxy)pentyl))piperidinylamino]-9-cyclopentylpurine 2-[Trans-(4-aminocyclohexyl)amino]-6-[4-(1-(5-(3-phenylpropyleneoxy)pentyl))piperidinylamino]-9-cyclopentylpurine is prepared from 2-chloro-6-[4-(1-(5-(3-phenylpropyleneoxy)pentyl))piperidinylamino]-9-cyclopentylpurine essentially as described in Example 1, Scheme A, step c.

EXAMPLE 88

2-[Trans-(4-aminocyclohexyl)amino]-6-[4-(1-(5-(4-phenylbutyleneoxy)pentyl))piperidinylamino]-9-cyclopentylpurine Preparation of 4-Amino-1-(5-(4-phenylbutyleneoxy)pentyl)piperidine Method 1

Scheme B, step a: 4-Carboxamide-1-(5-(4-phenylbutyleneoxy)pentyl)piperidine

4-Carboxamide-1-(5-(4-phenylbutyleneoxy)pentyl)piperidine may be prepared from isonipecotamide and 1-chloro-5-(4-phenylbutyleneoxy)pentane essentially as described above in Example 38, Scheme B, step a.

Scheme B step b: 4-Amino-1-(5-(4-phenylbutyleneoxy)pentyl)piperidine

4-Amino-1-(5-(4-phenylbutyleneoxy)pentyl)piperidine is prepared from 4-carboxamide-1-(5-(4-phenylbutyleneoxy)pentyl)piperidine essentially as described above in Example 38, Scheme B, step b.

Method 2

Scheme C, step a: 1-(5-(4-Phenylbutyleneoxy)pentyl)-4-piperidone 1-(5-(4-Phenylbutyleneoxy)pentyl)-4-piperidone is prepared from 4-piperidone and 1-chloro-5-(4-phenylbutyleneoxy)pentane essentially as described above in Example 38, Scheme C, step a.

Scheme C, step b: 1-(5-(4-Phenylbutyleneoxy)pentyl)-4-piperidone oxime 1-(5-(4-Phenylbutyleneoxy)pentyl)-4-piperidone oxime is prepared from 1-(5-(4-phenylbutyleneoxy)pentyl)-4-piperidone and hydroxylamine hydrochloride essentially as described above in Example 38, Scheme C, step b.

Scheme C, step c: 4-Amino-1-(5-(4-phenylbutyleneoxy)pentyl)piperidine

4-Amino-1-(5-(4-phenylbutyleneoxy)pentyl)piperidine is prepared from 1-(5-(4-phenylbutyleneoxy)pentyl)-4-piperidone oxime essentially as described above in Example 38, Scheme C, step c.

Scheme A, step b: 2-Chloro-6-[4-(1-(5-(4-phenylbutyleneoxy)pentyl))piperidinylamino]-9-cyclopentylpurine 2-Chloro-6-[4-(1-(5-(4-phenylbutyleneoxy)pentyl))piperidinylamino]-9-cyclopentylpurine is prepared from 2,6-dichloro-9-cyclopentylpurine, 4-amino-1-(5-(4-phenylbutyleneoxy)pentyl)piperidine, and triethylamine essentially as described above in Example 1, Scheme A, step b.

Scheme A, step c: 2-[Trans-(4-aminocyclohexyl)amino]-6-[4-(1-(5-(4-phenylbutyleneoxy)pentyl)piperidinylamino]-9-cyclopentylpurine 2-[Trans-(4-aminocyclohexyl)amino]-6-[4-(1-(5-(4-phenylbutyleneoxy)pentyl))piperidinylamino]-9- cyclopentylpurine is prepared from 2-chloro-6-[4-(1-(5-(4-phenylbutyleneoxy)pentyl))piperidinylamino]-9-cyclopentylpurine essentially as described in Example 1, Scheme A, step c.

EXAMPLE 89

2-[Trans-(4-aminocyclohexyl)amino]-6-[4-(1-(6-hydroxy)hexyl)piperidinylamino]-9-cyclopentylpurine Preparation of 4-Amino-1-(6-hydroxyhexyl)piperidine
Method 1
Scheme B, step a: 4-Carboxamide-1-(6-hydroxyhexyl)piperidine
  4-Carboxamide-1-(6-hydroxyhexyl)piperidine may be prepared from isonipecotamide and 6-chloro-1-hexanol essentially as described above in Example 38, Scheme B, step a.
Scheme B, step b: 4-Amino-1-(6-hydroxyhexyl)piperidine
  4-Amino-1-(6-hydroxyhexyl)piperidine is prepared from 4-carboxamide-1-(6-hydroxyhexyl)piperidine essentially as described above in Example 38, Scheme B, step b.
Method 2
Scheme C, step a: 1-(6-Hydroxyhexyl)-4-piperidone
  1-(6-Hydroxyhexyl)-4-piperidone is prepared from 4-piperidone and 6-chloro-1-hexanol essentially as described above in Example 38, Scheme C, step a.
Scheme C, step b: 1-(6-Hydroxyhexyl)-4-piperidone oxime
  1-(6-Hydroxyhexyl)-4-piperidone oxime is prepared from 1-(6-hydroxyhexyl)-4-piperidone and hydroxylamine hydrochloride essentially as described above in Example 38, Scheme C, step b.
Scheme C, step c: 4-Amino-1-(6-hydroxyhexyl)piperidine
  4-Amino-1-(6-hydroxyhexyl)piperidine is prepared from 1-(6-hydroxyhexyl)-4-piperidone oxime essentially as described above in Example 38, Scheme C, step c.
Scheme A, step b: 2-Chloro-6-[4-(1-(6-hydroxy)hexyl)piperidinylamino]-9-cyclopentylpurine
  2-Chloro-6-[4-(1-(6-hydroxy)hexyl)piperidinylamino]-9-cyclopentylpurine is prepared from 2,6-dichloro-9-cyclopentylpurine, 4-amino-1-(6-hydroxyhexyl)piperidine, and triethylamine essentially as described above in Example 1, Scheme A, step b.
Scheme A, step c: 2-[Trans-(4-aminocyclohexyl)amino]-6-[4-(1-(6-hydroxy)hexyl)piperidinylamino]-9-cyclopentylpurine
  2-[Trans-(4-aminocyclohexyl)amino]-6-[4-(1-(6-hydroxy)hexyl)piperidinylamino]-9-cyclopentylpurine is prepared from 2-chloro-6-[4-(1-(6-hydroxy)hexyl)piperidinylamino]-9-cyclopentylpurine essentially as described in Example 1, Scheme A, step c.

EXAMPLE 90

2-[Trans-(4-aminocyclohexyl)amino]-6-[4-(1-(6-methoxy)hexyl)piperidinylamino]-9-cyclopentylpurine Preparation of 4-Amino-1-(6-methoxyhexyl)piperidine
Method 1
Scheme B, step a: 4-Carboxamide-1-(6-methoxyhexyl)piperidine
  4-Carboxamide-1-(6-methoxyhexyl)piperidine may be prepared from isonipecotamide and 1-chloro-6-methoxyhexane essentially as described above in Example 38, Scheme B, step a.
Scheme B, step b: 4-Amino-1-(6-methoxyhexyl)piperidine
  4-Amino-1-(6-methoxyhexyl)piperidine is prepared from 4-carboxamide-1-(6-methoxyhexyl)piperidine essentially as described above in Example 38, Scheme B, step b.
Method 2
Scheme C, step a: 1-(6-Methoxyhexyl)-4-piperidone
  1-(6-Methoxyhexyl)-4-piperidone is prepared from 4-piperidone and 1-chloro-6-methoxyhexane essentially as described above in Example 38, Scheme C, step a.
Scheme C, step b: 1-(6-Methoxyhexyl)-4-piperidone oxime
  1-(6-Methoxyhexyl)-4-piperidone oxime is prepared from 1-(6-methoxyhexyl)-4-piperidone and hydroxylamine hydrochloride essentially as described above in Example 38, Scheme C, step b.
Scheme C, step c: 4-Amino-1-(6-methoxyhexyl)piperidine
  4-Amino-1-(6-methoxyhexyl)piperidine is prepared from 1-(6-methoxyhexyl)-4-piperidone oxime essentially as described above in Example 38, Scheme C, step c.
Scheme A, step b: 2-Chloro-6-[4-(1-(6-methoxy)hexyl)piperidinylamino]-9-cyclopentylpurine
  2-Chloro-6-[4-(1-(6-methoxy)hexyl)piperidinylamino]-9-cyclopentylpurine is prepared from 2,6-dichloro-9-cyclopentylpurine, 4-amino-1-(6-methoxyhexyl)piperidine, and triethylamine essentially as described above in Example 1, Scheme A, step b.
Scheme A, step c: 2-[Trans-(4-aminocyclohexyl)amino]-6-[4-(1-(6-methoxy)hexyl)piperidinylamino]-9-cyclopentylpurine
  2-[Trans-(4-aminocyclohexyl)amino]-6-[4-(1-(6-methoxy)hexyl)piperidinylamino]-9-cyclopentylpurine is prepared from 2-chloro-6-[4-(1-(6-methoxy)hexyl)piperidinylamino]-9-cyclopentylpurine essentially as described in Example 1, Scheme A, step c.

EXAMPLE 91

2-[Trans-(4-aminocyclohexyl)amino]-6-[4-(1-(6-ethoxy)hexyl)piperidinylamino]-9-cyclopentylpurine Preparation of 4-Amino-1-(6-ethoxyhexyl)piperidine
Method 1
Scheme B, step a: 4-Carboxamide-1-(6-ethoxyhexyl)piperidine
  4-Carboxamide-1-(6-ethoxyhexyl)piperidine may be prepared from isonipecotamide and 1-chloro-6-ethoxyhexane essentially as described above in Example 38, Scheme B, step a.
Scheme B, step b: 4-Amino-1-(6-ethoxyhexyl)piperidine
  4-Amino-1-(6-ethoxyhexyl)piperidine is prepared from 4-carboxamide-1-(6-ethoxyhexyl)piperidine essentially as described above in Example 38, Scheme B, step b.
Method 2
Scheme C, step a: 1-(6-Ethoxyhexyl)-4-piperidone
  1-(6-Ethoxyhexyl)-4-piperidone is prepared from 4-piperidone and 1-chloro-6-ethoxyhexane essentially as described above in Example 38, Scheme C, step a.
Scheme C, step b: 1-(6-Ethoxyhexyl)-4-piperidone oxime
  1-(6-Ethoxyhexyl)-4-piperidone oxime is prepared from 1-(6-ethoxyhexyl)-4-piperidone and hydroxylamine hydrochloride essentially as described above in Example 38, Scheme C, step b.
Scheme C, step c: 4-Amino-1-(6-ethoxyhexyl)piperidine
  4-Amino-1-(6-ethoxyhexyl)piperidine is prepared from 1-(6-ethoxyhexyl)-4-piperidone oxime essentially as described above in Example 38, Scheme C, step c.
Scheme A, step b: 2-Chloro-6-[4-(1-(6-ethoxy)hexyl)piperidinylamino]-9-cyclopentylpurine
  2-Chloro-6-[4-(1-(6-ethoxy)hexyl)piperidinylamino]-9-cyclopentylpurine is prepared from 2,6-dichloro-9-cyclopentylpurine, 4-amino-1-(6-ethoxyhexyl)piperidine, and triethylamine essentially as described above in Example 1, Scheme A, step b.

Scheme A, step c: 2-[Trans-(4-aminocyclohexyl)amino]-6-[4-(1-(6-ethoxy)hexyl)piperidinylamino]-9-cyclopentylpurine 2-[Trans-(4-aminocyclohexyl)amino]-6-[4-(1-(6-ethoxy)hexyl)piperidinylamino]-9-cyclopentylpurine is prepared from 2-chloro-6-[4-(1-(6-ethoxy)hexyl)piperidinylamino]-9-cyclopentylpurine essentially as described in Example 1, Scheme A, step c.

EXAMPLE 92

2-[Trans-(4-aminocyclohexyl)amino]-6-[4-(1-(6-propoxy)hexyl)piperidinylamino]-9-cyclopentylpurine Preparation of 4-Amino-1-(6-propoxyhexyl)piperidine
Method 1
Scheme B, step a: 4-Carboxamide-1-(6-propoxyhexyl)piperidine 4-Carboxamide-1-(6-propoxyhexyl)piperidine may be prepared from isonipecotamide and 1-chloro-6-propoxyhexane essentially as described above in Example 38, Scheme B, step a.

Scheme B, step b: 4-Amino-1-(6-propoxyhexyl)piperidine

4-Amino-1-(6-propoxyhexyl)piperidine is prepared from 4-carboxamide-1-(6-propoxyhexyl)piperidine essentially as described above in Example 38, Scheme B, step b.
Method 2
Scheme C, step a: 1-(6-Propoxyhexyl)-4-piperidone 1-(6-Propoxyhexyl)-4-piperidone is prepared from 4-piperidone and 1-chloro-6-propoxyhexane essentially as described above in Example 38, Scheme C, step a.

Scheme C, step b: 1-(6-Propoxyhexyl)-4-piperidone oxime 1-(6-Propoxyhexyl)-4-piperidone oxime is prepared from 1-(6-propoxyhexyl)-4-piperidone and hydroxylamine hydrochloride essentially as described above in Example 38, Scheme C, step b.

Scheme C, step, c: 4-Amino-1-(6-propoxyhexyl)piperidine

4-Amino-1-(6-propoxyhexyl)piperidine is prepared from 1-(6-propoxyhexyl)-4-piperidone oxime essentially as described above in Example 38, Scheme C, step c.

Scheme A, step b: 2-Chloro-6-[4-(1-(6-propoxy)hexyl)piperidinylamino]-9-cyclopentylpurine 2-Chloro-6-[4-(1-(6-propoxy)hexyl)piperidinylamino]-9-cyclopentylpurine is prepared from 2,6-dichloro-9-cyclopentylpurine, 4-amino-1-(6-propoxyhexyl)piperidine, and triethyl amine essentially as described above in Example 1, Scheme A, step b.

Scheme A, step c: 2-[Trans-(4-aminocyclohexyl)amino]-6-[4-(1-(6-propoxy)hexyl)piperidinylamino]-9-cyclopentylpurine 2-[Trans-(4-aminocyclohexyl)amino]-6-[4-(1-(6-propoxy)hexyl)piperidinylamino]-9-cyclopentylpurine is prepared from 2-chloro-6-[4-(1-(6-propoxy)hexyl)piperidinylamino]-9-cyclopentylpurine essentially as described in Example 1, Scheme A, step c.

EXAMPLE 93

2-[Trans-(4-aminocyclohexyl)amino]-6-[4-(1-(6-butoxy)hexyl)piperidinylamino]-9-cyclopentylpurine
Preparation of 4-Amino-1-(6-butoxyhexyl)piperidine
Method 1
Scheme B, step a: 4-Carboxamide-1-(6-butoxyhexyl)piperidine 4-Carboxamide-1-(6-butoxyhexyl)piperidine may be prepared from isonipecotamide and 1-chloro-6-butoxyhexane essentially as described above in Example 38, Scheme B, step a.

Scheme B, step b: 4-Amino-1-(6-butoxyhexyl)piperidine

4-Amino-1-(6-butoxyhexyl)piperidine is prepared from 4-carboxamide-1-(6-butoxyhexyl)piperidine essentially as described above in Example 38, Scheme B, step b.
Method 2
Scheme C, step a: 1-(6-Butoxyhexyl)-4-piperidone 1-(6-Butoxyhexyl)-4-piperidone is prepared from 4-piperidone and 1-chloro-6-butoxyhexane essentially as described above in Example 38, Scheme C, step a.

Scheme C, step b: 1-(6-Butoxyhexyl)-4-piperidone oxime 1-(6-Butoxyhexyl)-4-piperidone oxime is prepared from 1-(6-butoxyhexyl)-4-piperidone and hydroxylamine hydrochloride essentially as described above in Example 38, Scheme C, step b.

Scheme C, step c: 4-Amino-1-(6-butoxyhexyl)piperidine

4-Amino-1-(6-butoxyhexyl)piperidine is prepared from 1-(6-butoxyhexyl)-4-piperidone oxime essentially as described above in Example 38, Scheme C, step c.

Scheme A, step b: 2-Chloro-6-[4-(1-(6-butoxy)hexyl)piperidinylamino]-9-cyclopentylpurine 2-Chloro-6-[4-(1-(6-butoxy)hexyl)piperidinylamino]-9-cyclopentylpurine is prepared from 2,6-dichloro-9-cyclopentylpurine, 4-amino-1-(6-butoxyhexyl)piperidine, and triethylamine essentially as described above in Example 1, Scheme A, step b.

Scheme A, step c: 2-[Trans-(4-aminocyclohexyl)amino]-6-[4-(1-(6-butoxy)hexyl)piperidinylamino]-9-cyclopentylpurine 2-[Trans-(4-aminocyclohexyl)amino]-6-[4-(1-(6-butoxy)hexyl)piperidinylamino]-9-cyclopentylpurine is prepared from 2-chloro-6-[4-(1-(6-butoxy)hexyl)piperidinylamino]-9-cyclopentylpurine essentially as described in Example 1, Scheme A, step c.

EXAMPLE 94

2-[Trans-(4-aminocyclohexyl)amino]-6-[4-(1-(6-benzyloxy)hexyl)piperidinylamino]-9-cyclopentylpurine Preparation of 4-Amino-1-(6-benzyloxyhexyl)piperidine
Method 1
Scheme B, step a: 4-Carboxamide-1-(6-Benzyloxyhexyl)piperidine 4-Carboxamide-1-(6-Benzyloxyhexyl)piperidine may be prepared from isonipecotamide and 1-chloro-6-benzyloxyhexane essentially as described above in Example 38, Scheme B, step a.

Scheme B, step b: 4-Amino-1-(6-benzyloxyhexyl)piperidine

4-Amino-1-(6-benzyloxyhexyl)piperidine is prepared from 4-carboxamide-1-(6-benzyloxyhexyl)piperidine essentially as described above in Example 38, Scheme B, step b.
Method 2
Scheme C, step a: 1-(6-Benzyloxyhexyl)-4-piperidone 1-(6-Benzyloxyhexyl)-4-piperidone is prepared from 4-piperidone and 1-chloro-6-benzyloxyhexane essentially as described above in Example 38, Scheme C, step a.

Scheme C, step b: 1-(6-Benzyloxyhexyl)-4-piperidone oxime 1-(6-Benzyloxyhexyl)-4-piperidone oxime is prepared from 1-(6-benzyloxyhexyl)-4-piperidone and hydroxylamine hydrochloride essentially as described above in Example 38, Scheme C, step b.

Scheme C, step c: 4-Amino-1-(6-benzyloxyhexyl)piperidine

4-Amino-1-(6-benzyloxyhexyl)piperidine is prepared from 1-(6-benzyloxyhexyl)-4-piperidone oxime essentially as described above in Example 38, Scheme C, step c.

Scheme A, step b: 2-Chloro-6-[4-(1-(6-benzyloxy)hexyl)
piperidinylamino]-9-cyclopentylpurine 2-Chloro-6-[4-(1-(6-benzyloxy)hexyl)piperidinylamino]-9-cyclopentylpurine is prepared from 2,6-dichloro-9-cyclopentylpurine, 4-amino-1-(6-benzyloxyhexyl) piperidine, and triethylamine essentially as described above in Example 1, Scheme A, step b.

Scheme A, step c: 2-[Trans-(4-aminocyclohexyl)amino]-6-[4-(1-(6-benzyloxy)hexyl)piperidinylamino]-9-cyclopentylpurine 2-[Trans-(4-aminocyclohexyl)amino]-6-[4-(1-(6-benzyloxy)hexyl)piperidinylamino]-9-cyclopentylpurine is prepared from 2-chloro-6-[4-(1-(6-benzyloxy)hexyl)piperidinylamino]-9-cyclopentylpurine essentially as described in Example 1, Scheme A, step c.

EXAMPLE 95

2-[Trans-(4-aminocyclohexyl)amino]-6-[4-(1-(6-(2-phenylethyleneoxy)hexyl)piperidinylamino]-9-cyclopentylpurine Preparation of 4-Amino-1-(6-(2-phenylethyleneoxy)hexyl) piperidine Method 1

Scheme B, step a: 4-Carboxamide-1-(6-(2-phenylethyleneoxy)hexyl)piperidine

4-Carboxamide-1-(6-(2-phenylethyleneoxy)hexyl) piperidine may be prepared from isonipecotamide and 1-chloro-6-(2-phenylethyleneoxy)hexane essentially as described above in Example 38, Scheme B, step a.

Scheme B, step b: 4-Amino-1-(6-(2-phenylethyleneoxy)hexyl)piperidine

4-Amino-1-(6-(2-phenylethyleneoxy)hexyl)piperidine is prepared from 4-carboxamide-1-(6-(2-phenylethyleneoxy)hexyl)piperidine essentially as described above in Example 38, Scheme B, step b.

Method 2

Scheme C, step a: 1-(6-(2-Phenylethyleneoxy)hexyl)-4-piperidone 1-(6-(2-Phenylethyleneoxy)hexyl)-4-piperidone is prepared from 4-piperidone and 1-chloro-6-(2-phenylethyleneoxy)hexane essentially as described above in Example 38, Scheme C, step a.

Scheme C, step b: 1-(6-(2-Phenylethyleneoxy)hexyl)-4-piperidone oxime 1-(6-(2-Phenylethyleneoxy)hexyl)-4-piperidone oxime is prepared from 1-(6-(2-phenylethyleneoxy)hexyl)-4-piperidone and hydroxylamine hydrochloride essentially as described above in Example 38, Scheme C, step b.

Scheme C, step c: 4-Amino-1-(6-(2-phenylethyleneoxy) hexyl)piperidine

4-Amino-1-(6-(2-phenylethyleneoxy)hexyl)piperidine is prepared from 1-(6-(2-phenylethyleneoxy)hexyl)-4-piperidone oxime essentially as described above in Example 38, Scheme C, step c.

Scheme A, step b: 2-Chloro-6-[4-(1-(6-(2-phenylethyleneoxy)hexyl)piperidinylamino]-9-cyclopentylpurine 2-Chloro-6-[4-(1-(6-(2-phenylethyleneoxy)hexyl) piperidinylamino]-9-cyclopentylpurine is prepared from 2,6-dichloro-9-cyclopentylpurine, 4-amino-1-(6-(2-phenylethyleneoxy)hexyl)piperidine, and triethylamine essentially as described above in Example 1, Scheme A, step b.

Scheme A, step c: 2-[Trans-(4-aminocyclohexyl)amino]-6-[4-(1-(6-(2-phenylethyleneoxy)hexyl)piperidinylamino]-9-cyclopentylpurine 2-[Trans-(4-aminocyclohexyl)amino]-6-[4-(1-(6-(2-phenylethyleneoxy)hexyl)piperidinylamino]-9-cyclopentylpurine is prepared from 2-chloro-6-[4-(1-(6-(2-phenylethyleneoxy)hexyl)piperidinylamino]-9-cyclopentylpurine essentially as described in Example 1, Scheme A, step c.

EXAMPLE 96

2-[Trans-(4-aminocyclohexyl)amino]-6-[4-(1-(6-(3-phenylpropyleneoxy)hexyl)piperidinylamino]-9-cyclopentylpurine Preparation of 4-Amino-1-(6-(3-phenylpropyleneoxy) hexyl)piperidine Method 1

Scheme B, step a: 4-Carboxamide-1-(6-(3-phenylpropyleneoxy)hexyl)piperidine

4-Carboxamide-1-(6-(3-phenylpropyleneoxy)hexyl) piperidine may be prepared from isonipecotamide and 1-chloro-6-(3-phenylpropyleneoxy)hexane essentially as described above in Example 38, Scheme B, step a.

Scheme B, step b: 4-Amino-1-(6-(3-phenylpropyleneoxy) hexyl)piperidine

4-Amino-1-(6-(3-phenylpropyleneoxy)hexyl)piperidine is prepared from 4-carboxamide-1-(6-(3-phenylpropyleneoxy)hexyl)piperidine essentially as described above in Example 38, Scheme B, step b.

Method 2

Scheme C, step a: 1-(6-(3-Phenylpropyleneoxy)hexyl-4-piperidone 1-(6-(3-Phenylpropyleneoxy)hexyl-4-piperidone is prepared from 4-piperidone and 1-chloro-6-(3-phenylpropyleneoxy)hexane essentially as described above in Example 38, Scheme C, step a.

Scheme C, step b: 1-(6-(3-Phenylpropyleneoxy)hexyl-4-piperidone oxime 1-(6-(3-Phenylpropyleneoxy)hexyl-4-piperidone oxime is prepared from 1-(6-(3-phenylpropyleneoxy)hexyl-4-piperidone and hydroxylamine hydrochloride essentially as described above in Example 38, Scheme C, step b.

Scheme C, step c: 4-Amino-1-(6-(3-phenylpropyleneoxy) hexyl)piperidine

4-Amino-1-(6-(3-phenylpropyleneoxy)hexyl)piperidine is prepared from 1-(6-(3-phenylpropyleneoxy)hexyl-4-piperidone oxime essentially as described above in Example 38, Scheme C, step c.

Scheme A, step b: 2-Chloro-6-[4-(1-(6-(3-phenylpropyleneoxy)hexyl)piperidinylamino]-9-cyclopentylpurine 2-Chloro-6-[4-(1-(6-(3-phenylpropyleneoxy)hexyl) piperidinylamino]-9-cyclopentylpurine is prepared from 2,6-dichloro-9-cyclopentylpurine, 4-amino-1-(6-(3-phenylpropyleneoxy)hexyl)piperidine, and triethylamine essentially as described above in Example 1, Scheme A, step b.

Scheme A, step c: 2-[Trans-(4-aminocyclohexyl)amino]-6-[4-(1-(6-(3-phenylpropyleneoxy)hexyl)piperidinylamino]-9-cyclopentylpurine 2-[Trans-(4-aminocyclohexyl)amino]-6-[4-(1-(6-(3-phenylpropyleneoxy)hexyl)piperidinylamino]-9-cyclopentylpurine is prepared from 2-chloro-6-[4-(1-(6-(3-phenylpropyleneoxy)hexyl)piperidinylamino]-9-cyclopentylpurine essentially as described in Example 1, Scheme A, step c.

EXAMPLE 97

2-[Trans-(4-aminocyclohexyl)amino]-6-[4-(1-(6-(4-phenylbutyleneoxy)hexyl)piperidinylamino]-9-cyclopentylpurine Preparation of 4-Amino-1-(6-(4-phenylbutyleneoxy)hexyl)piperidine Method 1

Scheme B, step a: 4-Carboxamide-1-(6-(4-phenylbutyleneoxy)hexyl)piperidine

4-Carboxamide-1-(6-(4-phenylbutyleneoxy)hexyl)piperidine may be prepared from isonipecotamide and 1-chloro-6-(4-phenylbutyleneoxy)hexane essentially as described above in Example 38, Scheme B, step a.

Scheme B, step b: 4-Amino-1-(6-(4-phenylbutyleneoxy)hexyl)piperidine

4-Amino-1-(6-(4-phenylbutyleneoxy)hexyl)piperidine is prepared from 4-carboxamide-1-(6-(4-phenylbutyleneoxy)hexyl)piperidine essentially as described above in Example 38, Scheme B, step b.

Method 2

Scheme C, step a: 1-(6-(4-Phenylbutyleneoxy)hexyl)-4-piperidone 1-(6-(4-Phenylbutyleneoxy)hexyl)-4-piperidone is prepared from 4-piperidone and 1-chloro-(4-phenylbutyleneoxy)hexane essentially as described above in Example 38, Scheme C, step a.

Scheme C, step b: 1-(6-(4-Phenylbutyleneoxy)hexyl)-4-piperidone oxime 1-(6-(4-Phenylbutyleneoxy)hexyl)-4-piperidone oxime is prepared from 1-(6-(4-phenylbutyleneoxy)hexyl)-4-piperidone and hydroxylamine hydrochloride essentially as described above in Example 38, Scheme C, step b.

Scheme C, step c: 4-Amino-1-(6-(4-phenylbutyleneoxy)hexyl)piperidine

4-Amino-1-(6-(4-phenylbutyleneoxy)hexyl)piperidine is prepared from 1-(6-(4-phenylbutyleneoxy)hexyl)-4-piperidone oxime essentially as described above in Example 38, Scheme C, step c.

Scheme A, step b: 2-Chloro-6-[4-(1-(6-(4-phenylbutyleneoxy)hexyl)-1piperidinylamino]-9-cyclopentyl urine 2-Chloro-6-[4-(1-(6-(4-phenylbutyleneoxy)hexyl)piperidinylamino]-9-cyclopentylpurine is prepared from 2,6-dichloro-9-cyclopentylpurine, 4-amino-1-(6-(4-phenylbutyleneoxy)hexyl)piperidine, and triethylamine essentially as described above in Example 1, Scheme A, step b.

Scheme A, step c: 2-[Trans-(4-aminocyclohexyl)amino]-6-[4-(1-(6-(4-phenylbutyleneoxy)hexyl)piperidinylamino]-9-cyclopentylpurine 2-[Trans-(4-aminocyclohexyl)amino]-6-[4-(1-(6-(4-phenylbutyleneoxy)hexyl)piperidinylamino]9-cyclopentylpurine is prepared from 2-chloro-6-[4-(1-(6-(4-phenylbutyleneoxy)hexyl)piperidinylamino]-9-cyclopentylpurine essentially as described in Example 1, Scheme A, step c.

EXAMPLE 98

2-[Trans-(4-aminocyclohexyl)amino]-6-[4-(1-(allyl)piperidinylamino]-9-cyclopentylpurine Preparation of 4-Amino-1-(allyl)piperidine Method 1

Scheme B, step a: 4-Carboxamide-1-(allyl)piperidine

4-Carboxamide-1-(allyl)piperidine may be prepared from isonipecotamide and allyl chloride essentially as described above in Example 38, Scheme B, step a.

Scheme B, step b: 4-Amino-1-(allyl)piperidine

4-Amino-1-(allyl)piperidine is prepared from 4-carboxamide-1-(allyl)piperidine essentially as described above in Example 38, Scheme B, step b.

Method 2

Scheme C, step a: 1-(allyl)-4-piperidone 1-(allyl)-4-piperidone is prepared from 4-piperidone and allyl chloride essentially as described above in Example 38, Scheme C, step a.

Scheme C, step b: 1-(allyl)-4-piperidone oxime 1-(allyl)-4-piperidone oxime is prepared from 1-(allyl)-4-piperidone and hydroxylamine hydrochloride essentially as described above in Example 38, Scheme C, step b.

Scheme C, step c: 4-Amino-1-(allyl)piperidine

4-Amino-1-(allyl)piperidine is prepared from 1-(allyl)-4-piperidone oxime essentially as described above in Example 38, Scheme C, step c.

Scheme A, step b: 2-Chloro-6-[4-(1-(allyl)piperidinylamino]-9-cyclopentylpurine

2-Chloro-6-[4-(1-(allyl)piperidinylamino]-9-cyclopentylpurine is prepared from 2,6-dichloro-9-cyclopentylpurine, 4-amino-1-(allyl)piperidine, and triethylamine essentially as described above in Example 1, Scheme A, step b.

Scheme A, step c: 2-[Trans-(4-aminocyclohexyl)amino]-6-[4-(1-(allyl)piperidinylamino]-9-cyclopentylpurine 2-[Trans-(4-aminocyclohexyl)amino]-6-[4-(1-(allyl)piperidinylamino]-9-cyclopentylpurine is prepared from 2-chloro-6-[4-(1-(allyl)piperidinylamino]-9-cyclopentylpurine essentially as described in Example 1, Scheme A, step c.

EXAMPLE 99

2-[Trans-(4-aminocyclohexyl)amino]-6-[4-(1-(2-(2-hydroxyethyleneoxy)ethyl))piperidinylamino]-9-cyclopentylpurine Preparation of 4-Amino-1-(2-(2-hydroxyethyleneoxy)ethyl)piperidine Method 1

Scheme B, step a: 4-Carboxamide-1-(2-(2-hydroxyethyleneoxy)ethyl)piperidine

4-Carboxamide-1-(2-(2-hydroxyethyleneoxy)ethyl)piperidine may be prepared from isonipecotamide and 2-(2-chloroethoxy)ethanol essentially as described above in Example 38, Scheme B, step a.

Scheme B, step b: 4-Amino-1-(2-(2-hydroxyethyleneoxy)ethyl)piperidine

4-Amino-1-(2-(2-hydroxyethyleneoxy)ethyl)piperidine is prepared from 4-carboxamide-1-(2-(2-hydroxyethyleneoxy)ethyl)piperidine essentially as described above in Example 38, Scheme B, step b.

Method 2

Scheme C, step a: 1-(2-(2-Hydroxyethyleneoxy)ethyl)-4-piperidone 1-(2-(2-Hydroxyethyleneoxy)ethyl)-4-piperidone is prepared from 4-piperidone and 2-(2-chloroethoxy)ethanol essentially as described above in Example 38, Scheme C, step a.

Scheme C, step b: 1-(2-(2-Hydroxyethyleneoxy)ethyl)-4-piperidone oxime 1-(2-(2-Hydroxyethyleneoxy)ethyl)-4-piperidone oxime is prepared from 1-(2-(2-hydroxyethyleneoxy)ethyl)-4-piperidone and hydroxylamine hydrochloride essentially as described above in Example 38, Scheme C, step b.

Scheme C, step c: 4-Amino-1-(2-(2-hydroxyethyleneoxy)ethyl)piperidine

4-Amino-1-(2-(2-hydroxyethyleneoxy)ethyl)piperidine is prepared from 1-(2-(2-hydroxyethyleneoxy)ethyl)-4- piperidone oxime essentially as described above in Example 38, Scheme C, step c.

Scheme A, step b: 2-Chloro-6-[4-(1-(2-(2-hydroxyethyleneoxy ethyl))piperidinylamino]-9-cyclopentylpurine 2-Chloro-6-[4-(1-(2-(2-hydroxyethyleneoxy)ethyl))piperidinylamino]-9-cyclopentylpurine is prepared from 2,6-dichloro-9-cyclopentylpurine, 4-amino-1-(2-(2-hydroxyethyleneoxy)ethyl)piperidine, and triethylamine essentially as described above in Example 1, Scheme A, step b.

Scheme A, step c: 2-[Trans-(4-aminocyclohexyl)amino]-6-[4-(1-(2-(2-hydroxyethyleneoxy)piperidinylamino]-purine 2-[Trans-(4-aminocyclohexyl)amino]-6-[4-(1-(2-(2-hydroxyethyleneoxy)ethyl))piperidinylamino]-9-cyclopentylpurine is prepared from 2-chloro-6-[4-(1-(2-(2-hydroxyethyleneoxy)ethyl))piperidinylamino]-9-cyclopentylpurine essentially as described in Example 1, Scheme A, step c.

EXAMPLE 100

2-[Trans-(4-aminocyclohexyl)amino]-6-[4-(1-(2-N,N-dimethylaminoethyl)piperidinylamino]-9-cyclopentylpurine Preparation of 4-Amino-1-(2-N,N-dimethylaminoethyl)piperidine
Method 1
Scheme B, step a: 4-Carboxamide-1-(2-N,N-dimethylaminoethyl)piperidine 4-Carboxamide-1-(2-N,N-dimethylaminoethyl)piperidine may be prepared from isonipecotamide and 2-N,N-dimethylaminoethyl chloride essentially as described above in Example 38, Scheme B, step a.

Scheme B, step b: 4-Amino-1-(2-N,N-dimethylaminoethyl)piperidine

4-Amino-1-(2-N,N-dimethylaminoethyl)piperidine is prepared from 4-carboxamide-1-(2-N,N-dimethylaminoethyl)piperidine essentially as described above in Example 38, Scheme B, step b.

Method 2
Scheme C, step a: 1-(2-N,N-dimethylaminoethyl)-4-piperidone 1-(2-N,N-dimethylaminoethyl)-4-piperidone is prepared from 4-piperidone and 2-N,N-dimethylaminoethyl chloride essentially as described above in Example 38, Scheme C, step a.

Scheme C, step b: 1-(2-N,N-dimethylaminoethyl)-4-piperidone oxime 1-(2-N,N-dimethylaminoethyl)-4-piperidone oxime is prepared from 1-(2-N,N-dimethylaminoethyl)-4-piperidone and hydroxylamine hydrochloride essentially as described above in Example 38, Scheme C, step b.

Scheme C, step c: 4-Amino-1-(2-N,N-dimethylaminoethyl)piperidine

4-Amino-1-(2-N,N-dimethylaminoethyl)piperidine is prepared from 1-(2-N,N-dimethylaminoethyl)-4-piperidone oxime essentially as described above in Example 38, Scheme C, step c.

Scheme A, step b: 2-Chloro-6-[4-(1-(2-N,N-dimethylaminoethyl))piperidinylamino]-9-cyclopentylpurine 2-Chloro-6-[4-(1-(2-N,N-dimethylaminoethyl))piperidinylamino]-9-cyclopentylpurine is prepared from 2,6-dichloro-9-cyclopentylpurine, 4-amino-1-(2-N,N-dimethylaminoethyl)piperidine, and triethylamine essentially as described above in Example 1, Scheme A, step b.

Scheme A, step c: 2-[Trans-(4-aminocyclohexyl)amino]-6-[4-(1-(2-N,N-dimethylaminoethyl))piperidinylamino]-9-cyclopentylpurine 2-[Trans-(4-aminocyclohexyl)amino]-6-[4-(1-(2-N,N-dimethylaminoethyl))piperidinylamino]-9-cyclopentylpurine is prepared from 2-chloro-6-[4-(1-(2-N,N-dimethylaminoethyl))piperidinylamino]-9-cyclopentylpurine essentially as described in Example 1, Scheme A, step c.

EXAMPLE 101

2-[Trans-(4-aminocyclohexyl)amino]-6-[4-(1-(3-N,N-dimethylaminopropyl))piperidinylamino]-9-cyclopentylpurine Preparation of 4-Amino-1-(3-N,N-dimethylaminopropyl)piperidine
Method 1
Scheme B, step a: 4-Carboxamide-1-(3-N,N-dimethylaminopropyl)piperidine 4-Carboxamide-1-(3-N,N-dimethylaminopropyl)piperidine may be prepared from isonipecotamide and 3-N,N-dimethylaminopropyl chloride essentially as described above in Example 38, Scheme B, step a.

Scheme B, step b: 4-Amino-1-(3-N,N-dimethylaminopropyl)piperidine

4-Amino-1-(3-N,N-dimethylaminopropyl)piperidine is prepared from 4-carboxamide-1-(3-N,N-dimethylaminopropyl)piperidine essentially as described above in Example 38, Scheme B, step b.

Method 2
Scheme C, step a: 1-(3-N,N-dimethylaminopropyl)-4-piperidone 1-(3-N,N-dimethylaminopropyl)-4-piperidone is prepared from 4-piperidone and 3-N,N-dimethylaminopropyl chloride essentially as described above in Example 38, Scheme C, step a.

Scheme C, step b: 1-(3-N,N-dimethylaminopropyl)-4-piperidone oxime 1-(3-N,N-dimethylaminopropyl)-4-piperidone oxime is prepared from 1-(3-N,N-dimethylaminopropyl)-4-piperidone and hydroxylamine hydrochloride essentially as described above in Example 38, Scheme C, step b.

Scheme C, step c: 4-Amino-1-(3-N,N-dimethylaminopropyl)piperidine

4-Amino-1-(3-N,N-dimethylaminopropyl)piperidine is prepared from 1-(3-N,N-dimethylaminopropyl)-4-piperidone oxime essentially as described above in Example 38, Scheme C, step c.

Scheme A, step b: 2-Chloro-6-[4-(1-(3-N,N-dimethylaminopropyl))piperidinylamino]-9-cyclopentylpurine 2-Chloro-6-[4-(1-(3-N,N-dimethylaminopropyl))piperidinylamino]-9-cyclopentylpurine is prepared from 2,6-dichloro-9-cyclopentylpurine, 4-amino-1-(3-N,N-dimethylaminopropyl)piperidine, and triethylamine essentially as described above in Example 1, Scheme A, step b.

Scheme A, step c: 2-[Trans-(4-aminocyclohexyl)amino]-6-[4-(1-(3-N,N-dimethylaminopropyl))piperidinylamino]-9-cyclopentylpurine 2-[Trans-(4-aminocyclohexyl)amino]-6-[4-(1-(3-N,N-dimethylaminopropyl))piperidinylamino]-9-cyclopentylpurine is prepared from 2-chloro-6-[4-(1-(3-N,N-dimethylaminopropyl))piperidinylamino]-9-cyclopentylpurine essentially as described in Example 1, Scheme A, step c.

EXAMPLE 102

2-[Trans-(4-aminocyclohexyl)amino]-6-[4-(1-(4-N,N-dimethylaminobutyl))piperidinylamino]-9-cyclopentylpurine Preparation of 4-Amino-1-(4-N N-dimethylaminobutyl)piperidine Method 1

Scheme B, step a: 4-Carboxamide-1-(4-N,N-dimethylaminobutyl)piperidine

4-Carboxamide-1-(4-N,N-dimethylaminobutyl)piperidine may be prepared from isonipecotamide and 3-N,N-dimethylaminobutyl chloride essentially as described above in Example 38, Scheme B, step a.

Scheme B, step b: 4-Amino-1-(4-N,N-dimethylaminobutyl)piperidine

4-Amino-1-(4-N,N-dimethylaminobutyl)piperidine is prepared from 4-carboxamide-1-(4-N,N-dimethylaminobutyl)piperidine essentially as described above in Example 38, Scheme B, step b.

Method 2

Scheme C, step a: 1-(4-N,N-dimethylaminobutyl)-4-piperidone 1-(4-N,N-dimethylaminobutyl)-4-piperidone is prepared from 4-piperidone and 3-N,N-dimethylaminobutyl chloride essentially as described above in Example 38, Scheme C, step a.

Scheme C, step b: 1-(4-N,N-dimethylaminobutyl)-4-piperidone oxime 1-(4-N,N-dimethylaminobutyl)-4-piperidone oxime is prepared from 1-(4-N,N-dimethylaminobutyl)-4-piperidone and hydroxylamine hydrochloride essentially as described above in Example 38, Scheme C, step b.

Scheme C, step c: 4-Amino-1-(4-N,N-dimethylaminobutyl)piperidine

4-Amino-1-(4-N,N-dimethylaminobutyl)piperidine is prepared from 1-(4-N,N-dimethylaminobutyl)-4-piperidone oxime essentially as described above in Example 38, Scheme C, step c.

Scheme A, step b: 2-Chloro-6-[4-(1-(4-N,N-dimethylaminobutyl))piperidinylamino]-9-cyclopentylpurine 2-Chloro-6-[4-(1-(4-N,N-dimethylaminobutyl))piperidinylamino]-9-cyclopentylpurine is prepared from 2,6-dichloro-9-cyclopentylpurine, 4-amino-1-(4-N,N-dimethylaminobutyl)piperidine, and triethylamine essentially as described above in Example 1, Scheme A, step b.

Scheme A, step c: 2-[Trans-(4-aminocyclohexyl)amino]-6-[4-(1-(4-N,N-dimethylaminobutyl))piperidinylamino]-9-cyclopentylpurine 2-[Trans-(4-aminocyclohexyl)amino]-6-[4-(1-(4-N,N-dimethylaminobutyl))piperidinylamino]-9-cyclopentylpurine is prepared from 2-chloro-6-[4-(1-(4-N,N-dimethylaminobutyl))piperidinylamino]-9-cyclopentylpurine essentially as described in Example 1, Scheme A, step c.

EXAMPLE 103

2-[Trans-(4-aminocyclohexyl)amino]-6-[4-(1-(5-N,N-dimethylaminopentyl))piperidinylamino]-9-cyclopentylpurine Preparation of 4-Amino-1-(5-N,N-dimethylaminopentyl)piperidine Method 1

Scheme B, step a: 4-Carboxamide-1-(5-N,N-dimethylaminopentyl)piperidine

4-Carboxamide-1-(5-N,N-dimethylaminopentyl)piperidine may be prepared from isonipecotamide and 5-N,N-dimethylaminopentyl chloride essentially as described above in Example 38, Scheme B, step a.

Scheme B, step b: 4-Amino-1-(5-N,N-dimethylaminopentyl)piperidine

4-Amino-1-(5-N,N-dimethylaminopentyl)piperidine is prepared from 4-carboxamide-1-(5-N,N-dimethylaminopentyl)piperidine essentially as described above in Example 38, Scheme B, step b.

Method 2

Scheme C, step a: 1-(5-N,N-dimethylaminopentyl)-4-piperidone 1-(5-N,N-dimethylaminopentyl)-4-piperidone is prepared from 4-piperidone and 5-N,N-dimethylaminopentyl chloride essentially as described above in Example 38, Scheme C, step a.

Scheme C, step b: 1-(5-N,N-dimethylaminopentyl)-4'-piperidone oxime 1-(5-N,N-dimethylaminopentyl)-4-piperidone oxime is prepared from 1-(5-N,N-dimethylaminopentyl)-4-piperidone and hydroxylamine hydrochloride essentially as described above in Example 38, Scheme C, step b.

Scheme C, step c: 4-Amino-1-(5-N,N-dimethylaminopentyl)piperidine

4-Amino-1-(5-N,N-dimethylaminopentyl)piperidine is prepared from 1-(5-N,N-dimethylaminopentyl)-4-piperidone oxime essentially as described above in Example 38, Scheme C, step c.

Scheme A, step b: 2-Chloro-6-[4-(1-(5-N,N-dimethylaminopentyl))piperidinylamino]-9-cyclopentylpurine 2-Chloro-6-[4-(1-(5-N,N-dimethylaminopentyl))piperidinylamino]-9-cyclopentylpurine is prepared from 2,6-dichloro-9-cyclopentylpurine, 4-amino-1-(5-N,N-dimethylaminopentyl)piperidine, and triethylamine essentially as described above in Example 1, Scheme A, step b.

Scheme A, step c: 2-[Trans-(4-aminocyclohexyl)amino]-6-[4-(1-(5-N,N-dimethylaminopentyl))piperidinylamino]-9-cyclopentylpurine 2-[Trans-(4-aminocyclohexyl)amino]-6-[4-(1-(5-N,N-dimethylaminopentyl))piperidinylamino]-9-cyclopentylpurine is prepared from 2-chloro-6-[4-(1-(5-N,N-dimethylaminopentyl))piperidinylamino]-9-cyclopentylpurine essentially as described in Example 1, Scheme A, step c.

EXAMPLE 104

2-[Trans-(4-aminocyclohexyl)amino]-6-[4-(1-(2-N,N-diethylaminoethyl)piperidinylamino]-9-cyclopentylpurine Preparation of 4-Amino-1-(2-N,N-diethylaminoethyl)piperidine Method 1

Scheme B, step a: 4-Carboxamide-1-(2-N,N-diethylaminoethyl)piperidine

4-Carboxamide-1-(2-N,N-diethylaminoethyl)piperidine may be prepared from isonipecotamide and 2-N,N-diethylaminoethyl chloride essentially as described above in Example 38, Scheme B, step a.

Scheme B, step b: 4-Amino-1-(2-N,N-diethylaminoethyl)piperidine

4-Amino-1-(2-N,N-diethylaminoethyl)piperidine is prepared from 4-carboxamide-1-(2-N,N-diethylaminoethyl)piperidine essentially as described above in Example 38, Scheme B, step b.

Method 2
Scheme C, step a: 1-(2-N,N-diethylaminoethyl)-4-piperidone 1-(2-N,N-diethylaminoethyl)-4-piperidone is prepared from 4-piperidone and 2-N,N-diethylaminoethyl chloride essentially as described above in Example 38, Scheme C, step a.

Scheme C, step b: 1-(2-N,N-diethylaminoethyl)-4-piperidone oxime 1-(2-N,N-diethylaminoethyl)-4-piperidone oxime is prepared from 1-(2-N,N-diethylaminoethyl)-4-piperidone and hydroxylamine hydrochloride essentially as described above in Example 38, Scheme C, step b.

Scheme C, step c: 4-Amino-1-(2-N,N-diethylaminoethyl)piperidine

4-Amino-1-(2-N,N-diethylaminoethyl)piperidine is prepared from 1-(2-N,N-diethylaminoethyl)-4-piperidone oxime essentially as described above in Example 38, Scheme C, step c.

Scheme A, step b: 2-Chloro-6-[4-(1-(2-N,N-diethylaminoethyl))piperidinylamino]-9-cyclopentylpurine 2-Chloro-6-[4-(1-(2-N,N-diethylaminoethyl))piperidinylamino]-9-cyclopentylpurine is from 2,6-dichloro-9-cyclopentylpurine, 4-amino-1-(2-N,N-diethylaminoethyl)piperidine, and triethylamine essentially as described above in Example 1, Scheme A, step b.

Scheme A, step c: 2-[Trans-(4-aminocyclohexyl)amino]-6-[4-(1-(2-N,N-diethylaminoethyl))piperidinylamino]-9-cyclopentylpurine 2-[Trans-(4-aminocyclohexyl)amino]6-[4(1(2-N,N-diethylaminoethyl))piperidinylamino]-9-cyclopentylpurine is prepared from 2-chloro-6-[4-(1-(2-N,N-diethylaminoethyl))piperidinylamino]-9cyclopentylpurine essentially as described in Example 1, Scheme A, step c.

EXAMPLE 105

2-[Trans-(4-aminocyclohexyl)amino]-6-[4-(1-(3-N,N-diethylaminopropyl))piperidinylamino]-9-cyclopentylpurine Preparation of 4-Amino-1-(3-N,N-diethylaminopropyl)piperidine
Method 1
Scheme B, step a: 4-Carboxamide-1-(3-N,N-diethylaminopropyl)piperidine 4-Carboxamide-1-(3-N,N-diethylaminopropyl)piperidine may be prepared from isonipecotamide and 3-N,N-diethylaminopropyl chloride essentially as described above in Example 38, Scheme B, step a.

Scheme B, step b: 4-Amino-1-(3-N,N-diethylaminopropyl)piperidine

4-Amino-1-(3-N,N-diethylaminopropyl)piperidine is prepared from 4-carboxamide-1-(3-N,N-diethylaminopropyl)piperidine essentially as described above in Example 38, Scheme B, step b.

Method 2
Scheme C, step a: 1-(3-N,N-diethylaminopropyl)-4-piperidone 1-(3-N,N-diethylaminopropyl)-4-piperidone is prepared from 4-piperidone and 3-N,N-diethylaminopropyl chloride essentially as described above in Example 38, Scheme C, step a.

Scheme C, step b: 1-(3-N,N-diethylaminopropyl)-4-piperidone oxime 1-(3-N,N-diethylaminopropyl)-4-piperidone oxime is prepared from 1-(3-N,N-diethylaminopropyl)-4-piperidone and hydroxylamine hydrochloride essentially as described above in Example 38, Scheme C, step b.

Scheme C, step c: 4-Amino-1-(3-N,N-diethylaminopropyl)piperidine

4-Amino-1-(3-N,N-diethylaminopropyl)piperidine is prepared from 1-(3-N,N-diethylaminopropyl)-4-piperidone oxime essentially as described above in Example 38, Scheme C, step c.

Scheme A, step b: 2-Chloro-6-[4-(1-(3-N,N-diethylaminopropyl))piperidinylamino]-9-cyclopentylpurine 2-Chloro-6-[4-(1-(3-N,N-diethylaminopropyl))piperidinylamino]-9-cyclopentylpurine is prepared from 2,6-dichloro-9-cyclopentylpurine, 4-amino-1-(3-N,N-diethylaminopropyl)piperidine, and triethylamine essentially as described above in Example 1, Scheme A, step b.

Scheme A, step c: 2-[Trans-(4-aminocyclohexyl)amino]-6-[4-(1-(3-N,N-diethylaminopropyl))piperidinylamino]-9-cyclopentylpurine 2-[Trans-(4-aminocyclohexyl)amino]-6-[4-(1-(3-N,N-diethylaminopropyl))piperidinylamino]-9-cyclopentylpurine is prepared from 2-chloro-6-[4-(1-(3-N,N-diethylaminopropyl))piperidinylamino]-9-cyclopentylpurine essentially as described in Example 1, Scheme A, step c.

EXAMPLE 106

2-[Trans-(4-aminocyclohexyl)amino]-6-[4-(1-(4-N,N-diethylaminobutyl))piperidinylamino]-9-cyclopentylpurine Preparation of 4-Amino-1-(4-N,N-diethylaminobutyl)piperidine
Method 1
Scheme B, step a: 4-Carboxamide-1-(4-N,N-diethylaminobutyl)piperidine 4-Carboxamide-1-(4-N,N-diethylaminobutyl)piperidine may be prepared from isonipecotamide and 4-N,N-diethylaminobutyl chloride essentially as described above in Example 38, Scheme B, step a.

Scheme B, step b: 4-Amino-1-(4-N,N-diethylaminobutyl)piperidine

4-Amino-1-(4-N,N-diethylaminobutyl)piperidine is prepared from 4-carboxamide-1-(4-N,N-diethylaminobutyl)piperidine essentially as described above in Example 38, Scheme B, step b.

Method 2
Scheme C, step a: 1-(4-N N-diethylaminobutyl)-4-piperidone 1-(4-N,N-diethylaminobutyl)-4-piperidone is prepared from 4-piperidone and 4-N,N-diethylaminobutyl chloride essentially as described above in Example 38, Scheme C, step a.

Scheme C, step b: 1-(4-N,N-diethylaminobutyl)-4-piperidone oxime 1-(4-N,N-diethylaminobutyl)-4-piperidone oxime is prepared from 1-(4-N,N-diethylaminobutyl)-4-piperidone and hydroxylamine hydrochloride essentially as described above in Example 38, Scheme C, step b.

Scheme C, step c: 4-Amino-1-(4-N,N-diethylaminobutyl)piperidine

4-Amino-1-(4-N,N-diethylaminobutyl)piperidine is prepared from 1-(4-N,N-diethylaminobutyl)-4-piperidone oxime essentially as described above in Example 38, Scheme C, step c.

Scheme A, step b: 2-Chloro-6-[4-(1-(4-N,N-diethylaminobutyl))-piperidinylamino]-9-cyclopentylpurine 2-Chloro-6-[4-(1-(4-N,N-diethylaminobutyl))piperidinylamino]-9-cyclopentylpurine is prepared from 2,6-dichloro-9-cyclopentylpurine, 4-amino-1-(4-N,N-diethylaminobutyl)piperidine, and triethylamine essentially as described above in Example 1, Scheme A, step b.

Scheme A, step c: 2-[Trans-(4-aminocyclohexyl)amino]-6-[4-(1-(4-N,N-diethylaminobutyl))piperidinylamino]-9-cyclopentylpurine 2-[Trans-(4-aminocyclohexyl)amino]-6-[4-(1-(4-N,N-diethylaminobutyl))piperidinylamino]-9-cyclopentylpurine is prepared from 2-chloro-6-[4-(1-(4-N,N-diethylaminobutyl))piperidinylamino]-9-cyclopentylpurine essentially as described in Example 1, Scheme A, step c.

EXAMPLE 107

2-[Trans-(4-aminocyclohexyl)amino]-6-[4-(1-(5-N,N-diethylaminopentyl)piperidinylamino]-9-cyclopentylpurine Preparation of 4-Amino-1-(5-N,N-diethylaminopentyl)piperidine Method 1

Scheme B, step a: 4-Carboxamide-1-(5-N,N-diethylaminopentyl)piperidine

4-Carboxamide-1-(5-N,N-diethylaminopentyl)piperidine may be prepared from isonipecotamide and 5-N,N-diethylaminopentyl chloride essentially as described above in Example 38, Scheme B, step a.

Scheme B, step b: 4-Amino-1-(5-N,N-diethylaminopentyl)piperidine

4-Amino-1-(5-N,N-diethylaminopentyl)piperidine is prepared from 4-carboxamide-1-(5-N,N-diethylaminopentyl)piperidine essentially as described above in Example 38, Scheme B, step b.

Method 2

Scheme C, step a: 1-(5-N N-diethylaminopentyl)-4-piperidone 1-(5-N,N-diethylaminopentyl)-4-piperidone is prepared from 4-piperidone and 5-N,N-diethylaminopentyl chloride essentially as described above in Example 38, Scheme C, step a.

Scheme C, step b: 1-(5-N,N-diethylaminopentyl)-4-piperidone oxime 1-(5-N,N-diethylaminopentyl)-4-piperidone oxime is prepared from 1-(5-N,N-diethylaminopentyl)-4-piperidone and hydroxylamine hydrochloride essentially as described above in Example 38, Scheme C, step b.

Scheme C, step c: 4-Amino-1-(5-N,N-diethylaminopentyl)piperidine

4-Amino-1-(5-N,N-diethylaminopentyl)piperidine is prepared from 1-(5-N,N-diethylaminopentyl)-4-piperidone oxime essentially as described above in Example 38, Scheme C, step c.

Scheme A, step b: 2-Chloro-6-[4-(1-(5-N,N-diethylaminopentyl)piperidinylamino]-9-cyclopentylpurine 2-Chloro-6-[4-(1-(5-N,N-diethylaminopentyl)piperidinylamino]-9-cyclopentylpurine is prepared from 2,6-dichloro-9-cyclopentylpurine, 4-amino-1-(5-N,N-diethylaminopentyl)piperidine, and triethylamine essentially as described above in Example 1, Scheme A, step b.

Scheme A, step c: 2-[Trans-(4-aminocyclohexyl)amino]-6-[4-(1-(5-N,N-diethylaminopentyl)piperidinylamino]-9-cyclopentylpurine 2-[Trans-(4-aminocyclohexyl)amino]-6-[4-(1-(5-N,N-diethylaminopentyl)piperidinylamino]-9-cyclopentylpurine is prepared from 2-chloro-6-[4-(1-(5-N,N-diethylaminopentyl)piperidinylamino]-9-cyclopentylpurine essentially as described in Example 1, Scheme A, step c.

EXAMPLE 108

2-[Trans-(4-aminocyclohexyl)amino]-9-cyclopentylpurine

Preparation of 4-Amino-1-(2-N,N-dipropylaminoethyl)piperidine

Method 1

Scheme B, step a: 4-Carboxamide-1-(2-N,N-dipropylaminoethyl)piperidine

4-Carboxamide-1-(2-N,N-dipropylaminoethyl)piperidine may be prepared from isonipecotamide and 2-N,N-dipropylaminoethyl chloride essentially as described above in Example 38, Scheme B, step a.

Scheme B, step b: 4-Amino-1-(2-N,N-dipropylaminoethyl)piperidine

4-Amino-1-(2-N,N-dipropylaminoethyl)piperidine is prepared from 4-carboxamide-1-(2-N,N-dipropylaminoethyl)piperidine essentially as described above in Example 38, Scheme B, step b.

Method 2

Scheme C, step a: 1-(2-N,N-dipropylaminoethyl)-4-piperidone 1-(2-N,N-dipropylaminoethyl)-4-piperidone is prepared from 4-piperidone and 2-N,N-dipropylaminoethyl chloride essentially as described above in Example 38, Scheme C, step a.

Scheme C, step b: 1-(2-N,N-dipropylaminoethyl)-4-piperidone oxime 1-(2-N,N-dipropylaminoethyl)-4-piperidone oxime is prepared from 1-(2-N,N-dipropylaminoethyl)-4-piperidone and hydroxylamine hydrochloride essentially as described above in Example 38, Scheme C, step b.

Scheme C, step c: 4-Amino-1-(2-N,N-dipropylaminoethyl)piperidine

4-Amino-1-(2-N,N-dipropylaminoethyl)piperidine is prepared from 1-(2-N,N-dipropylaminoethyl)-4-piperidone oxime essentially as described above in Example 38, Scheme C, step c.

Scheme A, step b: 2-Chloro-6-[4-(1-(2-N,N-dipropylaminoethyl))piperidinylamino]-9-cyclopentylpurine 2-Chloro-6-[4-(1-(2-N,N-dipropylaminoethyl))piperidinylamino]-9-cyclopentylpurine is prepared from 2,6-dichloro-9-cyclopentylpurine, 4-amino-1-(2-N,N-dipropylaminoethyl)piperidine, and triethylamine essentially as described above in Example 1, Scheme A, step b.

Scheme A, step c: 2-[Trans-(4-aminocyclohexyl)amino]-6-[4-(1-(2-N,N-dipropylaminoethyl))piperidinylamino]-9-cyclopentylpurine 2-[Trans-(4-aminocyclohexyl)amino]-6-[4-(1-(2-N,N-dipropylaminoethyl))piperidinylamino]-9-cyclopentylpurine is prepared from 2-chloro-6-[4-(1-(2-N,N-dipropylaminoethyl))piperidinylamino]-9-cyclopentylpurine essentially as described in Example 1, Scheme A, step c.

EXAMPLE 109

2-[Trans-(4-aminocyclohexyl)amino]-6-[4-(1-(3-N,N-dipropylaminopropyl))piperidinylamino]-9-cyclopentylpurine Preparation of 4-Amino-1-(3-N,N-dipropylaminopropyl)piperidine Method 1

Scheme B, step a: 4-Carboxamide-1-(3-N,N-dipropylaminopropyl)piperidine

4-Carboxamide-1-(3-N,N-dipropylaminopropyl)piperidine may be prepared from isonipecotamide and 3-N, N-dipropylaminopropyl chloride essentially as described above in Example 38, Scheme B, step a.

Scheme B, step b: 4-Amino-1-(3-N,N-dipropylaminopropyl)piperidine

4-Amino-1-(3-N,N-dipropylaminopropyl)piperidine is prepared from 4-carboxamide-1-(3-N,N-dipropylaminopropyl)piperidine essentially as described above in Example 38, Scheme B, step b.

Method 2

Scheme C, step a: 1-(3-N,N-dipropylaminopropyl)-4-piperidone 1-(3-N,N-dipropylaminopropyl)-4-piperidone is prepared from 4-piperidone and 3-N,N-dipropylaminopropyl chloride essentially as described above in Example 38, Scheme C, step a.

Scheme C, step b: 1-(3-N,N-dipropylaminopropyl)-4-piperidone oxime 1-(3-N,N-dipropylaminopropyl)-4-piperidone oxime is prepared from 1-(3-N,N-dipropylaminopropyl)-4-piperidone and hydroxylamine hydrochloride essentially as described above in Example 38, Scheme C, step b.

Scheme C, step c: 4-Amino-1-(3-N,N-dipropylaminopropyl)piperidine

4-Amino-1-(3-N,N-dipropylaminopropyl)piperidine is prepared from 1-(3-N,N-dipropylaminopropyl)-4-piperidone oxime essentially as described above in Example 38, Scheme C, step c.

Scheme A, step b: 2-Chloro-6-[4-(1-(3-N,N-dipropylaminopropyl))piperidinylamino]-9-cyclopentylpurine 1-Chloro-6-[4-(1-(3-N,N-dipropylaminopropyl))piperidinylamino]-9-cyclopentylpurine is prepared from 2,6-dichloro-9-cyclopentylpurine, 4-amino-1-(3-N,N-dipropylaminopropyl)piperidine, and triethylamine essentially as described above in Example 1, Scheme A, step b.

Scheme A, steer c: 2-[Trans-(4-aminocyclohexyl)amino]-6-[4-(1-(3-N,N-dipropylaminopropyl))piperidinylamino]-9-cyclopentylpurine 2-[Trans-(4-aminocyclohexyl)amino]6-[4-(1-(3-N,N-dipropylaminopropyl))piperidinylamino]-9-cyclopentylpurine is prepared from 2-chloro-6-[4-(1-(3-N,N-dipropylaminopropyl))piperidinylamino]-9-cyclopentylpurine essentially as described in Example 1, Scheme A, step c.

EXAMPLE 110

2-[Trans-(4-aminocyclohexyl)amino]-6-[4-(1-(4-N,N-dipropylaminobutyl))piperidinylamino]-9-cyclopentylpurine Preparation of 4-Amino-1-(4-N,N-dipropylaminobutyl)piperidine Method 1

Scheme B, step a: 4-Carboxamide-1-(4-N,N-dipropylaminobutyl)piperidine

4-Carboxamide-1-(4-N,N-dipropylaminobutyl)piperidine may be prepared from isonipecotamide and 4-N,N-dipropylaminobutyl chloride essentially as described above in Example 38, Scheme B, step a.

Scheme B, step b: 4-Amino-1-(4-N,N-dipropylaminobutyl)piperidine

4-Amino-1-(4-N,N-dipropylaminobutyl)piperidine is prepared from 4-carboxamide-1-(4-N,N-dipropylaminobutyl)piperidine essentially as described above in Example 38, Scheme B, step b.

Method 2

Scheme C, step a: 1-(4-N,N-dipropylaminobutyl)-4-piperidone 1-(4-N,N-dipropylaminobutyl)-4-piperidone is prepared from 4-piperidone and 4-N,N-dipropylaminobutyl chloride essentially as described above in Example 38, Scheme C, step a.

Scheme C, step b: 1-(4-N,N-dipropylaminobutyl)-4-piperidone oxime 1-(4-N,N-dipropylaminobutyl)-4-piperidone oxime is prepared from 1-(4-N,N-dipropylaminobutyl)-4-piperidone and hydroxylamine hydrochloride essentially as described above in Example 38, Scheme C, step b.

Scheme C, step c: 4-Amino-1-(4-N,N-dipropylaminobutyl)piperidine

4-Amino-1-(4-N,N-dipropylaminobutyl)piperidine is prepared from 1-(4-N,N-dipropylaminobutyl)-4-piperidone oxime essentially as described above in Example 38, Scheme C, step c.

Scheme A, step b: 2-Chloro-6-[4-(1-(4-N,N-dipropylaminobutyl))piperidinylamino]-9-cyclopentylpurine 2-Chloro-6-[4-(1-(4-N,N-dipropylaminobutyl))piperidinylamino]-9-cyclopentylpurine is prepared from 2,6-dichloro-9-cyclopentylpurine, 4-amino-1-(4-N,N-dipropylaminobutyl)piperidine, and triethylamine essentially as described above in Example 1, Scheme A, step b.

Scheme A, step c: 2-[Trans-(4-aminocyclohexyl)amino]-6-[4-(1-(4-N,N-dipropylaminobutyl))piperidinylamino]-9-cyclopentylpurine 2-[Trans-(4-aminocyclohexyl)amino]-6-[4-(1-(4-N,N-dipropylaminobutyl))piperidinylamino]-9-cyclopentylpurine is prepared from 2-chloro-6-[4-(1-(4-N,N-dipropylaminobutyl))piperidinylamino]-9-cyclopentylpurine essentially as described in Example 1, Scheme A, step c.

EXAMPLE 111

2-[Trans-(4-aminocyclohexyl)amino]-6-[4-(1-(5-N,N-dipropylaminopentyl))piperidinylamino]-9-cyclopentylpurine Preparation of 4-Amino-1-(5-N,N-dipropylaminopentyl)piperidine Method 1

Scheme B, step a: 4-Carboxamide-1-(5-N,N-dipropylaminopentyl)piperidine

4-Carboxamide-1-(5-N,N-dipropylaminopentyl)piperidine may be prepared from isonipecotamide and 5-N,N-dipropylaminopentyl chloride essentially as described above in Example 38, Scheme B, step a.

Scheme B, step b: 4-Amino-1-(5-N,N-dipropylaminopentyl)piperidine

4-Amino-1-(5-N,N-dipropylaminopentyl)piperidine is prepared from 4-carboxamide-1-(5-N,N-dipropylaminopentyl)piperidine essentially as described above in Example 38, Scheme B, step b.

Method 2

Scheme C, step a: 1-(5-N,N-dipropylaminopentyl)-4-piperidone 1-(5-N,N-dipropylaminopentyl)-4-piperidone is prepared from 4-piperidone and 5-N,N-dipropylaminopentyl chloride essentially as described above in Example 38, Scheme C, step a.

Scheme C, step b: 1-(5-N,N-dipropylaminopentyl)-4-piperidone oxime 1-(5-N,N-dipropylaminopentyl)-4-piperidone oxime is prepared from 1-(5-N,N-dipropylaminopentyl)-4-piperidone and hydroxylamine hydrochloride essentially as described above in Example 38, Scheme C, step b.

Scheme C, step c: 4-Amino-1-(5-N,N-dipropylaminopentyl) piperidine

4-Amino-1-(5-N,N-dipropylaminopentyl)piperidine is prepared from 1-(5-N,N-dipropylaminopentyl)-4-piperidone oxime essentially as described above in Example 38, Scheme C, step c.

Scheme A, step b: 2-Chloro-6-[4-(1-(5-N,N-dipropylaminopentyl))piperidinylamino]-9-cyclopentylpurine 2-Chloro-6-[4-(1-(5-N,N-dipropylaminopentyl))piperidinylamino]-9-cyclopentylpurine is prepared from 2,6-dichloro-9-cyclopentylpurine, 4-amino-1-(5-N,N-dipropylaminopentyl)piperidine, and triethylamine essentially as described above in Example 1, Scheme A, step b.

Scheme A, step) c: 2-[Trans-(4-aminocyclohexyl)amino]-6-[4-(1-(5-N,N-dipropylaminopentyl))piperidinylamino]-9-cyclopentylpurine 2-[Trans-(4-aminocyclohexyl)amino]-6-[4-(1-(5-N,N-dipropylaminopentyl))piperidinylamino]-9-cyclopentylpurine is prepared from 2-chloro-6-[4-(1-(5-N,N-dipropylaminopentyl))piperidinylamino]-9-cyclopentylpurine essentially as described in Example 1, Scheme A, step c.

EXAMPLE 112

2-[Trans-(4-aminocyclohexyl)amino]-6-[4-(1-(2-N,N-dibutylaminoethyl))piperidinylamino]-9-cyclopentylpurine Preparation of 4-Amino-1-(2-N,N-dibutylaminoethyl) piperidine
Method 1
Scheme B, step a: 4-Carboxamide-1-(2-N,N-dibutylaminoethyl)piperidine 4-Carboxamide-1-(2-N,N-dibutylaminoethyl)piperidine may be prepared from isonipecotamide and 2-N,N-dibutylaminoethyl chloride essentially as described above in Example 38, Scheme B, step a.

Scheme B, step b: 4-Amino-1-(2-N,N-dibutylaminoethyl)piperidine

4-Amino-1-(2-N,N-dibutylaminoethyl)piperidine is prepared from 4-carboxamide-1-(2-N,N-dibutylaminoethyl)piperidine essentially as described above in Example 38, Scheme B, step b.

Method 2
Scheme C, step a: 1-(2-N,N-dibutylaminoethyl)-4-piperidone 1-(2-N,N-dibutylaminoethyl)-4-piperidone is prepared from 4-piperidone and 2-N,N-dibutylaminoethyl chloride essentially as described above in Example 38, Scheme C, step a.

Scheme C, step b: 1-(2-N,N-dibutylaminoethyl)-4-piperidone oxime 1-(2-N,N-dibutylaminoethyl)-4-piperidone oxime is prepared from 1-(2-N,N-dibutylaminoethyl)-4-piperidone and hydroxylamine hydrochloride essentially as described above in Example 38, Scheme C, step b.

Scheme C, step c: 4-Amino-1-(2-N,N-dibutylaminoethyl) piperidine

4-Amino-1-(2-N,N-dibutylaminoethyl)piperidine is prepared from 1-(2-N,N-dibutylaminoethyl)-4-piperidone oxime essentially as described above in Example 38, Scheme C, step c.

Scheme A, step b: 2-Chloro-6-[4-(1-(2-N,N-dibutylaminoethyl))piperidinylamino]-9-cyclopentylpurine 2-Chloro-6-[4-(1-(2-N,N-dibutylaminoethyl))piperidinylamino]-9-cyclopentylpurine is prepared from 2,6-dichloro-9-cyclopentylpurine, 4-amino-1-(2-N,N-dibutylaminoethyl)piperidine, and triethylamine essentially as described above in Example 1, Scheme A, step b.

Scheme A, step c: 2-[Trans-(4-aminocyclohexyl)amino]-6-[4-(1-(2-N,N-dibutylaminoethyl))piperidinylamino]-9-cyclopentylpurine 2-[Trans-(4-aminocyclohexyl)amino]-6-[4-(1-(2-N,N-dibutylaminoethyl))piperidinylamino]-9-cyclopentylpurine is prepared from 2-chloro-6-[4-(1-(2-N,N-dibutylaminoethyl))piperidinylamino]-9-cyclopentylpurine essentially as described in Example 1, Scheme A, step c.

EXAMPLE 113

2-[Trans-(4-aminocyclohexyl)amino]-6-[4-(1-(3-N,N-dibutylaminopropyl))piperidinylamino]-9-cyclopentylpurine Preparation of 4-Amino-1-(3-N,N-dibutylaminopropyl) piperidine
Method 1
Scheme B, step a: 4-Carboxamide-1-(3-N,N-dibutylaminopropyl)piperidine 4-Carboxamide-1-(3-N,N-dibutylaminopropyl)piperidine may be prepared from isonipecotamide and 3-N,N-dibutylaminopropyl chloride essentially as described above in Example 38, Scheme B, step a.

Scheme B, step b: 4-Amino-1-(3-N,N-dibutylaminopropyl) piperidine

4-Amino-1-(3-N,N-dibutylaminopropyl)piperidine is prepared from 4-carboxamide-1-(3-N,N-dibutylaminopropyl) piperidine essentially as described above in Example 38, Scheme B, step b.

Method 2
Scheme C, step a: 1-(3-N,N-dibutylaminopropyl)-4-piperidone 1-(3-N,N-dibutylaminopropyl)-4-piperidone is prepared from 4-piperidone and 3-N,N-dibutylaminopropyl chloride essentially as described above in Example 38, Scheme C, step a.

Scheme C, step b: 1-(3-N,N-dibutylaminopropyl)-4-piperidone oxime 1-(3-N,N-dibutylaminopropyl)-4-piperidone oxime is prepared from 1-(3-N,N-dibutylaminopropyl)-4-piperidone and hydroxylamine hydrochloride essentially as described above in Example 38, Scheme C, step b.

Scheme C, step c: 4-Amino-1-(3-N,N-dibutylaminopropyl) piperidine

4-Amino-1-(3-N,N-dibutylaminopropyl)piperidine is prepared from 1-(3-N,N-dibutylaminopropyl)-4-piperidone oxime essentially as described above in Example 38, Scheme C, step c.

Scheme A, step b: 2-Chloro-6-[4-(1-(3-N,N-dibutylaminopropyl))piperidinylamino]-9-cyclopentylpurine 2-Chloro-6-[4-(1-(3-N,N-dibutylaminopropyl))piperidinylamino]-9-cyclopentylpurine is prepared from 2,6-dichloro-9-cyclopentylpurine, 4-amino-1-(3-N,N-dibutylaminopropyl)piperidine, and triethylamine essentially as described above in Example 1, Scheme A, step b.

Scheme A, step c: 2-[Trans-(4-aminocyclohexyl)amino]-6-[4-(1-(3-N,N-dibutylaminopropyl))piperidinylamino]-9-cyclopentylpurine 2-[Trans-(4-aminocyclohexyl)amino]-6-[4-(1-(3-N,N-dibutylaminopropyl))piperidinylamino]-9-cyclopentylpurine is prepared from 2-chloro-6-[4-(1-(3-N,N-dibutylaminopropyl))piperidinylamino]-9-cyclopentylpurine essentially as described in Example 1, Scheme A, step c.

EXAMPLE 114

2-[Trans-(4-aminocyclohexyl)amino]-6-[4-(1-(4-N,N-dibutylaminobutyl)piperidinylamino]-9-cyclopentylpurine Preparation of 4-Amino-1-(4-N,N-dibutylaminobutyl)piperidine Method 1

Scheme B, step a: 4-Carboxamide-1-(4-N,N-dibutylaminobutyl)piperidine

4-Carboxamide-1-(4-N,N-dibutylaminobutyl)piperidine may be prepared from isonipecotamide and 4-N,N-dibutylaminobutyl chloride essentially as described above in Example 38, Scheme B, step a.

Scheme B, step b: 4-Amino-1-(4-N,N-dibutylaminobutyl)piperidine

4-Amino-1-(4-N,N-dibutylaminobutyl)piperidine is prepared from 4-carboxamide-1-(4-N,N-dibutylaminobutyl)piperidine essentially as described above in Example 38, Scheme B, step b.

Method 2

Scheme C, step a: 1-(4-N,N-dibutylaminobutyl)-4-piperidone 1-(4-N,N-dibutylaminobutyl)-4-piperidone is prepared from 4-piperidone and 4-N,N-dibutylaminobutyl chloride essentially as described above in Example 38, Scheme C, step a.

Scheme C, step b: 1-(4-N,N-dibutylaminobutyl-4-piperidone oxime 1-(4-N,N-dibutylaminobutyl)-4-piperidone oxime is prepared from 1-(4-N,N-dibutylaminobutyl)-4-piperidone and hydroxylamine hydrochloride essentially as described above in Example 38, Scheme C, step b.

Scheme C, step, c: 4-Amino-1-(4-N,N-dibutylaminobutyl)piperidine

4-Amino-1-(4-N,N-dibutylaminobutyl)piperidine is prepared from 1-(4-N,N-dibutylaminobutyl)-4-piperidone oxime essentially as described above in Example 38, Scheme C, step c.

Scheme A, step b: 2-Chloro-6-[4-(1-(4-N,N-dibutylaminobutyl)piperidinylamino]-9-cyclopentylpurine 2-Chloro-6-[4-(1-(4-N,N-dibutylaminobutyl)piperidinylamino]-9-cyclopentylpurine is prepared from 2,6-dichloro-9-cyclopentylpurine, 4-amino-1-(4-N,N-dibutylaminobutyl)piperidine, and triethylamine essentially as described above in Example 1, Scheme A, step b.

Scheme A, step c: 2-[Trans-(4-aminocyclohexyl)amino]-6-[4-(1-(4-N,N-dibutylaminobutyl)piperidinylamino]-9-cyclopentylpurine 2-[Trans-(4-aminocyclohexyl)amino]-6-[4-(1-(4-N,N-dibutylaminobutyl)piperidinylamino]-9-cyclopentylpurine is prepared from 2-chloro-6-[4-(1-(4-N,N-dibutylaminobutyl)piperidinylamino]-9-cyclopentylpurine essentially as described in Example 1, Scheme A, step c.

EXAMPLE 115

2-[Trans-(4-aminocyclohexyl)amino]-6-[4-(1-(5-N,N-dibutylaminopentyl))piperidinylamino]-9-cyclopentylpurine Preparation of 4-Amino-1-(5-N,N-dibutylaminopentyl)piperidine Method 1

Scheme B, step a: 4-Carboxamide-1-(5-N,N-dibutylaminopentyl)piperidine

4-Carboxamide-1-(5-N,N-dibutylaminopentyl)piperidine may be prepared from isonipecotamide and 5-N,N-dibutylaminopentyl chloride essentially as described above in Example 38, Scheme B, step a.

Scheme B, step b: 4-Amino-1-(5-N,N-dibutylaminopentyl)piperidine

4-Amino-1-(5-N,N-dibutylaminopentyl)piperidine is prepared from 4-carboxamide-1-(5-N,N-dibutylaminopentyl)piperidine essentially as described above in Example 38, Scheme B, step b.

Method 2

Scheme C, step a: 1-(5-N,N-dibutylaminopentyl)-4-piperidone 1-(5-N,N-dibutylaminopentyl)-4-piperidone is prepared from 4-piperidone and 5-N,N-dibutylaminopentyl chloride essentially as described above in Example 38, Scheme C, step a.

Scheme C, step b: 1-(5-N,N-dibutylaminopentyl)-4-piperidone oxime 1-(5-N,N-dibutylaminopentyl)-4-piperidone oxime is prepared from 1-(5-N,N-dibutylaminopentyl)-4-piperidone and hydroxylamine hydrochloride essentially as described above in Example 38, Scheme C, step b.

Scheme C -step c: 4-Amino-1-(5-N,N-dibutylaminopentyl)piperidine

4-Amino-1-(5-N,N-dibutylaminopentyl)piperidine is prepared from 1-(5-N,N-dibutylaminopentyl)-4-piperidone oxime essentially as described above in Example 38, Scheme C, step c.

Scheme A, step b: 2-Chloro-6-[4-(1-(5-N,.N-dibutylaminopentyl)piperidinylamino]-9-cyclopentylpurine 2-Chloro-6-[4-(1-(5-N,N-dibutylaminopentyl))piperidinylamino]-9-cyclopentylpurine is prepared from 2,6-dichloro-9-cyclopentylpurine, 4-amino-1-(5-N,N-dibutylaminopentyl)piperidine, and triethylamine essentially as described above in Example 1, Scheme A, step b.

Scheme A, step c: 2-[Trans-(4-aminocyclohexyl)amino]-6-[4-(1-(5-N,N-dibutylaminopentyl))piperidinylamino]-9-cyclopentylpurine 2-[Trans-(4-aminocyclohexyl)amino]-6-[4-(1-(5-N,N-dibutylaminopentyl))piperidinylamino]-9-cyclopentylpurine is prepared from 2-chloro-6-[4-(1-(5-N,N-dibutylaminopentyl))piperidinylamino]-9-cyclopentylpurine essentially as described in Example 1, Scheme A, step c.

EXAMPLE 116

2-[Trans-(4-aminocyclohexyl)amino]-6-[4-(1-(2-N,N-dibenzylaminoethyl))piperidinylamino]-9-cyclopentylpurine Preparation of 4-Amino-1-(2-N,N-dibenzylaminoethyl)piperidine Method 1

Scheme B, step a: 4-Carboxamide-1-(2-N N-dibenzylaminoethyl)piperidine

4-Carboxamide-1-(2-N,N-dibenzylaminoethyl)piperidine may be prepared from isonipecotamide and 2-N,N-dibenzylaminoethyl chloride essentially as described above in Example 38, Scheme B, step a.

Scheme B, step b: 4-Amino-1-(2-N,N-dibenzylaminoethyl)piperidine

4-Amino-1-(2-N,N-dibenzylaminoethyl)piperidine is prepared from 4-carboxamide-1-(2-N,N-dibenzylaminoethyl)piperidine essentially as described above in Example 38, Scheme B, step b.

Method 2

Scheme C, step a: 1-(2-N,N-dibenzylaminoethyl)-4-piperidone 1-(2-N,N-dibenzylaminoethyl)-4-piperidone is prepared from 4-piperidone and 2-N,N-dibenzylaminoethyl chloride essentially as described above in Example 38, Scheme C, step a.

Scheme C, step b: 1-(2-N,N-dibenzylaminoethyl)-4-piperidone oxime 1-(2-N,N-dibenzylaminoethyl)-4-piperidone oxime is prepared from 1-(2-N,N-dibenzylaminoethyl)-4-piperidone and hydroxylamine hydrochloride essentially as described above in Example 38, Scheme C, step b.

Scheme C, step c: 4-Amino-1-(2-N,N-dibenzylaminoethyl) piperidine

4-Amino-1-(2-N,N-dibenzylaminoethyl)piperidine is prepared from 1-(2-N,N-dibenzylaminoethyl)-4-piperidone oxime essentially as described above in Example 38, Scheme C, step c.

Scheme A, step b: 2-Chloro-6-[4-(1-(2-N,N-dibenzylaminoethyl))piperidinylamino]-9-cyclopentylpurine 2-Chloro-6-[4-(1-(2-N,N-dibenzylaminoethyl))piperidinylamino]-9-cyclopentylpurine is prepared from 2,6-dichloro-9-cyclopentylpurine, 4-amino-1-(2-N,N-dibenzylaminoethyl)piperidine, and triethylamine essentially as described above in Example 1, Scheme A, step b.

Scheme A, step c: 2-[Trans-(4-aminocyclohexyl)amino]-6-[4-(1-(2-N,N-dibenzylaminoethyl))piperidinylamino]-9-cyclopentylpurine 2-[Trans-(4-aminocyclohexyl)amino]-6-[4-(1-(2-N,N-dibenzylaminoethyl))piperidinylamino]-9-cyclopentylpurine is prepared from 2-chloro-6-[4-(1-(2-N,N-dibenzylaminoethyl))piperidinylamino]-9-cyclopentylpurine essentially as described in Example 1, Scheme A, step c.

EXAMPLE 117

2-[Trans-(4-aminocyclohexyl)amino]-6-[4-(1-(3-N,N-dibenzylaminopropyl))piperidinylamino]-9-cyclopentylpurine Preparation of 4-Amino-1-(3-N N-dibenzylaminopropyl)piperidine Method 1

Scheme B, step a: 4-Carboxamide-1-(3-N,N-dibenzylaminopropyl)piperidine

4-Carboxamide-1-(3-N,N-dibenzylaminopropyl)piperidine may be prepared from isonipecotamide and 3-N,N-dibenzylaminopropyl chloride essentially as described above in Example 38, Scheme B, step a.

Scheme B, step b: 4-Amino-1-(3-N,N-dibenzylaminopropyl)piperidine

4-Amino-1-(3-N,N-dibenzylaminopropyl)piperidine is prepared from 4-carboxamide-1-(3-N,N-dibenzylaminopropyl)piperidine essentially as described above in Example 38, Scheme B, step b.

Method 2

Scheme C, step a: 1-(3-N,N-dibenzylaminopropyl)-4-piperidone 1-(3-N,N-dibenzylaminopropyl)-4-piperidone is prepared from 4-piperidone and 3-N,N-dibenzylaminopropyl chloride essentially as described above in Example 38, Scheme C, step a.

Scheme C, step b: 1-(3-N,N-dibenzylaminopropyl)-4-piperidone oxime 1-(3-N,N-dibenzylaminopropyl)-4-piperidone oxime is prepared from 1-(3-N,N-dibenzylaminopropyl)-4-piperidone and hydroxylamine hydrochloride essentially as described above in Example 38, Scheme C, step b.

Scheme C, step c: 4-Amino-1-(3-N,N-dibenzylaminopropyl)piperidine

4-Amino-1-(3-N,N-dibenzylaminopropyl)piperidine is prepared from 1-(3-N,N-dibenzylaminopropyl)-4-piperidone oxime essentially as described above in Example 38, Scheme C, step c.

Scheme A, step b: 2-Chloro-6-[4-(1-(3-N,N-dibenzylaminopropyl))piperidinylamino]-9-cyclopentylpurine 2-Chloro-6-[4-(1-(3-N,N-dibenzylaminopropyl))piperidinylamino]-9-cyclopentylpurine is prepared from 2,6-dichloro-9-cyclopentylpurine, 4-amino-1-(3-N,N-dibenzylaminopropyl)piperidine, and triethylamine essentially as described above in Example 1, Scheme A, step b.

Scheme A, step c: 2-[Trans-(4-aminocyclohexyl)amino]-6-[4-(1-(3-N,N-dibenzylaminopropyl))piperidinylamino]-9-cyclopentylpurine 2-[Trans-(4-aminocyclohexyl)amino]-6-[4-(1-(3-N,N-dibenzylaminopropyl))piperidinylamino]-9-cyclopentylpurine is prepared from 2-chloro-6-[4-(1-(3-N,N-dibenzylaminopropyl))piperidinylamino]-9-cyclopentylpurine essentially as described in Example 1, Scheme A, step c.

EXAMPLE 118

2-[Trans-(4-aminocyclohexyl)amino]-6-[4-(1-(4-N,N-dibenzylaminobutyl)piperidinylamino]-9-cyclopentylpurine Preparation of 4-Amino-1-(4-N N-dibenzylaminobutyl) piperidine Method 1

Scheme B, step a: 4-Carboxamide-1-(4-N,N-dibenzylaminobutyl)piperidine

4-Carboxamide-1-(4-N,N-dibenzylaminobutyl)piperidine may be prepared from isonipecotamide and 4-N,N-dibenzylaminobutyl chloride essentially as described above in Example 38, Scheme B, step a.

Scheme B, step b: 4-Amino-1-(4-N,N-dibenzylaminobutyl)piperidine

4-Amino-1-(4-N,N-dibenzylaminobutyl)piperidine is prepared from 4-carboxamide-1-(4-N,N-dibenzylaminobutyl)piperidine essentially as described above in Example 38, Scheme B, step b.

Method 2

Scheme C, step) a: 1-(4-N,N-dibenzylaminobutyl)-4-piperidone 1-(4-N,N-dibenzylaminobutyl)-4-piperidone is prepared from 4-piperidone and 4-N,N-dibenzylaminobutyl chloride essentially as described above in Example 38, Scheme C, step a.

Scheme C, step b: 1-(4-N,N-dibenzylaminobutyl)-4-piperidone oxime 1-(4-N,N-dibenzylaminobutyl)-4-piperidone oxime is prepared from 1-(4-N,N-dibenzylaminobutyl)-4-piperidone and hydroxylamine hydrochloride essentially as described above in Example 38, Scheme C, step b.

Scheme C, step c: 4-Amino-1-(4-N,N-dibenzylaminobutyl) piperidine

4-Amino-1-(4-N,N-dibenzylaminobutyl)piperidine is prepared from 1-(4-N,N-dibenzylaminobutyl)-4-piperidone oxime essentially as described above in Example 38, Scheme C, step C.

Scheme A, step b: 2-Chloro-6-[4-(1-(4-N,N-dibenzylaminobutyl))piperidinylamino]-9-cyclopentylpurine 2-Chloro-6-[4-(1-(4-N,N-dibenzylaminobutyl))piperidinylamino]-9-cyclopentylpurine is prepared from 2,6-dichloro-9-cyclopentylpurine, 4-amino-1-(4-N,N-dibenzylaminobutyl)piperidine, and triethylamine essentially as described above in Example 1, Scheme A, step b.

Scheme A, step c: 2-[Trans-(4-aminocyclohexyl)amino]-6-[4-(1-(4-N,N-dibenzylaminobutyl))piperidinylamino]-9-cyclopentylpurine 2-[Trans-(4-aminocyclohexyl)amino]-6-[4-(1-(4-N,N-dibenzylaminobutyl))piperidinylamino]-9-cyclopentylpurine is prepared from 2-chloro-6-[4-(1-(4-N,N-dibenzylaminobutyl))piperidinylamino]-9-cyclopentylpurine essentially as described in Example 1, Scheme A, step c.

EXAMPLE 119

2-[Trans-(4-aminocyclohexyl)amino]-6-[4-(1-(5-N,N-dibenzylaminopentyl)piperidinylamino]-9-cyclopentylpurine Preparation of 4-Amino-1-(5-N,N-dibenzylaminopentyl)piperidine
Method 1
Scheme B, step a: 4-Carboxamide-1-(5-N,N-dibenzylaminopentyl)piperidine 4-Carboxamide-1-(5-N,N-dibenzylaminopentyl)piperidine may be prepared from isonipecotamide and 5-N,N-dibenzylaminopentyl chloride essentially as described above in Example 38, Scheme B, step a.
Scheme B, step b: 4-Amino-1-(5-N,N-dibenzylaminopentyl)piperidine 4-Amino-1-(5-N,N-dibenzylaminopentyl)piperidine is prepared from 4-carboxamide-1-(5-N,N-dibenzylaminopentyl)piperidine essentially as described above in Example 38, Scheme B, step b.
Method 2
Scheme C, step a: 1-(5-N,N-dibenzylaminopentyl)-4-piperidone 1-(5-N,N-dibenzylaminopentyl)-4-piperidone is prepared from 4-piperidone and 5-N,N-dibenzylaminopentyl chloride essentially as described above in Example 38, Scheme C, step a.
Scheme C, step b: 1-(5-N,N-dibenzylaminopentyl)-4-piperidone oxime 1-(5-N,N-dibenzylaminopentyl)-4-piperidone oxime is prepared from 1-(5-N,N-dibenzylaminopentyl)-4-piperidone and hydroxylamine hydrochloride essentially as described above in Example 38, Scheme C, step b.
Scheme C, step c: 4-Amino-1-(5-N,N-dibenzylaminopentyl)piperidine 4-Amino-1-(5-N,N-dibenzylaminopentyl)piperidine is prepared from 1-(5-N,N-dibenzylaminopentyl)-4-piperidone oxime essentially as described above in Example 38, Scheme C, step c.
Scheme A, step b: 2-Chloro-6-[4-(1-(5-N,N-dibenzylaminopentyl))piperidinylamino]-9-cyclopentylpurine 2-Chloro-6-[4-(1-(5-N,N-dibenzylaminopentyl))piperidinylamino]-9-cyclopentylpurine is prepared from 2,6-dichloro-9-cyclopentylpurine, 4-amino-1-(5-N,N-dibenzylaminopentyl)piperidine, and triethylamine essentially as described above in Example 1, Scheme A, step b.
Scheme A, step c: 2-[Trans-(4-aminocyclohexyl)amino]-6-[4-(1-(5-N,N-dibenzylaminopentyl))piperidinylamino]-9-cyclopentylpurine 2-[Trans-(4-aminocyclohexyl)amino]-6-[4-(1-(5-N,N-dibenzylaminopentyl))piperidinylamino]-9-cyclopentylpurine is prepared from 2-chloro-6-[4-(1-(5-N,N-dibenzylaminopentyl))piperidinylamino]-9-cyclopentylpurine essentially as described in Example 1, Scheme A, step c.

EXAMPLE 120

2-[Trans-(4-aminocyclohexyl)amino]-6-[4-(1-(2-N,N-di-(2-phenylethylene)aminoethyl))piperidinylamino]-9-cyclopentylpurine Preparation of 4-Amino-1-(2-N,N-di-(2-phenylethylene)aminoethyl)piperidine
Method 1
Scheme B, step a: 4-Carboxamide-1-(2-N,N-di-(2-phenylethylene)aminoethyl)piperidine 4-Carboxamide-1-(2-N,N-di-(2-phenylethylene)aminoethyl)piperidine may be prepared from isonipecotamide and 2-N,N-di-(2-phenylethyleneamino)ethyl chloride essentially as described above in Example 38, Scheme B, step a.
Scheme B, step b: 4-Amino-1-(2-N,N-di-(2-phenylethylene)aminoethyl)piperidine 4-Amino-1-(2-N,N-di-(2-phenylethylene)aminoethyl)piperidine is prepared from 4-carboxamide-1-(2-N,N-di-(2-phenylethylene)aminoethyl)piperidine essentially as described above in Example 38, Scheme B, step b.
Method 2
Scheme C, step a: 1-(2-N,N-di-(2-phenylethylene)aminoethyl)-4-piperidone 1-(2-N,N-di-(2-phenylethylene)aminoethyl)-4-piperidone is prepared from 4-piperidone and 2-N,N-di-(2-phenylethyleneamino)ethyl chloride essentially as described above in Example 38, Scheme C, step a.
Scheme C, step b: 1-(2-N,N-di-(2-phenylethylene)aminoethyl)-4-piperidone oxime 1-(2-N,N-di-(2-phenylethylene)aminoethyl)-4-piperidone oxime is prepared from 1-(2-N,N-di-(2-phenylethylene)aminoethyl)-4-piperidone and hydroxylamine hydrochloride essentially as described above in Example 38, Scheme C, step b.
Scheme C, step) c: 4-Amino-1-(2-N,N-di-(2-phenylethylene)aminoethyl)piperidine 4-Amino-1-(2-N,N-di-(2-phenylethylene)aminoethyl)piperidine is prepared from 1-(2-N,N-di-(2-phenylethylene)aminobutyl)-4-piperidone oxime essentially as described above in Example 38, Scheme C, step c.
Scheme A, step b: 2-Chloro-6-[4-(1-(2-N,N-di-(2-phenylethylene)aminoethyl))piperidinylamino]-9-cyclopentylpurine 2-Chloro-6-[4-(1-(2-N,N-di-(2-phenylethylene)aminoethyl))piperidinylamino]-9-cyclopentylpurine is prepared from 2,6-dichloro-9-cyclopentylpurine, 4-amino-1-(2-N,N-di-(2-phenylethylene)aminoethyl)piperidine, and triethylamine essentially as described above in Example 1, Scheme A, step b.
Scheme A, step c: 2-[Trans-(4-aminocyclohexyl)amino]-6-[4-(1-(2-N,N-di-(2-phenylethylene)aminoethyl)piperidinylamino]-9-cyclopentylpurine 2-[Trans-(4-aminocyclohexyl)amino]-6-[4-(1-(2-N,N-di-(2-phenylethylene)aminoethyl))piperidinylamino]-9-cyclopentylpurine is prepared from 2-chloro-6-[4-(1-(2-N,N-di-(2-phenylethylene)aminoethyl))piperidinylamino]-9-cyclopentylpurine essentially as described in Example 1, Scheme A, step c.

EXAMPLE 121

2-[Trans-(4-aminocyclohexyl)amino]-6-[4-(1-(3-N,N-di-(2-phenylethylene)aminopropyl))piperidinylamino]-9-cyclopentylpurine Preparation of 4-Amino-1-(3-N,N-di-(2-phenylethylene)aminopropyl)piperidine
Method 1
Scheme B, step a: 4-Carboxamide-1-(3-N,N-di-(2-phenylethylene)aminopropyl)piperidine 4-Carboxamide-1-(3-N,N-di-(2-phenylethylene)aminopropyl)piperidine may be prepared from isonipecotamide and 3-N,N-di-(2-phenylethyleneamino)propyl chloride essentially as described above in Example 38, Scheme B, step a.

Scheme B, step b: 4-Amino-1-(3-N,N-di-(2-phenylethylene)aminopropyl)piperidine

4-Amino-1-(3-N,N-di-(2-phenylethylene)aminopropyl)piperidine is prepared from 4-carboxamide-1-(3-N,N-di-(2-phenylethylene)aminopropyl)piperidine essentially as described above in Example 38, Scheme B, step b.

Method 2

Scheme C, step a: 1-(3-N,N-di-(2-phenylethylene)aminopropyl)-4-piperidone 1-(3-N,N-di-(2-phenylethylene)aminopropyl)-4-piperidone is prepared from 4-piperidone and 3-N,N-di-(2-phenylethyleneamino)propyl chloride essentially as described above in Example 38, Scheme C, step a.

Scheme C, step b: 1-(3-N,N-di-(2-phenylethylene)aminopropyl)-4-piperidone oxime 1-(3-N,N-di-(2-phenylethylene)aminopropyl)-4-piperidone oxime is prepared from 1-(3-N,N-di-(2-phenylethylene)aminopropyl)-4-piperidone and hydroxylamine hydrochloride essentially as described above in Example 38, Scheme C, step b.

Scheme C step c: 4-Amino-1-(3-N,N-di-(2-phenylethylene)aminopropyl)piperidine

4-Amino-1-(3-N,N-di-(2-phenylethylene)aminopropyl)piperidine is prepared from 1-(3-N,N-di-(2-phenylethylene)aminopropyl)-4-piperidone oxime essentially as described above in Example 38, Scheme C, step c.

Scheme A, step b: 2-Chloro-6-[4-(1-(3-N,N-di-(2-phenylethylene)aminopropyl))piperidinylamino]-9-cyclopentylpurine 2-Chloro-6-[4-(1-(3-N,N-di-(2-phenylethylene)aminopropyl))piperidinylamino]-9-cyclopentylpurine is prepared from 2,6-dichloro-9-cyclopentylpurine, 4-amino-1-(3-N,N-di-(2-phenylethylene)aminopropyl)piperidine, and triethylamine essentially as described above in Example 1, Scheme A, step b.

Scheme A, step c: 2-[Trans-(4-aminocyclohexyl)amino]-6-[4-(1-(3-N,N-di-(2-phenylethylene)aminopropyl))piperidinylamino]-9-cyclopentylpurine 2-[Trans-(4-aminocyclohexyl)amino]-6-[4-(1-(3-N,N-di-(2-phenylethylene)aminopropyl))piperidinylamino]-9-cyclopentylpurine is prepared from 2-chloro-6-[4-(1-(3-N,N-di-(2-phenylethylene)aminopropyl))piperidinylamino]-9-cyclopentylpurine essentially as described in Example 1, Scheme A, step c.

EXAMPLE 122

2-[Trans-(4-aminocyclohexyl)amino]-6-[4-(1-(4-N,N-di-(2-phenylethylene)aminobutyl))piperidinylamino]-9-cyclopentylpurine Preparation of 4-Amino-1-(4-N,N-di-(2-phenylethylene)aminobutyl)piperidine Method 1

Scheme B, step a: 4-Carboxamide-1-(4-N,N-di-(2-phenylethylene)aminobutyl)piperidine 4-Carboxamide-1-(4-N,N-di-(2-phenylethylene)aminobutyl)piperidine may be prepared from isonipecotamide and 4-N,N-di-(2-phenylethyleneamino)butyl chloride essentially as described above in Example 38, Scheme B, step a.

Scheme B, step b: 4-Amino-1-(4-N,N-di-(2-phenylethylene)aminobutyl)piperidine 4-Amino-1-(4-N,N-di-(2-phenylethylene)aminobutyl)piperidine is prepared from 4-carboxamide-1-(4-N,N-di-(2-phenylethylene)aminobutyl)piperidine essentially as described above in Example 38, Scheme B, step b.

Method 2

Scheme C, step a: 1-(4-N,N-di-(2-phenylethylene)aminobutyl)-4-piperidone 1-(4-N,N-di-(2-phenylethylene)aminobutyl)-4-piperidone is prepared from 4-piperidone and 4-N,N-di-(2-phenylethyleneamino)butyl chloride essentially as described above in Example 38, Scheme C, step a.

Scheme C, step b: 1-(4-N,N-di-(2-phenylethylene)aminobutyl)-4-piperidone oxime 1-(4-N,N-di-(2-phenylethylene)aminobutyl)-4-piperidone oxime is prepared from 1-(4-N,N-di-(2-phenylethylene)aminobutyl)-4-piperidone and hydroxylamine hydrochloride essentially as described above in Example 38, Scheme C, step b.

Scheme C, step c: 4-Amino-1-(4-N,N-di-(2-phenylethylene)aminobutyl)piperidine

4-Amino-1-(4-N,N-di-(2-phenylethylene)aminobutyl)piperidine is prepared from 1-(4-N,N-di-(2-phenylethylene)aminobutyl)-4-piperidone oxime essentially as described above in Example 38, Scheme C, step c.

Scheme A, step b: 2-Chloro-6-[4-(1-(4-N,N-di-(2-phenylethylene)aminobutyl))piperidinylamino]-9-cyclopentylpurine 2-Chloro-6-[4-(1-(4-N,N-di-(2-phenylethylene)aminobutyl))piperidinylamino]-9-cyclopentylpurine is prepared from 2,6-dichloro-9-cyclopentylpurine, 4-amino-1-(4-N,N-di-(2-phenylethylene)aminobutyl)piperidine, and triethylamine essentially as described above in Example 1, Scheme A, step b.

Scheme A, step c: 2-[Trans-(4-aminocyclohexyl)amino]-6-[4-(1-(4-N,N-di-(2-phenylethylene)aminobutyl))piperidinylamino]-9-cyclopentylpurine 2-[Trans-(4-aminocyclohexyl)amino]-6-[4-(1-(4-N,N-di-(2-phenylethylene)aminobutyl))piperidinylamino]-9-cyclopentylpurine is prepared from 2-chloro-6-[4-(1-(4-N,N-di-(2-phenylethylene)aminobutyl))piperidinylamino ]-9-cyclopentylpurine essentially as described in Example 1, Scheme A, step c.

EXAMPLE 123

2-[Trans-(4-aminocyclohexyl)amino]-6-[4-(1-(5-N,N-di-(2-phenylethylene)aminopentyl))-piperidinylamino]-9-cyclopentylpurine Preparation of 4-Amino-1-(5-N,N-di-(2-phenylethylene)aminopentyl)piperidine Method 1

Scheme B, step a: 4-Carboxamide-1-(5-N,N-di-(2-phenylethylene)aminopentyl)piperidine 4-Carboxamide-1-(5-N,N-di-(2-phenylethylene)aminopentyl)piperidine may be prepared from isonipecotamide and 5-N,N-di-(2-phenylethyleneamino)pentyl chloride essentially as described above in Example 38, Scheme B, step a.

Scheme B, step b: 4-Amino-1-(5-N,N-di-(2-phenylethylene)aminopentyl)piperidine

4-Amino-1-(5-N,N-di-(2-phenylethylene)aminopentyl)piperidine is prepared from 4-carboxamide-1-(5-N,N-di-(2-phenylethylene)aminopentyl)piperidine essentially as described above in Example 38, Scheme B, step b.

Method 2

Scheme C, step a: 1-(5-N,N-di-(2-phenylethylene)aminopentyl)-4-piperidone 1-(5-N,N-di-(2-phenylethylene)aminopentyl)-4-piperidone is prepared from 4-piperidone and 5-N,N-di-(2-phenylethyleneamino)pentyl chloride essentially as described above in Example 38, Scheme C, step a.

Scheme C, step b: 1-(5-N,N-di-(2-phenylethylene)aminopentyl)-4-piperidone oxime 1-(5-N,N-di-(2-phenylethylene)aminopentyl)-4-piperidone oxime is prepared from 1-(5-N,N-di-(2- phenylethylene)aminopentyl)-4-piperidone and hydroxylamine hydrochloride essentially as described above in Example 38, Scheme C, step b.
Scheme C, step c: 4-Amino-1-(5-N,N-di-(2-phenylethylene)aminopentyl)piperidine
4-Amino-1-(5-N,N-di-(2-phenylethylene)aminopentyl)piperidine is prepared from 1-(5-N,N-di-(2-phenylethylene)aminopentyl)-4-piperidone oxime essentially as described above in Example 38, Scheme C, step c.
Scheme A, step b: 2-Chloro-6-[4-(1-(5-N,N-di-(2-phenylethylene)aminopentyl))-piperidinylamino]-9-cyclopentylpurine
2-Chloro-6-[4-(1-(5-N,N-di-(2-phenylethylene)aminopentyl))-piperidinylamino]-9-cyclopentylpurine is prepared from 2,6-dichloro-9-cyclopentylpurine, 4-amino-1-(5-N,N-di-(2-phenylethylene)aminopentyl)piperidine, and triethylamine essentially as described above in Example 1, Scheme A, step b.
Scheme A, step c: 2-[Trans-(4-aminocyclohexyl)amino]-6-[4-(1-(5-N,N-di-(2-phenylethylene)aminopentyl))-piperidinylamino]-9-cyclopentylpurine
2-[Trans-(4-aminocyclohexyl)amino]-6-[4-(1-(5-N,N-di-(2-phenylethylene)aminopentyl))-piperidinylamino]-9-cyclopentylpurine is prepared from 2-chloro-6-[4-(1-(5-N,N-di-(2-phenylethylene)aminopentyl))-piperidinylamino]-9-cyclopentylpurine essentially as described in Example 1, Scheme A, step c.

EXAMPLE 124

2-[Trans-(4-aminocyclohexyl)amino]-6-[4-(1-(2-N,N-di-(3-phenylpropylene)aminoethyl))piperidinylamino]-9-cyclopentylpurine Preparation of 4-Amino-1-(2-N,N-di-(3-phenylpropylene)aminoethyl)piperidine
Method 1
Scheme B, step a: 4-Carboxamide-1-(2-N,N-di-(3-phenylpropylene)aminoethyl)piperidine
4-Carboxamide-1-(2-N,N-di-(3-phenylpropylene)aminoethyl)piperidine may be prepared from isonipecotamide and 2-N,N-di-(3-phenylpropyleneamino)ethyl chloride essentially as described above in Example 38, Scheme B, step a.
Scheme B, step b: 4-Amino-1-(2-N,N-di-(3-phenylpropylene)aminoethyl)piperidine
4-Amino-1-(2-N,N-di-(3-phenylpropylene)aminoethyl)piperidine is prepared from 4-carboxamide-1-(2-N,N-di-(3-phenylpropylene)aminoethyl)piperidine essentially as described above in Example 38, Scheme B, step b.
Method 2
Scheme C, step a: 1-(2-N N-di-(3-phenylpropylene)aminoethyl)-4-piperidone
1-(2-N,N-di-(3-phenylpropylene)aminoethyl)-4-piperidone is prepared from 4-piperidone and 2-N,N-di-(3-phenylpropyleneamino)ethyl chloride essentially as described above in Example 38, Scheme C, step a.
Scheme C, step b: 1-(2-N,N-di-(3-phenylpropylene)aminoethyl)-4-piperidone oxime
1-(2-N,N-di-(3-phenylpropylene)aminoethyl)-4-piperidone oxime is prepared from 1-(2-N,N-di-3-phenylpropylene)aminoethyl)-4-piperidone and hydroxylamine hydrochloride essentially as described above in Example 38, Scheme C, step b.
Scheme C, step c: 4-Amino-1-(2-N,N-di-(3-phenylpropylene)aminoethyl)piperidine
4-Amino-1-(2-N,N-di-(3-phenylpropylene)aminoethyl)piperidine is prepared from 1-(2-N,N-di-(3-phenylpropylene)aminoethyl)-4-piperidone oxime essentially as described above in Example 38, Scheme C, step c.
Scheme A, step b: 2-Chloro-6-[4-(1-(2-N,N-di-(3-phenylpropylene)aminoethyl))piperidinylamino]-9-cyclopentylpurine
2-Chloro-6-[4-(1-(2-N,N-di-(3-phenylpropylene)aminoethyl))piperidinylamino]-9-cyclopentylpurine is prepared from 2,6-dichloro-9-cyclopentylpurine, 4-amino-1-(2-N,N-di-(3-phenylpropylene)aminoethyl)piperidine, and triethylamine essentially as described above in Example 1, Scheme A, step b.
Scheme A, step c: 2-[Trans-(4-aminocyclohexyl)amino]-6-[4-(1-(2-N,N-di-(3-phenylpropylene)aminoethyl))piperidinylamino]-9-cyclopentylpurine
2-[Trans-(4-aminocyclohexyl)amino]-6-[4-(1-(2-N,N-di-(3-phenylpropylene)aminoethyl))piperidinylamino]-9-cyclopentylpurine is prepared from 2-chloro-6-[4-(1-(2-N,N-di-(3-phenylpropylene)aminoethyl))piperidinylamino]-9-cyclopentylpurine essentially as described in Example 1, Scheme A, step c.

EXAMPLE 125

2-[Trans-(4-aminocyclohexyl)amino]-6-[4-(1-(3-N,N-di-(3-phenylpropylene)aminopropyl))piperidinylamino]-9-cyclopentylpurine Preparation of 4-Amino-1-(3-N,N-di-(3-phenylpropylene)aminopropyl)piperidine
Method 1
Scheme B, step a: 4-Carboxamide-1-(3-N,N-di-(3-phenylpropylene)aminopropyl)piperidine
4-Carboxamide-1-(3-N,N-di-(3-phenylpropylene)aminopropyl)piperidine may be prepared from isonipecotamide and 3-N,N-di-(3-phenylpropyleneamino)propyl chloride essentially as described above in Example 38, Scheme B, step a.
Scheme B, step b: 4-Amino-1-(3-N,N-di-(3-phenylpropylene)aminopropyl)piperidine
4-Amino-1-(3-N,N-di-(3-phenylpropylene)aminopropyl)piperidine is prepared from 4-carboxamide-1-(3-N,N-di-(3-phenylpropylene)aminopropyl)piperidine essentially as described above in Example 38, Scheme B, step b.
Method 2
Scheme C, step a: 1-(3-N,N-di-(3-phenylpropylene)aminopropyl)-4-piperidone
1-(3-N,N-di-(3-phenylpropylene)aminopropyl)-4-piperidone is prepared from 4-piperidone and 3-N,N-di-(3-phenylpropyleneamino)propyl chloride essentially as described above in Example 38, Scheme C, step a.
Scheme C, step b: 1-(3-N,N-di-(3-phenylpropylene)aminopropyl)-4-piperidone oxime
1-(3-N,N-di-(3-phenylpropylene)aminopropyl)-4-piperidone oxime is prepared from 1-(3-N,N-di-(3-phenylpropylene)aminopropyl)-4-piperidone and hydroxylamine hydrochloride essentially as described above in Example 38, Scheme C, step b.
Scheme C, step c: 4-Amino-1-(3-N,N-di-(3-phenylpropylene)aminopropyl)piperidine
4-Amino-1-(3-N,N-di-(3-phenylpropylene)aminopropyl)piperidine is prepared from 1-(3-N,N-di-(3-phenylpropylene)aminopropyl)-4-piperidone oxime essentially as described above in Example 38, Scheme C, step c.
Scheme A, step b: 2-Chloro-6-[4-(1-(3-N,N-di-(3-phenylpropylene)aminopropyl))piperidinylamino]-9-cyclopentylpurine
2-Chloro-6-[4-(1-(3-N,N-di-(3-phenylpropylene)aminopropyl))piperidinylamino]-9-cyclopentylpurine is prepared from 2,6-dichloro-9-cyclopentylpurine, 4-amino-1-(3-N,N-di-(3-phenylpropylene)aminopropyl)piperidine, and triethylamine essentially as described above in Example 1, Scheme A, step b.

Scheme A, step c: 2-[Trans-(4-aminocyclohexyl)amino]-6-[4-(1-(3-N,N-di-(3-phenylpropylene)aminopropyl))piperidinylamino]-9-cyclopentylpurine 2-[Trans-(4-aminocyclohexyl)amino]-6-[4-(1-(3-N,N-di-(3-phenylpropylene)aminopropyl))piperidinylamino]-9-cyclopentylpurine is prepared from 2-chloro-6-[4-(1-(3-N,N-di-(3-phenylpropylene)aminopropyl))piperidinylamino]-9-cyclopentylpurine essentially as described in Example 1, Scheme A, step c.

EXAMPLE 126

2-[Trans-(4-aminocyclohexyl)amino]-6-[4-(1-(4-N,N-di-(3-phenylpropylene)aminobutyl))piperidinylamino]-9-cyclopentylpurine Preparation of 4-Amino-1-(4-N,N-di-(3-phenylpropylene)aminobutyl)piperidine Method 1

Scheme B, step a: 4-Carboxamide-1-(4-N,N-di-(3-phenylpropylene)aminobutyl)piperidine 4-Carboxamide-1-(4-N,N-di-(3-phenylpropylene)aminobutyl)piperidine may be prepared from isonipecotamide and 4-N,N-di-(3-phenylpropyleneamino)butyl chloride essentially as described above in Example 38, Scheme B, step a.

Scheme B, step b: 4-Amino-1-(4-N,N-di-(3-phenylpropylene)aminobutyl)piperidine

4-Amino-1-(4-N,N-di-(3-phenylpropylene)aminobutyl)piperidine is prepared from 4-carboxamide-1-(4-N,N-di-(3-phenylpropylene)aminobutyl)piperidine essentially as described above in Example 38, Scheme B, step b.

Method 2

Scheme C, step a: 1-(4-N,N-di-(3-phenylpropylene)aminobutyl-4-piperidone 1-(4-N,N-di-(3-phenylpropylene)aminobutyl)-4-piperidone is prepared from 4-piperidone and 4-N,N-di-(3-phenylpropyleneamino)butyl chloride essentially as described above in Example 38, Scheme C, step a.

Scheme C, step b: 1-(4-N,N-di-(3-phenylpropylene)aminobutyl)-4-piperidone oxime 1-(4-N,N-di-(3-phenylpropylene)aminobutyl)-4-piperidone oxime is prepared from 1-(4-N,N-di-(3-phenylpropylene)aminobutyl)-4-piperidone and hydroxylamine hydrochloride essentially as described above in Example 38, Scheme C, step b.

Scheme C, step c: 4-Amino-1-(4-N,N-di-(3-phenylpropylene)aminobutyl)piperidine

4-Amino-1-(4-N,N-di-(3-phenylpropylene)aminobutyl)piperidine is prepared from 1-(4-N,N-di-(3-phenylpropylene)aminobutyl)-4-piperidone oxime essentially as described above in Example 38, Scheme C, step c.

Scheme A, step b: 2-Chloro-6-[4-(1-(4-N,N-di-(3-phenylpropylene)aminobutyl)piperidinylamino]-9-cyclopentylpurine 2-Chloro-6-[4-(1-(4-N,N-di-(3-phenylpropylene)aminobutyl))piperidinylamino]-9-cyclopentylpurine is prepared from 2,6-dichloro-9-cyclopentylpurine, 4-amino-1-(4-N,N-di-(3-phenylpropylene)aminobutyl)piperidine, and triethylamine essentially as described above in Example 1, Scheme A, step b.

Scheme A, step c: 2-[Trans-(4-aminocyclohexyl)amino]-6-[4-(1-(4-N,N-di-(3-phenylpropylene)aminobutyl))piperidinylamino]-9-cyclopentylpurine 2-[Trans-(4-aminocyclohexyl)amino]-6-[4-(1-(4-N,N-di-(3-phenylpropylene)aminobutyl))piperidinylamino]-9-cyclopentylpurine is prepared from 2-chloro-6-[4-(1-(4-N,N-di-(3-phenylpropylene)aminobutyl))piperidinylamino]-9-cyclopentylpurine essentially as described in Example 1, Scheme A, step c.

EXAMPLE 127

2-[Trans-(4-aminocyclohexyl)amino]-6-[4-(1-(5-N,N-di-(3-phenylpropylene)aminopentyl))piperidinylamino]-9-cyclopentylpurine Preparation of 4-Amino-1-(5-N,N-di-(3-phenylpropylene)aminopentyl)piperidine Method 1

Scheme B, step a: 4-Carboxamide-1-(5-N,N-di-(3-phenylpropylene)aminopentyl)piperidine 4-Carboxamide-1-(5-N,N-di-(3-phenylpropylene)aminopentyl)piperidine may be prepared from isonipecotamide and 5-N,N-di-(3-phenylpropyleneamino)pentyl chloride essentially as described above in Example 38, Scheme B, step a.

Scheme B, step b: 4-Amino-1-(5-N,N-di-(3-phenylpropylene)aminopentyl)piperidine

4-Amino-1-(5-N,N-di-(3-phenylpropylene)aminopentyl)piperidine is prepared from 4-carboxamide-1-(5-N,N-di-(3-phenylpropylene)aminopentyl)piperidine essentially as described above in Example 38, Scheme B, step b.

Method 2

Scheme C, step a: 1-(5-N,N-di-(3-phenylpropylene)aminopentyl)-4-piperidone 1-(5-N,N-di-(3-phenylpropylene)aminopentyl)-4-piperidone is prepared from 4-piperidone and 5-N,N-di-(3-phenylpropyleneamino)pentyl chloride essentially as described above in Example 38, Scheme C, step a.

Scheme C, step b: 1-(5-N,N-di-(3-phenylpropylene)aminopentyl)-4-piperidone oxime 1-(5-N,N-di-(3-phenylpropylene)aminopentyl)-4-piperidone oxime is prepared from 1-(5-N,N-di-(3-phenylpropylene)aminopentyl)-4-piperidone and hydroxylamine hydrochloride essentially as described above in Example 38, Scheme C, step b.

Scheme C, step c: 4-Amino-1-(5-N,N-di-(3-phenylpropylene)aminopentyl)piperidine

4-Amino-1-(5-N,N-di-(3-phenylpropylene)aminopentyl)piperidine is prepared from 1-(5-N,N-di-(3-phenylpropylene)aminopentyl)-4-piperidone oxime essentially as described above in Example 38, Scheme C, step c.

Scheme A, step b: 2-Chloro-6-[4-(1-(5-N,N-di-(3-phenylpropylene)aminopentyl))piperidinylamino]-9-cyclopentylpurine 2-Chloro-6-[4-(1-(5-N,N-di-(3-phenylpropylene)aminopentyl))piperidinylamino]-9-cyclopentylpurine is prepared from 2,6-dichloro-9-cyclopentylpurine, 4-amino-1-(5-N,N-di-(3-phenylpropylene)aminopentyl)piperidine, and triethylamine essentially as described above in Example 1, Scheme A, step b.

Scheme A, step c: 2-[Trans-(4-aminocyclohexyl)amino]-6-[4-(1-(5-N,N-di-(3-phenylpropylene)aminopentyl)piperidinylamino]-9-cyclopentylpurine 2-[Trans-(4-aminocyclohexyl)amino]-6-[4-(1-(5-N,N-di-(3-phenylpropylene)aminopentyl))piperidinylamino]-9-cyclopentylpurine is prepared from 2-chloro-6-[4-(1-(5-N,N-di-(3-phenylpropylene)aminopentyl))piperidinylamino]-9-cyclopentylpurine essentially as described in Example 1, Scheme A, step c.

EXAMPLE 128

2-[Trans-(4-aminocyclohexyl)amino]-6-[4-(1-(2-N,
N-di-(4-phenylbutylene)aminoethyl))
piperidinylamino]-9-cyclopentylpurine Preparation of 4-Amino-1-(2-N,N-di-(4-phenylbutylene)
aminoethyl)piperidine Method 1

Scheme B, step a: 4-Carboxamide-1-(2-N N-di-(4-phenylbutylene)aminoethyl)piperidine 4-Carboxamide-1-(2-N,N-di-(4-phenylbutylene) aminoethyl)piperidine may be prepared from isonipecotamide and 2-N,N-di-(4-phenylbutyleneamino)ethyl chloride essentially as described above in Example 38, Scheme B, step a.

Scheme B, step b: 4-Amino-1-(2-N,N-di-(4-phenylbutylene)aminoethyl)piperidine

4-Amino-1-(2-N,N-di-(4-phenylbutylene)aminoethyl) piperidine is prepared from 4-carboxamide-1-(2-N,N-di-(4-phenylbutylene)aminoethyl)piperidine essentially as described above in Example 38, Scheme B, step b.

Method 2

Scheme C, step a: 1-(2-N,N-di-(4-phenylbutylene) aminoethyl)-4-piperidone 1-(2-N,N-di-(4-phenylbutylene)aminoethyl)-4-piperidone is prepared from 4-piperidone and 2-N,N-di-(4-phenylbutyleneamino)ethyl chloride essentially as described above in Example 38, Scheme C, step a.

Scheme C, step b: 1-(2-N,N-di-(4-phenylbutylene) aminoethyl)-4-piperidone oxime 1-(2-N,N-di-(4-phenylbutylene)aminoethyl)-4-piperidone oxime is prepared from 1-(2-N,N-di-(4-phenylbutylene)aminoethyl)-4-piperidone and hydroxylamine hydrochloride essentially as described above in Example 38, Scheme C, step b.

Scheme C, step c: 4-Amino-1-(2-N,N-di-(4-phenylbutylene)aminoethyl)piperidine

4-Amino-1-(2-N,N-di-(4-phenylbutylene)aminoethyl) piperidine is prepared from 1-(2-N,N-di-(4-phenylbutylene)aminoethyl)-4-piperidone oxime essentially as described above in Example 38, Scheme C, step c.

Scheme A, step b: 2-Chloro-6-[4-(1-(2-N,N-di-(4-phenylbutylene)aminoethyl))piperidinylamino]-9-cyclopentylpurine 2-Chloro-6-[4-(1-(2-N,N-di-(4-phenylbutylene) aminoethyl))piperidinylamino]-9-cyclopentylpurine is prepared from 2,6-dichloro-9-cyclopentylpurine, 4-amino-1-(2-N,N-di-(4-phenylbutylene)aminoethyl)piperidine, and triethylamine essentially as described above in Example 1, Scheme A, step b.

Scheme A, step c: 2-[Trans-(4-aminocyclohexyl)amino]-6-[4-(1-(2-N,N-di-(4-phenylbutylene)aminoethyl)) piperidinylamino]-9-cyclopentylpurine 2-[Trans-(4-aminocyclohexyl)amino]-6-[4-(1-(2-N,N-di-(4-phenylbutylene)aminoethyl))piperidinylamino]-9-cyclopentylpurine is prepared from 2-chloro-6-[4-(1-(2-N,N-di-(4-phenylbutylene)aminoethyl))piperidinylamino]-9-cyclopentylpurine essentially as described in Example 1, Scheme A, step c.

EXAMPLE 129

2-[Trans-(4-aminocyclohexyl)amino]-6-[4-(1-(3-N,
N-di-(4-phenylbutylene)aminopropyl))
piperidinylamino]-9-cyclopentylpurine Preparation of 4-Amino-1-(3-N,N-di-(4-phenylbutylene) aminopropyl)piperidine Method 1

Scheme B, step a: 4-Carboxamide-1-(3-N,N-di-(4-phenylbutylene)aminopropyl)piperidine 4-Carboxamide-1-(3-N,N-di-(4-phenylbutylene) aminopropyl)piperidine may be prepared from isonipecotamide and 3-N,N-di-(4-phenylbutyleneamino)propyl chloride essentially as described above in Example 38, Scheme B, step a.

Scheme B, step b: 4-Amino-1-(3-N,N-di-(4-phenylbutylene)aminopropyl)piperidine

4-Amino-1-(3-N,N-di-(4-phenylbutylene)aminopropyl) piperidine is prepared from 4-carboxamide-1-(3-N,N-di-(4-phenylbutylene)aminopropyl)piperidine essentially as described above in Example 38, Scheme B, step b.

Method 2

Scheme C, step a: 1-(3-N,N-di-(4-phenylbutylene) aminopropyl)-4-piperidone 1-(3-N,N-di-(4-phenylbutylene)aminopropyl)-4-piperidone is prepared from 4-piperidone and 3-N,N-di-(4-phenylbutyleneamino)propyl chloride essentially as described above in Example 38, Scheme C, step a.

Scheme C, step b: 1-(3-N,N-di-(4-phenylbutylene) aminopropyl)-4-piperidone oxime 1-(3-N,N-di-(4-phenylbutylene)aminopropyl)-4-piperidone oxime is prepared from 1-(3-N,N-di-(4-phenylbutylene)aminopropyl)-4-piperidone and hydroxylamine hydrochloride essentially as described above in Example 38, Scheme C, step b.

Scheme C, step c: 4-Amino-1-(3-N,N-di-(4-phenylbutylene)aminopropyl)piperidine

4-Amino-1-(3-N,N-di-(4-phenylbutylene)aminopropyl) piperidine is prepared from 1-(3-N,N-di-(4-phenylbutylene)aminopropyl)-4-piperidone oxime essentially as described above in Example 38, Scheme C, step c.

Scheme A, step b: 2-Chloro-6-[4-(1-(3-N,N-di-(4-phenylbutylene)aminopropyl))piperidinylamino]-9-cyclopentylpurine 2-Chloro-6-[4-(1-(3-N,N-di-(4-phenylbutylene) aminopropyl))piperidinylamino]-9-cyclopentylpurine is prepared from 2,6-dichloro-9-cyclopentylpurine, 4-amino-1-(3-N,N-di-(4-phenylbutylene)aminopropyl)piperidine, and triethylamine essentially as described above in Example 1, Scheme A, step b.

Scheme A, step c: 2-[Trans-(4-aminocyclohexyl)amino]-6-[4-(1-(3-N,N-di-(4-phenylbutylene)aminopropyl)) piperidinylamino]-9-cyclopentylpurine 2-[Trans-(4-aminocyclohexyl)amino]-6-[4-(1-(3-N,N-di-(4-phenylbutylene)aminopropyl))piperidinylamino]-9-cyclopentylpurine is prepared from 2-chloro-6-[4-(1-(3-N,N-di-(4-phenylbutylene)aminopropyl))piperidinylamino]-9-cyclopentylpurine essentially as described in Example 1, Scheme A, step c.

EXAMPLE 130

2-[Trans-(4-aminocyclohexyl)amino]-6-[4-(1-(4-N,
N-di-(4-phenylbutylene)aminobutyl))
piperidinylamino]-9-cyclopentylpurine Preparation of 4-Amino-1-(4-N,N-di-(4-phenylbutylene) aminobutyl)piperidine Method 1

Scheme B, step a: 4-Carboxamide-1-(4-N,N-di-(4-phenylbutylene)aminobutyl)piperidine 4-Carboxamide-1-(4-N,N-di-(4-phenylbutylene) aminobutyl)piperidine may be prepared from isonipecotamide and 4-N,N-di-(4-phenylbutyleneamino)butyl chloride essentially as described above in Example 38, Scheme B, step a.

Scheme B, step b: 4-Amino-1-(4-N,N-di-(4-phenylbutylene)aminobutyl)piperidine

4-Amino-1-(4-N,N-di-(4-phenylbutylene)aminobutyl) piperidine is prepared from 4-carboxamide-1-(4-N,N-di-(4-phenylbutylene)aminobutyl)piperidine essentially as described above in Example 38, Scheme B, step b.

Method 2
Scheme C, step a: 1-(4-(Di-(4-phenylbutylene)aminobutyl)-4-piperidone 1-(4-(Di-(4-phenylbutylene)aminobutyl)-4-piperidone is prepared from 4-piperidone and 4-N,N-di-(4-phenylbutyleneamino)butyl chloride essentially as described above in Example 38, Scheme C, step a.

Scheme C, step b: 1-(4-(Di-(4-phenylbutylene)aminobutyl)-4-piperidone oxime 1-(4-(Di-(4-phenylbutylene)aminobutyl)-4-piperidone oxime is prepared from 1-(4-(di-(4-phenylbutylene)aminobutyl)-4-piperidone and hydroxylamine hydrochloride essentially as described above in Example 38, Scheme C, step b.

Scheme C, step c: 4-Amino-1-(4-N,N-di-(4-phenylbutylene)aminobutyl)piperidine

4-Amino-1-(4-N,N-di-(4-phenylbutylene)aminobutyl)piperidine is prepared from 1-(4-(di-(4-phenylbutylene)aminobutyl)-4-piperidone oxime essentially as described above in Example 38, Scheme C, step c.

Scheme A, step b: 2-Chloro-6-[4-(1-(4-N,N-di-(4-phenylbutylene)aminobutyl))piperidinylamino]-9-cyclopentylpurine 2-Chloro-6-[4-(1-(4-N,N-di-(4-phenylbutylene)aminobutyl))piperidinylamino]-9-cyclopentylpurine is prepared from 2,6-dichloro-9-cyclopentylpurine, 4-amino-1-(4-N,N-di-(4-phenylbutylene)aminobutyl)piperidine, and triethylamine essentially as described above in Example 1, Scheme A, step b.

Scheme A, step c: 2-[Trans-(4-aminocyclohexyl)amino]-6-[4-(1-(4-N,N-di-(4-phenylbutylene)aminobutyl))piperidinylamino]-9-cyclopentylpurine 2-[Trans-(4-aminocyclohexyl)amino]-6-[4-(1-(4-N,N-di-(4-phenylbutylene)aminobutyl))piperidinylamino]-9-cyclopentylpurine is prepared from 2-chloro-6-[4-(1-(4-N,N-di-(4-phenylbutylene)aminobutyl))piperidinylamino]-9-cyclopentylpurine essentially as described in Example 1, Scheme A, step c.

EXAMPLE 131

2-[Trans-(4-aminocyclohexyl)amino]-6-[4-(1-(5-N,N-di-(4-phenylbutylene)aminopentyl))piperidinylamino]-9-cyclopentylpurine Preparation of 4-Amino-1-(5-N,N-di-(4-phenylbutylene)aminopentyl)piperidine Method 1
Scheme B, step a: 4-Carboxamide-1-(5-N N-di-(4-phenylbutylene)aminopentyl)piperidine 4-Carboxamide-1-(5-N,N-di-(4-phenylbutylene)aminopentyl)piperidine may be prepared from isonipecotamide and 5-N,N-di-(4-phenylbutyleneamino)pentyl chloride essentially as described above in Example 38, Scheme B, step a.

Scheme B, step b: 4-Amino-1-(5-N,N-di-(4-phenylbutylene)aminopentyl)piperidine

4-Amino-1-(5-N,N-di-(4-phenylbutylene)aminopentyl)piperidine is prepared from 4-carboxamide-1-(5-N,N-di-(4-phenylbutylene)aminopentyl)piperidine essentially as described above in Example 38, Scheme B, step b.

Method 2
Scheme C, step a: 1-(5-N,N-di-(4-phenylbutylene)aminopentyl)-4-piperidone 1-(5-N,N-di-(4-phenylbutylene)aminopentyl)-4-piperidone is prepared from 4-piperidone and 5-N,N-di-(4-phenylbutyleneamino)pentyl chloride essentially as described above in Example 38, Scheme C, step a.

Scheme C, step b: 1-(5-N,N-di-(4-phenylbutylene)aminopentyl)-4-piperidone oxime 1-(5-N,N-di-(4-phenylbutylene)aminopentyl)-4-piperidone oxime is prepared from 1-(5-N,N-di-5(4-phenylbutylene)aminopentyl)-4-piperidone and hydroxylamine hydrochloride essentially as described above in Example 38, Scheme C, step b.

Scheme C, step c: 4-Amino-1-(5-N,N-di-(4-phenylbutylene)aminopentyl)piperidine

4-Amino-1-(5-N,N-di-(4-phenylbutylene)aminopentyl)piperidine is prepared from 1-(5-N,N-di-(4-phenylbutylene)aminopentyl)-4-piperidone oxime essentially as described above in Example 38, Scheme C, step c.

Scheme A, step b: 2-Chloro-6-[4-(1-(5-N,N-di-(4-phenylbutylene)aminopentyl))piperidinylamino]-9-cyclopentylpurine 2-Chloro-6-[4-(1-(5-N,N-di-(4-phenylbutylene)aminopentyl))piperidinylamino]-9-cyclopentylpurine is prepared from 2,6-dichloro-9-cyclopentylpurine, 4-amino-1-(5-N,N-di-(4-phenylbutylene)aminopentyl)piperidine, and triethylamine essentially as described above in Example 1, Scheme A, step b.

Scheme A, step c: 2-[Trans-(4-aminocyclohexyl)amino]-6-[4-(1-(5-N N-di-(4-phenylbutylene)aminopentyl))piperidinylamino]-9-cyclopentylpurine 2-[Trans-(4-aminocyclohexyl)amino]-6-[4-(1-(5-N,N-di-(4-phenylbutylene)aminopentyl))piperidinylamino]-9-cyclopentylpurine is prepared from 2-chloro-6-[4-(1-(5-N,N-di-(4-phenylbutylene)aminopentyl))piperidinylamino]-9-cyclopentylpurine essentially as described in Example 1, Scheme A, step c.

EXAMPLE 132

2-[Trans-(4-aminocyclohexyl)amino]-6-[4-(1-(3-tetrahydrofuranyl)methyl)piperidinylamino]-9-cyclopentylpurine Preparation of 4-Amino-1-(3-tetrahydrofuranylmethyl)piperidine Method 1
Scheme B, step a: 4-Carboxamide-1-(3-tetrahydrofuranylmethyl)piperidine 4-Carboxamide-1-(3-tetrahydrofuranylmethyl)piperidine may be prepared from isonipecotamide and tetrahydrofurfuryl chloride essentially as described above in Example 38, Scheme B, step a.

Scheme B, step b: 4-Amino-1-(3-tetrahydrofuranylmethyl)piperidine

4-Amino-1-(3-tetrahydrofuranylmethyl)piperidine is prepared from 4-carboxamide-1-(3-tetrahydrofuranylmethyl)piperidine essentially as described above in Example 38, Scheme B, step b.

Method 2
Scheme C, step a: 1-(3-Tetrahydrofuranylmethyl)-4-piperidone 1-(3-Tetrahydrofuranylmethyl)-4-piperidone is prepared from 4-piperidone and tetrahydrofurfuryl chloride essentially as described above in Example 38, Scheme C, step a.

Scheme C, step b: 1-(3-Tetrahydrofuranylmethyl)-4-piperidone oxime 1-(3-Tetrahydrofuranylmethyl)-4-piperidone oxime is prepared from 1-(3-tetrahydrofuranylmethyl)-4-piperidone and hydroxylamine hydrochloride essentially as described above in Example 38, Scheme C, step b.

Scheme C, step c: 4-Amino-1-(3-tetrahydrofuranylmethyl)piperidine

4-Amino-1-(3-tetrahydrofuranylmethyl)piperidine is prepared from 1-(3-tetrahydrofuranylmethyl)-4-piperidone oxime essentially as described above in Example 38, Scheme C, step c.

Scheme A step b: 2-Chloro-6-[4-(1-(3-tetrahydrofuranyl)methyl)piperidinylamino]-9-cyclopentylpurine 2-Chloro-6-[4-(1-(3-tetrahydrofuranyl)methyl)piperidinylamino]-9-cyclopentylpurine is prepared from 2,6-dichloro-9-cyclopentylpurine, 4-amino-1-(3-tetrahydrofuranylmethyl)piperidine, and triethylamine essentially as described above in Example 1, Scheme A, step b.

Scheme A, step c: 2-[Trans-(4-aminocyclohexyl)amino]-6-[4-(1-(3-tetrahydrofuranyl)methyl)piperidinylamino]-9-cyclopentylpurine 2-[Trans-(4-aminocyclohexyl)amino]-6-[4-(1-(3-tetrahydrofuranyl)methyl)piperidinylamino]-9-cyclopentylpurine is prepared from 2-chloro-6-[4-(1-(3-tetrahydrofuranyl)methyl)piperidinylamino]-9-cyclopentylpurine essentially as described in Example 1, Scheme A, step c.

EXAMPLE 133

2-[Trans-(4-aminocyclohexyl)amino]-6-[4-(1-(2-(1-pyrrolidinyl)ethyl))piperidinylamino]-9-cyclopentylpurine Preparation of 4-Amino-1-(2-(1-pyrrolidinyl)ethyl)piperidine
Method 1
Scheme B, step a: 4-Carboxamide-1-(2-(1-pyrrolidinyl)ethyl)piperidine 4-Carboxamide-1-(2-(1-pyrrolidinyl)ethyl)piperidine may be prepared from isonipecotamide and 1-(2-chloroethyl)pyrrolidine essentially as described above in Example 38, Scheme B, step a.

Scheme B, step b: 4-Amino-1-(2-(1-pyrrolidinyl)ethyl)piperidine

4-Amino-1-(2-(1-pyrrolidinyl)ethyl)piperidine is prepared from 4-carboxamide-1-(2-(1-pyrrolidinyl)ethyl)piperidine essentially as described above in Example 38, Scheme B, step b.
Method 2
Scheme C, step a: 1-(2-(1-Pyrrolidinyl)ethyl)-4-piperidone 1-(2-(1-Pyrrolidinyl)ethyl)-4-piperidone is prepared from 4-piperidone and 1-(2-chloroethyl)pyrrolidine essentially as described above in Example 38, Scheme C, step a.

Scheme C, step b: 1-(2-(1-Pyrrolidinyl)ethyl)-4-piperidone oxime 1-(2-(1-Pyrrolidinyl)ethyl)-4-piperidone oxime is prepared from 1-(2-(1-pyrrolidinyl)ethyl)-4-piperidone and hydroxylamine hydrochloride essentially as described above in Example 38, Scheme C, step b.

Scheme C, step c: 4-Amino-1-(2-(1-pyrrolidinyl)ethyl)piperidine

4-Amino-1-(2-(1-pyrrolidinyl)ethyl)piperidine is prepared from 1-(2-(1-pyrrolidinyl)ethyl)-4-piperidone oxime essentially as described above in Example 38, Scheme C, step c.

Scheme A, step b: 2-Chloro-6-[4-(1-(2-(1-pyrrolidinyl)ethyl))piperidinylamino]-9-cyclopentylpurine 2-Chloro-6-[4-(1-(2-(1-pyrrolidinyl)ethyl))piperidinylamino]-9-cyclopentylpurine is prepared from 2,6-dichloro-9-cyclopentylpurine, 4-amino-1-(2-(1-pyrrolidinyl)ethyl)piperidine, and triethylamine essentially as described above in Example 1, Scheme A, step b.

Scheme A, step c: 2-[Trans-(4-aminocyclohexyl)amino]-6-[4-(1-(2-(1-pyrrolidinyl)ethyl))piperidinylamino]-9-cyclopentylpurine 2-[Trans-(4-aminocyclohexyl)amino]-6-[4-(1-(2-(1-pyrrolidinyl)ethyl))piperidinylamino]-9-cyclopentylpurine is prepared from 2-chloro-6-[4-(1-(2-(1-pyrrolidinyl)ethyl))piperidinylamino]-9-cyclopentylpurine essentially as described in Example 1, Scheme A, step c.

EXAMPLE 134

2-[Trans-(4-aminocyclohexyl)amino]-6-[4-(1-(2-(1-piperidinyl)ethyl))piperidinylamino]-9-cyclopentylpurine Preparation of 4-Amino-1-(2-(1-piperidinyl)ethyl)piperidine
Method 1
Scheme B, step a: 4-Carboxamide-1-(2-(1-piperidinyl)ethyl)piperidine 4-Carboxamide-1-(2-(1-piperidinyl)ethyl)piperidine may be prepared from isonipecotamide and 1-(2-chloroethyl)piperidine essentially as described above in Example 38, Scheme B, step a.

Scheme B, step b: 4-Amino-1-(2-(1-piperidinyl)ethyl)piperidine

4-Amino-1-(2-(1-piperidinyl)ethyl)piperidine is prepared from 4-carboxamide-1-(2-(1-piperidinyl)ethyl)piperidine essentially as described above in Example 38, Scheme B, step b.
Method 2
Scheme C, step a: 1-(2-(1-Piperidinyl)ethyl)-4-piperidone 1-(2-(1-Piperidinyl)ethyl)-4-piperidone is prepared from 4-piperidone and 1-(2-chloroethyl)piperidine essentially as described above in Example 38, Scheme C, step a.

Scheme C, step b: 1-(2-(1-Piperidinyl)ethyl)-4-piperidone oxime 1-(2-(1-Piperidinyl)ethyl)-4-piperidone oxime is prepared from 1-(2-(1-piperidinyl)ethyl)-4-piperidone and hydroxylamine hydrochloride essentially as described above in Example 38, Scheme C, step b.

Scheme C, step c: 4-Amino-1-(2-(1-piperidinyl)ethyl)piperidine

4-Amino-1-(2-(1-piperidinyl)ethyl)piperidine is prepared from 1-(2-(1-piperidinyl)ethyl)-4-piperidone oxime essentially as described above in Example 38, Scheme C, step c.

Scheme A, step b: 2-Chloro-6-[4-(1-(2-(1-piperidinyl)ethyl))piperidinylamino]-9-cyclopentylpurine 2-Chloro-6-[4-(1-(2-(1-piperidinyl)ethyl))piperidinylamino]-9-cyclopentylpurine is prepared from 2,6-dichloro-9-cyclopentylpurine, 4-amino-1-(2-(1-piperidinyl)ethyl)piperidine, and triethylamine essentially as described above in Example 1, Scheme A, step b.

Scheme A, step c: 2-[Trans-(4-aminocyclohexyl)amino]-6-[4-(1-(2-(1-piperidinyl)ethyl))piperidinylamino]-9-cyclopentylpurine 2-[Trans-(4-aminocyclohexyl)amino]-6-[4-(1-(2-(1-piperidinyl)ethyl))piperidinylamino]-9-cyclopentylpurine is prepared from 2-chloro-6-[4-(1-(2-(1-piperidinyl)ethyl))piperidinylamino]9-cyclopentylpurine essentially as described in Example 1, Scheme A, step c.

EXAMPLE 135

2-[Trans-(4-aminocyclohexyl)amino]-6-[4-(1-(2-(4-morpholinyl)ethyl))piperidinylamino]-9-cyclopentylpurine Preparation of 4-Amino-1-(2-(4-morpholinyl)ethyl)piperidine
Method 1
Scheme B, step a: 4-Carboxamide-1-(2-(4-morpholinyl)ethyl)piperidine 4-Carboxamide-1-(2-(4-morpholinyl)ethyl)piperidine may be prepared from isonipecotamide and 1-(2- chloroethyl)morpholine essentially as described above in Example 38, Scheme B, step a.

Scheme B, step b: 4-Amino-1-(2-(4-morpholinyl)ethyl)piperidine

4-Amino-1-(2-(4-morpholinyl)ethyl)piperidine is prepared from 4-carboxamide-1-(2-(4-morpholinyl)ethyl)piperidine essentially as described above in Example 38, Scheme B, step b.

Method 2

Scheme C, step a: 1-(2-(4-Morpholinyl)ethyl)-4-piperidone 1-(2-(4-Morpholinyl)ethyl)-4-piperidone is prepared from 4-piperidone and 1-(2-chloroethyl)morpholine essentially as described above in Example 38, Scheme C, step a.

Scheme C, step b: 1-(2-(4-Morpholinyl)ethyl)-4-piperidone oxime 1-(2-(4-Morpholinyl)ethyl)-4-piperidone oxime is prepared from 1-(2-(4-morpholinyl)ethyl)-4-piperidone and hydroxylamine hydrochloride essentially as described above in Example 38, Scheme C, step b.

Scheme C, step c: 4-Amino-1-(2-(4-morpholinyl)ethyl)piperidine

4-Amino-1-(2-(4-morpholinyl)ethyl)piperidine is prepared from 1-(2-(4-morpholinyl)ethyl)-4-piperidone oxime essentially as described above in Example 38, Scheme C, step c.

Scheme A, step b: 2-Chloro-6-[4-(1-(2-(4-morpholinyl)ethyl))piperidinylamino]-9-cyclopentylpurine 2-Chloro-6-[4-(1-(2-(4-morpholinyl)ethyl))piperidinylamino]-9-cyclopentylpurine is prepared from 2,6-dichloro-9-cyclopentylpurine, 4-amino-1-(2-(4-morpholinyl)ethyl)piperidine, and triethylamine essentially as described above in Example 1, Scheme A, step b.

Scheme A, step c: 2-[Trans-(4-aminocyclohexyl)amino]-6-[4-(1-(2-(4-morpholinyl)ethyl))piperidinylamino]-9-cyclopentylpurine 2-[Trans-(4-aminocyclohexyl)amino]-6-[4-(1-(2-(4-morpholinyl)ethyl))piperidinylamino]-9-cyclopentylpurine di is prepared from 2-chloro-6-[4-(1-(2-(4-morpholinyl)ethyl))piperidinylamino]-9-cyclopentylpurine essentially as described in Example 1, Scheme A, step c.

EXAMPLE 136

2-[Trans-(4-aminocyclohexyl)amino]-6-[4-(1-(3-(1-piperidinyl)propyl))piperidinylamino]-9-cyclopentylpurine Preparation of 4-Amino-1-(3-(1-piperidinyl)propyl)piperidine Method 1

Scheme B, step a: 4-Carboxamide-1-(3-(1-piperidinyl)propyl)piperidine

4-Carboxamide-1-(3-(1-piperidinyl)propyl)piperidine may be prepared from isonipecotamide and 1-(3-chloropropyl)piperidine essentially as described above in Example 38, Scheme B, step a.

Scheme B, step b: 4-Amino-1-(3-(1-piperidinyl)propyl)piperidine

4-Amino-1-(3-(1-piperidinyl)propyl)piperidine is prepared from 4-carboxamide-1-(3-(1-piperidinyl)propyl)piperidine essentially as described above in Example 38, Scheme B, step b.

Method 2

Scheme C, step a: 1-(3-(1-Piperidinyl)propyl)-4-piperidone 1-(3-(1-Piperidinyl)propyl)-4-piperidone is prepared from 4-piperidone and 1-(3-chloropropyl)piperidine essentially as described above in Example 38, Scheme C, step a.

Scheme C, step b: 1-(3-(1-Piperidinyl)propyl)-4-piperidone oxime 1-(3-(1-Piperidinyl)propyl)-4-piperidone oxime is prepared from 1-(3-(1-piperidinyl)propyl)-4-piperidone and hydroxylamine hydrochloride essentially as described above in Example 38, Scheme C, step b.

Scheme C, step c: 4-Amino-1-(3-(1-piperidinyl)propyl)piperidine

4-Amino-1-(3-(1-piperidinyl)propyl)piperidine is prepared from 1-(3-(1-piperidinyl)propyl)-4-piperidone oxime essentially as described above in Example 38, Scheme C, step c.

Scheme A, step b: 2-Chloro-6-[4-(1-(3-(1-piperidinyl)propyl))piperidinylamino]-9-cyclopentylpurine 2-Chloro-6-[4-(1-(3-(1-piperidinyl)propyl))piperidinylamino]-9-cyclopentylpurine is prepared from 2,6-dichloro-9-cyclopentylpurine, 4-amino-1-(3-(1-piperidinyl)propyl)piperidine, and triethylamine essentially as described above in Example 1, Scheme A, step b.

Scheme A, step c: 2-[Trans-(4-aminocyclohexyl)amino]-6-[4-(1-(3-(1-piperidinyl)propyl))piperidinylamino]-9-cyclopentylpurine 2-[Trans-(4-aminocyclohexyl)amino]-6-[4-(1-(3-(1-piperidinyl)propyl))piperidinylamino]-9-cyclopentylpurine is prepared from 2-chloro-6-[4-(1-(3-(1-piperidinyl)propyl))piperidinylamino]-9-cyclopentylpurine essentially as described in Example 1, Scheme A, step c.

EXAMPLE 137

(R,S)-2-[Trans-(4-aminocyclohexyl)amino]-6-[4-(1-(3-(1-methyl)piperidinyl)methyl))piperidinylamino]-9-cyclopentylpurine Preparation of (R,S)-4-Amino-1-(3-(1-methylpiperidinyl)methyl)piperidine Method 1

Scheme B, step a: (R,S)-4-Carboxamide-1-(3-(1-methylpiperidinyl)methyl)piperidine (R,S)-4-Carboxamide-1-(3-(1-methylpiperidinyl)methyl)piperidine may be prepared from isonipecotamide and (R,S)-3-chloromethyl-1-methylpiperidine essentially as described above in Example 38, Scheme B, step a.

Scheme B, step b: (R,S)-4-Amino-1-(3-(1-methylpiperidinyl)methyl)piperidine (R,S)-4-Amino-1-(3-(1-methylpiperidinyl)methyl)piperidine is prepared from (R,S)-4-carboxamide-1-(3-(1-methylpiperidinyl)methyl)piperidine essentially as described above in Example 38, Scheme B, step b.

Method 2

Scheme C, step a: (R,S)-1-(3-(1-Methylpiperidinyl)methyl)-4-piperidone (R,S)-1-(3-(1-Methylpiperidinyl)methyl)-4-piperidone is prepared from 4-piperidone and (R,S)-3-chloromethyl-1-methylpiperidine essentially as described above in Example 38, Scheme C, step a.

Scheme C, step b: (R,S)-1-(3-(1-Methylpiperidinyl)methyl)-4-piperidone oxime (R,S)-1-(3-(1-Methylpiperidinyl)methyl)-4-piperidone oxime is prepared from (R,S)-1-(3-(1-methylpiperidinyl)methyl)-4-piperidone and hydroxylamine hydrochloride essentially as described above in Example 38, Scheme C, step b.

Scheme C, step c: (R,S)-4-Amino-1-(3-(1-methylpiperidinyl)methyl)piperidine (R,S)-4-Amino-1-(3-(1-methylpiperidinyl)methyl)piperidine is prepared from (R,S)-1-(3-(1-methylpiperidinyl)methyl)-4-piperidone oxime essentially as described above in Example 38, Scheme C, step c.

Scheme A, step b: (R,S)-2-Chloro-6-[4-(1-(3-(1-methyl)piperidinyl)methyl))piperidinylamino]-9-cyclopentylpurine (R,S)-2-Chloro-6-[4-(1-(3-(1-methyl)piperidinyl)methyl))piperidinylamino]-9-cyclopentylpurine is prepared from 2,6-dichloro-9-cyclopentylpurine, (R,S)-4-amino-1-(3-(1-methylpiperidinyl)methyl)piperidine, and triethylamine essentially as described above in Example 1, Scheme A, step b.

Scheme A, step c: (R,S)-2-[Trans-(4-aminocyclohexyl)amino]-6-[4-(1-(3-(1-methyl)piperidinyl)methyl))piperidinylamino]-9-cyclopentylpurine (R,S)-2-[Trans-(4-aminocyclohexyl)amino]-6-[4-(1-(3-(1-methyl)piperidinyl)methyl))piperidinylamino]-9-cyclopentylpurine is prepared from (R,S)-2-chloro-6-[4-(1-(3-(1-methyl)piperidinyl)methyl))piperidinylamino]-9-cyclopentylpurine essentially as described in Example 1, Scheme A, step c.

EXAMPLE 138

(R,S)-2-[Trans-(4-aminocyclohexyl)amino]-6-[4-(1-(2-(3-(1-methyl)pyrrolidinyl)ethyl))piperidinylamino]-9-cyclopentylpurine Preparation of (R,S)-4-Amino-1-(2-(3-(1-methylpyrrolidinyl))ethyl)piperidine Method 1

Scheme B, step a: (R,S)-4-Carboxamide-1-(2-(3-(1-Methylpyrrolidinyl)ethyl)piperidine (R,S)-4-Carboxamide-1-(2-(3-(1-methylpyrrolidinyl)ethyl)piperidine may be prepared from isonipecotamide and (R,S)-3-(2-chloroethyl)-1-methylpyrrolidine essentially as described above in Example 38, Scheme B, step a.

Scheme B, step b: (R,S)-4-Amino-1-(2-(3-(1-methylpyrrolidinyl))ethyl)piperidine (R,S)-4-Amino-1-(2-(3-(1-methylpyrrolidinyl))ethyl)piperidine is prepared from (R,S)-4-carboxamide-1-(2-(3-(1-methylpyrrolidinyl)ethyl)piperidine essentially as described above in Example 38, Scheme B, step b.

Method 2

Scheme C, step a: (R,S)-1-(2-(3-(1-Methylpyrrolidinyl)ethyl)-4-piperidone (R,S)-1-(2-(3-(1-Methylpyrrolidinyl)ethyl)-4-piperidone is prepared from 4-piperidone and (R,S)-3-(2-chloroethyl)-1-methylpyrrolidine essentially as described above in Example 38, Scheme C, step a.

Scheme C, step b: (R,S)-1-(2-(3-(1-Methylpyrrolidinyl)ethyl)-4-piperidone oxime (R,S)-1-(2-(3-(1-Methylpyrrolidinyl)ethyl)-4-piperidone oxime is prepared from (R,S)-1-(2-(3-(1-methylpyrrolidinyl)ethyl)-4-piperidone and hydroxylamine hydrochloride essentially as described above in Example 38, Scheme C, step b.

Scheme C, step c: (R,S)-4-Amino-1-(2-(3-(1-methylpyrrolidinyl))ethyl)piperidine (R,S)-4-Amino-1-(2-(3-(1-methylpyrrolidinyl))ethyl)piperidine is prepared from (R,S)-1-(2-(3-(1-methylpyrrolidinyl)ethyl)-4-piperidone oxime essentially as described above in Example 38, Scheme C, step c.

Scheme A, step, b: (R,S)-2-Chloro-6-[4-(1-(2-(3-(1-methyl)pyrrolidinyl)ethyl))piperidinylamino]-9-cyclopentylpurine (R,S)-2-Chloro-6-[4-(1-(2-(3-(1-methyl)pyrrolidinyl)ethyl))piperidinylamino]-9-cyclopentylpurine is prepared from 2,6-dichloro-9-cyclopentylpurine, (R,S)-4-amino-1-(2-(3-(1-methylpyrrolidinyl))ethyl)piperidine, and triethylamine essentially as described above in Example 1, Scheme A, step b.

Scheme A, step c: (R,S)-2-[Trans-(4-aminocyclohexyl)amino]-6-[4-(1-(2-(3-(1-methyl)pyrrolidinyl)ethyl))piperidinylamino]-9-cyclopentylpurine (R,S)-2-[Trans-(4-aminocyclohexyl)amino]-6-[4-(1-(2-(3-(1-methyl)pyrrolidinyl)ethyl))piperidinylamino]-9-cyclopentylpurine is prepared from (R,S)-2-chloro-6-[4-(1-(2-(3-(1-methyl)pyrrolidinyl)ethyl))piperidinylamino]-9-cyclopentylpurine essentially as described in Example 1, Scheme A, step c.

EXAMPLE 139

2-[Trans-(4-aminocyclohexyl)amino]-6-[4-(1-(2-(1-(4-methyl)piperazinyl)ethyl))piperidinylamino]-9-cyclopentylpurine Preparation of 4-Amino-1-(2-(1-(4-methylpiperazinyl))ethyl)piperidine Method 1

Scheme B, step a: 4-Carboxamide-1-(2-(1-(4-methylpiperazinyl))ethyl)piperidine

4-Carboxamide-1-(2-(1-(4-methylpiperazinyl))ethyl)piperidine may be prepared from isonipecotamide and 1-(2-chloroethyl)-4-methylpiperazine essentially as described above in Example 38, Scheme B, step a.

Scheme B, step b: 4-Amino-1-(2-(1-(4-methylpiperazinyl))ethyl)piperidine

4-Amino-1-(2-(1-(4-methylpiperazinyl))ethyl)piperidine is prepared from 4-carboxamide-1-(2-(1-(4-methylpiperazinyl))ethyl)piperidine essentially as described above in Example 38, Scheme B, step b.

Method 2

Scheme C, step a: 1-(2-(1-(4-Methylpiperazinyl))ethyl)-4-piperidone 1-(2-(1-(4-Methylpiperazinyl))ethyl)-4-piperidone is prepared from 4-piperidone and 1-(2-chloroethyl)-4-methylpiperazine essentially as described above in Example 38, Scheme C, step a.

Scheme C, step b: 1-(2-(1-(4-Methylpiperazinyl))ethyl)-4-piperidone oxime 1-(2-(1-(4-Methylpiperazinyl))ethyl)-4-piperidone oxime is prepared from 1-(2-(1-(4-methylpiperazinyl))ethyl)-4-piperidone and hydroxylamine hydrochloride essentially as described above in Example 38, Scheme C, step b.

Scheme C, step c: 4-Amino-1-(2-(1-(4-methylpiperazinyl))ethyl)piperidine

4-Amino-1-(2-(1-(4-methylpiperazinyl))ethyl)piperidine is prepared from 1-(2-(1-(4-methylpiperazinyl))ethyl)-4-piperidone oxime essentially as described above in Example 38, Scheme C, step c.

Scheme A, step b: 2-Chloro-6-[4-(1-(2-(1-(4-methyl)piperazinyl)ethyl))piperidinylamino]-9-cyclopentylpurine 2-Chloro-6-[4-(1-(2-(1-(4-methyl)piperazinyl)ethyl))piperidinylamino]-9-cyclopentylpurine is prepared from 2,6-dichloro-9-cyclopentylpurine, 4-amino-1-(2-(1-(4-methylpiperazinyl))ethyl)piperidine, and triethylamine essentially as described above in Example 1, Scheme A, step b.

Scheme A, step c: 2-[Trans-(4-aminocyclohexyl)amino]-6-[4-(1-(2-(1-(4-methyl)piperazinyl)ethyl))piperidinylamino]-9-cyclopentylpurine 2-[Trans-(4-aminocyclohexyl)amino]-6-[4-(1-(2-(1-(4-methyl)piperazinyl)ethyl))piperidinylamino]-9-cyclopentylpurine is prepared from 2-chloro-6-[4-(1-(2-(1-(4-methyl)piperazinyl)ethyl))piperidinylamino]-9-cyclopentylpurine essentially as described in Example 1, Scheme A, step c.

EXAMPLE 140

(R,S)-2-[Trans-(4-aminocyclohexyl)amino]-6-[4-(1-(2-phenyl-2-hydroxyethyl))piperidinylamino]-9-cyclopentylpurine Preparation of (R,S)-4-Amino-1-(2-phenyl-2-hydroxyethyl)piperidine Method 1

Scheme B, step a: (R,S)-4-Carboxamide-1-(2-phenyl-2-hydroxyethyl)piperidine (R,S)-4-Carboxamide-1-(2-phenyl-2-hydroxyethyl)piperidine may be prepared from isonipecotamide and (R,S)-1-hydroxy-2-chloroethylbenzene essentially as described above in Example 38, Scheme B, step a.

Scheme B, step b: (R,S)-4-Amino-1-(2-phenyl-2-hydroxyethyl)piperidine (R,S)-4-Amino-1-(2-phenyl-2-hydroxyethyl)piperidine is prepared from (R,S)-4-carboxamide-1-(2-phenyl-2-hydroxyethyl)piperidine essentially as described above in Example 38, Scheme B, step b.

Method 2

Scheme C, step a: (R,S)-1-(2-Phenyl-2-hydroxyethyl)-4-piperidone (R,S)-1-(2-Phenyl-2-hydroxyethyl)-4-piperidone is prepared from 4-piperidone and (R,S)-1-hydroxy-2-chloroethylbenzene essentially as described above in Example 38, Scheme C, step a.

Scheme C, step b: (R,S)-1-(2-Phenyl-2-hydroxyethyl)-4-piperidone oxime (R,S)-1-(2-Phenyl-2-hydroxyethyl)-4-piperidone oxime is prepared from (R,S)-1-(2-phenyl-2-hydroxyethyl)-4-piperidone and hydroxylamine hydrochloride essentially as described above in Example 38, Scheme C, step b.

Scheme C, step c: (R,S)-4-Amino-1-(2-phenyl-2-hydroxyethyl)piperidine (R,S)-4-Amino-1-(2-phenyl-2-hydroxyethyl)piperidine is prepared from (R,S)-1-(2-phenyl-2-hydroxyethyl)-4-piperidone oxime essentially as described above in Example 38, Scheme C, step c.

Scheme A, step b: (R,S)-2-Chloro-6-[4-(1-(2-phenyl-2-hydroxyethyl))piperidinylamino]-9-cyclopentylpurine (R,S)-2-Chloro-6-[4-(1-(2-phenyl -2-hydroxyethyl))piperidinylamino]-9-cyclopentylpurine is prepared from 2,6-dichloro-9-cyclopentylpurine, (R,S)-4-amino-1-(2-phenyl-2-hydroxyethyl)piperidine, and triethylamine essentially as described above in Example 3, Scheme A, step b.

Scheme A, step c: (R,S)-2-[Trans-(4-aminocyclohexyl)amino]-6-[4-(1-(2-phenyl-2-hydroxyethyl))piperidinylamino]-9-cyclopentylpurine (R,S)-2-[Trans-(4-aminocyclohexyl)amino]-6-[4-(1-(2-phenyl-2-hydroxyethyl))piperidinylamino]-9-cyclopentylpurine di is prepared from (R,S)-2-chloro-6-[4-(1-(2-phenyl-2-hydroxyethyl))piperidinylamino]-9-cyclopentylpurine essentially as described in Example 1, Scheme A, step c.

EXAMPLE 141

2-[Trans-(4-aminocyclohexyl)amino]-6-[4-(1-(3,4-methylenedioxybenzyl))piperidinylamino]-9-cyclopentylpurine Preparation of 4-Amino-(3,4-methylenedioxybenzyl)piperidine Method 1

Scheme B, step a: 4-Carboxamide-1-(3,4-methylenedioxybenzyl)piperidine

4-Carboxamide-1-(3,4-methylenedioxybenzyl)piperidine may be prepared from isonipecotamide and 5-chloromethyl-1,3-benzodioxole essentially as described above in Example 38, Scheme B, step a.

Scheme B, step b: 4-Amino-(3,4-methylenedioxybenzyl)piperidine

4-Amino-(3,4-methylenedioxybenzyl)piperidine is prepared from 4-carboxamide-1-(3,4-methylenedioxybenzyl)piperidine essentially as described above in Example 38, Scheme B, step b.

Method 2

Scheme C, step a: 1-(3,4-Methylenedioxy)benzyl-4-piperidone 1-(3,4-Methylenedioxy)benzyl-4-piperidone is prepared from 4-piperidone and 5-chloromethyl-1,3-benzodioxole essentially as described above in Example 38, Scheme C, step a.

Scheme C, step b: 1-(3,4-Methylenedioxy)benzyl-4-piperidone oxime 1-(3,4-Methylenedioxy)benzyl-4-piperidone oxime is prepared from 1-(3,4-methylenedioxy)benzyl-4-piperidone and hydroxylamine hydrochloride essentially as described above in Example 38, Scheme C, step b.

Scheme C, step c: 4-Amino-(3,4-methylenedioxybenzyl)piperidine

4-Amino-(3,4-methylenedioxybenzyl)piperidine is prepared from 1-(3,4-methylenedioxy)benzyl-4-piperidone oxime essentially as described above in Example 38, Scheme C, step c.

Scheme A, step b: 2-Chloro-6-[4-(1-(3,4-methylenedioxybenzyll))piperidinylamino]-9-cyclopentylpurine 2-Chloro-6-[4-(1-(3,4-methylenedioxybenzyll))piperidinylamino]-9-cyclopentylpurine is prepared from 2,6-dichloro-9-cyclopentylpurine, 4-amino-(3,4-methylenedioxybenzyl)piperidine, and triethylamine essentially as described above in Example 1, Scheme A, step b.

Scheme A, step c: 2-[Trans-(4-aminocyclohexyl)amino]-6-[4-(1-(3,4-methylenedioxybenzyll))piperidinylamino]-9-cyclopentylpurine 2-[Trans-(4-aminocyclohexyl)amino]-6-[4-(1-(3,4-methylenedioxybenzyll))piperidinylamino]-9-cyclopentylpurine is prepared from 2-chloro-6-[4-(1-(3,4-methylenedioxybenzyll))piperidinylamino]-9-cyclopentylpurine essentially as described in Example 1, Scheme A, step c.

EXAMPLE 142

2-[Trans-(4-aminocyclohexyl)amino]-6-[4-(1-(2-benzimidazolinyl)methyl)piperidinylamino]-9-cyclopentylpurine Preparation of 4-Amino-1-(2-benzimidazolinyl)methylpiperidine Method 1

Scheme B, step a: 4-Carboxamide-1-(2-benzimidazolinyl)methylpiperidine

4-Carboxamide-1-(2-benzimidazolinyl)methylpiperidine may be prepared from isonipecotamide and 2-(chloromethyl)benzimidazole essentially as described above in Example 38, Scheme B, step a.

Scheme B, step b: 4-Amino-1-(2-benzimidazolinyl)methylpiperidine

4-Amino-1-(2-benzimidazolinyl)methylpiperidine is prepared from 4-carboxamide-1-(2-benzimidazolinyl)methylpiperidine essentially as described above in Example 38, Scheme B, step b.

Method 2
Scheme C, step a: 1-(2-Benzimidazolyl)methyl-4-piperidone 1-(2-Benzimidazolyl)methyl-4-piperidone is prepared from 4-piperidone and 2-(chloromethyl)benzimidazole essentially as described above in Example 38, Scheme C, step a.

Scheme C, step b: 1-(2-Benzimidazolyl)methyl-4-piperidone oxime 1-(2-Benzimidazolyl)methyl-4-piperidone oxime is prepared from 1-(2-benzimidazolyl)methyl-4-piperidone and hydroxylamine hydrochloride essentially as described above in Example 38, Scheme C, step b.

Scheme C, step c: 4-Amino-1-(2-benzimidazolinyl)methylpiperidine

4-Amino-1-(2-benzimidazolinyl)methylpiperidine is prepared from 1-(2-benzimidazolyl)methyl-4-piperidone oxime essentially as described above in Example 38, Scheme C, step c.

Scheme A, step b: 2-Chloro-6-[4-(1-(2-benzimidazolinyl)methyl)piperidinylamino]-9-cyclopentylpurine 2-Chloro-6-[4-(1-(2-benzimidazolinyl)methyl)piperidinylamino]-9-cyclopentylpurine is prepared from 2,6-dichloro-9-cyclopentylpurine, 4-amino-1-(2-benzimidazolinyl)methylpiperidine, and triethylamine essentially as described above in Example 1, Scheme A, step b.

Scheme A, step c: 2-[Trans-(4-aminocyclohexyl)amino]-6-[4-(1-(2-benzimidazolinyl)methyl)piperidinylamino]-9-cyclopentylpurine 2-[Trans-(4-aminocyclohexyl)amino]-6-[4-(1-(2-benzimidazolinyl)methyl)piperidinylamino]-9-cyclopentylpurine is prepared from 2-chloro-6-[4-(1-(2-benzimidazolinyl)methyl)piperidinylamino]-9-cyclopentylpurine essentially as described in Example 1, Scheme A, step c.

EXAMPLE 143

2-[Trans-(4-aminocyclohexyl)amino]-6-[4-(1-(4-(2-methyl)thiazolinyl)methyl)piperidinylamino]-9-cyclopentylpurine Preparation of 4-Amino-1-(4-(2-methylthiazolinyl)methyl)piperidine
Method 1
Scheme B, step a: 4-Carboxamide-1-(4-(2-methylthiazolinyl))methylpiperidine 4-Carboxamide-1-(4-(2-methylthiazolinyl))methylpiperidine may be prepared from isonipecotamide and 2-methyl-5-(chloromethyl)thiazole essentially as described above in Example 38, Scheme B, step a.

Scheme B, step b: 4-Amino-1-(4-(2-methylthiazolinyl)methyl)piperidine

4-Amino-1-(4-(2-methylthiazolinyl)methyl)piperidine is prepared from 4-carboxamide-1-(4-(2-methylthiazolinyl))methylpiperidine essentially as described above in Example 38, Scheme B, step b.

Method 2
Scheme C, step a: 1-(4-(2-Methylthiazolinyl)methyl)-4-piperidone 1-(4-(2-Methylthiazolinyl)methyl)-4-piperidone is prepared from 4-piperidone and 2-methyl-5-(chloromethyl)thiazole essentially as described above in Example 38, Scheme C, step a.

Scheme C, step b: 1-(4-(2-Methylthiazolinyl)methyl)-4-piperidone oxime 1-(4-(2-Methylthiazolinyl)methyl)-4-piperidone oxime is prepared from 1-(4-(2-methylthiazolinyl)methyl)-4-piperidone and hydroxylamine hydrochloride essentially as described above in Example 38, Scheme C, step b.

Scheme C, step c: 4-Amino-1-(4-(2-methylthiazolinyl)methyl)piperidine

4-Amino-1-(4-(2-methylthiazolinyl)methyl)piperidine is prepared from 1-(4-(2-methylthiazolinyl)methyl)-4-piperidone oxime essentially as described above in Example 38, Scheme C, step c.

Scheme A, step b: 2-Chloro-6-[4-(1-(4-(2-methyl)thiazolinyl)methyl)piperidinylamino]-9-cyclopentylpurine 2-Chloro-6-[4-(1-(4-(2-methyl)thiazolinyl)methyl)piperidinylamino]-9-cyclopentylpurine is prepared from 2,6-dichloro-9-cyclopentylpurine, 4-amino-1-(4-(2-methylthiazolinyl)methyl)piperidine, and triethylamine essentially as described above in Example 1, Scheme A, step b.

Scheme A, step c: 2-[Trans-(4-aminocyclohexyl)amino]-6-[4-(1-(4-(2-methyl)thiazolinyl)methyl)piperidinylamino]-9-cyclopentylpurine 2-[Trans-(4-aminocyclohexyl)amino]-6-[4-(1-(4-(2-methyl)thiazolinyl)methyl)piperidinylamino]-9-cyclopentylpurine is prepared from 2-chloro-6-[4-(1-(4-(2-methyl)thiazolinyl)methyl)piperidinylamino]-9-cyclopentylpurine essentially as described in Example 1, Scheme A, step c.

EXAMPLE 144

2-[Trans-(4-aminocyclohexyl)amino]-6-[4-(1-(2-thiopheneyl)methyl)piperidinylamino]-9-cyclopentylpurine Preparation of 4-Amino-1-(2-thiopheneyl)methylpiperidine
Method 1
Scheme B, step a: 4-Carboxamide-1-(2-thiopheneyl)methylpiperidine 4-Carboxamide-1-(2-thiopheneyl)methylpiperidine may be prepared from isonipecotamide and 2-(chloromethyl)thiophene essentially as described above in Example 38, Scheme B, step a.

Scheme B, step b: 4-Amino-1-(2-thiopheneyl)methylpiperidine

4-Amino-1-(2-thiopheneyl)methylpiperidine is prepared from 4-carboxamide-1-(2-thiopheneyl)methylpiperidine essentially as described above in Example 38, Scheme B, step b.

Method 2
Scheme C, step a: 1-(2-Thiopheneyl)methyl-4-piperidone 1-(2-Thiopheneyl)methyl-4-piperidone is prepared from 4-piperidone and 2-(chloromethyl)thiophene essentially as described above in Example 38, Scheme C, step a.

Scheme C, step b: 1-(2-Thiopheneyl)methyl-4-piperidone oxime 1-(2-Thiopheneyl)methyl-4-piperidone oxime is prepared from 1-(2-thiopheneyl)methyl-4-piperidone and hydroxylamine hydrochloride essentially as described above in Example 38, Scheme C, step b.

Scheme C, step c: 4-Amino-1-(2-thiopheneyl)methylpiperidine

4-Amino-1-(2-thiopheneyl)methylpiperidine is prepared from 1-(2-thiopheneyl)methyl-4-piperidone oxime essentially as described above in Example 38, Scheme C, step c.

Scheme A, step b: 2-Chloro-6-[4-(1-(2-thiopheneyl)methyl)piperidinylamino]-9-cyclopentylpurine 2-Chloro-6-[4-(1-(2-thiopheneyl)methyl)piperidinylamino]-9-cyclopentylpurine is prepared from 2,6-dichloro-9-cyclopentylpurine, 4-amino-1-(2-thiopheneyl)methylpiperidine, and triethylamine essentially as described above in Example 1, Scheme A, step b.

Scheme A, step c: 2-[Trans-(4-aminocyclohexyl)amino]-6-[4-(1-(2-thiopheneyl)methyl)piperidinylamino]-9-cyclopentylpurine 2-[Trans-(4-aminocyclohexyl)amino]-6-[4-(1-(2-thiopheneyl)methyl)piperidinylamino]-9-cyclopentylpurine is prepared from 2-chloro-6-[4-(1-(2-thiopheneyl)methyl) piperidinylamino]-9-cyclopentylpurine essentially as described in Example 1, Scheme A, step c.

EXAMPLE 145a

Trans-2-[Trans-(4-aminocyclohexyl)amino]-6-[(4-hydroxy)cyclohexylamino]-9-cyclopentylpurine dihydrochloride Scheme A, step b: Trans-2-chloro-6-[(4-hydroxy) cyclohexylamino]-9-cyclopentylpurine Trans-2-chloro-6-[(4-hydroxy)cyclohexylamino]-9-cyclopentylpurine is prepared from 2,6-dichloro-9-cyclopentylpurine, trans-4-(amino)cyclohexanol, and triethylamine essentially as described above in Example 1, Scheme A, step b.

Scheme A, step c: Trans-2-[trans-(4-aminocyclohexyl) amino]-6-[(4-hydroxy)cyclohexylamino]-9-cyclopentylpurine dihydrochloride Trans-2-[trans-(4-aminocyclohexyl)amino]-6-[(4-hydroxy)cyclohexylamino]-9-cyclopentylpurine dihydrochloride is prepared from trans-2-chloro-6-[(4-hydroxy) cyclohexylamino]-9-cyclopentylpurine essentially as described in Example 1, Scheme A, step c.

CIMS (NH$_3$) 414 (MH$^+$)
Rf (min.)=3.25

EXAMPLE 145b

Cis-2-[Trans-(4-aminocyclohexyl)amino]-6-[(4-hydroxy)cyclohexylamino]-9-cyclopentylpurine dihydrochloride Scheme A, step b: Cis-2-chloro-6-[(4-hydroxy) cyclohexylamino]-9-cyclopentylpurine Cis-2-chloro-6-[(4-hydroxy)cyclohexylamino]-9-cyclopentylpurine is prepared from 2,6-dichloro-9-cyclopentylpurine, cis-4-(amino)cyclohexanol, and triethylamine essentially as described above in Example 1, Scheme A, step b.

Scheme A, step c: Cis-2-[trans-(4-aminocyclohexyl)amino]-6-[(4-hydroxy)cyclohexylamino]-9-cyclopentylpurine dihydrochloride Cis-2-[trans-(4-aminocyclohexyl)amino]-6-[(4-hydroxy) cyclohexylamino-9-cyclopentylpurine dihydrochloride is prepared from cis-2-chloro-6-[(4-hydroxy) cyclohexylamino]-9-cyclopentylpurine hydrochloride essentially as described in Example 1, Scheme A, step c.

CIMS (NH$_3$) 414 (MH$^+$)
Rf (min.)=3.25

EXAMPLE 146

(R,S)-2-[Trans-(4-aminocyclohexyl)amino]-6-[(1-hydroxymethyl)cyclopentylamino]-9-cyclopentylpurine dihydrochloride Scheme A, step b: (R,S)-2-Chloro-6-[(1-hydroxymethyl) cyclopentylamino]-9-cyclopentylpurine (R,S)-2-Chloro-6-[(1-hydroxymethyl) cyclopentylamino]-9-cyclopentylpurine is prepared from 2,6-dichloro-9-cyclopentylpurine, (R,S)-2-hydroxymethyl-1-aminocyclopentane, and triethylamine essentially as described above in Example 1, Scheme A, step b.

Scheme A, step c: (R,S)-2-[Trans-(4-aminocyclohexyl) amino]-6-[(1-hydroxymethyl)cyclopentylamino]-9-cyclopentylpurine dihydrochloride (R,S)-2-[Trans-(4-aminocyclohexyl)amino]-6-[(1-hydroxymethyl)cyclopentylamino]-9-cyclopentylpurine dihydrochloride is prepared from (R,S)-2-chloro-6-[(1-hydroxymethyl)cyclopentylamino]-9-cyclopentylpurine essentially as described in Example 1, Scheme A, step c.

CIMS (NH3) 414 (MH$^+$)
Rf (min.)=3.27

EXAMPLE 147

2-[Trans-(4-aminocyclohexyl)amino]-6-(2,4-dichlorophenylhydrazino)-9-cyclopentylpurine dihydrochloride Scheme A, step b: 2-Chloro-6-(2,4-dichlorophenylhydrazino)-9-cyclopentylpurine 2-Chloro-6-(2,4-dichlorophenylhydrazino)-9-cyclopentylpurine is prepared from 2,6-dichloro-9-cyclopentylpurine, 2,4-dichlorophenylhydrazine, and triethylamine essentially as described above in Example 1, Scheme A, step b.

Scheme A, step c: 2-[Trans-(4-aminocyclohexyl)amino]-6-(2,4-dichlorophenylhydrazino)-9-cyclopentylpurine dihydrochloride 2-[Trans-(4-aminocyclohexyl)amino]-6-(2,4-dichlorophenylhydrazino)-9-cyclopentylpurine dihydrochloride is prepared from 2-chloro-6-(2,4-dichlorophenylhydrazino)-9-cyclopentylpurine essentially as described in Example 1, Scheme A, step c.

CIMS (NH$_3$) 47S (MH$^+$)
Rf(min.)=3.49

EXAMPLE 147-a

2-[Trans-(4-aminocyclohexyl)amino]-6-[4-[1-(1-naphthyl)methyl]piperidinylamino)-9-cyclopentylpurine trihydrochloride Scheme B, step a: 4-Carboxamide-1-(1-naphthyl) methylpiperidine 4-Carboxamide-1-(1-naphthyl)methylpiperidine may be prepared from isonipecotamide and 1-(chloromethyl) naphthalene (available from Aldrich Chemical Company) essentially as described above in Example 38, Scheme B, step a.

Scheme B, step b: 4-amino-1-(1-naphthyl)methylpiperidine

4-Amino-1-(1-naphthyl)methylpiperidine is prepared from 4-carboxamide-1-(1-naphthyl)methylpiperidine essentially as described above in Example 38, Scheme B, step b.

Scheme A, step b: 2-Chloro -6-[4-1-(1-naphthyl)methyl] piperidinylamino]-9-cyclopentylpurine 2-Chloro-6-[4-1-(1-naphthyl)methyl]piperidinylamino]-9-cyclopentylpurine is prepared from 2,6-dichloro-9-cyclopentylpurine, 4-amino-1-(1-naphthyl) methylpiperidine, and triethylamine essentially as described above in Example 1, Scheme A, step b.

Scheme A, step c: 2-[Trans-(4-aminocyclohexyl)amino]-6-[4-[1-(1-naphthyl)methyl]piperidinylamino]-9-cyclopentylpurine trihydrochloride 2-[Trans-(4-aminocyclohexyl)amino]-6-[4-[1-(1-naphthyl)methyl]piperidinylamino]-9-cyclopentylpurine trihydrochloride is prepared from 2-chloro-6-[4-1-(1-naphthyl)methyl]piperidinylamino]-9-cyclopentylpurine essentially as described in Example 1, Scheme A, step c.

APCI: 539 (M$^{+1}$)
R$_f$(min.)=2.33

EXAMPLE 147-b

2-[Trans-(4-aminocyclohexyl)amino]-6-[4-[1-(2-trifluoromethylbenzyl)]piperidinylamino]-9-cyclopentylpurine trihydrochloride Scheme B, step a: 4-Carboxamide-1-(2-trifluoromethylbenzyl)piperidine 4-Carboxamide-1-(2-trifluoromethylbenzyl)piperidine may be prepared from isonipecotamide and 2-(trifluoromethyl)benzyl bromide (available from Aldrich Chemical Company) essentially as described above in Example 38, Scheme B, step a.

Scheme B, step b: 4-amino-1-(2-trifluoromethylbenzyl) piperidine

4-Amino-1-(2-trifluoromethylbenzyl)piperidine is prepared from 4-carboxamide-1-(2-trifluoromethylbenzyl) piperidine essentially as described above in Example 38, Scheme B, step b.

Scheme A, step b: 2-Chloro-6-[4-[1-(2-trifluoromethylbenzyl)]piperidinylamino]-9-cyclopentylpurine 2-Chloro-6-[4-[1-(2-trifluoromethylbenzyl)] piperidinylamino]-9-cyclopentylpurine is prepared from 2,6-dichloro-9-cyclopentylpurine, 4-amino-1-(2-trifluoromethylbenzyl)piperidine, and triethylamine essentially as described above in Example 1, Scheme A, step b.

Scheme A, step c: 2-[Trans-(4-aminocyclohexyl)amino]-6-[4-[1-(2-trifluoromethylbenzyl)]piperidinylamino]-9-cyclopentylpurine trihydrochloride 2-[Trans-(4-aminocyclohexyl)amino]-6-[4-[1-(2-trifluoromethylbenzyl)]-piperidinylamino]-9-cyclopentylpurine trihydrochloride is prepared from 2-chloro-6-[4-[1-(2-trifluoromethylbenzyl)] piperidinylamino]-9-cyclopentylpurine essentially as described in Example 1, Scheme A, step c.

APCI: 557 ($M^{+1}$)
$R_f$(min.)=2.29

EXAMPLE 147-c

2-[Trans-(4-aminocyclohexyl)amino]-6-[4-[1-(3,5-dimethoxybenzyl)]piperidinylamino -9-cyclopentylpurine trihydrochloride Scheme B, step a: 4-Carboxamide-1-(3,5-dimethoxybenzyl) piperidine 4-Carboxamide-1-(3,5dimethoxybenzyl)piperidine may be prepared from isonipecotamide and 3,5-dimethoxybenzyl chloride (available from Aldrich Chemical Company) essentially as described above in Example 38, Scheme B, step a.

Scheme B, step b: 4-amino-1-(3,5-dimethoxybenzyl) piperidine

4-Amino-1-(3,5-dimethoxybenzyl)piperidine is prepared from 4-carboxamide-1-(3,5-dimethoxybenzyl)piperidine essentially as described above in Example 38, Scheme B, step b.

Scheme A, step b: 2-Chloro-6-[4-[1-(3,5-dimethoxybenzyl)]piperidinylamino]-9-cyclopentylpurine 2-Chloro-6-[4-[1-(3,5-dimethoxybenzyl)] piperidinylamino]-9-cyclopentylpurine is prepared from 2,6-dichloro-9-cyclopentylpurine, 4-amino-1-(3,5-dimethoxybenzyl)-piperidine, and triethylamine essentially as described above in Example 1, Scheme A, step b.

Scheme A, step c: 2-[Trans-(4-aminocyclohexyl)amino-6-[4-[1-(3,5-dimethoxybenzyl)]piperidinylamino]-9-cyclopentylpurine trihydrochloride 2-[Trans-(4-aminocyclohexyl)amino]-6-[4-[1-(3, 5-dimethoxybenzyl)]piperidinylamino]-9-cyclopentylpurine trihydrochloride is prepared from 2-chloro-6-[4-[1-(3,5-dimethoxybenzyl)]piperidinylamino]-9-cyclopentylpurine essentially as described in Example 1, Scheme A, step c.

APCI: 549 ($M^{+1}$)
$R_f$(min.)=2.27

EXAMPLE 147-d

2-[Trans-(4-aminocyclohexyl)amino]-6-[4-[1-[3,5-bis(trifluoromethyl)benzyl]]piperidinylamino]-9-cyclopentylpurine trihydrochloride Scheme B, step a: 4-Carboxamide-1-(3,5-bis-trifluoromethylbenzyl)piperidine 4-Carboxamide-1-(3,5-bis-trifluoromethylbenzyl) piperidine may be prepared from isonipecotamide and bis (3,5-trifluoromethyl)benzyl bromide (available from Aldrich Chemical Company) essentially as described above in Example 38, Scheme B, step a.

Scheme B, step b: 4-amino-1-(3,5-bis-trifluoromethylbenzyl)piperidine

4-Amino-1-(3,5-bis-trifluoromethylbenzyl)piperidine is prepared from 4-carboxamide-1-(3,5-bis-trifluoromethylbenzyl)piperidine essentially as described above in Example 38, Scheme B, step b.

Scheme A, step b: 2-Chloro-6-[4-[1-(3 5-bis-trifluoromethylbenzyl)]piperidinylamino]-9-cyclopentylpurine 2-Chloro-6-[4-[1-(3,5-bis-trifluoromethylbenzyl)] piperidinylamino]-9-cyclopentylpurine is prepared from 2,6-dichloro-9-cyclopentylpurine, 4-amino-1-(3,5-bis-trifluoromethylbenzyl)piperidine, and triethylamine essentially as described above in Example 1, Scheme A, step b.

Scheme A step c: 2-[Trans-(4-aminocyclohexyl)amino]-6-[4-[1-(3,5-bis-(trifluoromethylbenzyl)]piperidinylamino]-9-cyclopentylpurine trihydrochloride 2-[Trans-(4-aminocyclohexyl)amino]-6-[4-[1-[3,5-bis (trifluoromethyl)benzyl]]-piperidinylamino]-9-cyclopentylpurine trihydrochloride is prepared from 2-chloro-6-[4-[1-bis(3,5-trifluoromethyl)benzyl)] piperidinylamino]-9-cyclopentylpurine essentially as described in Example 1, Scheme A, step c.

APCI: 625 ($M^{+1}$)
$R_f$(min.)=2.37

EXAMPLE 147-e

2-[Trans-(4-aminocyclohexyl)amino]-6-[4-1-(2,3-difluorobenzyl)]piperidinylamino]-9-cyclopentylpurine trihydrochloride Scheme B, step a: 4-Carboxamide-1-(2,3-difluorobenzyl) piperidine 4-Carboxamide-1-(2,3-difluorobenzyl)piperidine may be prepared from isonipecotamide and 2,3-difluorobenzyl bromide (available from Aldrich Chemical Company) essentially as described above in Example 38, Scheme B, step a.

Scheme B, step b: 4-amino-1-(2,3-difluorobenzyl)piperidine

4-Amino-1-(2,3-difluorobenzyl)piperidine is prepared from 4-carboxamide-1-(2,3-difluorobenzyl)piperidine essentially as described above in Example 38, Scheme B, step b.

Scheme A, step b: 2-Chloro-6-[4-[1-(2,3-difluorobenzyl)] piperidinylamino]-9-cyclopentylpurine 2-Chloro-6-[4-[1-(2,3-difluorobenzyl)] piperidinylamino]-9-cyclopentylpurine is prepared from 2,6-dichloro-9-cyclopentylpurine, 4-amino-1-(2,3-difluorobenzyl)piperidine, and triethylamine essentially as described above in Example 1, Scheme A, step b.

Scheme A, step c: 2-[Trans-(4-aminocyclohexyl)amino]-6-[4-[1-(2.3-difluorobenzyl)]-piperidinylamino]-9-cyclopentylpurine trihydrochloride 2-[Trans-(4-aminocyclohexyl)amino]-6-[4-[1-(2,3-difluorobenzyl)]piperidinylamino]-9-cyclopentylpurine trihydrochloride is prepared from 2-chloro-6-[4-[1-(2,3-difluorobenzyl)]piperidinylamino]-9-cyclopentylpurine essentially as described in Example 1, Scheme A, step c.

APCI: 525 ($M^{+1}$)
$R_f$(min.)=2.26

EXAMPLE 147-f

2-[Trans-(4-aminocyclohexyl)amino]-6-[4-[1-(2,5-difluorobenzyl)]piperidinylamino-9-cyclopentylpurine trihydrochloride Scheme B, step a: 4-Carboxamide-1-(2,5-difluorobenzyl) piperidine 4-Carboxamide-1-(2,5-difluorobenzyl)piperidine may be prepared from isonipecotamide and 2,5-difluorobenzyl bromide (available from Aldrich Chemical Company) essentially as described above in Example 38, Scheme B, step a.

Scheme B, step b: 4-amino-1-(2,5-difluorobenzyl)piperidine

4-Amino-1-(2,5-difluorobenzyl)piperidine is prepared from 4-carboxamide-1-(2,5-difluorobenzyl)piperidine essentially as described above in Example 39, Scheme B, step b.

Scheme A, step b: 2-Chloro-6-[4-[1-(2,5-difluorobenzyl)]piperidinylamino]-9-cyclopentylpurine 2-Chloro-6-[4-[1-(2,5-difluorobenzyl)]piperidinylamino]-9-cyclopentylpurine is prepared from 2,6-dichloro-9-cyclopentylpurine, 4-amino-1-(2,5-difluorobenzyl)piperidine, and triethylamine essentially as described above in Example 1, Scheme A, step b.

Scheme A, step c: 2-[Trans-(4-aminocyclohexyl)amino]-6-[4-[1-(2,5-difluorobenzyl)]-piperidinylamino]-9-cyclopentylpurine trihydrochloride 2-[Trans-(4-aminocyclohexyl)amino]-6-[4-[1-(2,5-difluorobenzyl)]piperidinylamino]-9-cyclopentylpurine trihydrochloride is prepared from 2-chloro-6-[4-[1-(2,5-difluorobenzyl)]piperidinylamino]-9-cyclopentylpurine essentially as described in Example 1, Scheme A, step c.

APCI: 525 ($M^{+1}$)

$R_f$ (min.)=2.26

EXAMPLE 147-g

2-[Trans-(4-aminocyclohexyl)amino]-6-[4-1 1-(3.5-difluorobenzyl)]piperidinylamino]-9-cyclopentylpurine trihydrochloride Scheme B, step a: 4-Carboxamide-1-(3,5-difluorobenzyl)piperidine 4-Carboxamide-1-(3,5-difluorobenzyl)piperidine may be prepared from isonipecotamide and 3,5-difluorobenzyl bromide (available from Aldrich Chemical Company) essentially as described above in Example 38, Scheme B, step a.

Scheme B, step b: 4-amino-1-(3,5-difluorobenzyl)piperidine

4-Amino-1-(3,5-difluorobenzyl)piperidine is prepared from 4-carboxamide-1-(3,5-difluorobenzyl)piperidine essentially as described above in Example 38, Scheme B, step b.

Scheme A step b: 2-Chloro-6-[4-[1-(3,5-difluorobenzyl)]piperidinylamino]-9-cyclopentylpurine 2-Chloro-6-[4-[1-(3,5-difluorobenzyl)]piperidinylamino]-9-cyclopentylpurine is prepared from 2,6-dichloro-9-cyclopentylpurine, 4-amino-1-(3,5-difluorobenzyl)piperidine, and triethylamine essentially as described above in Example 1, Scheme A, step b.

Scheme A, step c: 2-[Trans-(4-aminocyclohexyl)amino]-6-[4-[1-(3,5-difluorobenzyl)]-piperidinylamino]-9-cyclopentylpurine trihydrochloride 2-[Trans-(4-aminocyclohexyl)amino]-6-[4-[1-(3,5-difluorobenzyl)]piperidinylamino]-9-cyclopentylpurine trihydrochloride is prepared from 2-chloro-6-[4-[1-(3,5-difluorobenzyl)]piperidinylamino]-9-cyclopentylpurine essentially as described in Example 1, Scheme A, step c.

APCI: 525 ($M^{+1}$)

$R_f$(min.)=2.25

EXAMPLE 147-h

2-[Trans-(4-aminocyclohexyl)amino]-6-[4-[1-(2,4-difluorobenzyl)piperidinylamino]-9-cyclopentylpurine trihydrochloride Scheme B, step a: 4-Carboxamide-1-(2.4-difluorobenzyl)piperidine 4-Carboxamide-1-(2,4-difluorobenzyl)piperidine may be prepared from isonipecotamide and 2,4-difluorobenzyl bromide (available from Aldrich Chemical Company) essentially as described above in Example 38, Scheme B, step a.

Scheme B, step b: 4-amino-1-(2,4-difluorobenzyl)piperidine

4-Amino-1-(2,4-difluorobenzyl)piperidine is prepared from 4-carboxamide-1-(2,4-difluorobenzyl)piperidine essentially as described above in Example 38, Scheme B, step b.

Scheme A, step b: 2-Chloro-6-[4-[1-(2,4-difluorobenzyl)]piperidinylamino]-9-cyclopentylpurine 2-Chloro-6-[4-[1-(2,4-difluorobenzyl)]piperidinylamino]-9-cyclopentylpurine is prepared from 2,6-dichloro-9-cyclopentylpurine, 4-amino-1-(2,4-difluorobenzyl)piperidine, and triethylamine essentially as described above in Example 1, Scheme A, step b.

Scheme A, step c: 2-[Trans-(4-aminocyclohexyl)amino]-6-[4-[1-(2,4-difluorobenzyl)]-piperidinylamino]-9-cyclopentylpurine trihydrochloride 2-[Trans-(4-aminocyclohexyl)amino]-6-[4-[1-(2,4-difluorobenzyl)]piperidinylamino]-9-cyclopentylpurine trihydrochloride is prepared from 2-chloro-6-[4-[1-(2,4-difluorobenzyl)]piperidinylamino]-9-cyclopentylpurine essentially as described in Example 1, Scheme A, step c.

APCI: 525 ($M^{+1}$)

$R_f$(min.)=2.25

EXAMPLE 147-i

2-[Trans-(4-aminocyclohexyl)amino]-6-[4-[1-(3-methylbenzyl)]piperidinylamino]-9-cyclopentylpurine trihydrochloride Scheme B, step a: 4-Carboxamide-1-(3-methylbenzyl)piperidine 4-Carboxamide-1-(3-methylbenzyl)piperidine may be prepared from isonipecotamide and 3-methylbenzyl bromide (available from Aldrich Chemical Company) essentially as described above in Example 38, Scheme B, step a.

Scheme B, step b: 4-amino-1-(3-methylbenzyl)piperidine

4-Amino-1-(3-methylbenzyl)piperidine is prepared from 4-carboxamide-1-(3-methylbenzyl)piperidine essentially as described above in Example 38, Scheme B, step b.

Scheme A, step b: 2-Chloro-6-[4-[1-(3-methylbenzyl)]piperidinylamino]-9-cyclopentylpurine 2-Chloro-6-[4-[1-(3-methylbenzyl)]piperidinylamino]-9-cyclopentylpurine is prepared from 2,6-dichloro-9-cyclopentylpurine, 4-amino-1-(3-methylbenzyl)piperidine, and triethylamine essentially as described above in Example 1, Scheme A, step b.

Scheme A, step c: 2-[Trans-(4-aminocyclohexyl)amino]-6-[4-[1-(3-methylbenzyl)]-piperidinylamino]-9-cyclopentylpurine trihydrochloride 2-[Trans-(4-aminocyclohexyl)amino]-6-[4-[1-(3-methylbenzyl)]piperidinylamino]-9-cyclopentylpurine trihydrochloride is prepared from 2-chloro-6-[4-[1-(3-methylbenzyl)]-piperidinylamino]-9-cyclopentylpurine essentially as described in Example 1, Scheme A, step c.

APCI: 503 ($M^{+1}$)

$R_f$(min.)=2.24

EXAMPLE 147-j

2-[Trans-(4-aminocyclohexyl)amino]-6-[4-[1-(3-fluorobenzyl)]piperidinylamino]-9-cyclopentylpurine trihydrochloride Scheme B, step a: 4-Carboxamide-1-(3-fluorobenzyl)piperidine 4-Carboxamide-1-(3-fluorobenzyl)piperidine may be prepared from isonipecotamide and 3-fluorobenzyl bromide (available from Aldrich Chemical Company) essentially as described above in Example 38, Scheme B, step a.

Scheme B, step b: 4-amino-1-(3-fluorobenzyl)piperidine

4-Amino-1-(3-fluorobenzyl)piperidine is prepared from 4-carboxamide-1-(3-fluorobenzyl)piperidine essentially as described above in Example 38, Scheme B, step b.

Scheme A, step b: 2-Chloro-6-[4-[1-(3-fluorobenzyl)] piperidinylamino]-9-cyclopentylpurine 2-Chloro-6-[4-[1-(3-fluorobenzyl)]piperidinylamino-9-cyclopentylpurine is prepared from 2,6-dichloro-9-cyclopentylpurine, 4-amino-1-(3-fluorobenzyl)piperidine, and triethylamine essentially as described above in Example 1, Scheme A, step b.

Scheme A, step c: 2-[Trans-(4-aminocyclohexyl)amino]-6-[4-[1-(3-fluorobenzyl)]-piperidinylamino]-9-cyclopentylpurine trihydrochloride 2-[Trans-(4-aminocyclohexyl)amino]-6-[4-[1-(3-fluorobenzyl)]piperidinylamino]-9-cyclopentylpurine trihydrochloride is prepared from 2-chloro-6-[4-[1-(3-fluorobenzyl)]-piperidinylamino]-9-cyclopentylpurine essentially as described in Example 1, Scheme A, step c.

APCI: 507 (M$^{+1}$)

R$_f$(min.)=2.25

EXAMPLE 147-k

2-[Trans-(4-aminocyclohexyl)amino]-6-[4-[1-(2-fluorobenzyl)]piperidinylamino]-9-cyclopentylpurine trihydrochloride Scheme B, step a: 4-Carboxamide-1-(2-fluorobenzyl) piperidine 4-Carboxamide-1-(2-fluorobenzyl)piperidine may be prepared from isonipecotamide and 2-fluorobenzyl bromide (available from Aldrich Chemical Company) essentially as described above in Example 38, Scheme B, step a.

Scheme B, step b: 4-amino-1-(2-fluorobenzyl)piperidine

4-Amino-1-(2-fluorobenzyl)piperidine is prepared from 4-carboxamide-1-(2-fluorobenzyl)piperidine essentially as described above in Example 38, Scheme B, step b.

Scheme A, step b: 2-Chloro-6-[4-[1-(2-fluorobenzyl)] piperidinylamino]-9-cyclopentylpurine 2-Chloro-6-[4-[1-(2-fluorobenzyl)]piperidinylamino]-9-cyclopentylpurine is prepared from 2,6-dichloro-9-cyclopentylpurine, 4-amino-1-(2-fluorobenzyl)piperidine, and triethylamine essentially as described above in Example 1, Scheme A, step b.

Scheme A, step c: 2-[Trans-(4-aminocyclohexyl)amino]-6-[4-11-(2-fluorobenzyl)]-piperidinylamino]-9-cyclopentylpurine trihydrochloride 2-[Trans-(4-aminocyclohexyl)amino]-6-[4-[1-(2-fluorobenzyl)]piperidinylamino]-9-cyclopentylpurine trihydrochloride is prepared from 2-chloro-6-[4-[1-(2-fluorobenzyl)]-piperidinylamino]-9-cyclopentylpurine essentially as described in Example 1, Scheme A, step c.

APCI: 507 (M$^{+1}$)

R$_f$(min.)=2.22

EXAMPLE 147-l

2-[Trans-(4-aminocyclohexyl)amino]-6-[4-[1-(4-fluorobenzyl)]piperidinylamino]-9-cyclopentylpurine trihydrochloride Scheme B, step a: 4-Carboxamide-1-(4-fluorobenzyl) piperidine 4-Carboxamide-1-(4-fluorobenzyl)piperidine may be prepared from isonipecotamide and 4-fluorobenzyl bromide (available from Aldrich Chemical Company) essentially as described above in Example 38, Scheme B, step a.

Scheme B, step b: 4-amino-1-(4-fluorobenzyl)piperidine

4-Amino-1-(4-fluorobenzyl)piperidine is prepared from 4-carboxamide-1-(4-fluorobenzyl)piperidine essentially as described above in Example 38, Scheme B, step b.

Scheme A, step b: 2-Chloro-6-[4-[1-(4-fluorobenzyl)] piperidinylamino]-9-cyclopentylpurine 2-Chloro-6-[4-[1-(4-fluorobenzyl)]piperidinylamino]-9-cyclopentylpurine is prepared from 2,6-dichloro-9-cyclopentylpurine, 4-amino-1-(4-fluorobenzyl)piperidine, and triethylamine essentially as described above in Example 1, Scheme A, step b Scheme A, step c: 2-[Trans-(4-aminocyclohexyl)amino]-6-[4-[1-(4-fluorobenzyl)]-piperidinylamino]-9-cyclopentylpurine trihydrochloride 2-[Trans-(4-aminocyclohexyl)amino]-6-[4-[1-(4-fluorobenzyl)]piperidinylamino]-9-cyclopentylpurine trihydrochloride is prepared from 2-chloro-6-[4-[1-(4-fluorobenzyl)]-piperidinylamino]-9-cyclopentylpurine essentially as described in Example 1, Scheme A, step c.

APCI: 507 (M$^{+1}$)

R$_f$(min.)=2.23

EXAMPLE 147-m

2-[Trans-(4-aminocyclohexyl)amino]-6-[4-[1-(3-trifluoromethylbenzyl)]piperidinylamino]-cyclopentylpurine trihydrochloride Scheme B, step a: 4-Carboxamide-1-(3-trifluoromethylbenzyl)piperidine 4-Carboxamide-1-(3-trifluoromethylbenzyl)piperidine may be prepared from isonipecotamide and 3-(trifluoromethyl)benzyl bromide (available from Aldrich Chemical Company) essentially as described above in Example 38, Scheme B, step a.

Scheme B, step b: 4-amino-1-(3-trifluoromethylbenzyl) piperidine

4-Amino-1-(3-trifluoromethylbenzyl)piperidine is prepared from 4-carboxamide-1-(3-trifluoromethylbenzyl) piperidine essentially as described above in Example 38, Scheme B, step b.

Scheme A, step b: 2-Chloro-6-[4-[1-(3-trifluoromethylbenzyl)]piperidinylamino]-9-cyclopentylpurine 2-Chloro-6-[4-[1-(3-trifluoromethylbenzyl)] piperidinylamino]-9-cyclopentylpurine is prepared from 2,6-dichloro-9-cyclopentylpurine, 4-amino-1-(3-trifluoromethylbenzyl)piperidine, and triethylamine essentially as described above in Example 1, Scheme A, step b.

Scheme A, step c: 2-[Trans-(4-aminocyclohexyl)amino]-6-[4-[1-(3-trifluoromethylbenzyl)]piperidinylamino]-9-cyclopentylpurine trihydrochloride 2-[Trans-(4-aminocyclohexyl)amino]-6-[4-[1-(3-trifluoromethylbenzyl)]-piperidinylamino]-9-cyclopentylpurine trihydrochloride is prepared from 2-chloro-6-[4-[1-(3-trifluoromethylbenzyl)] piperidinylamino]-9-cyclopentylpurine essentially as described in Example 1, Scheme A, step c.

APCI: 557 (M$^{+1}$)

R$_f$(min.) 2.31

EXAMPLE 147-n

2-[Trans-(4-aminocyclohexyl)amino]-6-[4-[1-(2-chloro-6-fluorobenzyl)]piperidinylamino]-cyclopentylpurine trihydrochloride Scheme B, step a: 4-Carboxamide-1-(2-chloro-6-fluorobenzyl)piperidine 4-Carboxamide-1-(2-chloro-6-fluorobenzyl)piperidine may be prepared from isonipecotamide and 2-chloro-6-fluorobenzyl chloride (available from Aldrich Chemical Company) essentially as described above in Example 38, Scheme B, step a.

Scheme B, step b: 4-amino-1-(2-chloro-6-fluorobenzyl) piperidine

4-Amino-1-(2-chloro-6-fluorobenzyl)piperidine is prepared from 4-carboxamide-1-(2-chloro-6-fluorobenzyl) piperidine essentially as described above in Example 38, Scheme B, step b.

Scheme A, step b: 2-Chloro-6-[4-[1-(2-chloro-6-fluorobenzyl)]piperidinylamino]-9-cyclopentylpurine 2-Chloro-6-[4-[1-(2-chloro-6-fluorobenzyl)] piperidinylamino]-9-cyclopentylpurine is prepared from 2,6-dichloro-9-cyclopentylpurine, 4-amino-1-(2-chloro-6-fluorobenzyl)piperidine, and triethylamine essentially as described above in Example 1, Scheme A, step b.

Scheme A, step c: 2-[Trans-(4-aminocyclohexyl)amino]-6-[4-[1-(2-chloro-6-fluorobenzyl)]piperidinylamino]-9-cyclopentylpurine trihydrochloride 2-[Trans-(4-aminocyclohexyl)amino]-6-[4-[1-(2-chloro-6-fluorobenzyl)]-piperidinylamino]-cyclopentylpurine trihydrochloride is prepared from 2-chloro-6-[4-[1-(2-chloro-6-fluorobenzyl)]piperidinylamino]-9-cyclopentylpurine essentially as described in Example 1, Scheme A, step c.

APCI: 541 ($M^{+1}$)

$R_f$(min.) 2.22

EXAMPLE 147-o

2-[Trans-(4-aminocyclohexyl)amino]-6-[4-[1-(3,4-dichlorobenzyl)]piperidinylamino]-9-cyclopentylpurine trihydrochloride Scheme B, step a: 4-Carboxamide-1-(3,4-dichlorobenzyl) piperidine 4-Carboxamide-1-(3,4-dichlorobenzyl)piperidine may be prepared from isonipecotamide and 3,4-dichlorobenzyl chloride (available from Aldrich Chemical Company) essentially as described above in Example 38, Scheme B, step a.

Scheme B, step b: 4-amino-1-(3,4-dichlorobenzyl) piperidine

4-Amino-1-(3,4-dichlorobenzyl)piperidine is prepared from 4-carboxamide-1-(3,4-dichlorobenzyl)piperidine essentially as described above in Example 38, Scheme B, step b.

Scheme A, step b: 2-Chloro-6-[4-[1-(3,4-dichlorobenzyl)] piperidinylamino]-9-cyclopentylpurine 2-Chloro-6-[4-[1-(3,4-dichlorobenzyl)] piperidinylamino]-9-cyclopentylpurine is prepared from 2,6-dichloro-9-cyclopentylpurine, 4-amino-1-(3,4-dichlorobenzyl)piperidine, and triethylamine essentially as described above in Example 1, Scheme A, step b.

Scheme A, step c: 2-[Trans-(4-aminocyclohexyl)amino]-6-[4-[1-(3,4-dichlorobenzyl)]-piperidinylamino]-9-cyclopentylpurine trihydrochloride 2-[Trans-(4-aminocyclohexyl)amino]-6-[4-[1-(3,4-dichlorobenzyl)]piperidinylamino]-9-cyclopentylpurine trihydrochloride is prepared from 2-chloro-6-[4-[1-(3,4-dichlorobenzyl)]piperidinylamino]-9-cyclopentylpurine essentially as described in Example 1, Scheme A, step c.

APCI; 557 ($M^{+1}$)

$R_f$(min.)=2.33

EXAMPLE 147-p

2-[Trans-(4-aminocyclohexyl)amino]-6-[4-[1-(2-naphthyl)methyl]piperidinylamino]-9-cyclopentylpurine trihydrochloride Scheme B, step a: 4-Carboxamide-1-(2-naphthyl) methylpiperidine 4-Carboxamide-1-(2-naphthyl)methylpiperidine may be prepared from isonipecotamide and 2-(chloromethyl) naphthalene (available from Aldrich Chemical Company) essentially as described above in Example 38, Scheme B, step a.

Scheme B, step b: 4-amino-1-(2-naphthyl)methylpiperidine

4-Amino-1-(2-naphthyl)methylpiperidine is prepared from 4-carboxamide-1-(2-naphthyl)methylpiperidine essentially as described above in Example 38, Scheme B, step b.

Scheme A, step b: 2-Chloro-6-[4-1-(2-naphthyl)methyl] piperidinylamino]-9-cyclopentylpurine 2-Chloro-6-[4-1-(2-naphthyl)methyl]piperidinylamino]-9-cyclopentylpurine is prepared from 2,6-dichloro-9-cyclopentylpurine, 4-amino-1-(2-naphthyl)methylpiperidine, and triethylamine essentially as described above in Example 1, Scheme A, step b.

Scheme A, step c: 2-[Trans-(4-aminocyclohexyl)amino]-6-[4-[1-(2-naphthyl)methyl]piperidinylamino]-9-cyclopentylpurine trihydrochloride 2-[Trans-(4-aminocyclohexyl)amino]-6-[4-[1-(2-naphthyl)methyl]piperidinylamino]-9-cyclopentylpurine trihydrochloride is prepared from 2-chloro-6-[4-1-(2-naphthyl)methyl]piperidinylamino]-9-cyclopentylpurine essentially as described in Example 1, Scheme A, step c.

APCI: 539 ($M^{+1}$)

$R_f$(min.)=2.30

EXAMPLE 147-q

2-[Trans-(4-aminocyclohexyl)amino]-6-[4-1-(2-methoxybenzyl)]piperidinylamino -9-cyclopentylpurine trihydrochloride Scheme B, step a: 4-Carboxamide-1-(2-methoxybenzyl) piperidine 4-Carboxamide-1-(2-methoxybenzyl)piperidine may be prepared from isonipecotamide and 2-methoxybenzyl bromide (available from Aldrich Chemical Company) essentially as described above in Example 38, Scheme B, step a.

Scheme B, step b: 4-amino-1-(2-methoxybenzyl)piperidine

4-Amino-1-(2-methoxybenzyl)piperidine is prepared from 4-carboxamide-1-(2-methoxybenzyl)piperidine essentially as described above in Example 38, Scheme B, step b.

Scheme A, step b: 2-Chloro-6-[4-[1-(2-methoxybenzyl)] piperidinylamino]-9-cyclopentylpurine 2-Chloro-6-[4-[1-(2-methoxybenzyl)]piperidinylamino]-9-cyclopentylpurine is prepared from 2,6-dichloro-9-cyclopentylpurine, 4-amino-1-(2-methoxybenzyl) piperidine, and triethylamine essentially as described above in Example 1, Scheme A, step b.

Scheme A, step c: 2-[Trans-(4-aminocyclohexyl)amino]-6-[4-[1-(2-methoxybenzyl)]-piperidinylamino]-9-cyclopentylpurine trihydrochloride 2-[Trans-(4-aminocyclohexyl)amino]-6-[4-[1-(2-methoxybenzyl)]piperidinylamino]-cyclopentylpurine trihydrochloride is prepared from 2-chloro-6-[4-[1-(2-methoxybenzyl)]-piperidinylamino]-9-cyclopentylpurine essentially as described in Example 1, Scheme A, step c.

APCI: 519 ($M^{+1}$)

$R_f$(min.)=2.19

EXAMPLE 147-r

2-[Trans-(4-aminocyclohexyl)amino]-6-[4-[1-(2,5-dichlorobenzyl)]piperidinylamino]-9-cyclopentylpurine trihydrochloride Scheme B, step a: 4-Carboxamide-1-(2,5-dichlorobenzyl) piperidine 4-Carboxamide-1-(2,5-dichlorobenzyl)piperidine may be prepared from isonipecotamide and 2,5-dichlorobenzyl chloride (available from Lancaster) essentially as described above in Example 38, Scheme B, step a.

Scheme B, step b: 4-amino-1-(2,5-dichlorobenzyl) piperidine

4-Amino-1-(2,5-dichlorobenzyl)piperidine is prepared from 4-carboxamide-1-(2,5-dichlorobenzyl)piperidine essentially as described above in Example 38, Scheme B, step b.

Scheme A, step b; 2-Chloro-6-[4-[1-(2,5-dichlorobenzyl)]piperidinylamino]-9-cyclopentylpurine 2-Chloro-6-[4-[1-(2,5-dichlorobenzyl)]piperidinylamino]-9-cyclopentylpurine is prepared from 2,6-dichloro-9-cyclopentylpurine, 4-amino-1-(2,5-dichlorobenzyl)piperidine, and triethylamine essentially as described above in Example 1, Scheme A, step b.

Scheme A, step c: 2-[Trans-(4-aminocyclohexyl)amino]-6-[4-[1-(2,5-dichlorobenzyl)]-piperidinylamino]-9-cyclopentylpurine trihydrochloride 2-[Trans-(4-aminocyclohexyl)amino]-6-[4-[1-(2,5-dichlorobenzyl)]piperidinylamino]-9-cyclopentylpurine trihydrochloride is prepared from 2-chloro-6-[4-[1-(2,5-dichlorobenzyl)]piperidinylamino]-9-cyclopentylpurine essentially as described in Example 1, Scheme A, step c.

APCI: 557 ($M^{+1}$)
$R_f$(min.)=2.22

EXAMPLE 147-s

2-[Trans-(4-aminocyclohexyl)amino]-6-[4-(1-cyclohexylmethyl)piperidinylamino]-9-cyclopentylpurine trihydrochloride Scheme B, step a: 4-Carboxamide-1-cyclohexylmethylpiperidine 4-Carboxamide-1-cyclohexylmethylpiperidine may be prepared from isonipecotamide and cyclohexylmethyl bromide (available from Aldrich Chemical Company) essentially as described above in Example 38, Scheme B, step a.

Scheme B, step b: 4-amino-1-cyclohexylmethylpiperidine

4-Amino-1-cyclohexylmethylpiperidine is prepared from 4-carboxamide-1-cyclohexylmethylpiperidine essentially as described above in Example 38, Scheme B, step b.

Scheme A, step b: 2-Chloro-6-[4-(1-cyclohexylmethyl)piperidinylamino]-9-cyclopentylpurine 2-Chloro-6-[4-(1-cyclohexylmethyl)piperidinylamino]-9-cyclopentylpurine is prepared from 2,6-dichloro-9-cyclopentylpurine, 4-amino-1-cyclohexylmethylpiperidine, and triethylamine essentially as described above in Example 1, Scheme A, step b.

Scheme A, step c: 2-[Trans-(4-aminocyclohexyl)amino]-6-[4-(1-cyclohexylmethyl)piperidinylamino]-9-cyclopentylpurine trihydrochloride 2-[Trans-(4-aminocyclohexyl)amino]-6-[4-(1-cyclohexylmethyl)piperidinylamino]-9-cyclopentylpurine trihydrochloride is prepared from 2-chloro-6-[4-(1-cyclohexylmethyl)piperidinylamino]-9-cyclopentylpurine essentially as described in Example 1, Scheme A, step c.

APCI: 495 ($M^{+1}$)
$R_f$(min.)=2.25

EXAMPLE 147-t

2-[Trans-(4-aminocyclohexyl)amino]-6-[4-[1-(2-chloro-4-fluorobenzyl)]piperidinylamino]-9-cyclopentylpurine trihydrochloride Scheme B, step a: 4-Carboxamide-1-(2-chloro-4-fluorobenzyl)piperidine 4-Carboxamide-1-(2-chloro-4-fluorobenzyl)piperidine may be prepared from isonipecotamide and 2-chloro-4-fluorobenzyl chloride (available from Lancaster or Acros) essentially as described above in Example 38, Scheme B, step a.

Scheme B, step b: 4-amino-1-(2-chloro-4-fluorobenzyl) piperidine

4-Amino-1-(2-chloro4-fluorobenzyl)piperidine is prepared from 4-carboxamide-1-(2-chloro-4-fluorobenzyl) piperidine essentially as described above in Example 38, Scheme B, step b.

Scheme A, step b: 2-Chloro-6-[4-[1-(2-chloro-4-fluorobenzyl)]piperidinylamino]-9-cyclopentylpurine 2-Chloro-6-[4-[1-(2-chloro-4-fluorobenzyl)]piperidinylamino]-9-cyclopentylpurine is prepared from 2,6-dichloro-9-cyclopentylpurine, 4-amino-1-(2-chloro-4-fluorobenzyl)piperidine, and triethylamine essentially as described above in Example 1, Scheme A, step b.

Scheme A, step c: 2-[Trans-(4-aminocyclohexyl)amino]-6-[4-[1-(2-chloro-4-fluorobenzyl)]piperidinylamino]-9-cyclopentylpurine trihydrochloride 2-[Trans-(4-aminocyclohexyl)amino]-6-[4-[1-(2-chloro-4-fluorobenzyl)]-piperidinylamino]-9-cyclopentylpurine trihydrochloride is prepared from 2-chloro-6-[4-[1-(2-chloro-4-fluorobenzyl)]piperidinylamino]-9-cyclopentylpurine essentially as described in Example 1, Scheme A, step c.

APCI: 541 ($M^{+1}$)
$R_f$(min.)=2.28

EXAMPLE 147-u

2-[Trans-(4-aminocyclohexyl)amino]-6-[4-[1-(3,4-difluorobenzyl)]piperidinylamino]-9-cyclopentylpurine trihydrochloride Scheme B, step a: 4-Carboxamide-1-(3,4-difluorobenzyl) piperidine 4-Carboxamide-1-(3,4-difluorobenzyl)piperidine may be prepared from isonipecotamide and 3,4-difluorobenzyl bromide (available from Aldrich Chemical Company) essentially as described above in Example 38, Scheme B, step a.

Scheme B step b: 4-amino-1-(3,4-difluorobenzyl)piperidine

4-Amino-1-(3,4-difluorobenzyl)piperidine is prepared from 4-carboxamide-1-(3,4-difluorobenzyl)piperidine essentially as described above in Example 38, Scheme B, step b.

Scheme A, step b: 2-Chloro-6-[4-[1-(3,4-difluorobenzyl)]piperidinylamino]-9-cyclopentylpurine 2-Chloro-6-[4-[1-(3,4-difluorobenzyl)]piperidinylamino]-9-cyclopentylpurine is prepared from 2,6-dichloro-9-cyclopentylpurine, 4-amino-1-(3,4-difluorobenzyl)piperidine, and triethylamine essentially as described above in Example 1, Scheme A, step b.

Scheme A, step c: 2-[Trans-(4-aminocyclohexyl)amino]-6-[4-[1-(3,4-difluorobenzyl)]-piperidinylamino]-9-cyclopentylpurine trihydrochloride 2-[Trans-(4-aminocyclohexyl)amino]-6-[4-[1-(3,4-difluorobenzyl)]piperidinylamino]-9-cyclopentylpurine trihydrochloride is prepared from 2-chloro-6-[4-[1-(3,4-difluorobenzyl)]piperidinylamino]-9-cyclopentylpurine essentially as described in Example 1, Scheme A, step c.

APCI: 525 ($M^{+1}$)
$R_f$(min.)=2.29

EXAMPLE 147-v

2-[Trans-(4-aminocyclohexyl)amino]-6-[4-[1-(2,6-difluorobenzyl)]piperidinylamino]-9-cyclopentylpurine trihydrochloride Scheme B, step a: 4-Carboxamide-1-(2,6-difluorobenzyl) piperidine 4-Carboxamide-1-(2,6-difluorobenzyl)piperidine may be prepared from isonipecotamide and 2,6-difluorobenzyl bromide (available from Aldrich Chemical Company) essentially as described above in Example 38, Scheme B, step a.

Scheme B, step b: 4-amino-1-(2,6-difluorobenzyl)piperidine

4-Amino-1-(2,6-difluorobenzyl)piperidine is prepared from 4-carboxamide-1-(2,6-difluorobenzyl)piperidine essentially as described above in Example 38, Scheme B, step b.

Scheme A, step b: 2-Chloro-6-[4-[1-(2,6-difluorobenzyl)]piperidinylamino]-9-cyclopentylpurine 2-Chloro-6-[4-[1-(2,6-difluorobenzyl)]piperidinylamino]-9-cyclopentylpurine is prepared from 2,6-dichloro-9-cyclopentylpurine, 4-amino-1-(2,6-difluorobenzyl)piperidine, and triethylamine essentially as described above in Example 1, Scheme A, step b.

Scheme A, step c: 2-[Trans-(4-aminocyclohexyl)amino]-6-[4-[1-(2,6-difluorobenzyl]-piperidinylamino]-9-cyclopentylpurine trihydrochloride 2-[Trans-(4-aminocyclohexyl)amino]-6-[4-[1-(2,6-difluorobenzyl)]piperidinylamino]-9-cyclopentylpurine trihydrochloride is prepared from 2-chloro-6-[4-[1-(2,6-difluorobenzyl)]piperidinylamino]-9-cyclopentylpurine essentially as described in Example 1, Scheme A, step c.

APCI: 525 ($M^{+1}$)
$R_f$(min.)=2.26

EXAMPLE 147-w

2-[Trans-(4-aminocyclohexyl)amino]-6-[4-[1-(3,5-dichlorobenzyl)]piperidinylamino]-9-cyclopentylpurine trihydrochloride Scheme B, step a: 4-Carboxamide-1-(3,5-dichlorobenzyl)piperidine 4-Carboxamide-1-(3,5-dichlorobenzyl)piperidine may be prepared from isonipecotamide and 3,5-dichlorobenzyl chloride (available from Trans World Chemicals or Fluorochem Ltd.) essentially as described above in Example 38, Scheme B, step a.

Scheme B, step b: 4-amino-1-(3,5-dichlorobenzyl)piperidine

4-Amino-1-(3,5-dichlorobenzyl)piperidine is prepared from 4-carboxamide-1-(3,5-dichlorobenzyl)piperidine essentially as described above in Example 38, Scheme B, step b.

Scheme A, step b: 2-Chloro-6-[4-[1-(3,5-dichlorobenzyl)]piperidinylamino]-9-cyclopentylpurine 2-Chloro-6-[4-[1-(3,5-dichlorobenzyl)]piperidinylamino]-9-cyclopentylpurine is prepared from 2,6-dichloro-9-cyclopentylpurine, 4-amino-1-(3,5-dichlorobenzyl)piperidine, and triethylamine essentially as described above in Example 1, Scheme A, step b.

Scheme A, step c: 2-[Trans-(4-aminocyclohexyl)amino]-6-[4-[1-(3,5-dichlorobenzyl)]-piperidinylamino]-9-cyclopentylpurine trihydrochloride 2-[Trans-(4-aminocyclohexyl)amino]-6-[4-[1-(3,5-dichlorobenzyl)]piperidinylamino]-9-cyclopentylpurine trihydrochloride is prepared from 2-chloro-6-[4-[1-(3,5-dichlorobenzyl)]piperidinylamino]-9-cyclopentylpurine essentially as described in Example 1, Scheme A, step c.

APCI: 557 ($M^{+1}$)
$R_f$(min.)=2.31

EXAMPLE 147-x

2-[Trans-(4-aminocyclohexyl)amino]-6-[4-[1-(2,4-dichlorobenzyl)]piperidinylamino]-9-cyclopentylpurine trihydrochloride Scheme B, step a: 4-Carboxamide-1-(2,4-dichlorobenzyl)piperidine 4-Carboxamide-1-(2,4-dichlorobenzyl)piperidine may be prepared from isonipecotamide and 2,4-dichlorobenzyl chloride (available from Aldrich Chemical Company) essentially as described above in Example 38, Scheme B, step a.

Scheme B, step b: 4-amino-1-(2,4-dichlorobenzyl)piperidine

4-Amino-1-(2,4-dichlorobenzyl)piperidine is prepared from 4-carboxamide-1-(2,4-dichlorobenzyl)piperidine essentially as described above in Example 38, Scheme B, step b.

Scheme A, step b: 2-Chloro-6-[4-[1-(2,4-dichlorobenzyl)]piperidinylamino]-9-cyclopentylpurine 2-Chloro-6-[4-[1-(2,4-dichlorobenzyl)]piperidinylamino]-9-cyclopentylpurine is prepared from 2,6-dichloro-9-cyclopentylpurine, 4-amino-1-(2,4-dichlorobenzyl)piperidine, and triethylamine essentially as described above in Example 1, Scheme A, step b.

Scheme A, step c: 2-[Trans-(4-aminocyclohexyl)amino]-6-[4-[1-(2,4-dichlorobenzyl)]-piperidinylamino]-9-cyclopentylpurine trihydrochloride 2-[Trans-(4-aminocyclohexyl)amino]-6-[4-[1-(2,4-dichlorobenzyl)]piperidinylamino]-9-cyclopentylpurine trihydrochloride is prepared from 2-chloro-6-[4-[1-(2,4-dichlorobenzyl)]piperidinylamino]-9-cyclopentylpurine essentially as described in Example 1, Scheme A, step c.

APCI: 557 ($M^{+1}$)
$R_f$(min.)=2.31

EXAMPLE 147-y

2-[Trans-(4-aminocyclohexyl)amino]-6-[4-[1-(3-chloro-4-methylbenzyl)]piperidinylamino]-9-cyclopentylpurine trihydrochloride Scheme B, step a: 4-Carboxamide-1-(3-chloro-4-methylbenzyl)piperidine 4-Carboxamide-1-(3-chloro-4-methylbenzyl)piperidine may be prepared from isonipecotamide and 3-chloro-4-methylbenzyl chloride (available from Pfaltz-Bauer) essentially as described above in Example 38, Scheme B, step a.

Scheme B, step b: 4-amino-1-(3-chloro-4-methylbenzyl)piperidine

4-Amino-1-(3-chloro-4-methylbenzyl)piperidine is prepared from 4-carboxamide-1-(3-chloro-4-methylbenzyl)piperidine essentially as described above in Example 38, Scheme B, step b.

Scheme A, step b: 2-Chloro-6-[4-[1-(3-chloro-4-methylbenzyl)]piperidinylamino]-9-cyclopentylpurine 2-Chloro-6-[4-[1-(3-chloro-4-methylbenzyl)]piperidinylamino]-9-cyclopentylpurine is prepared from 2,6-dichloro-9-cyclopentylpurine, 4-amino-1-(3-chloro-4-methylbenzyl)piperidine, and triethylamine essentially as described above in Example 1, Scheme A, step b.

Scheme A, step c: 2-[Trans-(4-aminocyclohexyl)amino]-6-[4-[1-(3-chloro-4-methylbenzyl)]-piperidinylamino]-9-cyclopentylpurine trihydrochloride 2-[Trans-(4-aminocyclohexyl)amino]-6-[4-[1-(3-chloro-4-methylbenzyl)]piperidinylamino]-9-cyclopentylpurine trihydrochloride is prepared from 2-chloro-6-[4-[1-(3-chloro-4-methylbenzyl)]piperidinylamino]-9-cyclopentylpurine essentially as described in Example 1, Scheme A, step c.

APCI: 537 ($M^{+1}$)
$R_f$(min.)=2.25

EXAMPLE 147-z

2-[Trans-(4-aminocyclohexyl)amino]-6-[4-[1-(4-trifluoromethoxybenzyl)]piperidinylamino]-9-cyclopentylpurine trihydrochloride Scheme B, step a: 4-Carboxamide-1-(4-trifluoromethoxybenzyl)piperidine 4-Carboxamide-1-(4-trifluoromethoxybenzyl)piperidine may be prepared from isonipecotamide and 4-(trifluoromethoxy)benzyl bromide (available from Aldrich Chemical Company) essentially as described above in Example 38, Scheme B, step a.

Scheme B, step b: 4-amino-1-(4-trifluoromethoxybenzyl)piperidine

4-Amino-1-(4-trifluoromethoxybenzyl)piperidine is prepared from 4-carboxamide-1-(4-trifluoromethoxybenzyl)piperidine essentially as described above in Example 38, Scheme B, step b.

Scheme A, step b: 2-Chloro-6-[4-[1-(4-trifluoromethoxybenzyl)]piperidinylamino]-9-cyclopentylpurine 2-Chloro-6-[4-[1-(4-trifluoromethoxybenzyl)]piperidinylamino]-9-cyclopentylpurine is prepared from 2,6-dichloro-9-cyclopentylpurine, 4-amino-1-(4-trifluoromethoxybenzyl)piperidine, and triethylamine essentially as described above in Example 1, Scheme A, step b.

Scheme A, step c: 2-[Trans-(4-aminocyclohexyl)amino]-6-[4-[1-(4-trifluoromethoxybenzyl)]piperidinylamino]-9-cyclopentylpurine trihydrochloride 2-[Trans-(4-aminocyclohexyl)amino]-6-[4-[1-(4-trifluoromethoxybenzyl)]-piperidinylamino]-9-cyclopentylpurine trihydrochloride is prepared from 2-chloro-6-[4-[1-(4-trifluoromethoxybenzyl)]piperidinylamino]-9-cyclopentylpurine essentially as described in Example 1, Scheme A, step c.

APCI: 573 (M$^{+1}$)

R$_f$(min.)=2.23

EXAMPLE 147-aa

2-[Trans-(4-aminocyclohexyl)amino]-6-[4-[1-(2,4-bis-trifluoromethylbenzyl)]piperidinylamino]-9-cyclopentylpurine trihydrochloride Scheme B, step a: 4-Carboxamide-1-(2,4-bis-trifluoromethylbenzyl)piperidine 4-Carboxamide-1-(2,4-bis-trifluoromethylbenzyl)piperidine may be prepared from isonipecotamide and bis(2,4-trifluoromethyl)benzyl bromide (available from Aldrich Chemical Company) essentially as described above in Example 38, Scheme B, step a.

Scheme B step b: 4-amino-1-(2,4-bis-trifluoromethylbenzyl)piperidine

4-Amino-1-(2,4-bis-trifluoromethylbenzyl)piperidine is prepared from 4-carboxamide-1-(2,4-bis-trifluoromethylbenzyl)piperidine essentially as described above in Example 38, Scheme B, step b.

Scheme A, step b: 2-Chloro-6-[4-[1-(2,4-bis-trifluoromethylbenzyl)]piperidinylamino]-9-cyclopentylpurine 2-Chloro-6-[4-[1-(2,4-bis-trifluoromethylbenzyl)]piperidinylamino]-9-cyclopentylpurine is prepared from 2,6-dichloro-9-cyclopentylpurine, 4-amino-1-(2,4-bis-trifluoromethylbenzyl)]piperidine, and triethylamine essentially as described above in Example 1, Scheme A, step b.

Scheme A, step c: 2-[Trans-(4-aminocyclohexyl)amino]-6-[4-[1-(2,4-bis-trifluoromethylbenzyl)]piperidinylamino]-9-cyclopentylpurine trihydrochloride 2-[Trans-(4-aminocyclohexyl)amino]-6-[4-[1-(2,4-bis-trifluoromethylbenzyl)]-piperidinylamino]-9-cyclopentylpurine trihydrochloride is prepared from 2-chloro-6-[4-[1-(2,4-bis-trifluoromethylbenzyl)]piperidinylamino]-9-cyclopentylpurine essentially as described in Example 1, Scheme A, step c.

APCI: 625 (M$^{+1}$)

R$_f$(min.)=1.44

EXAMPLE 147-ab

2-[Trans-(4-aminocyclohexyl)amino]-6-[4-[1-(2-trifluoromethoxybenzyl)]piperidinylamino]-9-cyclopentylpurine trihydrochloride Scheme B, step a: 4-Carboxamide-1-(2-trifluoromethoxybenzyl)piperidine 4-Carboxamide-1-(2-trifluoromethoxybenzyl)piperidine may be prepared from isonipecotamide and 2-(trifluoromethoxy)benzyl bromide (available from Fluorochem Ltd.) essentially as described above in Example 38, Scheme B, step a.

Scheme B, step b: 4-amino-1-(2-trifluoromethoxybenzyl)piperidine

4-Amino-1-(2-trifluoromethoxybenzyl)piperidine is prepared from 4-carboxamide-1-(2-trifluoromethoxybenzyl)piperidine essentially as described above in Example 38, Scheme B, step b.

Scheme A, step b: 2-Chloro-6-[4-[1-(2-trifluoromethoxybenzyl)]piperidinylamino]-9-cyclopentylpurine 2-Chloro-6-[4-[1-(2-trifluoromethoxybenzyl)]piperidinylamino]-9-cyclopentylpurine is prepared from 2,6-dichloro-9-cyclopentylpurine, 4-amino-1-(2-trifluoromethoxybenzyl)piperidine, and triethylamine essentially as described above in Example 1, Scheme A, step b.

Scheme A, step c: 2-[Trans-(4-aminocyclohexyl)amino]-6-[4-[1-(2-trifluoromethoxybenzyl)]piperidinylamino]-9-cyclopentylpurine trihydrochloride 2-[Trans-(4-aminocyclohexyl)amino]-6-[4-[1-(2-trifluoromethoxybenzyl)]-piperidinylamino]-9-cyclopentylpurine trihydrochloride is prepared from 2-chloro-6-[4-[1-(2-trifluoromethoxybenzyl)]piperidinylamino]-9-cyclopentylpurine essentially as described in Example 1, Scheme A, step c.

APCI: 573 (M$^{+1}$)

R$_f$(min.)=2.26

EXAMPLE 147-ac

2-[Trans-(4-aminocyclohexyl)amino]-6-[4-(1-benzyl)piperidinylmethylamino]-9-cyclopentylpurine trihydrochloride N-Benzyl-4-(aminomethyl)piperidine N-Benzyl-4-aminomethylpiperidine is prepared from 4-(aminomethyl)piperidine (available from Aldrich Chemical Company) as described by L. G. Humber [J. Med. Chem., 92, 441–443 (1966)]

Scheme A, step b: 2-Chloro-6-[4-(1-benzyl)piperidinylmethylamino]-9-cyclopentylpurine 2-Chloro-6-[4-(1-benzyl)piperidinylmethylamino]-9-cyclopentylpurine is prepared from 2,6-dichloro-9-cyclopentylpurine, N-benzyl-4-aminomethylpiperidine, and triethylamine essentially as described above in Example 1, Scheme A, step b.

Scheme A, step c: 2-[Trans-(4-aminocyclohexyl)amino]-6-[4-(1-benzyl)piperidinylmethylamino]-9-cyclopentylpurine trihydrochloride 2-[Trans-(4-aminocyclohexyl)amino]-6-[4-(1-benzyl)piperidinylmethylamino]-9-cyclopentylpurine trihydrochloride is prepared from 2-chloro-6-[4-(1-benzyl)piperidinylmethylamino]-9-cyclopentylpurine essentially as described in Example 1, Scheme A, step c.

APCI: 503 (M$^{+1}$)

R$_f$(min.)=2.24

EXAMPLE 147-ad

2-[Trans-(4-aminocyclohexyl)amino]-6-[4-[1-(3-phenoxybenzyl)]piperidinylamino]-9-cyclopentylpurine trihydrochloride Scheme B, step a: 4-Carboxamide-1-(3-phenoxybenzyl) piperidine 4-Carboxamide-1-(3-phenoxybenzyl)piperidine may be prepared from isonipecotamide and 3-phenoxybenzyl chloride (available from Lancaster) essentially as described above in Example 38, Scheme B, step a.

Scheme B, step b: 4-amino-1-(3-phenoxybenzyl)piperidine

4-Amino-1-(3-phenoxybenzyl)piperidine is prepared from 4-carboxamide-1-(4-phenoxybenzyl)piperidine essentially as described above in Example 38, Scheme B, step b.

Scheme A, step b: 2-Chloro-6-[4-[1-(3-phenoxybenzyl)] piperidinylamino]-9-cyclopentylpurine 2-Chloro-6-[4-[1-(3-phenoxybenzyl)]piperidinylamino]-9-cyclopentylpurine is prepared from 2,6-dichloro-9-cyclopentylpurine, 4-amino-1-(3-phenoxybenzyl) piperidine, and triethylamine essentially as described above in Example 1, Scheme A, step b.

Scheme A, step c: 2-[Trans-(4-aminocyclohexyl)amino]-6-[4-[1-(3-phenoxybenzyl)]-piperidinylamino]-9-cyclopentylpurine trihydrochloride 2-[Trans-(4-aminocyclohexyl)amino]-6-[4-[1-(3-phenoxybenzyl)]piperidinylamino]-9-cyclopentylpurine trihydrochloride is prepared from 2-chloro-6-[4-[1-(3-phenoxybenzyl)]piperidinylamino]-9-cyclopentylpurine essentially as described in Example 1, Scheme A, step c.

APCI: 581 ($M^{+1}$)

$R_f$(min.)=2.35

The term "neoplastic disease state" as used herein refers to an abnormal state or condition characterized by uncontrolled proliferation. Neoplastic disease states include leukemias, carcinomas and adenocarcinomas, sarcomas, melanomas, and mixed types of neoplasms.

Leukemias include, but are not limited to, acute lymphoblastic, chronic lymphocytic, acute myeloblastic and chronic myelocytic leukemias.

Carcinomas and adenocarcinomas include, but are not limited to, those of the cervis, breast, prostate, esophagus, stomach, small intestines, colon, ovary and lungs.

Sarcomas include, but are not limited to, oesteromas, osteosarcoma, lipoma, lipsarcoma, hemangiomas and hemangiosarcoma.

Melanomas include, but are not limited to, amelanotic and melanotic melanomas.

Mixed types of neoplasms include, but are not limited to, carcinosarcoma, lymphoid tissue type, folicullar reticulum, cell sarcoma and Hodgkins Disease.

The term "therapeutically effective amount" of a compound of the formula (1) refers to an amount which is effective, upon single or multiple dose administration to the patient, in controlling the growth of the neoplasm or metastases of the neoplasm or preventing apoptosis. A therapeutically effective amount of a compound of the formula will vary according to the age, weight, type of neoplasm to be treated, the combination of other antineoplastic agents, and other criteria well known to those skilled in the art using standard clinical and laboratory tests and procedures. A therapeutically effective amount of a compound of the formula will vary according to the type of cell susceptible to apoptosis, the location of the infarct, as well as the age, weight and other criteria well known to those skilled in the art.

The term "controlling the growth" of the neoplasm refers to slowing, interrupting, arresting or stopping the growth of the neoplasm or metastates of the neoplasm. The term "controlling the growth" of the neoplasm also refers to killing the neoplasia or metastates of the neoplasia.

An effective amount of a compound of the formula is that amount which is effective, upon single or multiple dose administration to a patient in providing an antineoplastic effect or in preventing apoptosis. An "antineoplastic effect" refers to the slowing, interrupting, preventing or destruction of further growth of neoplastic cells.

An effective antineoplastic amount of a compound of the formula can be readily determined by an attending diagnostician, as one skilled in the art, by the use of known techniques and by observing results obtained under analogous circumstances. In determining the effective amount, a number of factors are considered by the attending diagnostician, including but not limited to, the species of mammal; its size, age and general health; the specific disease involved; the degree of or involvement or the severity of the disease; the response of the individual patient; the particular compound of the formula administered; the mode of administration; the bioavailability characteristics of the preparation administered; the dose regimen selected; the use of concomitant medication; and other relevant circumstances.

A further embodiment of the present invention includes a method for the prophylactic treatment of a patient at risk of developing a neoplastic disease state comprising administering a prophylactically effective antineoplastic amount of a compound of the formula. The term "a patient at risk of developing a neoplastic disease state" refers to a patient who, because of an identified genetic predisposition to neoplasms, had or currently have neoplasms, exposure of carcinogenic agents, diet, age or has other risk factors associated with the development of neoplastic disease states. Preferred patients at risk of developing a neoplastic disease state include patients who are positive for oncogenic viruses, are in remission from prior treatment of neoplasm(s), use tobacco products or have previously been exposed to carcinogens such as asbestos, or are positive for various neoplastic genetic markers.

Oncogenic viruses are those viruses associated with cancers. For example, Rous sarcoma of chickens, Shope rabbit papilloma, murine leukemia viruses are animal viruses recognized as having a role in development of various cancers. Human papillomavirus is associated with genital cancer. Molluscum contagiosum virus is associated with molluscum contagiosum tumors. The JC virus, a human papovirus, is associated with disorders of reticulendothelial system such as leukemia and lymphoma. Human retroviruses such as human T-cell lymphotropic viruses (HTLV) types 1 and 2 are associated with some human leukemias and lymphomas. Human immunodeficiency viruses (HIV) types 1 and 2 are the causes of AIDS. Epstein-Barr virus has been associated with various malignancies, including nasopharyngeal carcinoma, African Burkitt's lymphoma and lymphomas in immunosuppressed organ transplant recipients.

Genetic markers such as mutations, rearrangments and the like in BRCA 1, bcl-1/PRAD1, cyclin D1/CCND1, p16, cdk4, especially an Arg24Cys mutation, p16$^{INK4a}$. Genetic markers are associated with predispositions to various neoplasms. For example, alterations in the BRCA 1 gene are associated with a higher risk for breast and ovarian cancer. Other genetic markers include alterations in the MMSC1 gene, which interracts with the MMCA1 brain and prostate cancer gene, in the CtIP gene, which is linked to the BRACA1 gene in breast and ovarian cancer, binds to the BRCA1 gene and is linked to the E1A oncogene pathway, and in the MKK3 gene, which is a cell cycle control gene that acts as a tumor supressor in lung cancer by activating apoptosis. Patients at risk of developing a neoplastic disease state also include patients who overexpress various cell cycle proteins, including cdk4, cyclins B1 and E. Patients at risk of developing a neoplastic disease state include those with elevated levels of tumor markers. Known tumor markers include prostate specific antigen (PSA) and plasma insulin-like growth factor-1 (IGF-1), which are markers for prostate cancer. Nuclear matrix proteins (NMPs) are associated with the presence of cancer, particularly bladder and colon cancers.

An effective amount of a compound of the formula is expected to vary from about 25 nonograms per kilogram of body weight per day (ng/kg/day) to about 500 mg/kg/day. Preferred effective amounts of a compound of the formula is from about 1 µg/kg/day to about 500 µg/kg/day. A more preferred amount of a compound of the formula is from about 1 µg/kg/day to about 50 µg/kg/day.

A compound of the formula may be administered in any form or mode which makes the compound bioavailable in effective amounts. Compounds of the formula may be administered by oral or parental routes. Compounds of the formula may be administered orally, subcutaneously, intramuscularly, intravenously, transdermally, intranasally, rectally, ocularly and the like. Oral administration is preferred. One skilled in the art of preparing pharmacuetical formulations may readily determine appropriate forms of a compound of the formula by determining particular characteristics of the compound, the disease to be treated, the stage of the disease, response of other patients and other relevant circumstances.

A compound of the formula may be combined with carriers, excipients or other compounds to prepare compositions of a compound of the formula. A composition of the formula comprise a compound of the formula in admixture or otherwise in association with one or more inert carriers. Compositions of the formula are useful, for example, as convenient means of making bulk shipments, or for storing, a compound of the formula. An inert carrier is a material which does not degrade or otherwise covalently react with a compound of the formula. An inert carrier may be a solid, semi-solid or liquid material. Preferred carriers are water, aqueous buffers, organic solvents and pharmaceutically acceptable carriers or excipients. Preferred aqueous buffers provide a buffering range at which a compound of the formula does not degrade. Preferred buffering ranges are about pH 4 to about pH 9. Preferred organic solvents are acetonitrile, ethyl acetate, hexane.

A pharmaceutical composition of a compound of the formula comprises a compound of the formula in admixture or otherwise in association with one or more pharmaceutically acceptable carrier or excipient. A pharmaceutically acceptable carrier or excipient may be a solid, semi-solid or liquid material which can serve as a vehicle or medium for the compound of the formula. Suitable pharmaceutically acceptable carriers or excipients are well-known to those skilled in the art.

A pharmaceutical composition of a compound of the formula may be adapted for the route of administration. A preferred pharmaceutical composition of a compound of the formula is a tablet, troche, capsule, elixir, syrup, wafer, chewing gum, suppository, solution or suspension if the route of administration is oral, parental or topical.

A preferred oral pharmaceutical composition of a compound of the formula comprises a compound of the formula with an inert diluent or with an edible carrier. Preferred forms of oral pharmaceutical compositions of a compound of the formula are tablets, troches, capsules, elixirs, syrups, wafers, chewing gum, solutions or suspensions.

Preferred pharmaceutical compositions of a compound of the formula contain from about 4% to about 80% of the compound. Preferred pharmaceutical compositions contain an amount of the compound of the formula from about 50 ηg to about 500 µg; more preferred pharmaceutical composition contain an amount of the compound of the formula from about 1 µg to about 200 µg.

A compound of the formula may be administered alone or in the form of a pharmaceutical composition in combination with pharmaceutically acceptable carriers or excipients.

The following abbreviations are used herein: mg, milligram; µg, microgram; ηg, nanogram; TEA, triethlyamine; mmol, millimole: mL, milliliter; C., Celsius; hr, hour; TLC, thin layer chromatography; $CH_2CL_2$, methylene chloride; MeOH, methanol; EtOH, ethanol; N, Normal; HCl, hydrogen chloride; TFA, trifluoroacetic acid, DIEA, diisopropylethylamine; RT PCR, reverse transcription polymerase chain reaction; HEPES, 4-(2-hydoxyethyl0-1-piperazine ethanesulfonic acid); $MgCl_2$, Magnesium chloride; EGTA, ethylene glycol-bis(β-aminoethylether)-N,N,N',N'-tetraacetic acid; EDTA, ethylenediaminetetraacetic acid; DTT, dithiothreitol; MOI, multiplicity of infection; NaF, Sodium flouride; BSA, bovine serum albumin; p.o., oral(ly) i.v., intravenous(ly); s.c., subcutaneous(ly).

EXAMPLE 148

Cyclin-dependent Kinase 4 Assay

The $IC_{50}$ values for cdk4 inhibition were by the following method:
Substrate
Glutathione S-transferase—retinoblastoma fusion protein (GST-Rb) (Kaelin, W. G., Jr., et al., Cell 64: 521–532, 1991) was obtained from Dr. William Kaelin. GST-Rb was prepared by transformation of E. coli with the plasmid pGEX-Rb (379–928). The transformed bacteria were grown overnight to saturation, then diluted in YT broth and incubated at 37° C. for 2 h. The protein was induced by incubation with 0.1 mM isopropylthioglycoside for 3 h. Following sedimentation by centrifugation, the cells were lysed by sonication in STE buffer (0.1 mM NaCl, 10 mM Tris, pH 8.0, 1 mM EDTA) containing 10% sarkosyl. Particulate matter was removed by centrifugation and the lysate was incubated with glutathione-Sepharose at 4° C. The beads were washed with kinase buffer and then quantitation of Coomassie blue-stained proteins separated by SDS-PAGE was performed using a protein standard of known concentration.
Expression of CDK4/Cyclin D1 in Insect Cells
Human cyclin-dependent kinase 4 (cdk4) was cloned by RT PCR using degenerate primers based on the published amino acid sequence (Matsushime, H, et al., Cell, 71: 323–334, 1992). The cDNA for human cyclin D1 was cloned by RT PCR using genomic DNA from MCF-7 cells. The sequence was consistent with the published sequence (Xiong, Y., et al., Cell, 65: 691–699, 1991.). Both the cDNAs for cdk4 and cyclin D1 were cloned into pFastBac (Life Technologies) and recombinant Bacmid DNA containing the cDNAs was produced by site-specific transposition using the Bac-to-Bac Baculovirus expression system purchased from Life Technologies (catalog # 10359-016). Bacmid DNA was used to transfect Sf9 insect cells to produce recombinant virus. Following plaque purification of the virus, the viral preparations were amplified until high titer stocks were acheived. Optimum coexpression of the recombinant proteins was determined to be acheived with an MOI of 0.1 for both cdk4 and cyclin D1 at 72 h post infection.

Lysates were prepared by lysis of Sf9 cells coinfected with cdk4 and cyclin D1 in 50 mM HEPES, pH 7.5, 10 mM $MgCl_2$, 1 mM DTT, 0.1 mM phenylmethylsulfonyl fluoride, 5 µg/ml aprotinin, and 5 µg/ml leupeptin using a PARR bomb under 500 p.s.i nitrogen pressure for 5 min at 4° C. Insoluble material was sedimented at 10,000×g for 20 min at 4° C. Glycerol was added to the supernatant to 10% and stored at −80° C. in aliquots.

Kinase Assay

Pre-wet Millipore Multiscreen 96-well filter plates (0.65 µm Durapore filters) with 200 µl kinase buffer (50 mM HEPES, pH 7.5, 10 mM $MgCl_2$, 1 mM EGTA). GST-Rb (0.5 µg) bound to glutathione-Sepharose beads is added in 50 µl per well and the solution removed by application of vacuum. The assay contains 50 mM HEPES, pH 7.5, 10 mM $MgCl_2$, 1 mM EDTA, 1 mM DTT, 1 mM EGTA, 10 mM β-glycerophosphate, 0.1 mM sodium orthovanadate, 0.1 mM NaF, 0.25% BSA, 10 µM ATP and 0.25 µCi of [$\gamma^{33}$P]-ATP. Add 0.1 µg cdk4/cyclin D1 (insect cell lysate) to initiate assay. Incubate 30 min at 37° C. Terminate reaction by filtration on Millipore Vacuum Manifold. Wash four times with TNEN (20 mM Tris, pH 8.0, 100 mM Na Cl, 1 mM EDTA, 0.5% nonidet P-40). After drying the plates at room temperature, the filter plates were placed in adapter plates (Packard) and 40 µl of Microscint-O® (Packard) was added to each well. Top Seal A film was used to cover the plates before counting in a Top Count Scintillation Counter.

The results are provided in Table 1.

EXAMPLE 149 cdk-2 Inhibition Studies

The $IC_{50}$ values for CDK-2 inhibition were determined by the following method:

Cyclin-Dependent Kinase 2 Assay
Substrate: GST-Rb as described above for cdk4/cyclin D1
Expression of CDK2/Cyclin E in Insect Cells Recombinant baculoviruses for human cdk2 and cyclin E were obtained from Dr. David Morgan at UC, Berkeley (Desai, D. et al. Molec. Biol. Cell, 3:571–582, 1992). Optimum coexpression in insect cells was obtained at MOI's of 0.1 and 1.0 for cdk2 and cyclin E, respectively, at 72 h post infection.

Kinase Assay

Assay conditions for cdk2/cyclin E were identical to those for cdk4/cyclin D1 including the substrate. The concentration of recombinant cdk2/cyclin E in the assay was 0.1 µg per 100 µl assay. Incubation was for 30 min at 30° C.

The results are provided in Table 1.

EXAMPLE 150

Cdk7/Cyclin H Assay Protocol
Substrate: Peptide Substrate $H_2N$—RRR(YSPTSPS)$_4$-COOH Based on Sequence of CTD of RNA Polymerase II
Expression of CDK7/Cyclin H in Insect Cells Human cdk7 was cloned by reverse transcription PCR. The sequence was consistent with that reported by Tassan, J. P., et al., *J. Cell Biol.* 127: 467–478, 1994 and Darbon, J. M. et al. *Oncogene*, 9: 3127–3138, 1994. The cDNA for cyclin H was also cloned by reverse transcription PCR and the sequence was consistent with that reported by Fisher & Morgan, *Cell*, 78: 713–724, 1994. Recombinant Bacmid DNA and viral stocks were prepared as described above for cdk4 and cyclin D1. Optimum coexpression was achieved at MOI's of 1 and 2 for cdk7 and cyclin H, respectively at 48 h post infection.

Kinase Assay

The assay measures the phosphorylation of a peptide substrate (based on the C-terminal domain of RNA polymerase II) by cyclin-dependent kinase 7 which is activated by cyclin H. [$\gamma^{33}$P]-phosphate is transferred from [$\gamma^{33}$P]-ATP to the peptide substrate by the enzyme. The assay is run in 96-well V-bottom plates, then following termination the reaction is transferred to 96-well Millipore Multiscreen phosphocellulose filter plates. The peptide is retained on the phosphocellulose membrane after washing with a phosphoric acid solution.

Method

Enzyme assay is run in 96-well V-bottom plates in a total volume of 100 µl. Assay contains 15 µM ATP, 0.5 µCi [$\gamma^{33}$P]-ATP, 50 mM Hepes, pH 7.5, 10 mM $MgCl_2$, 1 mM EDTA, 1 mM DTT, 10 mM β-glycerophosphate, 0.1 mM sodium orthovanadate, 0.1 mM NaF, 10 µM peptide substrate. To initiate the assay, 0.125 ng cdk7 and cyclin H (insect cell lysate) is added. Incubation is for 5 min at 24° C. Reaction is terminated by addition of 40 µl cold 300 mM phosphoric acid to each sample. Contents of V-bottom wells were then transferred to a Millipore 96-well phosphocellulose filter plate. After sitting for 15 min at room temperature vacuum was applied to the filter plate and the wells were washed 4× with 100 µl of cold 75 mM phosphoric acid. After removal of the underdrain assembly, filters were dried completely, placed in Multiscreen microplate adapters, and 40 µl of Micro-Scint O added to each well. Plates were covered with Top-Seal A film and counted for 1.5 min using a Packard Top Count Scintillation Counter.

The results are provided in Table 1

EXAMPLE 151

CDK1/cyclin B [$^{33}$P]SPA Assay Protocol

Substrate

The assay uses a biotinylated substrate peptide (biotin-PKTPKKAKKL) derived from the in vitro p34$^{cdc2}$ phosphorylation site of histone H1.

Expression of Cdk1/Cyclin B1 in Insect Cells

Human cdk1 was cloned by reverse transcription PCR. The sequence was consistent with that reported by Lee, M. G. and Nurse, P. *Nature*, 327:31–33, 1987. The cDNA for cyclin H was also cloned by RT PCR and the sequence was consistent with that reported by Pines, J. and Hunter, T., *Cell*, 58: 833–846, 1989. Recombinant Bacmid DNA and viral stocks were prepared as described above for cdk4 and cyclin D1. Optimum coexpression was achieved at an MOI of 0.1 for both cdk1 and cyclin B1 at 48 h post infection.
Kinase Assay: p34$^{cdc2}$ SPA [$^{33}$P] kinase enzyme assay kit was purchased from Amersham Life Science (catalog # RPNQ0170) and the protocol was performed as a 96-well format assay as suggested by the manufacturer. Each assay contained 50 mM Tris HCl, pH 8.0, 10 mM $MgCl_2$, 0.1 mM $Na_3VO_4$ (sodium orthovanadate), 0.5 uM ATP, 0.2 µCi $^{33}$P-ATP, 2 µM DTT and 0.75 uM biotinylated peptide and 3 µg cdk1/cyclin B insect cell lysate in a total assay volume of 100 µl. Incubation was for 30 min at 30° C. The reaction was terminated by addition of 200 uL of stop buffer (50 uM ATP, 5 mM EDTA, 0.1%(v/v) Triton X-100 in phosphate buffered saline),/streptavidin-coated SPA beads (2.5 mg/ml). The plate was left at room temperature overnight then covered with a Packard TopSeal and counted on a Packard TopCount. The $IC_{50}$ value was determined by fitting the data into a sigmodial curve using GraphPad Prism software.

EXAMPLE 152

In Vitro Tumor Inhibition
In Vitro Proliferation Assay

The proliferation of tumor cells was measured using a sulforhodamine B assay as described in Skehan, P., et al., *J. Natl. Cancer Inst.* 82: 1107–1112, 1990. Tumor cells were harvested with trypsin-EDTA, cells that excluded trypan blue were counted, added to 96-well plates and incubated overnight at 37° C. Drug was added to the wells following dilution in culture medium. Three days later, the medium was removed and replenished with medium containing fresh drug and incubated an additional 4 days. The cells were then fixed with 0.1 ml 10% trichloroacetic acid for 60 min at 4° C. The plates were rinsed five times with tap water, air-dried and stained for 30 min with 0.4% sulforhodamine B in 1% acetic acid and air-dried. Bound dye was solubilized with 0.1 ml 10 mM Tris (pH 10.5) for 5 min and the absorbance measured at 490 nm using a Titertek Multiscan MCC/340 plate reader.

Alternatively, the CyQUANT cell proliferation assay was used to quantitate cell proliferation.

CyQUANT Cell Proliferation Assay

Alternatively, the CyQUANT cell proliferation assay was used to quantify tumor cell proliferation. Tumor cells were harvested with trypsin-EDTA, cells that excluded trypan blue were counted, added to 96-well plates and incubated overnight at 37° C. Drug was added to the wells following dilution in culture medium. Three days later the medium was removed and the plates frozen at −80° C. for at least 30 minutes. After thawing the plates, 200 μL of CyQUANT-GR in Cell Lysis Buffer (Molecular Probes # C-7026) was added to each well and incubated 3–5 minutes at room temperature. Fluorescence of CyQUANT-GR was measured on a Molecular Devices Fmax fluorescence microplate reader (excitation 485 nm, emission 530 nm).

Cell Lines

MCF7 is a human breast adenocarcinoma, hormone-dependent (HTB 22);

MDA-MB-23 1 is a human breast adenocarcinoma, hormone-independent (HTB 26);

HT-29 is a human colon adenocarcinoma, moderately well-differentiated grade II (HTB 38);

HCT-15 is a human colon adenocarcinoma (CCL 225);

A549 is a human non-small cell lung carcinoma (CCL 185);

PC-3 is a human prostate adenocarcinoma, hormone-independent (CRL 1435); and

DU 145 is a human prostate carcinoma, hormone-independent (HTB 81).

All of the cell lines were obtained from American Type Tissue Collection, with the ATCC accession number in parentheticals.

MCF-7, MDA-MB-435 and and MDA-MB-231 cells were grown in improved minimum essential medium (Biofluids) without phenol red, supplemented with 5% fetal bovine serum, 0.01 mg/ml gentamicin and 3 mM L-glutamine. All of the other cell lines were grown in RPMI 1640 medium (Life Technologies) supplemented with 5% fetal bovine serum, 0.01 mg/ml gentamicin and 3 mM L-glutamine.

The results are provided in Table 1.

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | | |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 29 | | 0.011 0.04 | 1.0 0.71 | | 4.2* 3.6* | 5.9* 6.0* | 4.4* 4.2* | | 2.8* 4.6* | 2.9* 2.6* | 2.6* 3.3* | 3.2* 3.5* | 3.0* 2.9* |
| Example 10 | | 0.016 0.013 | 1.6 | | 1.4* 5.2* | | 1.6* 1.7* | | 1.3* 2.6* | 1.3* 2.6* | 1.5* 1.4* | 1.1* 1.0* | 1.3* 2.6* |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 32 | | 0.054<br>0.025<br>0.027<br>0.014 | 1.3<br>1.6 | | 0.85*<br>0.68* | 1.59*<br>1.39* | 1.0*<br>1.1* | | 0.82*<br>1.2* | 0.37*<br>0.68* | 0.61*<br>0.51* | 1.2*<br>0.57* | 0.39*<br>0.64* |
| Example 15 | | 0.016<br>(n = 1) | 0.04 | | 1.8*<br>3.8* | | 2.1*<br>2.1* | | 1.6*<br>1.7* | 1.2*<br>3.1* | 1.8*<br>1.9* | 1.4*<br>1.2* | 1.8*<br>3.7* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) ||||||||| 
|---|---|---|---|---|---|---|---|---|---|---|---|
| | | | | Breast |||| Colon || Lung || Prostate |
| | | | | MCF-7 | MDA-MB-231 | MDA-MB-435 | HT-29 | HCT-15 | Colo-205 | A549 | DMS-114 | PC-3 | DU145 |
| Example 8 | (4-methoxybenzyl)-cyclopentyl purine with trans-4-aminocyclohexylamine | 0.030<br>0.048<br>0.030<br>0.022 | 6.6<br>3.2 | 0.2<br>1<br>0.9<br>8 | 0.88<br>1.2 | | 1.3<br>1.4 | 4.5<br>3.5 | | 0.80<br>1.1 | 0.80<br>0.89 | 0.98<br>0.63 | 0.88<br>1.2 |
| Example 16 | (2-methoxyethyl)-cyclopentyl purine with trans-4-aminocyclohexylamine | 0.055<br>0.030 | 0.23<br>0.28 | | 4.7*<br>4.1* | 9.2*<br>7.6* | 6.4*<br>6.3* | | 3.4*<br>7.1* | 0.5*<br>6.2* | 4.8*<br>4.4* | 8.2*<br>3.3* | 2.5*<br>3.3* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) |  |  |  |  |  |  |  |  |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 145a | | 0.050 | 1.5 1.6 | | 3.0* 2.9* | 3.3* 3.8* | 3.4* 2.3* | | 1.7* 1.6* | 4.4* 4.8* | 4.6* 3.1* | 1.9* 2.1* | 3.9* 3.8* |
| Example 13 | | 0.050 | 2.9 | 0.95 2.0 | 2.2 2.6 | | 3.1 3.4 | 2.0 7.1 | | 1.7 1.7 | 1.0 1.4 | 1.9 1.3 | 0.99 1.7 |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-m | | 0.065 0.077 | 0.37 | | 0.32* 0.33* | 0.42* 0.56* | 0.34* 0.35* | | 0.18* 0.17* | 0.17* 0.22* | 0.29* 0.32* | 0.25* 0.50* | 0.32* 0.35* |
| Example 34 | | 0.080 | 1.2 0.80 | 2.3 3.5 | 3.4 5.8 | 3.4 6.0 | 7.7 13 | | 3.4 4.8 | 4.2 4.5 | 1.0 2.0 | 2.7 4.3 |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 21 | | 0.082 0.080 | 0.23 0.97 | | 1.3* 1.3* | 1.9* 2.3* | 1.6* 1.7* | | 1.2* 1.1* | 0.6* 1.0* | 1.1* 0.7* | 1.3* 0.7* | 0.7* 0.9* |
| Example 14 | | 0.100 (n = 1) | 1.5 | | 3.0* | | 2.7* | | 2.4* | 1.4* | 1.3* | 2.3* | 2.8* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | | |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 11 | | 0.10 | 8.9 5.8 | | 5.0* 6.7* | 13* 10* | 6.5* 7.8* | | 6.5* 5.2* | 4.5* 3.4* | 6.8* 4.9* | 3.6* 3.6* | 4.6* 4.7* |
| Example 147-s | | 0.12 0.10 | 1.3 0.62 | | 0.31* 0.33* | 0.42* 0.43* | 0.35* 0.33* | | 0.28* 0.23* | 0.22* 0.20 | 0.57* 0.30* | 0.31* 0.37* | 0.29* 0.27* |
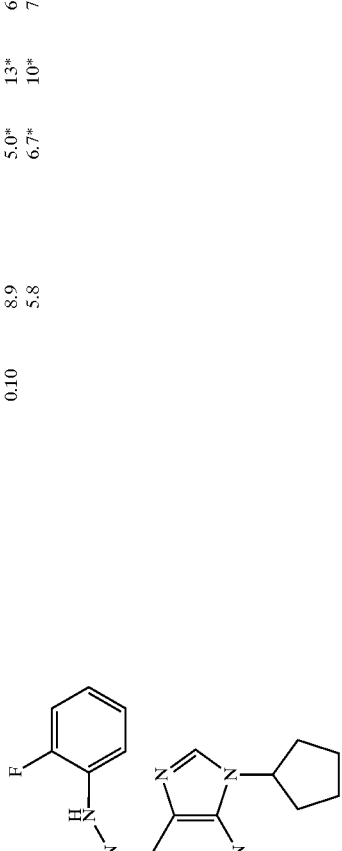

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | | |
|---|---|---|---|---|---|---|---|---|---|---|---|---|
| | | | | Breast | | | Colon | | Lung | | Prostate | |
| | | | | MC F-7 | MDA-MB-231 | MDA-MB-435 | HT-29 | HCT-15 | Colo-205 | A549 | DMS-114 | PC-3 | DU145 |
| Example 26 |  | 0.11 (n = 1) | 0.53 0.52 | | 14* 13* | 23* 22* | 18* 22* | 13* 15* | 13* 15* | 13* 17* | 17* 15* | 15* 8* | 18* 13* |
| Example 2 | 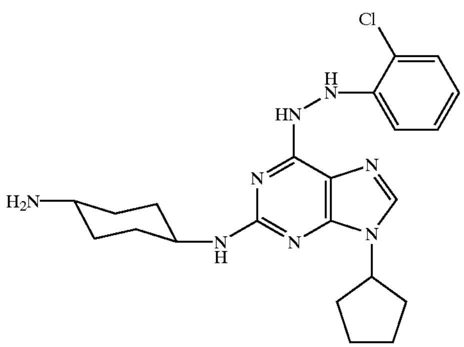 | 0.12 0.10 | 1.3 1.0 | | 2.3* 2.5* 3.5* 5.5* | 8.0* 8.2* | 2.4* 2.5* 2.4* 4.1* | 2.2* 3.2* 4.6* 3.0* | 1.7* 2.2* 1.8* | 1.2* 1.4* 3.6* 3.0* | 4.4* 2.5* 1.8* 2.2* | 1.3* 1.5* 2.3* 2.8* |

-continued

| MDL Number | Structure | CDK-2 Inhibition IC₅₀ ($\mu M$) | CDK4 Inhibition IC₅₀ ($\mu M$) | In vitro Tumor Cell Proliferation (IC$_{50}$, $\mu M$) | | | | | | | | |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 1 | (structure: 4-CF₃-benzyl-aminopurine with cyclopentyl and trans-4-aminocyclohexyl) | 0.120 0.081 | 2.0 2.7 1.7 | 1.2 1.6 | 1.4 1.5 | | 1.5 1.6 | 2.4 2.5 | | 0.97 0.90 | 1.1 0.86 | 0.96 1.0 | 1.4 1.5 |
| Example 147-u | (structure: 3,4-difluorobenzyl-piperidinyl-aminopurine with cyclopentyl and trans-4-aminocyclohexyl) | 0.15 0.11 | 2.8 2.6 | | 0.33* 0.36* | 0.47* 0.48* | 0.41* 0.33* | | 0.28* 0.22* | 0.27* 0.19* | 0.62* 0.35* | 0.35* 0.43* | 0.38* 0.28* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) |||||||||
|---|---|---|---|---|---|---|---|---|---|---|---|
| | | | | Breast ||| Colon || Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 52 | | 0.19 | 0.74 1.4 1.1 | | 1.0* 1.2* | 2.1* 2.4* | 1.6* 2.0* | | 1.5* 1.1* | 0.57* 0.68* | 1.4* 0.63* | 1.7* 2.1* | 1.4* 1.5* |
| Example 27 | | 0.13 0.130 | 1.4 | | 10* 6* | 9.3* 7.2* | 3.8* 5.2* | | 4.9* 4.6* | 3.1* 1.6* | 2.1* 2.1* | 2.6* 3.0* | 5.0* 2.4* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-q | 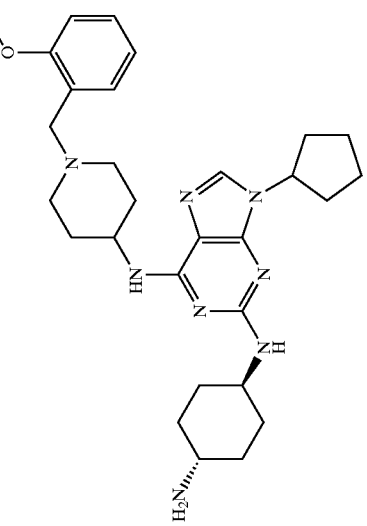 | 0.11<br>0.24<br>0.08 | 0.69<br>1.3 | | 0.19*<br>0.25* | 0.36*<br>0.33* | 0.32*<br>0.38* | | 0.17*<br>0.19* | 0.18*<br>0.19* | 0.40*<br>0.21* | 0.33*<br>0.40* | 0.29*<br>0.32* |
| Example 147-ae | 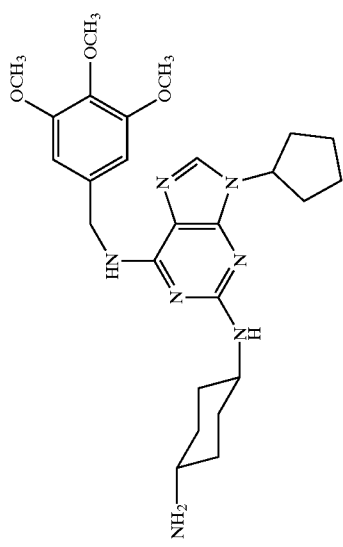 | 0.140<br>(n = 1) | | | 6.5*<br>6.6* | 14*<br>11* | 10*<br>10* | | 11*<br>8.6* | 11*<br>11* | 8.7* | 11*<br>5.1* | 12*<br>6.7* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-w | | 0.13 0.18 | 4.0 2.1 | 0.35* 0.40* | 0.57* 0.51* | 0.37* 0.39* | | 0.32* 0.32* | 0.21* 0.21* | 0.45* 0.31* | 0.44* 0.46* | 0.35* 0.39* |
| Example 7 | 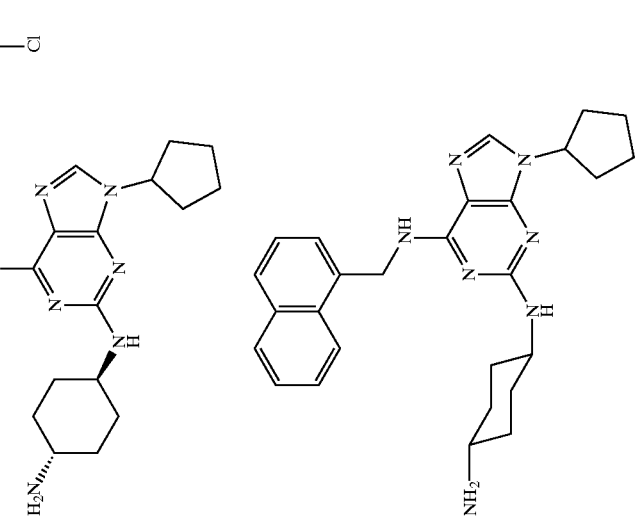 | 0.160 (n = 1) | 1.4 | 4.4* 4.9* | 11* 10* | 4.6* 4.8* | | 3.4* 3.5* | 3.4* 3.4* | 2.8* 3.3* | 4.2* 4.8* | 5.5* 5.2* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) ||||||||
|---|---|---|---|---|---|---|---|---|---|---|---|
| | | | | Breast ||| Colon || Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 146 | 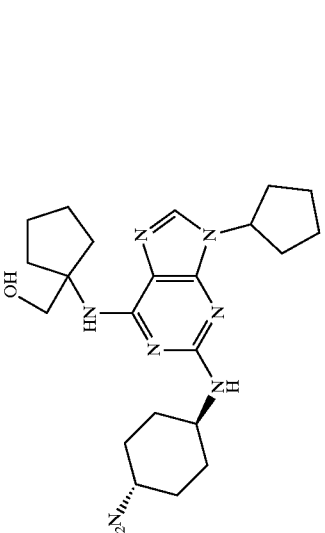 | 0.164 | 1.6 0.81 0.50 | | 14* 12* | 18* 21* | 16* 11* | | 12* 14* | 12* 12* | 13* 11* | 11* 10* | 12* 16* |
| Example 9 | 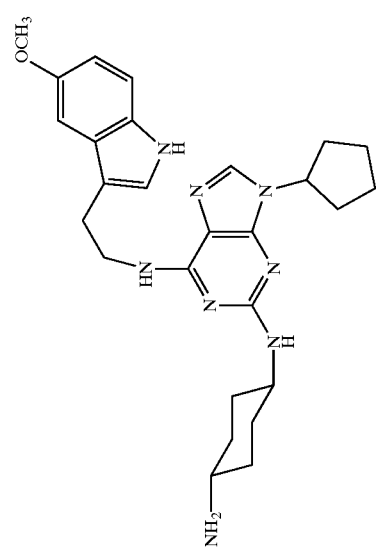 | 0.165 (n = 1) | 3.9 2.0 | | 0.7* 1.1* | >10* >10* | 0.87* 0.96* | | 0.76* 0.94* | 1.2* 2.0* | 1.0* 1.4* | 0.41* 0.28* | 3.5* 4.0* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 42 | 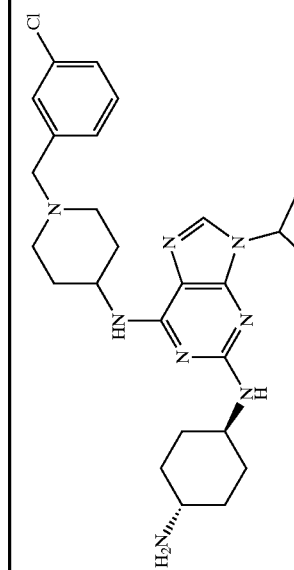 | 0.20 0.15 | 1.0 1.2 2.0 | | 0.24* 0.30* | 0.37* 0.44* | 0.25* 0.28* | | 0.19* 0.19* | 0.16* 0.14* | 0.27* 0.20* | 0.21* 0.34* | 0.22* 0.23* |
| Example 147-h | 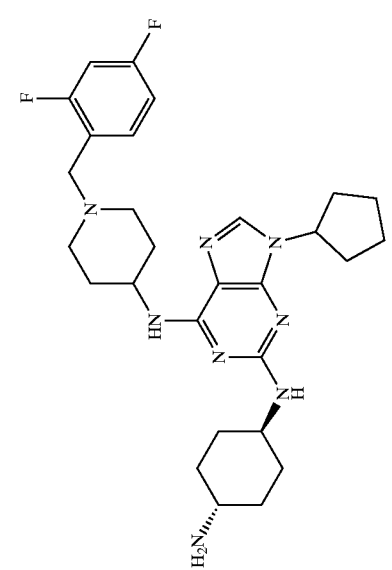 | 0.10 0.24 | 2.8 1.8 | | 0.47* 0.47* | 0.48* 0.78* | 0.42* 0.47* | | 0.34* 0.21* | 0.22* 0.16* | 0.94* 0.47* | 0.33* 0.58* | 0.34* 0.36* |

-continued

| MDL Number | Structure | CDK-2 Inhibition IC$_{50}$ (μM) | CDK4 Inhibition IC$_{50}$ (μM) | In vitro Tumor Cell Proliferation (IC$_{50}$, μM) ||||||||
|---|---|---|---|---|---|---|---|---|---|---|---|
| | | | | Breast ||| Colon ||| Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 39 | | 0.15 0.20 | 0.37 0.20 | | 0.31* 0.18* | 0.23* 0.35* | 0.32* 0.22* | | 0.28* 0.17* | 0.17* 0.15* | 0.32* 0.22* | 0.28* 0.36* | 0.28* 0.27* |
| Example 43 | | 0.15 0.20 | 3.9 7.7 | | 0.37* 0.43* | 0.33* 0.57* | 1.1* 0.36* | | 0.28* 0.23* | 0.25* 0.23* | 0.43* 0.41* | 0.29* 0.59* | 0.30* 0.32* |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-k | | 0.20<br>0.17 | 2.9<br>2.9 | | 0.31*<br>0.32* | 0.39*<br>0.39* | 0.40*<br>0.26* | | 0.26*<br>0.15* | 0.29*<br>0.16* | 0.45*<br>0.29* | 0.35*<br>0.34* | 0.30*<br>0.15* |
| Example 147-o | | 0.20<br>0.16 | 1.8<br>1.8 | | 0.77*<br>0.90* | 0.92*<br>1.1* | 0.83*<br>0.77* | | 0.63*<br>0.45* | 0.42*<br>0.44* | 0.78*<br>0.71* | 0.64*<br>0.92* | 0.76*<br>0.69* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 33 | | 0.190 0.140 | 0.41 | | 0.17* 0.21* | 0.26* 0.28* | 0.19* 0.21* | | 0.18* | 0.12* 0.13* | 0.19* | 0.20* 0.18* | 0.15* 0.15* |
| Example 40 | | 0.23 0.17 | 1.0 2.0 | | 0.19* 0.28* | 0.27* 0.37* | 0.29* 0.27* | | 0.16* 0.18* | 0.15* 0.18* | 0.26* 0.21* | 0.20* 0.34* | 0.24* 0.21* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-j | | 0.20 0.21 | 1.3 0.72 | | 0.20* 0.21* | 0.27* 0.30* | 0.30* 0.22* | | 0.17* 0.17* | 0.15* 0.14* | 0.37* 0.25* | 0.17* 0.26* | 0.21* 0.20* |
| Example 147-i | | 0.20 0.21 | 0.61 2.2 1.2 | | 0.30* 0.34* | 0.30* 0.45* | 0.31* 0.33* | | 0.24* 0.27* | 0.17* 0.18* | 0.39* 0.26* | 0.23* 0.41* | 0.23* 0.21* |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 12 | | 0.230 | 4.5 6.2 | 3.3 7.1 | 8.6 11 | | 7.3 8.5 | 16 18 | | 5.6 3.5 | 5.4 5.4 | 4.4 3.5 | 3.5 6.7 |
| Example 5 | | 0.230 (n = 1) | 0.4 0.7 | | 0.78* 0.87* | 1.3* 1.5* | 1.0* 1.1* | | 1.0* 1.2* | 0.35* 0.53* | 0.47* 0.47* | 1.1* 0.7* | 0.56* 0.7* |

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | | |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 44 | 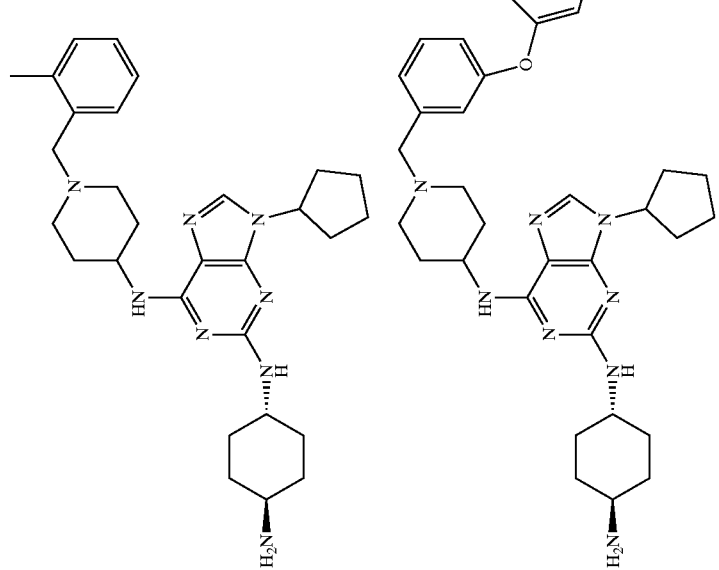 | 0.23<br>0.13<br>0.34 | 2.3 | | 0.20*<br>0.22* | 0.24*<br>0.27* | 0.22*<br>0.22* | | 0.16*<br>0.17* | 0.15*<br>0.09* | 0.28*<br>0.21* | 0.16*<br>0.22* | 0.16*<br>0.16* |
| Example 147-ad Correct structure | 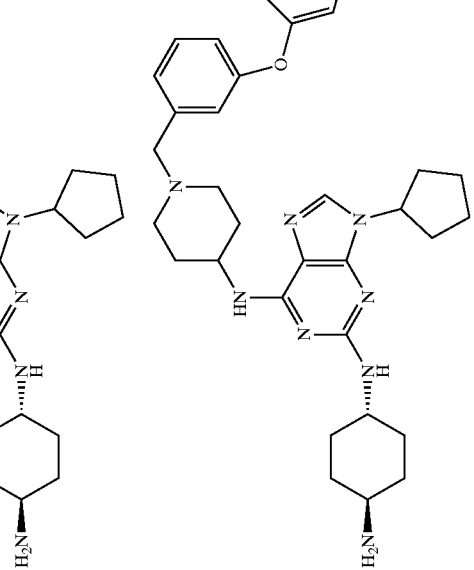 | 0.28<br>0.19 | 3.0<br>3.2 | | 0.64*<br>0.64* | 0.87*<br>1.0* | 0.79*<br>0.70* | | 0.53*<br>0.58* | 0.39*<br>0.43* | 0.82*<br>0.62* | 0.48*<br>0.86* | 0.54*<br>0.62* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-v |  | 0.24<br>0.24 | 2.0<br>3.4 | | 0.63*<br>1.2* | 1.0*<br>1.3* | 0.76*<br>0.83* | | 0.58*<br>0.77* | 0.50*<br>0.63* | 1.9*<br>1.1* | 0.85*<br>1.1* | 0.52*<br>0.57 |
| Example 147-1 | 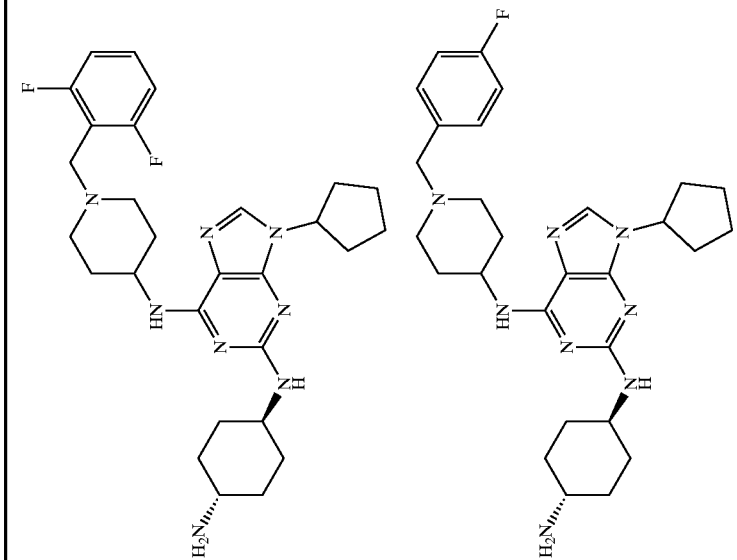 | 0.26<br>0.17<br>0.28 | 2.0<br>2.7<br>1.3 | | 0.33*<br>0.29* | 0.46*<br>0.46* | 0.37*<br>0.40* | | 0.26*<br>0.19* | 0.26*<br>0.19* | 0.48*<br>0.43* | 0.31*<br>0.41* | 0.30*<br>0.29* |

-continued
| MDL Number | Structure | CDK-2 Inhibition IC$_{50}$ ($\mu$M) | CDK4 Inhibition IC$_{50}$ ($\mu$M) | Breast | | | Colon | | Lung | | Prostate | |
|---|---|---|---|---|---|---|---|---|---|---|---|---|
| | | | | MCF-7 | MDA-MB-231 | MDA-MB-435 | HT-29 | HCT-15 | Colo-205 | A549 | DMS-114 | PC-3 | DU145 |
| Example 147-t | | 0.25 0.16 0.34 | 2.2 1.7 | | 0.37* 0.37* | 0.41* 0.69* | 0.42* 0.48* | | 0.31* 0.36* | 0.30* 0.28* | 0.71* 0.46* | 0.37* 0.45* | 0.33* 0.38* |
| Example 147-p | | 0.30 0.11 0.36 | 3.1 3.9 | | 0.57* 0.60* | 0.59* 0.68* | 0.71* 0.72* | | 0.45* 0.48* | 0.39* 0.34* | 0.91* 0.68* | 0.46* 0.66* | 0.54* 0.54* |
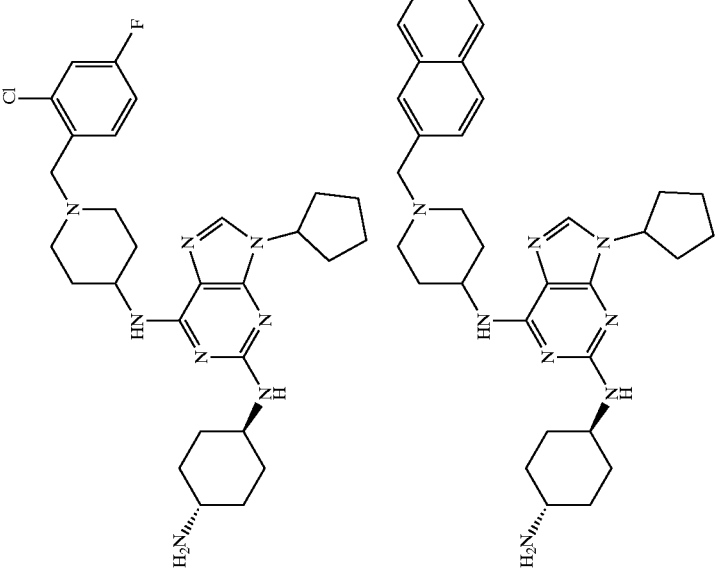

-continued
| MDL Number | Structure | CDK-2 Inhibition IC$_{50}$ (μM) | CDK4 Inhibition IC$_{50}$ (μM) | Breast MCF-7 | Breast MDA-MB-231 | Breast MDA-MB-435 | Colon HT-29 | Colon HCT-15 | Colon Colo-205 | Lung A549 | Lung DMS-114 | Prostate PC-3 | Prostate DU145 |
|---|---|---|---|---|---|---|---|---|---|---|---|---|---|
| Example 41 | 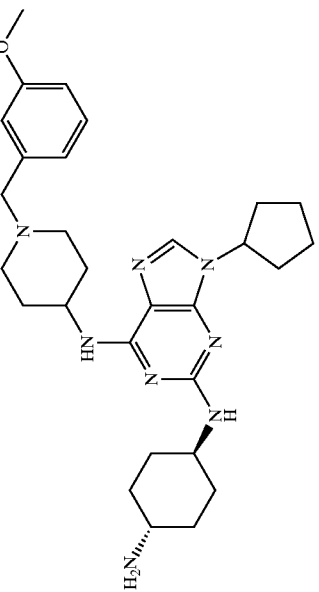 | 0.30<br>0.14<br>0.34 | 0.75<br>1.4 | | 0.29*<br>0.32* | 0.35*<br>0.36* | 0.32*<br>0.31* | | 0.25*<br>0.21* | 0.19*<br>0.19* | 0.38*<br>0.29* | 0.27*<br>0.42* | 0.29*<br>0.23* |
| Example 25 | 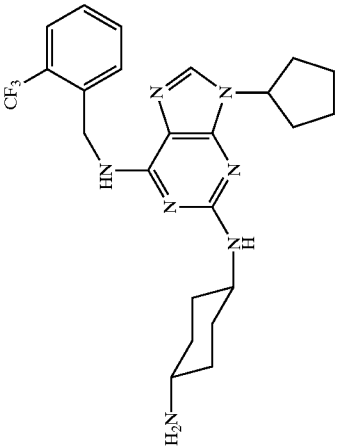 | 0.260 | 6.4<br>6.9 | 1.0<br>2.7 | 4.5<br>4.3 | | 2.6<br>3.0 | 4.0<br>3.7 | | 1.9 | 0.85<br>0.95 | 1.1<br>1.7 | 0.95<br>1.7 |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147 | | 0.268 | 5.7<br>6.1 | | 5.1*<br>3.2* | 5.6*<br>6.0* | 2.8*<br>2.0* | | 5.7*<br>3.5* | 2.7*<br>2.6* | 5.2*<br>1.9* | 3.2*<br>2.3* | 3.1*<br>5.7* |
| Example 147-e | | 0.34<br>0.23<br>0.46 | 2.7<br>4.6 | | 0.58*<br>0.30* | 0.62*<br>0.60* | 0.59*<br>0.30* | | 0.34*<br>0.32* | 0.35*<br>0.30* | 0.58*<br>0.50* | 0.47*<br>0.35* | 0.35*<br>0.41* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) ||||||||
|---|---|---|---|---|---|---|---|---|---|---|
| | | | | Breast |||  Colon || Lung || Prostate |
| | | | | MCF-7 | MDA-MB-231 | MDA-MB-435 | HT-29 | HCT-15 | Colo-205 | A549 | DMS-114 | PC-3 | DU145 |
| 816384ta | | 0.32, 0.12 | 7.4, 7.1 | | 0.43*, 0.29* | 0.38*, 0.35* | 0.40*, 0.30* | | 0.32*, 0.25* | 0.27*, 0.22* | 0.40*, 0.26* | 0.28*, 0.32* | 0.31*, 0.32* |
| Example 23 | | 2, 0.95, 0.76 | 4 | | 2.7*, 2.6*, 2.5*, 2.7* | 3.1*, 3.5*, 3.0*, 3.3* | 2.5*, 2.4*, 2.3*, 2.3* | | 2.9*, 2.8*, 2.7*, 2.8* | 2.3*, 2.5*, 2.3* | 2.6*, 2.6*, 2.1*, 2.1* | 3.1*, 2.7*, 2.5*, 2.2* | 3.1*, 3.2*, 3.0*, 3.0* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) ||||||||
|---|---|---|---|---|---|---|---|---|---|---|---|
| | | | | Breast |||  Colon || Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 147-g | | 0.33 0.29 | 3.5 2.0 | | 0.29* 0.31* | 0.30* 0.41* | 0.31* 0.29* | | 0.18* 0.13* | 0.19* 0.14* | 0.32* 0.26* | 0.21* 0.39* | 0.22* 0.25* |
| Example 147-n | | 0.16 0.34 0.44 | 1.6 3.1 | | 0.81* 0.72* | 0.89* 1.0* | 0.71* 0.64* | | 0.44* 0.32* | 0.39* 0.33* | 1.1* 0.80* | 0.73* 0.93* | 0.60* 0.59* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-x | | 0.32<br>0.32 | 3.8<br>3.9 | | 0.85*<br>0.67* | 0.75*<br>0.92* | 0.72*<br>0.60* | | 0.59*<br>0.62* | 0.44*<br>0.45* | 1.0*<br>0.70* | 0.54*<br>0.65* | 0.49*<br>0.53* |
| Example 147-a | | 0.41<br>0.097<br>0.44 | 2.9<br>2.1 | | 0.35*<br>0.34* | 0.42*<br>0.408 | 0.32*<br>0.32* | | 0.20*<br>0.31* | 0.17*<br>0.17* | 0.32*<br>0.33* | 0.24*<br>0.34* | 0.22*<br>0.33* |

-continued

| MDL Number | Structure | CDK-2 Inhibition IC$_{50}$ (µM) | CDK4 Inhibition IC$_{50}$ (µM) | Breast MCF-7 | Breast MDA-MB-231 | Breast MDA-MB-435 | Colon HT-29 | Colon HCT-15 | Colon Colo-205 | Lung A549 | Lung DMS-114 | Prostate PC-3 | Prostate DU145 |
|---|---|---|---|---|---|---|---|---|---|---|---|---|---|
| Example 17 | 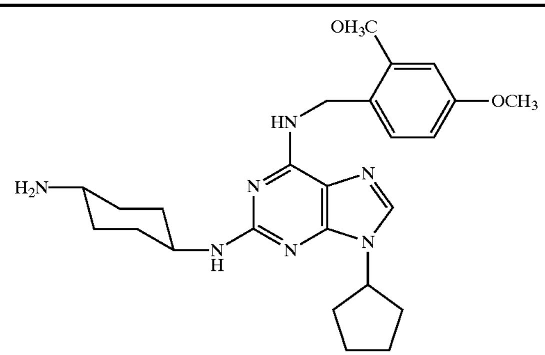 | 0.350 | | 3.1<br>6.4 | 6.1<br>7.9 | | 6.8<br>6.8 | 9.9 | | 6.8<br>7.5 | 5.3<br>5.8 | 4.0 | 3.6<br>6.9 |
| Example 22 | 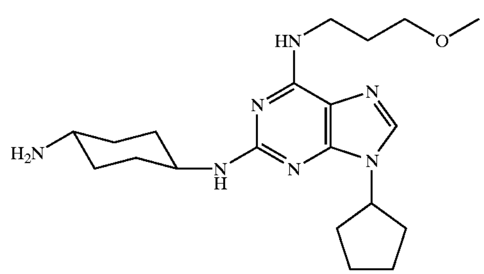 | 0.37<br>0.37 | 0.4<br>1.3<br>0.57 | 4.2*<br>8.2* | | 10*<br>11* | 4.0*<br>4.4* | | 3.9*<br>5.3* | 2.6*<br>6.0* | 2.7*<br>2.8* | 2.5*<br>2.3* | 3.7*<br>7.6* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | | |
|---|---|---|---|---|---|---|---|---|---|---|---|---|
| | | | | Breast | | | Colon | | Lung | | Prostate | |
| | | | | MCF-7 | MDA-MB-231 | MDA-MB-435 | HT-29 | HCT-15 | Colo-205 | A549 | DMS-114 | PC-3 | DU145 |
| Example 147-ac | 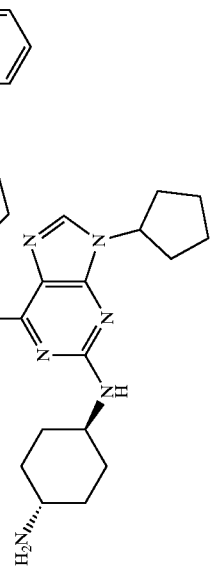 | 0.17<br>0.37<br>0.53<br>0.40 | 3.3<br>1.2 | | 0.79*<br>0.75* | 0.97*<br>1.1* | 1.0*<br>0.93* | | 0.61*<br>0.66* | 0.47*<br>0.62* | 1.4*<br>1.0* | 0.78*<br>0.82* | 0.71*<br>0.66* |
| Example 31 | 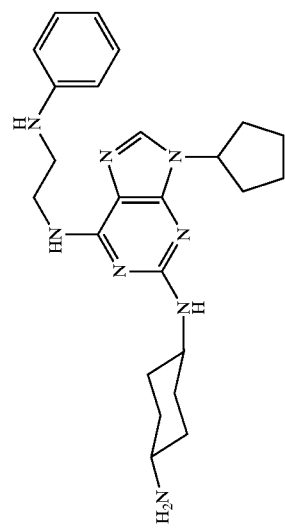 | 0.4<br>0.4 | 0.1<br>0.1 | | 2.1*<br>2.4* | 3.1*<br>2.6* | 2.4*<br>2.5* | | 1.4*<br>1.7* | 1.6*<br>2.1* | 2.4*<br>1.8* | 2.3*<br>1.9* | 1.9*<br>1.8* |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-c | | 0.56 0.27 0.45 | 0.67 0.60 | 0.23* 0.27* | 0.33* 0.34* | 0.32* 0.30* | | 0.19* 0.20* | 0.18* 0.24* | 0.30* 0.32* | 0.22* 0.33* | 0.21* 0.30* |
| Example 147-r | | 0.09 0.58 0.55 0.61 | 7.2 4.3 | 0.31* 0.48* | 0.60* 0.65* | 0.49* 0.47* | | 0.32* 0.38* | 0.33* 0.33* | 0.62* 0.48* | 0.39* 0.55* | 0.45* 0.40* |

-continued
| MDL Number | Structure | CDK-2 Inhibition IC$_{50}$ (μM) | CDK4 Inhibition IC$_{50}$ (μM) | In vitro Tumor Cell Proliferation (IC$_{50}$, μM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-f | | 0.51 0.22 0.67 | 1.1 2.1 | | 0.41* 0.38* | 0.50* 0.49* | 0.40* 0.34* | | 0.31* 0.25* | 0.30* 0.21* | 0.67* 0.36* | 0.36* 0.45* | 0.31* 0.29* |
| Example 46 | 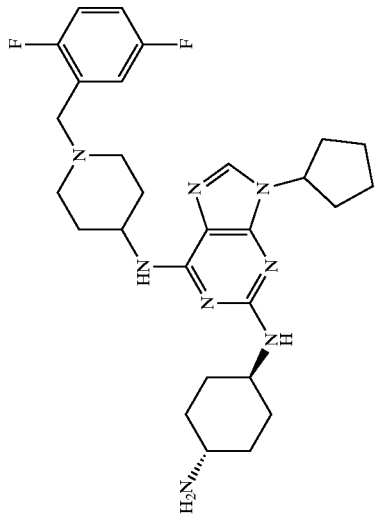 | 0.50 0.45 | 20 | | 0.46* 0.53* | 0.61* 0.62* | 0.53* 0.44* | | 0.44* 0.46* | 0.28* 0.33* | 0.35* 0.58* | 0.39* 0.46* | 0.36* 0.49* |

-continued

| MDL Number | Structure | CDK-2 Inhibition IC$_{50}$ (μM) | CDK4 Inhibition IC$_{50}$ (μM) | In vitro Tumor Cell Proliferation (IC$_{50}$, μM) ||||||||
|---|---|---|---|---|---|---|---|---|---|---|---|
| | | | | Breast |||| Colon || Lung || Prostate ||
| | | | | MCF-7 | MDA-MB-231 | MDA-MB-435 | | HT-29 | HCT-15 | Colo-205 | A549 | DMS-114 | PC-3 | DU145 |
| Example 28 | | 0.480 | 2.2 / 2.6 | 5.6 / 11 | 12 / 14 | | | 12 / 13 | >20 / >20 | | 1.9 | 6.1 / 7.7 | 4.8 / 6.4 | 6.4 / 9.1 |
| Example 20 | | 0.497 | | | 4.8* | 11* | | 7.6* | | 13* | 5.6* / 4.8* | 7.5* | 7.9* | 6.5* / 13* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) |||||||||
|---|---|---|---|---|---|---|---|---|---|---|---|---|
| | | | | Breast |||| Colon ||| Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 36 | 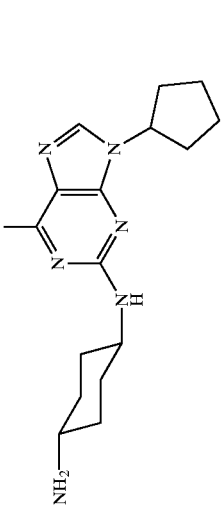 | 0.52 (n = 1) | 4.5 | | 3.2* | 4.2* 2.2* | 4.0* 4* | | 3.1* 3.1* | 5.6* 3.1* | 3.6* 3.1* | 3.1* 3.8* | 5.4* 3.4* |
| Example 19 | 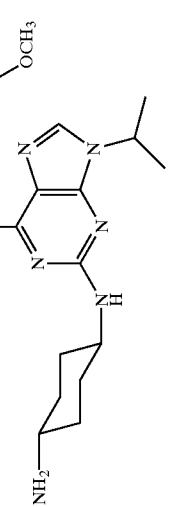 | 0.540 (n = 1) | 20 | | 15* 14* | 20* 18* | 18* 14* | | 12* 10* | 22* 13* | 12* 15* | 14* 14* | 14* 13* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) ||||||||
|---|---|---|---|---|---|---|---|---|---|---|
| | | | | Breast ||| Colon ||| Lung || Prostate ||
| | | | | MCF-7 | MDA-MB-231 | MDA-MB-435 | HT-29 | HCT-15 | Colo-205 | A549 | DMS-114 | PC-3 | DU145 |
| Example 147-ab | | 0.25 0.90 | 4.5 2.7 | | 0.62* 0.70* | 0.84* 0.91* | 0.73* 0.62* | | 0.43* 0.45* | 0.33* 0.39* | 0.74* 0.64* | 0.69* 0.69* | 0.59* 0.60* |
| Example 147-y | | 0.51 0.67 | 5.4 4.8 | | 0.34* 0.35* | 0.47* 0.55* | 0.41* 0.38* | | 0.32* 0.35* | 0.16* 0.29* | 0.40* 0.45* | 0.35* 0.46* | 0.33* 0.35* |

-continued

| MDL Number | Structure | CDK-2 Inhibition IC$_{50}$ (µM) | CDK4 Inhibition IC$_{50}$ (µM) | In vitro Tumor Cell Proliferation (IC$_{50}$, µM) | | | | | | | |
|---|---|---|---|---|---|---|---|---|---|---|---|
| | | | | Breast | | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 6 | | 0.690 (n = 1) | 0.3 0.7 | | 6.2* 6.4* | 14* 11* | 13* 7.7* | | 5.4* 4.7* | 7.2* 9.6* | 6.3* | 6.4* 8.2* | 7.8* 7.9* |
| Example 37 | | 0.690 (n = 1) | 5.2 | | 3.0* 3.0* 3.0* | 3.4* 3.2* 2.7* | 3.2* 1.8* 2.5* | | 1.7* 1.6* 1.3* | 1.3* 1.3* | 1.3* 1.7* 1.5* | 2.3* 2.8* 2.5* | 2.7* 2.6* 3.0* |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-d | | 0.89 0.53 0.75 | 64 | | 0.47* 0.42* | 0.69* 0.94* | 0.44* 0.34* | 0.38* 0.52* | 0.23* 0.25* | 0.34* 0.36* | 0.66* 0.66* | 0.69* 0.58* |
| Example 147-z | | 0.72 1.0 | 7.9 5.7 | | 0.37* 0.35* | 0.50* 0.57* | 0.43* 0.44* | 0.38* 0.46* | 0.18* 0.30* | 0.34* 0.42* | 0.33* 0.44* | 0.28* 0.36* |

-continued
| MDL Number | Structure | CDK-2 Inhibition IC$_{50}$ (μM) | CDK4 Inhibition IC$_{50}$ (μM) | In vitro Tumor Cell Proliferation (IC$_{50}$, μM) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 18 | 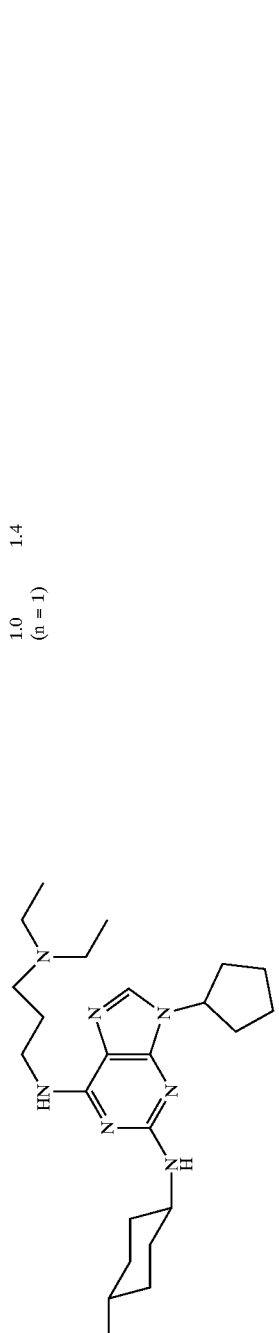 | 1.0 (n = 1) | 1.4 | | | | | | | | |
| Example 45 | 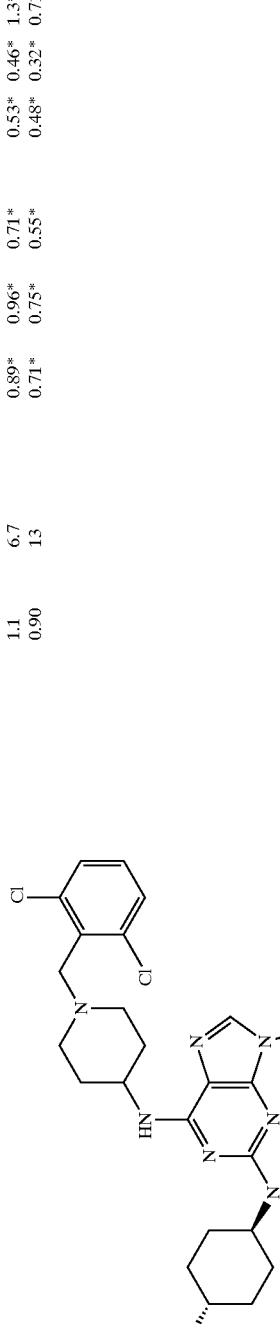 | 1.1 0.90 | 6.7 13 | 0.89* 0.71* | 0.96* 0.75* | 0.71* 0.55* | 0.53* 0.48* | 0.46* 0.32* | 1.3* 0.71* | 0.63* 0.74* | 0.51* 0.46* |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 147-b | 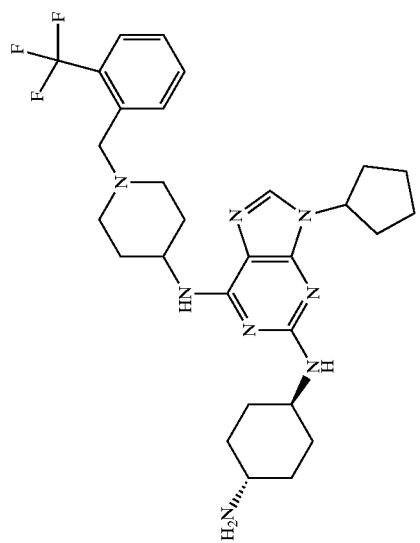 | 1.2 0.92 | 2.4 4.5 | | 0.64* 0.73* | 0.99* 0.95* | 0.65* 0.61* | | 0.48* 0.62* | 0.42* 0.40* | 0.92* 0.82* | 0.63* 0.78* | 0.46* 0.61* |
| Example 30 | 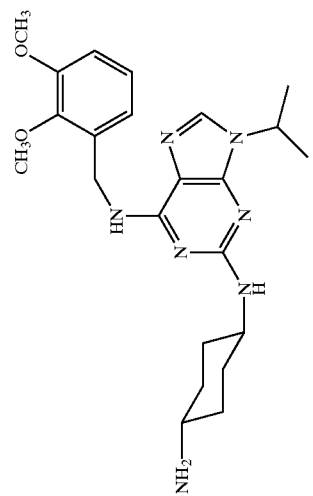 | 1.40 (n = 1) | 2.4 | | | | | | | | | | |

-continued

| MDL Number | Structure | CDK-2 Inhibition IC$_{50}$ ($\mu$M) | CDK4 Inhibition IC$_{50}$ ($\mu$M) | Breast MCF-7 | Breast MDA-MB-231 | Breast MDA-MB-435 | Colon HT-29 | Colon HCT-15 | Colon Colo-205 | Lung A549 | Lung DMS-114 | Prostate PC-3 | Prostate DU145 |
|---|---|---|---|---|---|---|---|---|---|---|---|---|---|
| Example 147-aa | 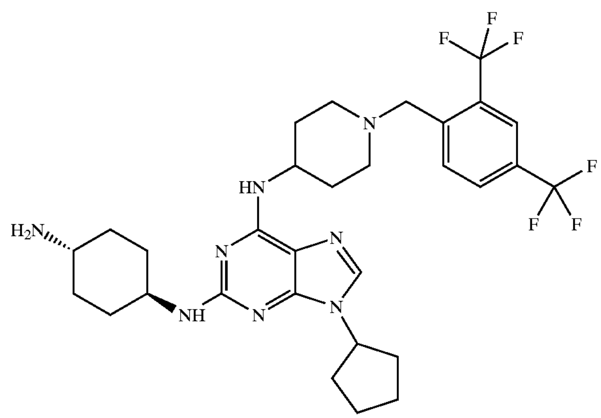 | 1.6<br>2.6 | 10<br>8.4 | | 2.5*<br>3.1* | 5.8*<br>4.9* | 2.8*<br>2.3* | | 4.0*<br>2.9* | 4.1*<br>3.6* | 2.7*<br>2.9* | 3.8*<br>4.6* | 4.4*<br>4.3* |
| Example 4 | 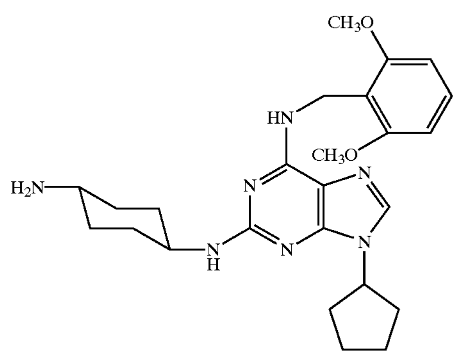 | 19.4 | 46<br>>100 | | | | | | | | | | |

-continued

| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | | |
|---|---|---|---|---|---|---|---|---|---|---|---|
| | | | | Breast | | | Colon | | Lung | | Prostate |
| | | | | MCF-7 | MDA-MB-231 | MDA-MB-435 | HT-29 | HCT-15 | Colo-205 | A549 | DMS-114 | PC-3 | DU145 |
| Example 24 | 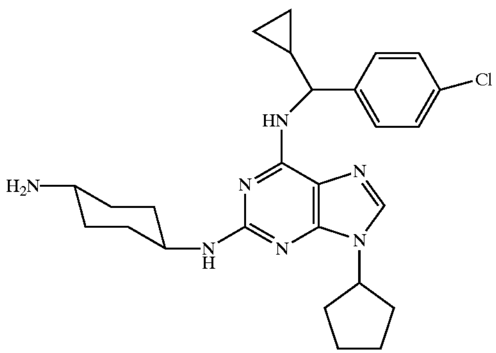 | 27.1 | 4.6 10 | | | | | | | | |
| 107,466 roscovitine | | 0.31 | 36 | 13 >20 | 157 >20 | 51 >20 | 18 >20 | 14 >20 | 13 >20 | 18 18 | >20 |
| Olomoucine | 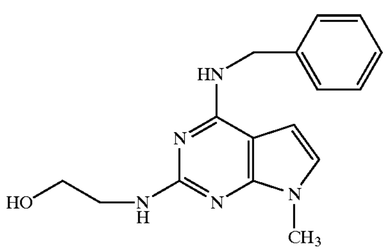 | 5 | >1000 | 35 35 | | 53 58 | 62 63 | 69 69 | 50 76 | 55 | >100 |

-continued
| MDL Number | Structure | CDK-2 Inhibition IC$_{50}$ ($\mu$M) | CDK4 Inhibition IC$_{50}$ ($\mu$M) | In vitro Tumor Cell Proliferation (IC$_{50}$, $\mu$M) | | | | | | |
|---|---|---|---|---|---|---|---|---|---|---|
| | | | | Breast | | | Colon | | Lung | Prostate |
| | | | | MCF-7 | MDA-MB-231 | MDA-MB-435 | HT-29 | HCT-15 | Colo-205 | A549 | DMS-114 | PC-3 | DU145 |
| Flavopiridol | | 0.130 | 0.017 | 0.06 | 0.095 | | 0.17 | 0.1 | | 0.08 | 0.08 | 0.07 | 0.08 |
| | | n = 2 | n = 1 | n = 1 | n = 1 | | n = 1 | n = 1 | | n = 1 | n = 1 | n = 1 | n = 1 |
| Example 35 | 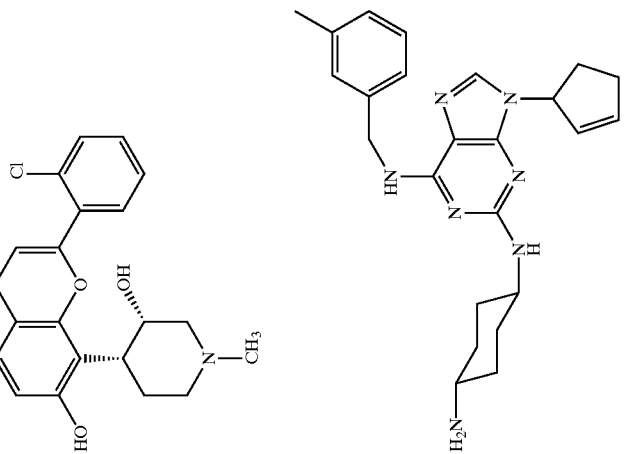 | 0.49<br>0.14 | 9.4<br>7.7 | 2.9<br>1.9 | | | 2.1<br>1.9 | 5.7<br>4.0 | | | | | |

What is claimed is:

1. A compound of the formula

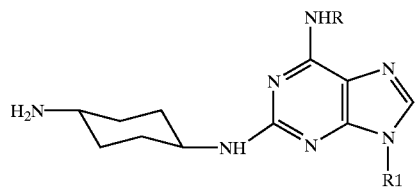

wherein R is selected from the group consisting of R2, R2NH—, or R3R4N—R5- wherein

R2 is selected from the group consisting of $C_9$–$C_{12}$ alkyl,

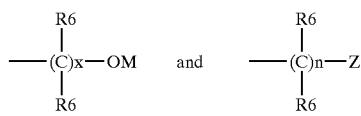

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; n is an integer 0–8; Z is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; and M is selected from the group consisting of hydrogen, $C_1$–$C_4$ alkyl,

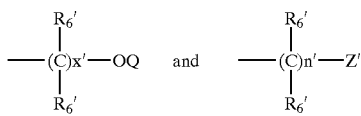

wherein each R6' is independently selected from the group consisting of hydrogen, $C_3$–$C_8$ cycloalkyl, $C_1$–$C_4$ alkyl, and $(CH_2)_{m'}$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; and wherein each $C_9$–$C_2$ alkyl or Z is optionally substituted with 1 to 3 substituents, which may be the same or different, and which are selected from the group consisting of D, E,

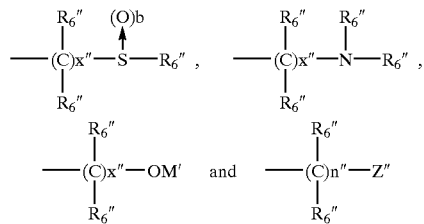

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

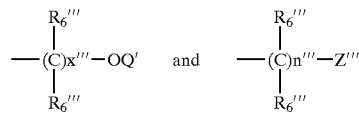

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl, wherein the groups M' and Z" may be optionally substituted with the groups D', E' or

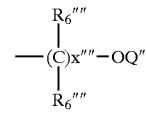

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl;

R3 and R4 are selected from the group consisting of hydrogen, $C_1$–$C_4$ alkyl and $(CH_2)_y$-phenyl, wherein y is an integer 0–8, with the proviso that R3 and R4 not both be hydrogen;

R5 is $C_1$–$C_8$ alkylene; and

R1 is selected from the group consisting of cyclopentyl and cyclopentenyl, and the pharmaceutically acceptable salts, optical isomers, and hydrates thereof, with the proviso that when R2 is the group

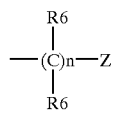

wherein n is 1 or greater; R1 is cyclopentyl; R6 is hydrogen, $C_1$–$C_4$ alkyl, or $(CH_2)_m$-phenyl; and Z is phenyl, heterocycle, or cycloalkyl, that Z is substituted with 1 to 3 substituents, which may be the same or different, and which are selected from the group consisting of

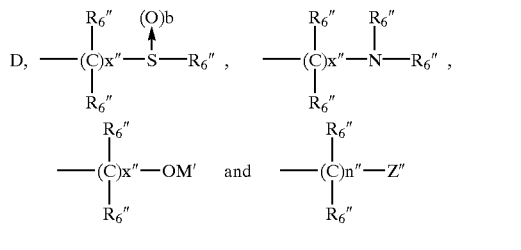

wherein D, b, R6", x", n", M', and Z" are as previously defined.

2. A compound according to claim 1 which is

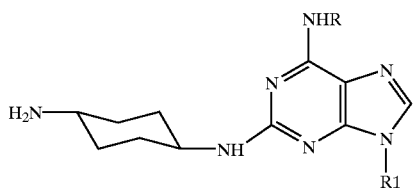

wherein R is R2, wherein

R2 is $C_9$–$C_{12}$ alkyl, which may be optionally substituted with 1 to 3 substituents, which may be the same or different, and which are selected from the group consisting of D, E,

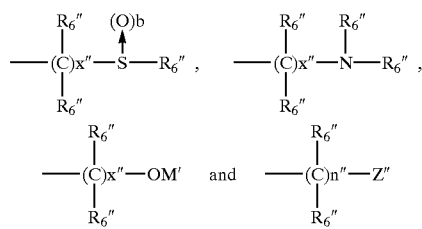

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl, each R6" is independently selected from the group consisting of hydrogen, $C_3$–$C_8$ cycloalkyl, $C_1$–$C_4$ alkyl, and $(CH_2)_{m"}$-phenyl, wherein m" is an integer 0–8; n" is an integer 0–8; x" is an integer 1–8; and M' is selected from the group consisting of hydrogen, $C_1$–$C_4$ alkyl,

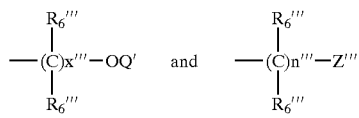

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

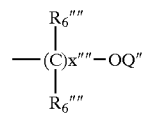

provided M' is not hydrogen, wherein each R6"" is independently selected from the group consisting of hydrogen, $C_3$–$C_8$ cycloalkyl, $C_1$–$C_4$ alkyl, and $(CH_2)_{m""}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl;

R1 is selected from the group consisting of cyclopentyl and cyclopentenyl, and the pharmaceutically acceptable salts, optical isomers, and hydrates thereof.

3. A compound according to claim 2 wherein R2 is $C_{11}$–$C_{12}$ alkyl.

4. A compound according to claim 3 wherein R2 is $C_{12}$ alkyl.

5. A compound according to claim 4 which is 2-[trans-(4-aminocyclohexyl)amino]-6-(dodecylamino)-9-cyclopentylpurine dihydrochloride.

6. A compound according to claim 1 which is

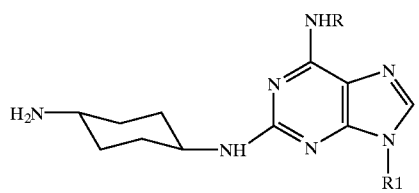

wherein R is R2, wherein

R2 is

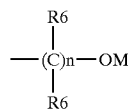

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; and M is selected from the group consisting of hydrogen, $C_1$–$C_4$ alkyl,

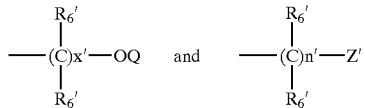

wherein each R6' is independently selected from the group consisting of hydrogen, $C_3$–$C_8$ cycloalkyl, $C_1$–$C_4$ alkyl, and $(CH_2)_{m'}$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and naphthyl; and R1 is selected from the group consisting of cyclopentyl and cyclopentenyl, and the pharmaceutically acceptable salts, optical isomers, and hydrates thereof.

7. A compound according to claim 6 wherein M is hydrogen.

8. A compound according to claim 6 wherein M is $C_1$–$C_4$ alkyl.

9. A compound according to claim 8 which is 2-[trans-(4-aminocyclohexyl)amino]-6-(2-methoxyethylamino)-9-cyclopentylpurine dihydrochloride; 2-[trans-(4aminocyclohexyl)amino]-6-(3-methoxypropylamino)-9-cyclopentylpurine dihydrochloride; or 2-[trans-(4-aminocyclohexyl)amino]-6-(4-methoxybutylamino)-9-cyclopentylpurine dihydrochlorides.

10. A compound according to claim 6 wherein M is the group

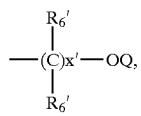

wherein R6', x', and Q are as defined in claim 6.

11. A compound according to claim 10 wherein Q is hydrogen.

12. A compound according to claim 11 which is 2-[trans-(4-aminocyclohexyl)amino]-6-(2-hydroxyethoxyethylamino)-9-cyclopentylpurine dihydrochloride.

13. A compound according to claim 10 wherein Q is $C_1$–$C_4$ alkyl.

14. A compound according to claim 13 which is 2-[trans-(4-aminocyclohexyl)amino]-6-[3-(2-methoxyethoxy)propylamino]-9-cyclopentylpurine dihydrochloride.

15. A compound according to claim 6 wherein M is the group

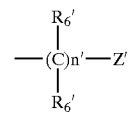

wherein R6', n', and Z' are as defined in claim 6.

16. A compound according to claim 1 wherein R is R2, wherein R2 is

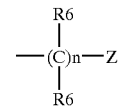

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; n is an integer 0–8; Z is naphthyl, wherein Z is optionally substituted with 1 to 3 substituents, which may be the same or different, and which are selected from the group consisting of D, E,

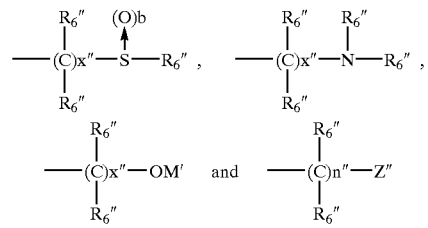

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; x'' is an integer 1–8; n'' is an integer 0–8; Z'' is selected from the group consisting of phenyl, heterocycle, cycloalkyl, and naphthyl; and M' is selected from the group consisting of hydrogen, $C_1$–$C_4$ alkyl,

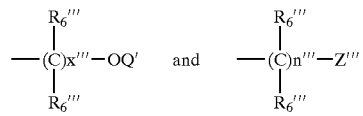

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

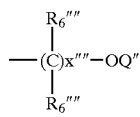

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

17. A compound according to claim 16 which is 2-[trans-(4-aminocyclohexyl)amino]-6-[(1-naphthyl)methylamino]-9-cyclopentylpurine dihydrochloride.

18. The compound according to claim 1, wherein R is R2, wherein

R2 is Z, wherein Z is phenyl, wherein Z may be optionally substituted with 1 to 3 substituents, which may be the same of different, and which are selected from the group consisting of D, E,

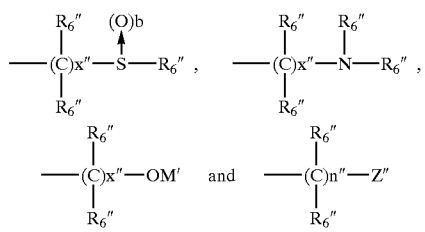

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; each R6" is independently selected from the group consisting of hydrogen, $C_3$–$C_8$ cycloalkyl, $C_1$–$C_4$ alkyl, and $(CH_2)_m$"-phenyl, wherein m" is an integer 0–8; x" is an integer 1–8; n" is an integer 0–8; Z" is selected from the group consisting of phenyl, heterocycle, cycloalkyl, and naphthyl; and M' is selected from the group consisting of hydrogen, $C_1$–$C_4$ alkyl,

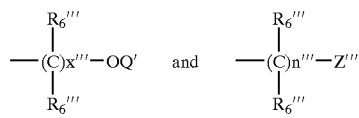

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

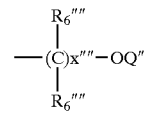

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

19. A compound according to claim 18 which is 2-[trans-(4-aminocyclohexyl)amino]-6-(phenylamino)-9-cyclopentylpurine dihydrochloride.

20. A compound according to claim 18 wherein Z is substituted with the group D.

21. A compound according to claim 20 which is 2-[trans-(4-aminocyclohexyl)amino]-6-[(4-trifluoromethoxy) phenylamino]-9-cyclopentylpurine dihydrochloride.

22. A compound according to claim 18 wherein Z is substituted with the group E.

23. A compound according to claim 22 wherein E is Hal.

24. A compound according to claim 23 which is 2-[trans-(4-aminocyclohexyl)amino]-6-(3-fluorophenylamino)-9-cyclopentylpurine dihydrochloride.

25. A compound according to claim 22 wherein E is $C_1$–$C_8$ alkyl.

26. A compound according to claim 25 which is 2-[trans-(4-aminocyclohexyl)amino]-6-[(4-pentyl)phenylamino]-9-cyclopentylpurine dihydrochloride.

27. A compound according to claim 1 wherein R is R2, R2 is

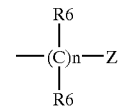

wherein each R6 is independently hydrogen or $C_3$–$C_8$ cycloalkyl, with the proviso that at least one of R6 is $C_3$–$C_8$ cycloalkyl; n is an integer 1–8; and Z is phenyl, wherein Z may be optionally substituted with 1 to 3 substituents, which may be the same or different, and which are selected from the group consisting of D,E

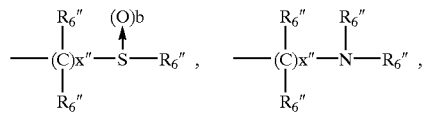

-continued

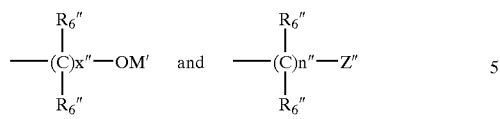

wherein each D is independently selected from the group consisting of trifluoromethyl, trifluoromethoxy, and $C_1-C_4$ alkoxy; each E is independently selected from the group consisting of Hal, OH, $C_2-C_6$ alkenyl, and $C_1-C_8$ alkyl; b is an integer 0–2; each R6" is independently selected from the group consisting of hydrogen, $C_3-C_8$ cycloalkyl, $C_1-C_4$ alkyl, and $(CH_2)_{m''}$-phenyl, wherein m" is an integer 0–8; x" is an integer 1–8; n" is an integer 0–8; Z" is selected from the group consisting of phenyl, heterocycle, cycloalkyl, and naphthyl; and M' is selected from the group consisting of hydrogen, $C_1-C_4$ alkyl,

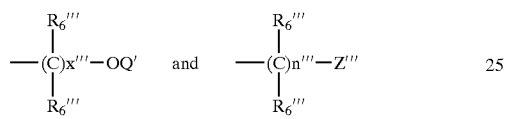

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and naphthyl, wherein the groups M' and Z" may be optionally substituted with the groups D', E' or

provided M' is not hydrogen, wherein each R6"" is independently selected from the group consisting of hydrogen, $C_3-C_8$ cycloalkyl, $C_1-C_4$ alkyl, and $(CH_2)_{m''''}$-phenyl, wherein m'''' is an integer 0–8; x'''' is an integer 0–8; Q" is hydrogen, $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1-C_8$ alkyl; and R1 is selected from the group consisting of cyclopentyl and cyclopentenyl, and the pharmaceutically acceptable salts, optical isomers, and hydrates thereof.

28. A compound according to claim 27 which is (+/−)-2-[trans-(4-aminocyclohexyl)amino]-6-[(α-cyclopropyl-4-chlorobenzyl)amino]-9-cyclopentylpurine dihydrochloride.

29. A compound according to claim 1 wherein R is R2, R2 is

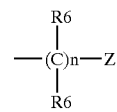

wherein each R6 is independently selected from the group consisting of hydrogen, $C_1-C_4$ alkyl, and $(CH_2)_m$-phenyl, wherein m is an integer 0–8; n is an integer 1–8; and Z is phenyl, wherein Z may be optionally substituted with 1 to 3 substituents, which may be the same or different, and which are selected from the group consisting of

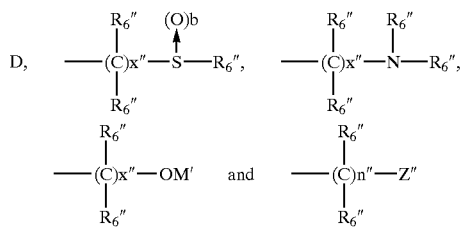

wherein each D is independently selected from the group consisting of trifluoromethyl, trifluoromethoxy, and $C_1-C_4$ alkoxy; b is an integer 0–2; Z" is selected from the group consisting of phenyl, heterocycle, cycloalkyl, and naphthyl; each R6" is independently selected from the group consisting of hydrogen, $C_3-C_8$ cycloalkyl, $C_1-C_4$ alkyl, and $(CH_2)_{m''}$-phenyl, wherein m" is an integer 0–8; x" is an integer 1–8; n" is an integer 0–8; and M' is selected from the group consisting of hydrogen, $C_1-C_4$ alkyl,

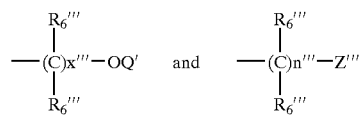

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and naphthyl, wherein the groups M' and Z" may be optionally substituted with the groups D', E' or

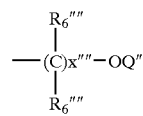

provided M' is not hydrogen, wherein each R6"" is independently selected from the group consisting of hydrogen, $C_3-C_8$ cycloalkyl, $C_1-C_4$ alkyl, and $(CH_2)_{m''''}$-phenyl, wherein m'''' is an integer 0–8; x'''' is an integer 0–8; Q" is hydrogen, $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1$–$C_8$ alkyl; and R1 is cyclopentyl, and the pharmaceutically acceptable salts, optical isomers, and hydrates thereof.

30. A compound according to claim 29 wherein Z is substituted with the group D.

31. A compound according to claim 30 wherein D is trifluoromethyl.

32. A compound according to claim 31 which is 2-[trans-(4-aminocyclohexyl)amino]-6-[(4-trifluorobenzyl)amino]-9-cyclopentylpurine dihydrochloride or 2-[trans-(4-aminocyclohexyl)amino]-6-[(2-trifluorobenzyl)amino]-9-cyclopentylpurine dihydrochloride.

33. A compound according to claim 30 wherein D is $C_1$–$C_4$ alkoxy.

34. The compound according to claim 33, which is 2-(trans-(4-aminocyclohexyl)amino)-6-(3,4,5-trimethoxybenzylamino)-9-cyclopentylpurine dihydrochloride; 2-(trans-(4-aminocyclohexyl)amino)-6-((2,6-dimethoxybenzyl)amino)-9-cyclopentylpurine dihydrochloride; 2-(trans-(4-aminocyclohexyl)amino)-6-((4-methoxybenzyl)amino)-9-cyclopentylpurine dihydrochloride; 2-(trans-(4-aminocyclohexyl)amino)-6-((2-methoxybenzyl)amino)-9-cyclopentylpurine dihydrochloride; 2-(trans-(4-aminocyclohexyl)amino)-6-((2,3-dimethoxybenzyl)amino)-9-cyclopentylpurine dihydrochloride; 2-(trans-(4-aminocyclohexyl)amino)-6-(2-(4-methoxyphenyl)ethylamino)-9-cyclopentylpurine dihydrochloride; 2-(trans-(4-aminocyclohexyl)amino)-6-((2,4-dimethoxybenzyl)amino)-9-cyclopentylpurine dihydrochloride; 2-(trans-(4-aminocyclohexyl)amino)-6-(2-(3-methoxyphenyl)ethylamino)-9-cyclopentylpurine dihydrochloride; 2-(trans-(4-aminocyclohexyl)amino)-6-((3,5-dimethoxybenzyl)-amino)-9-cyclopentylpurine dihydrochloride; or 2-(trans-(4-aminocyclohexyl)amino)-6-(3,4-dimethoxybenzyl)amino)-9-cyclopentylpurine dihydrochloride.

35. A compound according to claim 1 wherein R is R2, R2 is

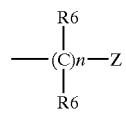

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8, n is an integer 0–8; and Z is phenyl, wherein Z may be optionally substituted with 1 to 3 substituents, which may be the same or different, and which are selected from the group consisting of D, E,

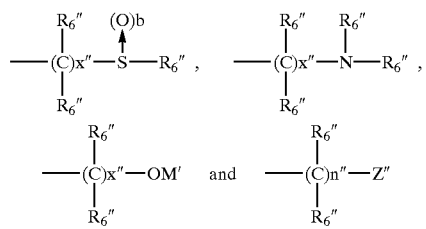

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; x" is an integer 1–8; n" is an integer 0–8; and M' is selected from the group consisting of hydrogen, $C_1$–$C_4$ alkyl,

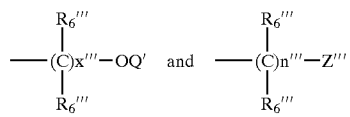

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

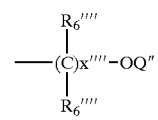

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R2 is cyclopentenyl, and the pharmaceutically acceptable salts, optical isomers, and hydrates thereof.

36. A compound according to claim 35 wherein Z is substituted with the group E.

37. A compound according to claim 36 wherein E is Hal.

38. A compound according to claim 37 which is 2-[trans-(4-aminocyclohexyl)amino]-6-[(3-iodobenzyl)amino]-9-(2-cyclopentenyl)purine hydrochloride.

39. A compound according to claim 1 wherein R is R2, wherein R2 is Z wherein Z is heterocycle, wherein Z may be optionally substituted with 1 to 3 substituents, which may be the same or different, and which are selected from the group consisting of D, E,

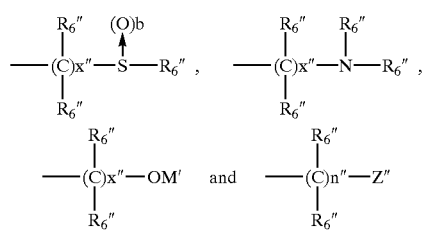

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; x" is an integer 1–8; n" is an integer 0–8; and M' is selected from the group consisting of hydrogen, $C_1$–$C_4$ alkyl, $$\begin{array}{cc} R_6''' & R_6''' \\ | & | \\ -(C)x'''-OQ' \text{ and } -(C)n'''-Z''' \\ | & | \\ R_6''' & R_6''' \end{array}$$

wherein each R6"' is independently selected from the group consisting of hydrogen, $C_3$–$C_8$ cycloalkyl, $C_1$–$C_4$ alkyl, and $(CH_2)_{m'''}$-phenyl, wherein m'" is an integer 0–8; n'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl, wherein the groups M' and Z" may be optionally substituted with the groups D', E' or $$\begin{array}{c} R_6'''' \\ | \\ -(C)x''''-OQ'' \\ | \\ R_6'''' \end{array}$$

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

40. A compound according to claim 39 wherein Z is piperidine or optionally substituted piperidine as defined in claim 39.

41. A compound according to claim 40 wherein Z is substituted with the group D.

42. A compound according to claim 40 wherein Z is substituted with the group E.

43. A compound according to claim 42 wherein E is $C_1$–$C_8$ alkyl.

44. A compound according to claim 43 which is 2-[trans-(4-aminocyclohexyl)amino]-6-[4-(1-propyl)piperidinylamino]-9-cyclopentylpurine; 2-[trans-(4-aminocyclohexyl)amino]-6-[4-(1-butyl)piperidinylamino]-9-cyclopentylpurine; or 2-[trans-(4-aminocyclohexyl)amino]-6-[4-(1-(allyl)piperidinylamino]-9-cyclopentylpurine.

45. A compound according to claim 40 wherein Z is substituted with the group $$\begin{array}{cc} R_6'' & (O)b \\ | & \uparrow \\ -(C)x''-S-R_6'' \\ | \\ R_6'' \end{array}$$

wherein R6", x", and b are defined as in claim, 40.

46. A compound according to claim 45 wherein b is 0.

47. A compound according to claim 46 which is 2-(trans-(4-aminocyclohexyl)amino)-6-(4-(1-(2-methylthioethyl)piperidinylamino)-9-cyclopentylpurine.

48. A compound according to claim 45 wherein b is 1.

49. A compound according to claim 48 which is 2-[trans-(4-aminocyclohexyl)amino]-6-[4-(1-(2-phenylsulfinyl)ethyl)piperidinylamino]-9-cyclopentylpurine.

50. A compound according to claim 40 wherein Z is substituted with the group $$\begin{array}{cc} R_6'' & R_6'' \\ | & | \\ -(C)x''-N-R_6'' \\ | \\ R_6'' \end{array}$$

wherein R6" and x" are defined as in claim 40.

51. A compound according to claim 50 which is 2-[trans-(4-aminocyclohexyl)amino]-6-[4-(1-(2-N,N-dimethylaminoethyl))piperidinylamino]-9-cyclopentylpurine; 2-[trans-(4-aminocyclohexyl)amino]-6-[4-(1-(3-N,N-dimethylaminopropyl))piperidinylamino]-9-cyclopentylpurine; 2-[trans-(4-aminocyclohexyl)amino]-6-[4-(1-(4-N,N-dimethylaminobutyl))piperidinylamino]-9-cyclopentylpurine; 2-[trans-(4-aminocyclohexyl)amino]-6-[4-(1-(5-N,N-dimethylaminopentyl))piperidinylamino]-9-cyclopentylpurine; 2-[trans-(4-aminocyclohexyl)amino]-6-[4-(1-(2-N,N-diethylaminoethyl))piperidinylamino]-9-cyclopentylpurine; 2-[trans-(4-aminocyclohexyl)amino]-6-[4-(1-(3-N,N-diethylaminopropyl))piperidinylamino]-9-cyclopentylpurine; 2-[trans-(4-aminocyclohexyl)amino]-6-[4-(1(4-N,N-diethylaminobutyl))piperidinylamino]-9-cyclopentylpurine; 2-[trans-(4-aminocyclohexyl)amino]-6-[4-(1-(5-N,N-diethylaminopentyl)piperidinylamino]-9-cyclopentylpurine; 2-[trans-(4-aminocyclohexyl)amino]-6-[4-(1-(2-N,N-dipropylaminoethyl))piperidinylamino]-9-cyclopentylpurine; 2-[trans-(4-aminocyclohexyl)amino]-6-[4-(1-(3-N,N-dipropylaminopropyl))piperidinylamino]-9-cyclopentylpurine; 2-[trans-(4-aminocyclohexyl)amino]-6-[4-(1-(4-N,N-dipropylaminobutyl))piperidinylamino]-9-cyclopentylpurine; 2-[trans-(4-aminocyclohexyl)amino]-6-[4-(1-(5-N,N-dipropylaminopentyl))piperidinylamino]-9-cyclopentylpurine; 2-[trans-(4-aminocyclohexyl)amino]-6-[4-(1-(2-N,N-dibutylaminoethyl))piperidinylamino]-9-cyclopentylpurine; 2-[trans-(4-aminocyclohexyl)amino]-6-[4-(1-(3-N,N-dibutylaminopropyl))piperidinylamino]-9-cyclopentylpurine; 2-[trans-(4-aminocyclohexyl)amino]-6-[4-(1-(4-N,N-dibutylaminobutyl)piperidinylamino]-9-cyclopentylpurine; 2-[trans-(4-aminocyclohexyl)amino]-6-[4-(1-(5-N,N-dibutylaminopentyl))piperidinylamino]-9-cyclopentylpurine; 2-[trans-(4-aminocyclohexyl)amino]-6-[4-(1-(2-N,N-dibenzylaminoethyl))piperidinylamino]-9-cyclopentylpurine; 2-[trans-(4-aminocyclohexyl)amino]-6-[4-(1-(3-N,N-dibenzylaminopropyl))piperidinylamino]-9-cyclopentylpurine; 2-[trans-(4-aminocyclohexyl)amino]-6-[4-(1-(4-N,N-dibenzylaminobutyl))piperidinylamino]-9-cyclopentylpurine; 2-[trans-(4-aminocyclohexyl)amino]-6-[4-(1-(5-N,N-dibenzylaminopentyl)piperidinylamino]-9-cyclopentylpurine; 2-[trans-(4-aminocyclohexyl)amino]-6-

[4-(1-(2-N,N-di-(2-phenylethylene)aminoethyl))piperidinylamino]-9-cyclopentylpurine; 2-[trans-(4-aminocyclohexyl)amino]-6-[4-(1-(3-N,N-di-(2-phenylethylene)aminopropyl))piperidinylamino]-9-cyclopentylpurine; 2-[trans-(4-aminocyclohexyl)amino]-6-[4-(1(4-N,N-di-(2-phenylethylene)aminobutyl))piperidinylamino]-9-cyclopentylpurine; 2-[trans-(4-aminocyclohexyl)amino]-6-[4-(1(5-N,N-di-(2-phenylethylene)aminopentyl))-piperidinylamino]-9-cyclopentylpurine; 2-[trans-(4-aminocyclohexyl)amino]-6-[4-(1-(2-N,N-di-(3-phenylpropylene)aminoethyl))piperidinylamino]-9-cyclopentylpurine; 2-[trans-(4-aminocyclohexyl)amino]-6-[4-(1-(3-N,N-di-(3-phenylpropylene)aminopropyl))piperidinylamino]-9-cyclopentylpurine; 2-[trans-(4-aminocyclohexyl)amino]-6-[4-(1-(4-N,N-di-(3-phenylpropylene)aminobutyl))piperidinylamino]-9-cyclopentylpurine; 2-[trans-(4-aminocyclohexyl)amino]-6-[4-(1(5-N,N-di-(3-phenylpropylene)aminopentyl))piperidinylamino]-9-cyclopentylpurine; 2-[trans-(4-aminocyclohexyl)amino]-6-[4-(1-(2-N,N-di-(4-phenylbutylene)aminoethyl))piperidinylamino]-9-cyclopentylpurine; 2-[trans-(4-aminocyclohexyl)amino]-6-[4-(1-(3-N,N-di-(4-phenylbutylene)aminopropyl))piperidinylamino]-9-cyclopentylpurine; 2-[trans-(4-aminocyclohexyl)amino]-6-[4-(1(4-N,N-di-(4-phenylbutylene)aminobutyl))piperidinylamino]-9-cyclopentylpurine; or 2-[trans-(4-aminocyclohexyl)amino]-6-[4-(1-(5-N,N-di-(4-phenylbutylene)aminopentyl))piperidinylamino]-9-cyclopentylpurine.

52. A compound according to claim 40 wherein Z is substituted with the group

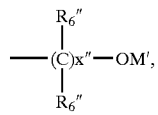

wherein $R_6''$, $x''$ and $M'$ are defined as in claim 40.

53. A compound according to claim 52 wherein $M'$ is hydrogen.

54. A compound according to claim 53 wherein $x''$ is 2.

55. A compound according to claim 54 which is (R,S)-2-[trans-(4-aminocyclohexyl)amino]-6-[4-(1(2-phenyl-2-hydroxyethyl))piperidinylamino]-9-cyclopentylpurine.

56. A compound according to claim 53 wherein $x''$ is 3.

57. A compound according to claim 56 which is 2-[trans-(4-aminocyclohexyl)amino]-6-[4-(1-(3-hydroxy)propyl)piperidinylamino]-9-cyclopentylpurine.

58. A compound according to claim 53 wherein $x''$ is 4.

59. A compound according to claim 58 which is 2-[trans-(4-aminocyclohexyl)amino]-6-[4-(1-(4-hydroxy)butyl)piperidinylamino]-9-cyclopentylpurine.

60. A compound according to claim 53 wherein $x''$ is 5.

61. A compound according to claim 60 which is 2-[trans-(4-aminocyclohexyl)amino]-6-[4-(1-(5-hydroxypentyl))piperidinylamino]-9-cyclopentylpurine.

62. A compound according to claim 53 wherein $x''$ is 6.

63. A compound according to claim 62 which is 2-[trans-(4-aminocyclohexyl)amino]-6-[4-(1-(6-hydroxy)hexyl)piperidinylamino]-9-cyclopentylpurine.

64. A compound according to claim 52 wherein $M'$ is $C_1$–$C_4$ alkyl.

65. A compound according to claim 64 wherein $x''$ is 1.

66. The compound according to claim 1, wherein Z is heterocycle substituted with —$(C(R_6'')_2)_n$—Z''.

67. A compound according to claim 64 wherein $x''$ is 2.

68. A compound according to claim 65 wherein $x''$ is 3.

69. A compound according to claim 68 which is 2-[trans-(4-aminocyclohexyl)amino]-6-[4-(1-(3-methoxy)propyl)piperidinylamino]-9-cyclopentylpurine; 2-[trans-(4-aminocyclohexyl)amino]-6-[4-(1-(3-ethoxy)propyl)piperidinylamino]-9-cyclopentylpurine; 2-[trans-(4-aminocyclohexyl)amino]-6-[4-(1-(3-propoxy)propyl)piperidinylamino]-9-cyclopentylpurine; or 2-[trans-(4-aminocyclohexyl)amino]-6-[4-(1-(3-butoxy)propyl)piperidinylamino]-9-cyclopentylpurine.

70. A compound according to claim 65 wherein $x''$ is 4.

71. A compound according to claim 70 which is 2-[trans-(4-aminocyclohexyl)amino]-6-[4-(1-(4-methoxy)butyl)piperidinylamino]-9-cyclopentylpurine; 2-[trans-(4-aminocyclohexyl)amino]-6-[4-(1-(4-ethoxy)butyl)piperidinylamino]-9-cyclopentylpurine; 2-[trans-(4-aminocyclohexyl)amino]-6-[4-(1-(4-propoxy)butyl)piperidinylamino]-9-cyclopentylpurine; or 2-[trans-(4-aminocyclohexyl)amino]-6-[4-(1-(4-butoxy)butyl)piperidinylamino]-9-cyclopentylpurine.

72. A compound according to claim 65 wherein $x''$ is 5.

73. A compound according to claim 72 which is 2-[trans-(4-aminocyclohexyl)amino]-6-[4-(1-(5-methoxypentyl))piperidinylamino]-9-cyclopentylpurine; 2-[trans-(4-aminocyclohexyl)amino]-6-[4-(1-(5-ethoxypentyl))piperidinylamino]-9-cyclopentylpurine; 2-[trans-(4-aminocyclohexyl)amino]-6-[4-(1-(5-propoxypentyl))piperidinylamino]-9-cyclopentylpurine; or 2-[trans-(4-aminocyclohexyl)amino]-6-[4-(1-(5-butoxypentyl))piperidinylamino]-9-cyclopentylpurine.

74. A compound according to claim 65 wherein $x''$ is 6.

75. A compound according to claim 74 which is 2-[trans-(4-aminocyclohexyl)amino]-6-[4-(1-(6-methoxy)hexyl)piperidinylamino]-9-cyclopentylpurine; 2-[trans-(4-aminocyclohexyl)amino]-6-[4-(1-(6-ethoxy)hexyl)piperidinylamino]-9-cyclopentylpurine; 2-[trans-(4-aminocyclohexyl)amino]-6-[4-(1-(6-propoxy)hexyl)piperidinylamino]-9-cyclopentylpurine; or 2-[trans-(4-aminocyclohexyl)amino]-6-[4-(1-(6-butoxy)hexyl)piperidinylamino]-9-cyclopentylpurine.

76. A compound according to claim 52 wherein $M'$ is a group of the formula

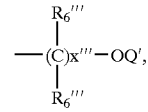

wherein $R_6'''$, $x'''$ and $Q'$ are as defined in claim 52.

77. A compound according to claim 76 wherein $Q'$ is hydrogen.

78. A compound according to claim 77 which is 2-[trans-(4-aminocyclohexyl)amino]6-[4-(1(2-(2-hydroxyethyleneoxy)ethyl))piperidinylamino]-9-cyclopentylpurine.

79. A compound according to claim 76 wherein $Q'$ is $C_1$–$C_4$ alkyl.

80. A compound according to claim 52 wherein $M'$ is a group of the formula

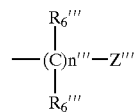

wherein R6''', n''' and Z''' are defined as in claim 52.

81. A compound according to claim 80 wherein Z''' is phenyl.

82. A compound according to claim 81 wherein x'' is 2.

83. A compound according to claim 82 which is 2-[trans-(4-aminocyclohexyl)amino]-6-[4-(1-(2-phenoxyethyl))piperidinylamino]-9-cyclopentylpurine.

84. A compound according to claim 81 wherein x'' is 3.

85. A compound according to claim 84 which is 2-[trans-(4-aminocyclohexyl)amino]-6-[4-(1-(3-phenoxypropyl))piperidinylamino]-9-cyclopentylpurine; 2-[trans-(4-aminocyclohexyl)amino]-6-[4-(1-(3-benzyloxy)propyl)piperidinylamino]-9-cyclopentylpurine; 2-[trans-(4-aminocyclohexyl)amino]-6-[4-(1-(3-(2-phenylethyleneoxy)propyl)piperidinylamino]-9-cyclopentylpurine; 2-[trans-(4-aminocyclohexyl)amino]-6-[4-(1-(3-(3-phenylpropyleneoxy)propyl)piperidinylamino]-9-cyclopentylpurine; or 2-[trans-(4-aminocyclohexyl)amino]-6-[4-(1-(3-(4-phenylbutyleneoxy)propyl)piperidinylamino]-9-cyclopentylpurine.

86. A compound according to claim 81 wherein x'' is 4.

87. A compound according to claim 86 which is 2-[trans-(4-aminocyclohexyl)amino]-6-[4-(1-(4-benzyloxy)butyl)piperidinylamino]-9-cyclopentylpurine; 2-[trans-(4-aminocyclohexyl)amino]-6-[4-(1(4-(2-phenylethyleneoxy)butyl)piperidinylamino]-9-cyclopentylpurine; 2-[trans-(4-aminocyclohexyl)amino]-6-[4-(1-(4-(3-phenylpropyleneoxy)butyl)piperidinylamino]-9-cyclopentylpurine; or 2-[trans-(4-aminocyclohexyl)amino]-6-[4-(1-(4-(4-phenylbutyleneoxy)butyl)piperidinylamino]-9-cyclopentylpurine.

88. A compound according to claim 81 wherein x'' is 5.

89. A compound according to claim 88 which is 2-[trans-(4-aminocyclohexyl)amino]-6-[4-(1-(5-benzyloxypentyl))piperidinylamino]-9-cyclopentylpurine; 2-[trans-(4-aminocyclohexyl)amino]-6-[4-(1-(5-(2-phenylethyleneoxy)pentyl))piperidinylamino]-9-cyclopentylpurine; 2-[trans-(4-aminocyclohexyl)amino]-6-[4-(1-(5-(3-phenylpropyleneoxy)pentyl))piperidinylamino]-9-cyclopentylpurine; or 2-[trans-(4-aminocyclohexyl)amino]-6-[4-(1-(5-(4-phenylbutyleneoxy)pentyl))piperidinylamino]-9-cyclopentylpurine.

90. A compound according to claim 81 wherein x'' is 6.

91. A compound according to claim 90 which is 2-[trans-(4-aminocyclohexyl)amino]-6-[4-(1-(6-benzyloxy)hexyl)piperidinylamino]-9-cyclopentylpurine; 2-[trans-(4-aminocyclohexyl)amino]-6-[4-(1-(6-(2-phenylethyleneoxy)hexyl)piperidinylamino]-9-cyclopentylpurine; 2-[trans-(4-aminocyclohexyl)amino]-6-[4-(1-(6-(3-phenylpropyleneoxy)hexyl)piperidinylamino]-9-cyclopentylpurine; or 2-[trans-(4-aminocyclohexyl)amino]-6-[4-(1-(6-(4-phenylbutyleneoxy)hexyl)piperidinylamino]-9-cyclopentylpurine.

92. A compound according to claim 40 wherein Z is substituted with the group

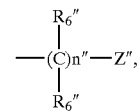

wherein R6'', n'' and Z'' are defined as in claim 40.

93. A compound according to claim 92 wherein Z'' is phenyl.

94. A compound according to claim 93 wherein n''=1.

95. A compound according to claim 94 which is 2-[trans-(4-aminocyclohexyl)amino]-6-[4-(1-benzyl)piperidinylamino]-9-cyclopentylpurine trihydrochloride; (R,S)-2-[trans-(4-aminocyclohexyl)amino]-6-[4-(1-benzyl-3-methyl)piperidinylamino]-9-cyclopentylpurine or (+/−)-2-[trans-(4-aminocyclohexyl)amino]-6-[4-(1-(α-methylbenzyl))piperidinylamino]-9-cyclopentylpurine.

96. A compound according to claim 93 wherein n''=2.

97. A compound according to claim 96 which is 2-[trans-(4-aminocyclohexyl)amino]-6-[4-(1-(2-phenylethyl))piperidinylamino]-9-cyclopentylpurine trihydrochloride.

98. A compound according to claim 63 wherein Z'' is substituted with the group D'.

99. A compound according to claim 98 wherein D' is $C_1$–$C_4$ alkoxy.

100. A compound according to claim 99 which is 2-[trans-(4-aminocyclohexyl)amino]-6-[4-(1-(4-methoxybenzyl))piperidinylamino]-9-cyclopentylpurine or 2-[trans-(4-aminocyclohexyl)amino]-6-[4-(1-(3-methoxybenzyl))piperidinylamino]-9-cyclopentylpurine 2-[Trans-(4-aminocyclohexyl)amino]-6-[4-[1-(3,5-dimethoxybenzyl)]piperidinylamino]-9-cyclopentylpurine trihydrochloride; 2-[Trans-(4-aminocyclohexyl)amino]-6-[4-[1-(2-methoxybenzyl)]piperidinylamino]-9-cyclopentylpurine trihydrochloride.

101. A compound according to claim 98 wherein D' is trifluoromethyl.

102. A compound according to claim 101 which is 2-[trans-(4-aminocyclohexyl)amino]-6-[4-(1(4-trifluoromethylbenzyl))piperidinylamino]-9-cyclopentylpurine; 2-[Trans-(4-aminocyclohexyl)amino]6-[4-[1-(2-trifluoromethylbenzyl)]-piperidinylamino]-9-cyclopentylpurine trihydrochloride; 2-[Trans-(4-aminocyclohexyl)amino]-6-[4-[1-[3,5-bis(trifluoromethyl)benzyl]]piperidinylamino]-9-cyclopentylpurine trihydrochloride;2-[Trans-(4-aminocyclohexyl)amino]-6-[4-[1-(3-trifluoromethylbenzyl)]piperidinylamino]-9-cyclopentylpurine trihydrochloride;2-[Trans-(4-aminocyclohexyl)amino]-6-[4-[1-(2,4-bis-trifluoromethylbenzyl)]piperidinylamino]-9-cyclopentylpurine trihydrochloride.

103. A compound according to claim 93 wherein Z'' is substituted with the group E'.

104. A compound according to claim 103 wherein E' is $C_1$–$C_8$ alkyl.

105. A compound according to claim 104 which is 2-(trans-(4-aminocyclohexyl)amino)-6-(4-(1-(4-methylbenzyl))piperidinylamino)-9-cyclopentylpurine; 2-(trans-(4-aminocyclohexyl)amino)-6-(4-(1-(2-methylbenzyl))piperidinylamino)-9-cyclopentylpurine; 2-(Trans-(4-aminocyclohexyl)amino)-6-(4-(1-(3-methylbenzyl))piperidinylamino)-9-cyclopentylpurine trihydrochloride; 2-(Trans-(4-aminocyclohexyl)amino)-6-(4-(1-(3-chloro-4-methylbenzyl))piperidinylamino)-9-cyclopentylpurine trihydrochloride.

106. A compound according to claim 103 wherein E' is Hal.

107. The compound according to claim 106, which is 2-(trans-(4-aminocyclohexyl)amino)-6-(4-(1-(4-chlorobenzyl))piperidinylamino)-9-cyclopentylpurine; 2-(trans-(4-aminocyclohexyl)amino)-6-(4-(1-(3-chlorobenzyl))piperidinylamino)-9-cyclopentylpurine; 2-(trans-(4-aminocyclohexyl)amino)-6-(4-(1-(2-chlorobenzyl))piperidinylamino)-9-cyclopentylpurine; 2-(trans-(4-aminocyclohexyl)amino)-6-(4-(1-(2,6dichlorobenzyl))piperidinylamino)-9-cyclopentylpurine or 2-(trans-(4-aminocyclohexyl)amino)-6-(4-(1-(3,4-difluorobenzyl))piperidinylamino)-9-cyclopentylpurine trihydrochloride; 2-(Trans-(4-aminocyclohexyl)amino)-6-(4-(1-(2,4-difluorobenzyl))piperidinylamino)-9-cyclopentylpurine trihydrochloride; 2-(Trans-(4-aminocyclohexyl)amino)-6-(4-(1-(2-fluorobenzyl))piperidinylamino)-9-cyclopentylpurine trihydrochloride; 2-(Trans-(4-aminocyclohexyl)amino)-6-(4-(1-(3,4-dichlorobenzyl))piperidinylamino)-9-cyclopentylpurine trihydrochloride; 2-(Trans-(4-aminocyclohexyl)amino)-6-(4-(1-(3-fluorobenzyl))piperidinylamino)-9-cyclopentylpurine trihydrochloride; 2-(Trans-(4-aminocyclohexyl)amino)-6-(4-(1-(2-chloro-4-fluorobenzyl))piperidinylamino)-9-cyclopentylpurine trihydrochloride; 2-(Trans-(4-aminocyclohexyl)amino)-6-(4-(1-(3-chloro-4-methylbenzyl))piperidinylamino)-9-cyclopentylpurine trihydrochloride; 2-(Trans-(4-aminocyclohexyl)amino)-6-(4-(1-(3,5-difluorobenzyl))piperidinylamino)-9-cyclopentylpurine trihydrochloride; 2-(Trans-(4-aminocyclohexyl)amino)-6-(4-(1-(2-chloro-6-fluorobenzyl))piperidinylamino)-9-cyclopentylpurine trihydrochloride; 2-(Trans-(4-aminocyclohexyl)amino)-6-(4-(1-(2,4-dichlorobenzyl))piperidinylamino)-9-cyclopentylpurine trihydrochloride; 2-(Trans-(4-aminocyclohexyl)amino)-6-(4-(1-(2,3-difluorobenzyl))piperidinylamino)-9-cyclopentylpurine trihydrochloride; 2-(Trans-(4-aminocyclohexyl)amino)-6-(4-(1-(2,6-difluorobenzyl))piperidinylamino)-9-cyclopentylpurine trihydrochloride; 2-(Trans-(4-aminocyclohexyl)amino)-6-(4-(1-(4-fluorobenzyl))piperidinylamino)-9-cyclopentylpurine trihydrochloride; 2-(Trans-(4-aminocyclohexyl)amino)-6-(4-(1-(2,5-dichlorobenzyl))piperidinylamino)-9-cyclopentylpurine trihydrochloride; 2-(Trans-(4-aminocyclohexyl)amino)-6-(4-(1-(2,5-difluorobenzyl))piperidinylamino)-9-cyclopentylpurine trihydrochloride; or 2-(Trans-(4aminocyclohexyl)amino)-6-(4-(1-(2,4-difluorobenzyl))piperidinylamino)-9-cyclopentylpurine trihydrochloride.

108. A compound according to claim 92 wherein Z" is heterocycle.

109. A compound according to claim 108 wherein Z" is 1,3-benzodioxolyl.

110. A compound according to claim 109 which is 2-[trans-(4-aminocyclohexyl)amino]-6-[4-(1-(3,4-methylenedioxybenzyl))piperidinylamino]-9-cyclopentylpurine.

111. A compound according to claim 108 wherein Z" is pyridinyl.

112. A compound according to claim 111 which is 2-[trans-(4-aminocyclohexyl)amino]-6-[4-(1-(2-pyridinylmethyl))piperidinylamino]-9-cyclopentylpurine; 2-[trans-(4-aminocyclohexyl)amino]-6-[4-(1-(3-pyridinylmethyl))piperidinylamino]-9-cyclopentylpurine; or 2-[trans-(4-aminocyclohexyl)amino]-6-[4-(1-(4-pyridinylmethyl))piperidinylamino]-9-cyclopentylpurine.

113. A compound according to claim 108 wherein Z" is isoxazolyl, or optionally substituted isoxazolyl as defined in claim 108.

114. A compound according to claim 113 which is 2-[trans-(4-aminocyclohexyl)amino]-6-[4-(1-(3-(2,4-dimethylisoxazolyl))methyl)piperidinylamino]-9-cyclopentylpurine.

115. A compound according to claim 108 wherein Z" is tetrahydrofuranyl, or optionally substituted tetrahydrofuranyl as defined in claim 108.

116. A compound according to claim 115 which is 2-[trans-(4-aminocyclohexyl)amino]-6-[4-(1-(3-tetrahydrofuranyl)methyl)piperidinylamino]-9-cyclopentylpurine.

117. A compound according to claim 108 wherein Z" is pyrrolidinyl, or optionally substituted pyrrolidinyl as defined in claim 108.

118. A compound according to claim 117 which is 2-[trans-(4-aminocyclohexyl)amino]-6-[4-(1-(2-(1-pyrrolidinyl)ethyl))piperidinylamino]-9-cyclopentylpurine or (R,S)-2-[trans-(4-aminocyclohexyl)amino]-6-[4-(1-(2-(3-(1-methyl)pyrrolidinyl)ethyl))piperidinylamino]-9-cyclopentylpurine.

119. A compound according to claim 108 wherein Z" is piperidinyl, or optionally substituted piperidinyl as defined in claim 108.

120. A compound according to claim 119 which is 2-[trans-(4-aminocyclohexyl)amino]-6-[4-(1-(2-(1-piperidinyl)ethyl))piperidinylamino]-9-cyclopentylpurine; 2-[trans-(4-aminocyclohexyl)amino]-6-[4-(1-(3-(1-piperidinyl)propyl))piperidinylamino]-9-cyclopentylpurine; or (R,S)-2-[trans-(4-aminocyclohexyl)amino]-6-[4-(1-(3-(1-methyl)piperidinyl)methyl))piperidinylamino]-9-cyclopentylpurine.

121. A compound according to claim 108 wherein Z" is morpholinyl, or optionally substituted morpholinyl as defined in claim 108.

122. A compound according to claim 121 which is 2-[trans-(4-aminocyclohexyl)-amino]-6-[4-(1-(2-(4-morpholinyl)ethyl))piperidinylamino]-9-cyclopentylpurine.

123. A compound according to claim 108 wherein Z" is piperazinyl, or optionally substituted piperazinyl as defined in claim 108.

124. A compound according to claim 123 which is 2-[trans-(4-aminocyclohexyl)-amino]-6-[4-(1-(2-(1-(4-methyl)piperazinyl)ethyl))piperidinylamino]-9-cyclopentylpurine.

125. A compound according to claim 108 wherein Z" is benzimidazolinyl, or optionally substituted benzimidazolinyl as defined in claim 108.

126. A compound according to claim 125 which is 2-[trans-(4-aminocyclohexyl)amino]-6-[4-(1-(2-benzimidazolinyl)methyl)piperidinylamino]-9-cyclopentylpurine.

127. A compound according to claim 108 wherein Z" is thiazolinyl, or optionally substituted thiazolinyl as defined in claim 108.

128. A compound according to claim 127 which is 2-[trans-(4-aminocyclohexyl)amino]-6-[4-(1-(4-(2-methyl)thiazolinyl)methyl)piperidinylamino]-9-cyclopentylpurine.

129. A compound according to claim 108 wherein Z" is thiophenyl, or optionally substituted thiophenyl as defined in claim 108.

130. A compound according to claim 129 which is 2-[trans-(4-aminocyclohexyl)amino]-6-[4-(1-(2-thipheneyl)methyl)piperidinylamino]-9-cyclopentylpurine.

131. A compound according to claim 92 wherein Z" is cycloalkyl, or optionally substituted cycloalkyl as defined in claim 92.

132. A compound according to claim 131 which is 2-[trans-(4-aminocyclohexyl)amino]-6-[4-(1-cyclopropylmethyl)piperidinylamino]-9-cyclopentylpurine; 2-[Trans-(4-aminocyclohexyl)amino]-6-[4-(1-cyclohexylmethyl)piperidinylamino]-9-cyclopentylpurine trihydrochloride.

133. A compound according to claim 39 wherein Z is pyrrolidine, or optionally substituted pyrrolidine as defined in claim 39.

134. A compound according to claim 133 wherein Z is substituted with the group

wherein R6", n" and Z" are as defined in claim 133.

135. A compound according to claim 134 wherein Z" phenyl, or optionally substituted phenyl as defined in claim 134.

136. A compound according to claim 135 which is (R)-2-[trans-(4-aminocyclohexyl)amino]-6-[3-(1-benzyl)pyrrolidinylamino]-9-cyclopentylpurine or (S)-2-[trans-(4-aminocyclohexyl)amino]-6-[3-(1-benzyl)pyrrolidinylamino]-9-cyclopentylpurine.

137. A compound according to claim 1, wherein R is R2, R2 is

wherein each R6 is independently hydrogen, $C_3-C_8$ cycloalkyl, with the proviso that at least one of R6 is $C_3-C_6$ cycloalkyl; n is an integer 1–8; and Z is heterocycle,
wherein Z may be optionally substituted with 1 to 3 substituents, which may be the same or different, and which are selected from the group consisting of D, E,

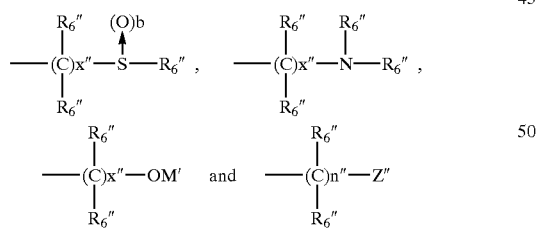

wherein each D is independently selected from the group consisting of trifluoromethyl, trifluoromethoxy, and $C_1-C_4$ alkoxy; each E is independently selected from the group consisting of Hal, OH, $C_2-C_6$ alkenyl, and $C_1-C_8$ alkyl; b is an integer 0–2; Z" is selected from the group consisting of phenyl, heterocycle, cycloalkyl, and naphthyl; each R6" is independently selected from the group consisting of hydrogen, $C_3-C_8$ cycloalkyl, $C_1-C_4$ alkyl, and $(CH_2)_{m''}$-phenyl, wherein m" is an integer 0–8; n" is an integer 0–8; x" is an integer 1–8; and M' is selected from the group consisting of hydrogen, $C_1-C_4$ alkyl,

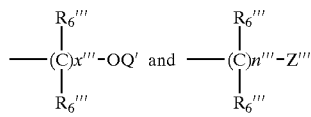

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and naphthyl, wherein the groups M' and Z" may be optionally substituted with the groups D', E' or

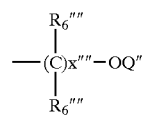

provided M' is not hydrogen,
wherein each R6'''' is independently selected from the group consisting of hydrogen, $C_3-C_8$ cycloalkyl, $C_1-C_4$ alkyl, and $(CH_2)_{m''''}$-phenyl, wherein m'''' is an integer 0–8; x'''' is an integer 0–8; Q'' is hydrogen, $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1-C_8$ alkyl; and R1 is selected from the group consisting of cyclopentyl and cyclopentenyl, and the pharmaceutically acceptable salts, optical isomers, and hydrates thereof.

138. A compound according to claim 1, wherein R is R2, R2 is

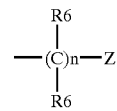

wherein each R6 is independently selected from the group consisting of hydrogen, $C_1-C_4$ alkyl, and $(CH_2)_{n'}$-phenyl, wherein n' is an integer 0–8; n; is an integer 1–8; and Z is heterocycle,
wherein Z is substituted with 1 to 3 substituents, which may be the same or different, and which are selected from the group consisting of

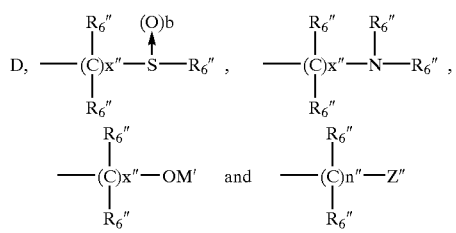

wherein each D is independently selected from the group consisting of trifluoromethyl, trifluoromethoxy, and $C_1-C_4$ alkoxy; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

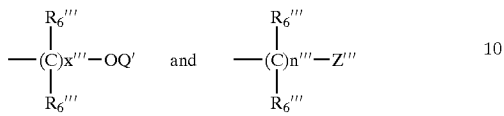

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl, and the pharmaceutically acceptable salts, optical isomers, and hydrates thereof.

139. A compound according to claim 138 wherein Z is substituted with the group D.

140. A compound according to claim 139 wherein D is $C_1$–$C_4$ alkoxy.

141. A compound according to claim 140 which is 2-[trans-(4-aminocyclohexyl)amino]-6-[(3-(5-methoxyindolyl))-2-ethylamino]-9-cyclopentylpurine dihydrochloride.

142. A compound according to claim 1 wherein R is R2, R2 is

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8, n is an integer 0–8; and Z is phenyl,
wherein Z may be optionally substituted with 1 to 3 substituents, which may be the same or different, and which are selected from the group consisting of D, E,

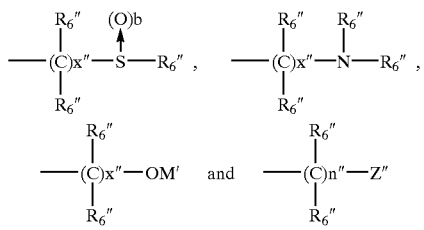

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

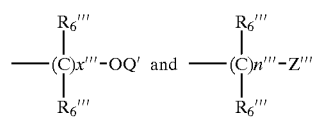

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

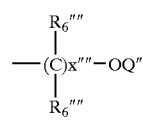

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentenyl,
and the pharmaceutically acceptable salts, optical isomers, and hydrates thereof.

143. A compound according to claim 1, wherein R is R2, R2 is Z, wherein Z is cycloalkyl, wherein Z may be optionally substituted with 1 to 3 substituents, which may be the same or different, and which are selected from the group consisting of D, E,

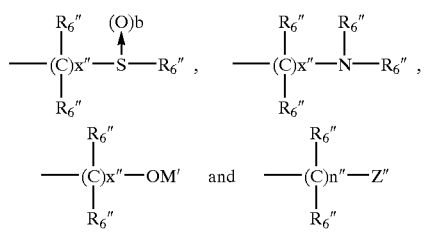

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

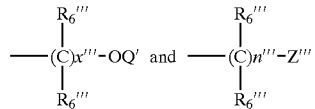

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

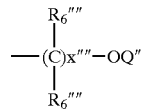

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen, $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

144. A compound according to claim 143 wherein Z is substituted with the group E.

145. A compound according to claim 144 wherein E is OH.

146. A compound according to claim 145 which is trans-2-[tran-(4-aminocyclohexyl)-amino]-6-[(4-hydroxy)cyclohexylamino]-9-cyclopentylpurine dihydrochloride or cis-2-[trans-(4-aminocyclohexyl)amino]-6-[(4-hydroxy)cyclohexylamino]-9-cyclopentylpurine dihydrochloride.

147. A compound according to claim 143 wherein Z is substituted with the group

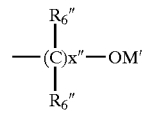

wherein R6'', x'', and M' are as defined in claim 143.

148. A compound according to claim 147 wherein M' is hydrogen.

149. A compound according to claim 148 which is (R,S)-2-[trans-(4-aminocyclohexyl)amino]-6-[(1-hydroxymethyl)cyclopentylamino]-9-cyclopentylpurine dihydrochloride.

150. A compound according to claim 1 wherein R is R2, R2 is

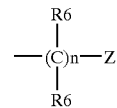

wherein each R6 is independently hydrogen or $C_3$–$C_8$ cycloalkyl, with the proviso that at least one of R6 is $C_3$–$C_8$ cycloalkyl; n is an integer 1–8; and Z is cycloalkyl, wherein Z may be optionally substituted with 1 to 3 substituents, which may be the same or different, and which are selected from the group consisting of D, E,

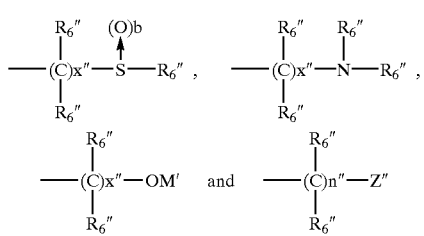

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

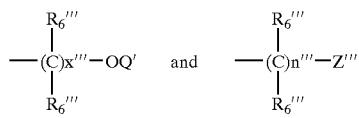

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

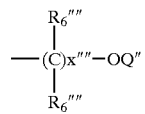

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

151. A compound according to claim 1, wherein R is R2, R2 is

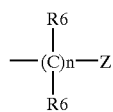

wherein each R6 is independently selected from the group consisting of hydrogen, $C_1$–$C_4$ alkyl, and $(CH_2)_{n'}$-phenyl, wherein n' is an integer 0–8; n; is an integer 1–8; and Z is cycloalkyl, wherein Z is substituted with 1 to 3 substituents, which may be the same or different, and which are selected from the group consisting of

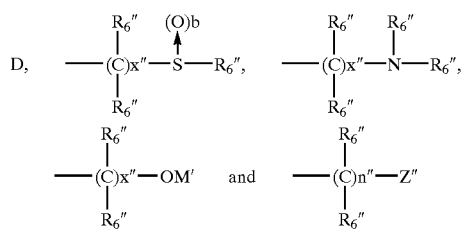

wherein each D is independently selected from the group consisting of trifluoromethyl, trifluoromethoxy, and $C_1$–$C_4$ alkoxy; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

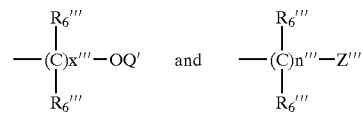

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

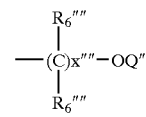

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentyl, and the pharmaceutically acceptable salts, optical isomers, and hydrates thereof.

152. A compound according to claim 151 wherein Z is substituted with the group

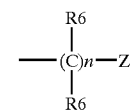

wherein R6", x", and M' are as defined in claim 146.

153. A compound according to claim 152 wherein M' is hydrogen.

154. A compound according to claim 153 which is 2-[trans-(4-aminocyclohexyl)-amino]-6-[4-(hydroxymethyl)cyclohexanemethylamino]-9-cyclopentylpurine dihydrochloride.

155. A compound according to claim 1 wherein R is R2, R2 is

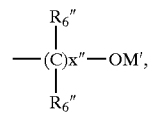

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; n is an integer 0–8; and Z is cycloalkyl, wherein Z may be optionally substituted with 1 to 3 substituents, which may be the same or different, and which are selected from the group consisting of D, E,

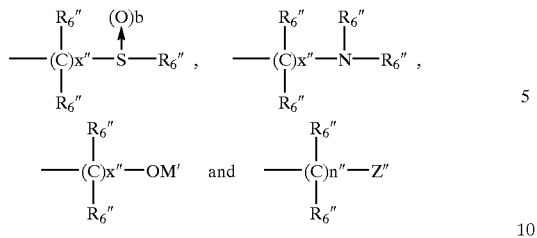

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m"}$-phenyl, wherein m" is an integer 0–8; n" is an integer 0–8; x" is an integer 1–8; and M' is selected from the group consisting of hydrogen, $C_1$–$C_4$ alkyl,

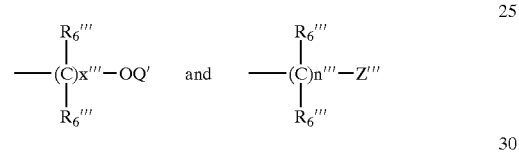

wherein each R6'" is independently selected from the group consisting of hydrogen, $C_3$–$C_8$ cycloalkyl, $C_1$–$C_4$ alkyl, and $(CH_2)_{m'"}$-phenyl, wherein m'" is an integer 0–8; n'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl, wherein the groups M' and Z" may be optionally substituted with the groups D', E' or

provided M' is not hydrogen, wherein each R6"" is independently selected from the group consisting of hydrogen, $C_3$–$C_8$ cycloalkyl, $C_1$–$C_4$ alkyl, and $(CH_2)_{m""}$-phenyl, wherein m"" is an integer 1–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentenyl, and the pharmaceutically acceptable salts, optical isomers, and hydrates thereof.

156. A compound according to claim 1, wherein R is R2NH—, wherein R2 is $C_9$–$C_{12}$ alkyl, which may be optionally substituted with 1 to 3 substituents, which may be the same or different, and which are selected from the group consisting of D, E,

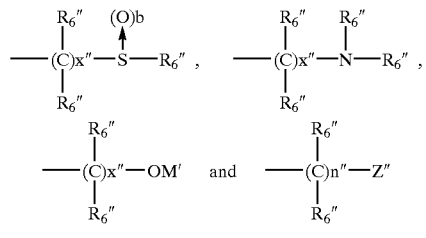

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m"}$-phenyl, wherein m" is an integer 0–8; n" is an integer 0–8; x" is an integer 1–8; and M' is selected from the group consisting of hydrogen, $C_1$–$C_4$ alkyl,

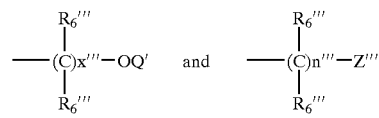

wherein each R6'" is independently selected from the group consisting of hydrogen, $C_3$–$C_8$ cycloalkyl, $C_1$–$C_4$ alkyl, and $(CH_2)_{m'"}$-phenyl, wherein m'" is an integer 0–8; n'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl, wherein the groups M' and Z" may be optionally substituted with the groups D', E' or

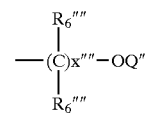

provided M' is not hydrogen, wherein each R6"" is independently selected from the group consisting of hydrogen, $C_3$–$C_8$ cycloalkyl, $C_1$–$C_4$ alkyl, and $(CH_2)_{m""}$-phenyl, wherein m"" is an integer 0–8; x"" is an integer 0–8; Q" is hydrogen or $C_1$–$C_4$ alkyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

157. A compound according to claim 1 wherein R is R2NH—, wherein R2 is

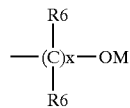

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; and M is selected from the group consisting of hydrogen, $C_1$–$C_4$ alkyl,

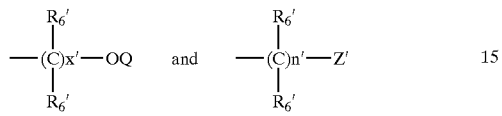

wherein each R6' is independently selected from the group consisting of hydrogen, $C_3$–$C_8$ cycloalkyl, $C_1$–$C_4$ alkyl, and $(CH_2)_m$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and naphthyl; and R1 is selected from the group consisting of cyclopentyl and cyclopentenyl, and the pharmaceutically acceptable salts, optical isomers, and hydrates thereof.

158. A compound according to claim 1 wherein R is R2NH—, wherein R2 is

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8, n is an integer 0–8; and Z is naphthyl, wherein Z may be optionally substituted with 1 to 3 substituents, which may be the same or different, and which are selected from the group consisting of D, E,

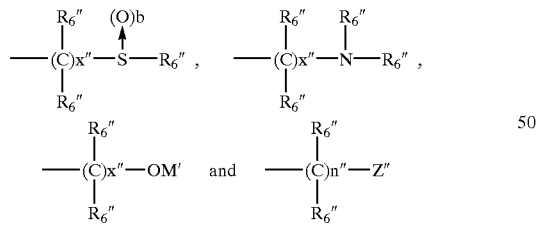

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

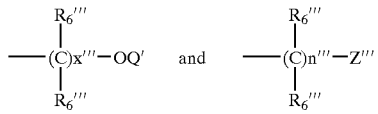

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

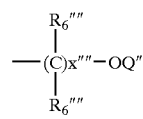

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

159. A compound according to claim 1, wherein R is R2NH—, wherein R2 is Z, wherein Z is phenyl, wherein Z may be optionally substituted with 1 to 3 substituents, which may be the same or different, and which are selected from the group consisting of D, E,

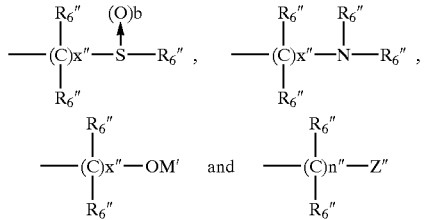

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

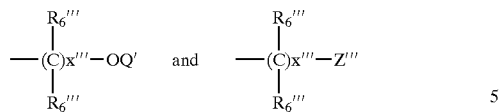

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and naphthyl, wherein the groups M' and Z'' may be optionally substituted with the groups D', E' or

provided M' is not hydrogen, wherein each R6'''' is independently selected from the group consisting of hydrogen, $C_3-C_8$ cycloalkyl, $C_1-C_4$ alkyl, and $(CH_2)_{m''''}$-phenyl, wherein m'''' is an integer 0–8; x'''' is an integer 0–8; Q'' is hydrogen or $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1-C_8$ alkyl; and R1 is selected from the group consisting of cyclopentyl and cyclopentenyl, and the pharmaceutically acceptable salts, optical isomers, and hydrates thereof.

160. A compound according to claim 159 wherein Z is substituted with the group E.

161. A compound according to claim 160 wherein E is Hal.

162. The compound according to claim 161, which is 2-(trans-(4-aminocyclohexyl)amino)-6-(2,6-dichlorophenylhydrazino)-9-cyclopentylpurine dihydrochloride; 2-(trans-(4-aminocyclohexyl)amino)-6-(2-chlorophenylhydrazino)-9-cyclopentylpurine dihydrochloride; 2-(trans-(4-aminocyclohexyl)amino)-6-(-2-fluorophenylhydrazino)-9-cyclopentylpurine dihydrochloride; or 2-(trans-(4-aminocyclohexyl)amino)-6-(2,4-dichlorophenylhydrazino)-9-cyclopentylpurine dihydrochloride.

163. A compound according to claim 1, wherein R is R2NH—, wherein R2 is

wherein each R6 is independently hydrogen or $C_3-C_8$ cycloalkyl, with the proviso that at least one of R6 is $C_3-C_8$ cycloalkyl; n is an integer 1–8; and Z is phenyl, wherein Z may be optionally substituted with 1 to 3 substituents, which may be the same or different, and which are selected from the group consisting of D, E,

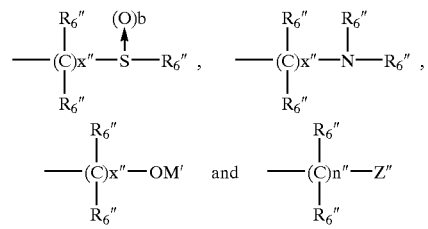

wherein each D is independently selected from the group consisting of trifluoromethyl, trifluoromethoxy, and $C_1-C_4$ alkoxy; each E is independently selected from the group consisting of Hal, OH, $C_2-C_6$ alkenyl, and $C_1-C_8$ alkyl; b is an integer 0–2; Z'' is selected from the group consisting of phenyl, heterocycle, cycloalkyl, and naphthyl; each R6'' is independently selected from the group consisting of hydrogen, $C_3-C_8$ cycloalkyl, $C_1-C_4$ alkyl, and $(CH_2)_{m''}$-phenyl, wherein m'' is an integer 0–8; n'' is an integer 0–8; x'' is an integer 1–8; and M'' is selected from the group consisting of hydrogen, $C_1-C_4$ alkyl,

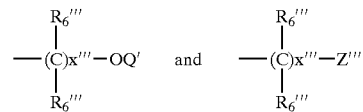

wherein each R6''' is independently selected from the group consisting of hydrogen, $C_3-C_8$ cycloalkyl, $C_1-C_4$ alkyl, and $(CH_2)_{m'''}$-phenyl, wherein m''' is an integer 0–8; n''' is an integer 0–8; x''' is an integer 1–8; Q' is hydrogen or $C_1-C_4$ alkyl; and Z''' is selected from the group consisting of phenyl, heterocycle, cycloalkyl, and naphthyl, wherein the groups M' and Z'' may be optionally substituted with the groups D', E' or

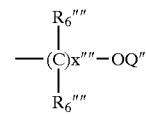

provided M' is not hydrogen, wherein each R6'''' is independently selected from the group consisting of hydrogen, $C_3-C_8$ cycloalkyl, $C_1-C_4$ alkyl, and $(CH_2)_{m''''}$-phenyl, wherein m'''' is an integer 0–8; x'''' is an integer 0–8; Q'' is hydrogen or $C_1-C_4$ alkyl or phenyl; each D' is independently selected from the group consisting of trifluoromethyl, trifluoromethoxy, and $C_1-C_4$ alkoxy; each E' is independently selected from the group consisting of Hal, OH, and $C_1-C_8$ alkyl; and R1 is selected from the group consisting of cyclopentyl and cyclopentenyl, and the pharmaceutically acceptable salts, optical isomers, and hydrates thereof.

164. A compound according to claim 1, wherein R is R2NH—, wherein R2 is

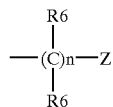

wherein each R6 is independently selected from the group consisting of hydrogen; $C_1$–$C_4$ alkyl, and $(CH_2)_m$-phenyl, wherein m is an integer 0–8; n is an integer 1–8; and Z is phenyl,
  wherein Z is substituted with 1 to 3 substituents, which may be the same or different, and which are selected from the group consisting of

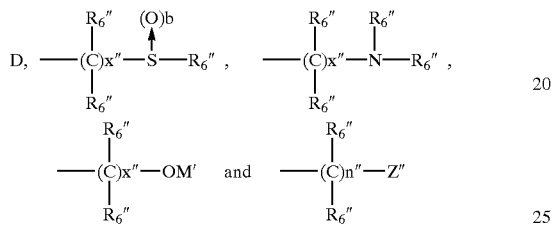

wherein each D is independently selected from the group consisting of trifluoromethyl, trifluoromethoxy, and $C_1$–$C_4$ alkoxy; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m"}$-phenyl, wherein m" is an integer 0–8; n" is an integer 0–8; x" is an integer 1–8; and M' is selected from the group consisting of hydrogen, $C_1$–$C_4$ alkyl,

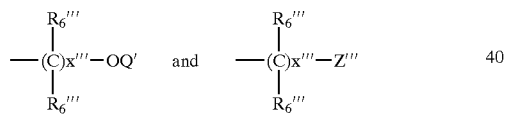

wherein each R6'" is independently selected from the group consisting of hydrogen, $C_3$–$C_8$ cycloalkyl, $C_1$–$C_4$ alkyl, and $(CH_2)_{m'"}$-phenyl, wherein m'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl,
wherein the groups M' and Z" may be optionally substituted with the groups D', E' or

provided M' is not hydrogen,
  wherein each R6"" is independently selected from the group consisting of hydrogen, $C_3$–$C_8$ cycloalkyl, $C_1$–$C_4$ alkyl, and $(CH_2)_{m""}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and
R1 is cyclopentyl,
and the pharmaceutically acceptable salts, optical isomers, and hydrates thereof.

165. A compound according to claim 1, wherein R is R2NH—, wherein R2 is

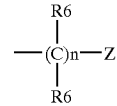

wherein each R6 is independently selected from the group consisting of hydrogen; $C_3$–$C_8$ cycloalkyl, $C_1$–$C_4$ alkyl and $(CH_2)_m$-phenyl, wherein m is an integer 0–8; n is an integer 0–8; and Z is phenyl,
wherein Z may be optionally substituted with 1 to 3 substituents, which may be the same or different, and which are selected from the group consisting of D, E,

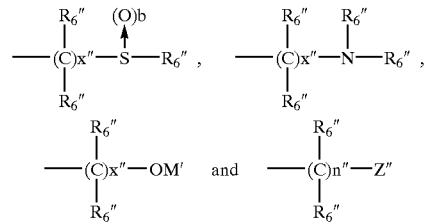

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m"}$-phenyl, wherein m" is an integer 0–8; n" is an integer 0–8; x" is an integer 1–8; and M' is selected from the group consisting of hydrogen, $C_1$–$C_4$ alkyl,

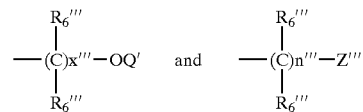

wherein each R6'" is independently selected from the group consisting of hydrogen, $C_3$–$C_8$ cycloalkyl, $C_1$–$C_4$ alkyl, and $(CH_2)_{m'"}$-phenyl, wherein m'" is an integer 0–8; n'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl,
  wherein the groups M' and Z" may be optionally substituted with the groups D', E' or

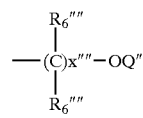

provided M' is not hydrogen,
  wherein each R6"" is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentenyl, and the pharmaceutically acceptable salts, optical isomers, and hydrates thereof.

166. A compound according to claim 1, wherein R is R2NH—, wherein R2 is Z, wherein Z is heterocycle, optionally substituted with 1 to 3 substituents, which may be the same or different, and which are selected from the group consisting of D, E,

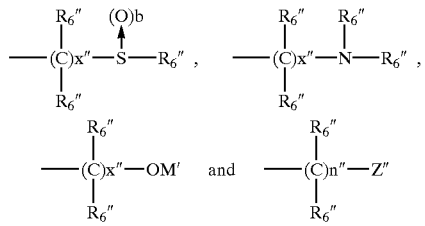

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

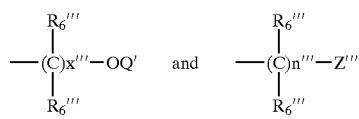

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_0$–$C_4$ alkyl; and Z''' is selected from the group consisting of phenyl, heterocycle, cycloalkyl, and naphthyl, wherein the groups M' and Z'' may be optionally substituted with the groups D', E' or

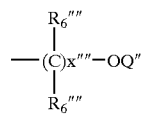

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

167. A compound according to claim 1, wherein R is R2NH—, wherein R2 is

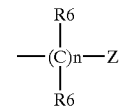

wherein each R6 is independently hydrogen or $C_3$–$C_8$ cycloalkyl, with the proviso that at least one of R6 is $C_3$–$C_8$ cycloalkyl; n is an integer 1–8; and Z is heterocycle, wherein Z may be optionally substituted with 1 to 3 substituents, which may be the same or different, and which are selected from the group consisting of D, E,

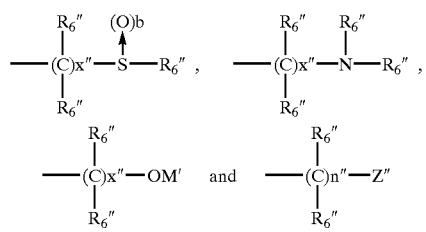

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

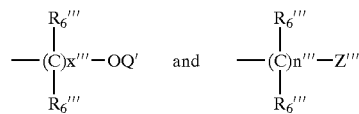

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

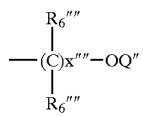

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

168. A compound according to claim 1, wherein R is R2NH—, wherein R2 is

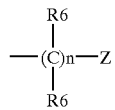

wherein each R6 is independently selected from the group consisting of hydrogen; $C_1$–$C_4$ alkyl, and $(CH_2)_m$-phenyl, wherein m is an integer 0–8; n is an integer 1–8; and Z is heterocycle, wherein Z is substituted with 1 to 3 substituents, which may be the same or different, and which are selected from the group consisting of

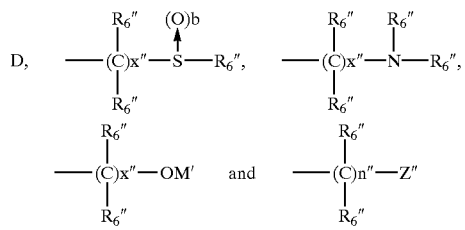

wherein each D is independently selected from the group consisting of trifluoromethyl, trifluoromethoxy, and $C_1$–$C_4$ alkoxy; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

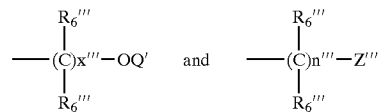

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z" may be optionally substituted with the groups D', E' or

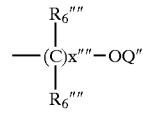

provided M' is not hydrogen,
wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q" is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentyl, and the pharmaceutically acceptable salts, optical isomers, and hydrates thereof.

169. A compound according to claim 1, wherein R is R2NH—, wherein R2 is

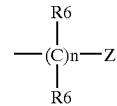

wherein each R6 is independently selected from the group consisting of hydrogen; $C_3$–$C_8$ cycloalkyl, $C_1$–$C_4$ alkyl and $(CH_2)_m$-phenyl, wherein m is an integer 0–8; n is an integer 0–8; and Z is heterocycle, wherein Z may be optionally substituted with 1 to 3 substituents, which may be the same or different, and which are selected from the group consisting of D, E,

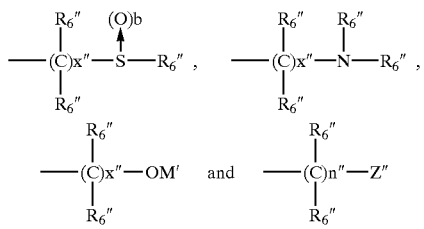

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

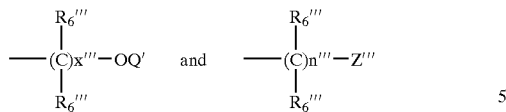

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 0–8; Q' is hydrogen or $C_1$–$C_4$ alkyl or phenyl; and Z''' is selected from the group consisting of phenyl, heterocycle, cycloalkyl, and naphthyl, wherein the groups M' and Z'' may be optionally substituted with the groups D', E' or

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 1–8; Q'' is hydrogen or $C_1$–$C_4$ alkyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is cyclopentenyl, and the pharmaceutically acceptable salts, optical isomers, and hydrates thereof.

170. A compound according to claim 1, wherein R is R2NH—, wherein R2 is Z, wherein Z is cycloalkyl, wherein Z may be optionally substituted with 1 to 3 substituents, which may be the same or different, and which are selected from the group consisting of D, E,

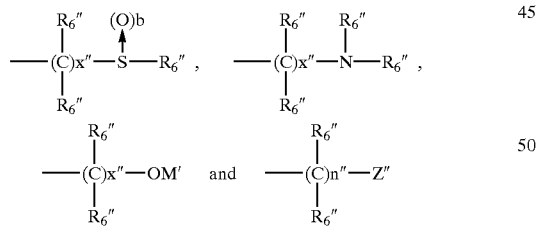

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

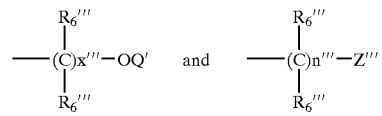

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

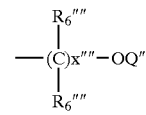

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

171. A compound according to claim 1, wherein R is R2NH—, wherein R2 is

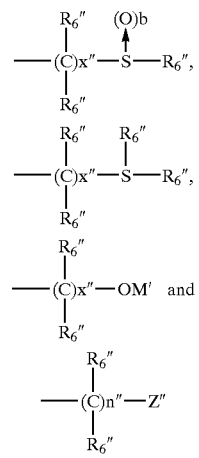

wherein each R6 is independently hydrogen or $C_3$–$C_8$ cycloalkyl, with the proviso that at least one of R6 is $C_3$–$C_8$ cycloalkyl; n is an integer 1–8; and Z is cycloalkyl, wherein Z may be optionally substituted with 1 to 3 substituents, which may be the same or different, and which are selected from the group consisting of D, E,

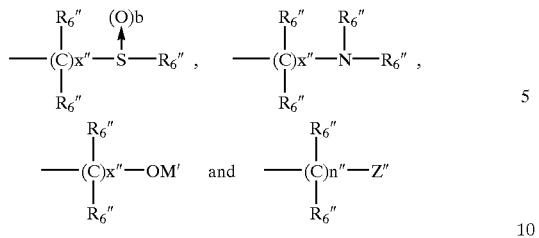

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

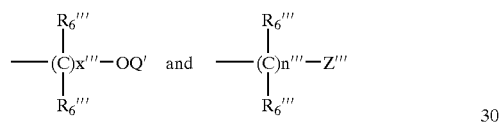

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 0–8; Q' is hydrogen or $C_1$–$C_4$ alkyl or phenyl; and Z''' is selected from the group consisting of phenyl, heterocycle, cycloalkyl, and naphthyl, wherein the groups M' and Z'' may be optionally substituted with the groups D', E' or

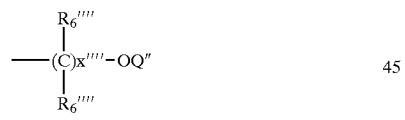

provided M' is not hydrogen,
wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 1–8; Q'' is hydrogen or $C_1$–$C_4$ alkyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl and cyclopentenyl, and the pharmaceutically acceptable salts, optical isomers, and hydrates thereof.

172. A compound according to claim 1, wherein R is R2NH—, wherein R2 is $$\begin{array}{c} R6 \\ | \\ -(C)n-Z \\ | \\ R6 \end{array}$$

wherein each R6 is independently selected from the group consisting of hydrogen, $C_1$–$C_4$ alkyl and $(CH_2)_m$-phenyl, wherein m is an integer 0–8; n is an integer 1–8; and Z is cycloalkyl, wherein Z is substituted with 1 to 3 substituents, which may be the same or different, and which are selected from the group consisting of

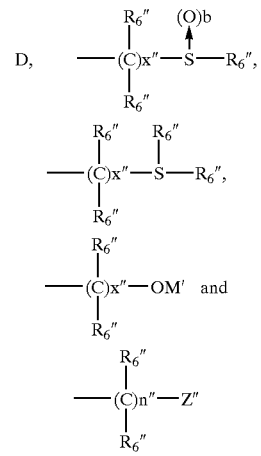

wherein each D is independently selected from the group consisting of trifluoromethyl, trifluoromethoxy, and $C_1$–$C_4$ alkoxy; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

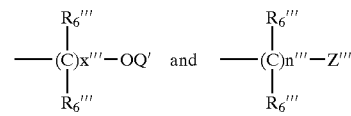

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

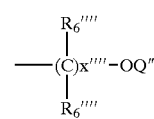

provided M' is not hydrogen,
wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl; and R1 is selected from the group consisting of cyclopentyl, and the pharmaceutically acceptable salts, optical isomers, and hydrates thereof.

173. A compound according to claim 1, wherein R is R2NH—, wherein R2 is

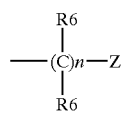

wherein each R6 is independently selected from the group consisting of hydrogen, $C_3$–$C_8$ cycloalkyl, $C_1$–$C_4$ alkyl and $(CH_2)_m$-phenyl, wherein m is an integer 0–8; n is an integer 0–8; and Z is cycloalkyl, optionally substituted with 1 to 3 substituents independently selected from the group consisting of D, E,

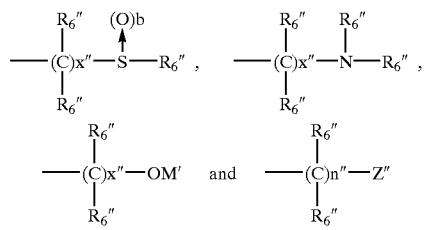

wherein each D is independently selected from the group consisting of trifluoromethyl, trifluoromethoxy, and $C_1$–$C_4$ alkoxy; each E is independently selected from the group consisting of Hal, OH, $CH_2$–$CH_6$ alkenyl, and $C_1$–$C_8$ alkyl; b is an integer 0–2; Z'' is selected from the group consisting of phenyl, heterocycle, cycloalkyl, and naphthyl; each R6'' is independently selected from the group consisting of hydrogen, $C_3$–$C_8$ cycloalkyl, $C_1$–$C_4$ alkyl, and $(CH_2)_{m''}$-phenyl, wherein m'' is an integer 0–8; n'' is an integer 0–8; x'' is an integer 1–8; and M' is selected from the group consisting of hydrogen, $C_1$–$C_4$ alkyl,

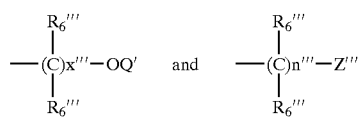

wherein each R6''' is independently selected from the group consisting of hydrogen, $C_3$–$C_8$ cycloalkyl, $C_1$–$C_4$ alkyl, and $(CH_2)_{m'''}$-phenyl, wherein m''' is an integer 0–8; n''' is an integer 0–8; x''' is an integer 1–8; Q' is hydrogen or $C_1$–$C_4$ alkyl; and Z''' is selected from the group consisting of phenyl, heterocycle, cycloalkyl, and naphthyl, wherein the groups M' and Z'' may be optionally substituted with the groups D', E' or

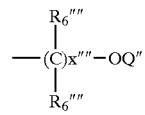

provided M' is not hydrogen, wherein each R6'''' is independently selected from the group consisting of hydrogen, $C_3$–$C_8$ cycloalkyl, $C_1$–$C_4$ alkyl, and $(CH_2)_{m''''}$-phenyl, wherein m'''' is an integer 0–8; x'''' is an integer 0–8; Q'' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$CH_8$ alkyl; and R1 is cyclopentenyl, and the pharmaceutically acceptable salts, optical isomers, and hydrates thereof.

174. A compound according to claim 1, wherein R is R3R4N—R5— wherein R3 and R4 are selected from the group consisting of hydrogen, $C_1$–$C_4$ alkyl and $(CH_2)_n$-phenyl, wherein n is an integer 0–8, with the proviso that R3 and R4 not both be hydrogen;

R5 is $C_1$–$C_8$ alkylene; and

R1 is selected from the group consisting of cyclopentyl and cyclopentenyl, and the pharmaceutically acceptable salts, optical isomers, and hydrates thereof.

175. A compound according to claim 174 which is 2-[trans-(4-aminocyclohexyl)-amino]-6-[(2-N,N-diethylamino)ethylamino]-9-cyclopentylpurine trihydrochloride; 2-[trans-(4-aminocyclohexyl)amino]-6-[(3-N,N-diethylamino)propylamino]-9-cyclopentylpurine trihydrochloride; or 2-[trans-(4-aminocyclohexyl)amino]-6-[2-(phenylamino)ethylamino]-9-cyclopentylpurine trihydrochloride.

176. A compound of the formula

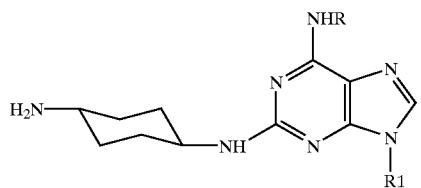

wherein R is selected from the group consisting of R2, R2NH—, or R3R4N—R5— wherein R2 is selected from the group consisting of $C_9$–$C_{12}$ alkyl,

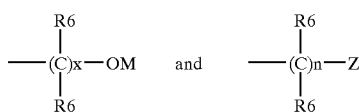

wherein each R6 is independently selected from the group consisting of hydrogen, $C_3$–$C_8$ cycloalkyl, $C_1$–$C_4$ alkyl, and $(CH_2)_m$-phenyl, wherein m is an integer 0–8; x is an integer 1–8; n is an integer 1–8; Z is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; and M is selected from the group consisting of hydrogen, $C_1$–$C_4$ alkyl,

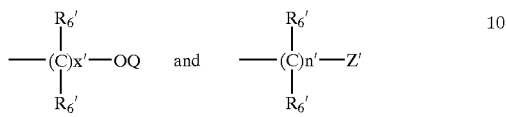

wherein each R6' is independently selected from the group consisting of hydrogen, $C_3$–$C_8$ cycloalkyl, $C_1$–$C_4$ alkyl, and $(CH_2)_{m'}$-phenyl, wherein m' is an integer 0–8; n' is an integer 0–8; x' is an integer 1–8; Q is hydrogen or $C_1$–$C_4$ alkyl; and Z' is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; and wherein each $C_9$–$C_{12}$ alkyl or Z is optionally substituted with 1 to 3 substituents, which may be the same or different, and which are selected from the group consisting of D, E,

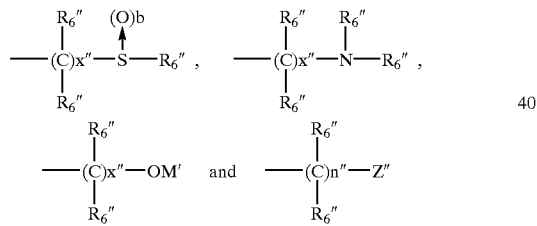

wherein each D is independently selected from the group consisting of trifluoromethyl, trifluoromethoxy, and $C_1$–$C_4$ alkoxy; each E is independently selected from the group consisting of Hal, OH, $C_2$–$C_6$ alkenyl, and $C_1$–$C_8$ alkyl; b is an integer 0–2; Z" is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl; each R6" is independently selected from the group consisting of hydrogen, $C_3$–$C_8$ cycloalkyl, $C_1$–$C_4$ alkyl, and $(CH_2)_{m''}$-phenyl, wherein m" is an integer 0–8; n" is an integer 0–8; x" is an integer 1–8; and M' is selected from the group consisting of hydrogen, $C_1$–$C_4$ alkyl,

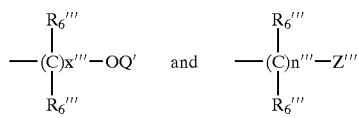

wherein each R6'" is independently selected from the group consisting of hydrogen, $C_3$–$C_8$ cycloalkyl, $C_1$–$C_4$ alkyl, and $(CH_2)_{m'''}$-phenyl, wherein m'" is an integer 0–8; n'" is an integer 0–8; x'" is an integer 1–8; Q' is hydrogen or $C_1$–$C_4$ alkyl; and Z'" is selected from the group consisting of phenyl, heterocycle, cycloalkyl, and naphthyl, where heterocycle is piperidinyl, pyridinyl, isoxazolyl, tetrahydrofuranyl, pyrrolidinyl, morpholinyl, piperazinyl, benzimidazolyl, thiazolyl, thiophene, furanyl, indolyl, 1,3-benzodioxolyl, tetrahydropyranyl, imidazolyl, tetrahydrothiophene, pyranyl, dioxanyl, pyrrolyl, pyrimidinyl, pyrazinyl, triazinyl, oxazolyl, purinyl, quinolinyl, or isoquinolinyl, wherein the groups M' and Z" may be optionally substituted with the groups D', E' or

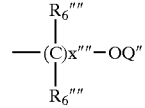

provided M' is not hydrogen, wherein each R6"" is independently selected from the group consisting of hydrogen, $C_3$–$C_8$ cycloalkyl, $C_1$–$C_4$ alkyl, and $(CH_2)_{m''''}$-phenyl, wherein m"" is an integer 0–8; x"" is an integer 0–8; Q' is hydrogen or $C_1$–$C_4$ alkyl or phenyl; each D' is independently selected from the group consisting of trifluoromethyl, trifluoromethoxy, and $C_1$–$C_4$ alkoxy; each E' is independently selected from the group consisting of Hal, OH, and $C_1$–$C_8$ alkyl;

R3 and R4 are selected from the group consisting of hydrogen, $C_1$–$C_4$ alkyl and $(CH_2)_y$-phenyl, wherein y is an integer 0–8, with the proviso that R3 and R4 not both be hydrogen;

R5 is $C_1$–$C_8$ alkylene; and

R1 is isopropyl, and the pharmaceutically acceptable salts, optical isomers, and hydrates thereof.

177. The compound according to claim 176 wherein R is R2, R2 is

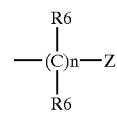

wherein each R6 is hydrogen and Z is phenyl, wherein Z may be optionally substituted with 1 to 3 substituents, which may be the same or different, and which are selected from the group consisting of trifluoromethyl, trifluoromethoxy, and $C_1$–$C_4$ alkoxy, and the pharmaceutically acceptable salts, optical isomers, and hydrates thereof.

178. The compound according to claim 176, wherein the compound is 2-(trans-(4-aminocyclohexyl)amino)-6-(3,4- dimethoxybenzyl)amino)-9-(2-propyl)purine dihydrochloride; 2-(trans-(4-aminocyclohexyl)amino)-6-(2,3-dimethoxybenzyl)amino)-9-(2-propyl)purine dihydrochloride; or 2-(trans-(4-aminocyclohexyl)amino)-6-(4-methoxybenzyl)amino)-9-(2-propyl)purine dihydrochloride.

179. A method a treating carcinoma selected from the group consisting of cervix carcinoma, breast carcinoma, prostate carcinoma, esophageal carcinoma, small intestine carcinoma, colon carcinoma, ovary carcinoma, lung carcinoma, comprising administering to a patient in need of said treatment an effective amount of a compound according to claim 1 or a pharmaceutically acceptable salt thereof, optionally in combination with the pharmaceutically acceptable carrier.

180. A method of treating adenocarcinoma selected from the group consisting of cervix adenocarcinoma, breast adenocarcinoma, prostate adenocarcinoma, esophageal adenocarcinoma, small intestine adenocarcinoma, colon adenocarcinoma, ovary adenocarcinoma, lung adenocarcinoma, comprising administering to a patient in need of said treatment an effective amount of a compound according to claim 1 or a pharmaceutically acceptable salt thereof, optionally in combination with the pharmaceutically acceptable carrier.

181. A method of treating a disease condition selected from the group consisting of osteosarcoma, liposarcoma, hemangiosarcoma, carcinosarcoma and reticulum cell sarcoma comprising administering to a patient in need of said treatment an effective amount of a compound according to claim 1 or a pharmaceutically acceptable salt thereof, optionally in combination with the pharmaceutically acceptable carrier.

182. A method of treating amelanotic melanoma or melanotic melanoma comprising administering to a patient in need of said treatment an effective amount of a compound according to claim 1 or a pharmaceutically acceptable salt thereof, optionally in combination with the pharmaceutically acceptable carrier.

183. The compound according to claim 66, wherein Z" is naphthyl.

184. The compound according to claim 183, wherein n" is 1.

185. The compound according to claim 66, wherein the compound is; 2-(Trans-(4-aminocyclohexyl)amino)-6-(4-(1-(2-naphthyl)methyl)piperidinylamino)-9-cyclopentylpurine trihydrochloride; or 2-(Trans-(4-aminocyclohexyl)amino)-6-(4-(1-(1-naphthyl)methyl)piperidinylamino)-9-cyclopentylpurine trihydrochloride.

186. A method of preventing apoptosis in neuronal cells in a patient by administration of a compound according to claim 1.

187. The method according to claim 186, wherein the apoptosis is induced by antineoplastic agents.

188. The method according to claim 186, wherein the apoptosis is induced by cerebrovascular disease.

189. The method according to claim 186, wherein the apoptosis is induced by stroke or infarction.

190. A method of protecting method of protecting neuronal cells from apoptosis comprising administering a compound according to claim 1.

191. A method of protecting neuronal cells from damage induced by antineoplastic agents, comprising administering a compound according to claim 1.

192. A composition comprising a compound of claim 1 in admixture or otherwise in association with an inert carrier.

193. A pharmaceutical composition comprising an effective cdk-2 inhibiting amount of a compound of claim 1 in admixture or otherwise in association with one or more pharmaceutically acceptable carriers or excipients.

* * * * *